(12) United States Patent
Wu et al.

(10) Patent No.: US 8,633,297 B2
(45) Date of Patent: Jan. 21, 2014

(54) PROTEIN SCAFFOLDS

(75) Inventors: Herren Wu, Boyds, MD (US); Manuel Baca, Gaithersburg, MD (US); Jeffrey Swers, Rockville, MD (US); Benoy Chacko, Gaithersburg, MD (US)

(73) Assignee: MedImmune, LLC, Gaithersburg, MD (US)

(*) Notice: Subject to any disclaimer, the term of this patent is extended or adjusted under 35 U.S.C. 154(b) by 540 days.

(21) Appl. No.: 12/739,149

(22) PCT Filed: Oct. 31, 2008

(86) PCT No.: PCT/US2008/012398
§ 371 (c)(1),
(2), (4) Date: Aug. 12, 2010

(87) PCT Pub. No.: WO2009/058379
PCT Pub. Date: May 7, 2009

(65) Prior Publication Data
US 2010/0298541 A1 Nov. 25, 2010

Related U.S. Application Data

(60) Provisional application No. 60/984,209, filed on Oct. 31, 2007.

(51) Int. Cl.
*C07K 14/00* (2006.01)
*A61K 38/00* (2006.01)

(52) U.S. Cl.
USPC ............................................ 530/300; 514/1.1

(58) Field of Classification Search
USPC ............................................ 530/300; 514/1.1
See application file for complete search history.

(56) References Cited

U.S. PATENT DOCUMENTS

| | | | |
|---|---|---|---|
| 6,160,089 A | 12/2000 | Honjo et al. | |
| 6,482,410 B1 | 11/2002 | Crossin et al. | |
| 6,818,418 B1 | 11/2004 | Lipovsek et al. | |
| 2005/0038229 A1* | 2/2005 | Lipovsek et al. | 530/350 |
| 2006/0073559 A1 | 4/2006 | Ferrari et al. | |
| 2007/0098681 A1 | 5/2007 | Kelley et al. | |
| 2008/0108798 A1* | 5/2008 | Lipovsek et al. | 530/402 |
| 2009/0176654 A1* | 7/2009 | Cappuccilli et al. | 506/9 |

FOREIGN PATENT DOCUMENTS

| | | | |
|---|---|---|---|
| KR | 10-2006-0005595 * | 1/2006 | C07K 2/00 |
| WO | WO 9856915 A2 | 12/1998 | |
| WO | WO 0034784 A1 | 6/2000 | |
| WO | WO 0164942 A1 | 9/2001 | |
| WO | WO 0204523 A2 | 1/2002 | |
| WO | WO 0232925 A2 | 4/2002 | |
| WO | WO 03104418 A2 | 12/2003 | |
| WO | WO 2005056764 A2 | 6/2005 | |
| WO | WO 2006013468 A2 | 2/2006 | |
| WO | WO 2008031098 A1 | 3/2008 | |
| WO | WO 2008066752 A2 | 6/2008 | |
| WO | WO 2009023184 A2 | 2/2009 | |
| WO | WO 2009058379 A2 | 5/2009 | |
| WO | WO 2009058379 A3 | 5/2009 | |
| WO | WO 2009083804 A2 | 7/2009 | |
| WO | WO 2009133208 A1 | 11/2009 | |
| WO | WO 2009142773 A2 | 11/2009 | |
| WO | WO 2010051274 A2 | 5/2010 | |
| WO | WO 2010060095 A1 | 5/2010 | |
| WO | WO 2010093627 A2 | 8/2010 | |
| WO | WO 2011020033 A2 | 2/2011 | |
| WO | WO 2011035202 A2 | 3/2011 | |

OTHER PUBLICATIONS

Baca, M., "A New Platform for Non-antibody Protein Drugs," 15thHuman Antibodies & Hybridomas Conference, pp. 1-22 (2010).
Baca, M., "Beyond Antibodies: Challenges and Opportunities for Alternative Scaffold Protein Drugs," Antibody Interest Group, NIH, pp. 1-24 (2010).
Baca, M., "Tn3: A New Platform for Non-antibody Protein Drugs," Protein and Antibody Engineering Summit, pp. 1-2 (2010).
Batori, V., et al., "Exploring the potential of the monobody scaffold: effects of loop elongation on the stability of a fibronectin type III domain," Protein Engineering, vol. 15, No. 12, pp. 1015-1020, Oxford University Press (2002).
Binz, H.K., et al., "Engineering novel binding proteins from nonimmunoglobulin domains," Nature Biotechnology, vol. 23, No. 10, pp. 1257-1268, Nature publishing Group (2005).
Bloom, L, and Calabro, V., "FN3: a new protein scaffold reaches the clinic," Drug Discovery Today, vol. 14, No. 19-20, pp. 949-955, Elsevier Ltd. (2009).
Bork, P, and Doolittle, R.F., "Proposed acquisition of an animal protein domain by bacteria," Proc. Natl. Acad. Sci, vol. 89, pp. 8990-8994, (1992).
Bork, P., et al., "The Immunoglobulin Fold Structural Classification, Sequence Patterns and Common Core," J. Mol. Bio., vol. 242, pp. 309-320, Academic Press Limited (1994).
Chothia, C, and Jones, E.Y., "The Molecular Structure of Cell Adhesion Molecules," Annu. Rev. Biochem., vol. 66, pp. 823-862, Annual Reviews Inc., (1997).
Coussen, F., et al., "Trimers of the fibronectin cell adhesion domain localize to actin filament bundles and undergo rearward translocation," Journal of Cell Science, vol. 115, pp. 2581-2590, The Company of Biologists Ltd (2002).
Duan, J., et al., "Fibronectin Type III Domain Based Monobody with High Avidity," Biochemistry, vol. 46, No. 44, pp. 12656-12664, American Chemical Society (2007).
Dutta, S., "High-affinity fragment complementation of a fibronectin type III domain and its application to stability enhancement," Protein Science, vol. 14, pp. 2838-2848, The Protein Society (2005).
Emanuel, S.L., et al., "Functional activity of a bispecific Adnectin inhibitor to EGFR and IGFR," AACR, p. 1, Denver, CO (2009).
Friedman, M, and Ståhl, S., "Engineered affinity proteins for tumour-targeting applications," Biotechnol. Appl. Biochem. vol. 53, pp. 1-29, Portland Press Ltd (2009).
Gebauer, M, and Skerra, A., "Engineered protein scaffolds as next-generation antibody therapeutics," Current Opinion in Chemical Biology, vol. 13, pp. 245-255, Elsevier Ltd. (2009).

(Continued)

*Primary Examiner* — Amber D Steele

(57) ABSTRACT

The invention provides protein scaffolds and methods of preparing, screening, engineering and using such protein scaffolds.

17 Claims, 70 Drawing Sheets

(56) References Cited

OTHER PUBLICATIONS

Getmanova, E.V., et al., "Antagonists to Human and Mouse Vascular Endothelial Growth Factor Receptor 2 Generated by Directed Protein Evolution In Vitro," Chemistry & Biology, vol. 13, Issue 5, pp. 549-556, Elsevier Ltd (2006).

Gill, D.S and Damle, N.K., "Biopharmaceutical drug discovery using novel protein scaffolds," Current Opinion in Biotechnology, vol. 17, pp. 653-658, Elsevier Ltd. (2006).

Hackel, B.J, and Wittrup, K.D., "High Affinity Fn3 Domains Using Loop Length Diversity and Population Maturation," AIChE SBE's 1st International Converence on Biomolecular Engineering (2007).

Hackel, B.J., et al., "Picomolar Affinity Fibronectin Domains Engineered Utilizing Loop Length Diversity, Recursive Mutagenesis, and Loop Shuffling," J. Mol. Biol., vol. 381, pp. 1238-1252, Elsevier Ltd. (2008).

Hsia, H.C, and Schwarzbauer, J.E., "Meet the Tenascins: Multifunctional and Mysterious," The Journal of Biological Chemistry, vol. 280, No. 29, pp. 26641-26644, The American Society for Biochemistry and Molecular Biology, Inc. (2005).

Karatan, E., et al., "Molecular Recognition Properties of FN3 Monobodies that Bind the Src SH3 Domain," Chemistry & Biology, vol. 11, pp. 835-844, Elsevier Ltd. (2004).

Kashiwagi, K., et al., "Frame shuffling: a novel method for in vitro protein evolution," Protein Engineering, Design & Selection, vol. 19, No. 3, pp. 135-140 (2006).

Koide, A, and Koide, S., "Antibody Mimics based on the Scaffold of the Fibronectin Type III Domain," Methods in Molecular Biology, vol. 352, pp. 95-96, Humana Press Inc. (2007).

Koide, A., et al., "High-affinity single-domain binding proteins with a binary-code interface," PNAS, vol. 104, No. 16, pp. 6632-6637, The National Academy of Sciences of the USA (2007).

Koide, A., et al., "The Fibronectin Type III Domain as a Scaffold for Novel Binding Proteins," J. Mol. Biol., vol. 284, pp. 1141-1151, Academic Press (1998).

Kolkman, J.A, and Stemmer, W.P.C., "Directed evolution of proteins by exon shuffling," Nature Biotechnology, vol. 19, pp. 423-428, Nature Publishing Group (2001).

Lipovšek "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," J. Mol. Biol., vol. 368, pp. 1024-1041, Elsevier Ltd. (2007).

Meinke, A., et al., "Cellulose-Binding Polypeptides from *Cellulomonas fimi*: Endoglucanase D (CenD), a Family A β-1,4-Glucanase," Journal of Bacteriology, vol. 175, No. 7, pp. 1910-1918, American Society for Microbiology (1993).

Ng. S.P., et al., "Designing an extracellular matrix protein with enhanced mechanical stability," PNAS, vol. 104, No. 23, pp. 9633-9637, The National Academy of Sciences of the USA (2007).

Nuttall, S.D, and Walsh, R.B., "Display scaffolds: protein engineering for novel therapeutics," Current Opinion in Pharmacology, vol. 8, pp. 609-615, Elsevier Ltd. (2008).

O'Neil, K., "Centyrin Alternative Scaffolds: A New Biotherapeutic Platform for J&J," Beyond Antibodies conference, pp. 1-24 (2009).

Olson, C.A, and Roberts, R.W., "Design, expression, and stability of a diverse protein library based on the human fibronectin type III domain," Protein Science, vol. 16, pp. 476-484, The Protein Society (2007).

Parker, M.H., et al., "Antibody mimics based on human fibronectin type three domain engineered for thermostability and high-affinity binding to vascular endothelial growth factor receptor two," Protein Engineering, Design & Selection, vol. 18, No. 9, pp. 435-444 (2005).

Peleshok, J, and Saragovi, H.U., "Functional mimetics of neurotrophins and their receptors," Biochemical Society Transactions, vol. 34, Part 4, pp. 612-617, Biochemical Society (2006).

Schellenberger, V., "Tuning the Half-life of Protein Therapeutics by Fusion to XTEN," VP Drug Discovery, Amunix Inc., pp. 1-25 (2010).

Sheridan, C., "Pharma consolidates its grip on post-antibody landscape," Nature Biotechnology, vol. 25, No. 4, pp. 365-366, Nature Publishing Group (2007).

Silverman, J., et al., "Multivalent avimer proteins evolved by exon shuffling of a family of human receptor domains," vol. 23, No. 12, Nature Biotechnology, pp. 1556-1561, Nature Publishing Group (2005).

Skerra, A., "Alternative non-antibody scaffolds for molecular recognition", Current Opinion in Biotechnology, 18:295-304, (2007).

Thisted, T., "Tn3: A New Platform for Non-antibody Protein Drugs," 5th Annual Biological Therapeutics Conference, pp. 1-21 (2010).

Thøgersen, H.C, and Holldack, J., "A Tetranectin-Based Platform for Protein Engineering," Innovations in Pharmaceutical Technology, pp. 27-31 (2005).

Watanabe, T., et al., "Gene Cloning of Chitinase A1 from *Bacillus circulans* WL-12 Revealed Its Evolutionary Relationship to *Serratia* Chitinase and to the Type III Homology Units Fibronectin," The Journal of Biological Chemistry, vol. 265, No. 26, pp. 15659-15665, The American Society for Biochemistry and Molecular Biology, Inc. (1990).

Wurch, T., et al., "Development of Novel Protein Scaffolds as Alternatives to Whole Antibodies for Imaging and Therapy: Status on Discovery Research and Clinical Validation," Current Pharmaceutical Biotechnology, vol. 9, No. 6, pp. 502-509, Bentham Science Publishers Ltd (2008).

International Preliminary Report on Patentability (IPRP) with Written Opinion for International Application No. PCT/US2008/012398, The International Bureau of WIPO, Switzerland, mailed on Apr. 24, 2009.

* cited by examiner

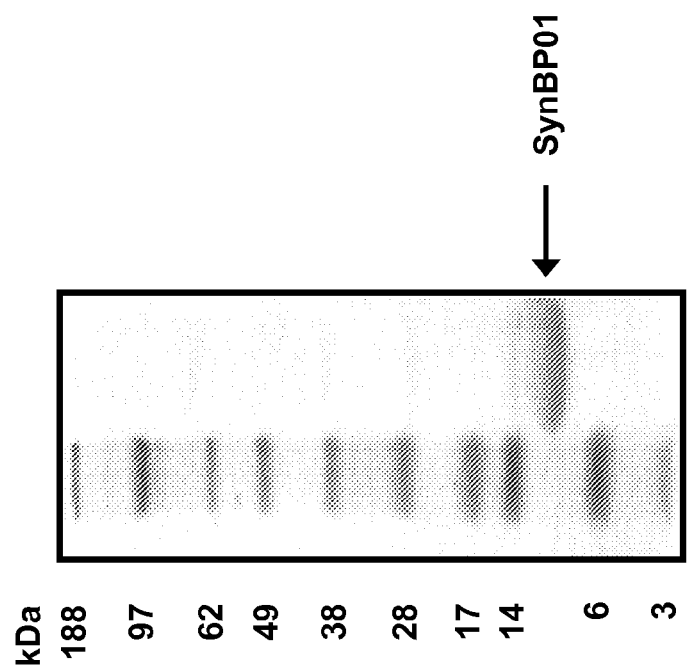

IEVKDVTDTTALITWEKPLAEIDGIELTYGIKDVPGDRTTI
DLTEDENQYSIGNLKPDTEYEVSLISRRGDMSSNPAKETFTT (SEQ ID NO: 61)

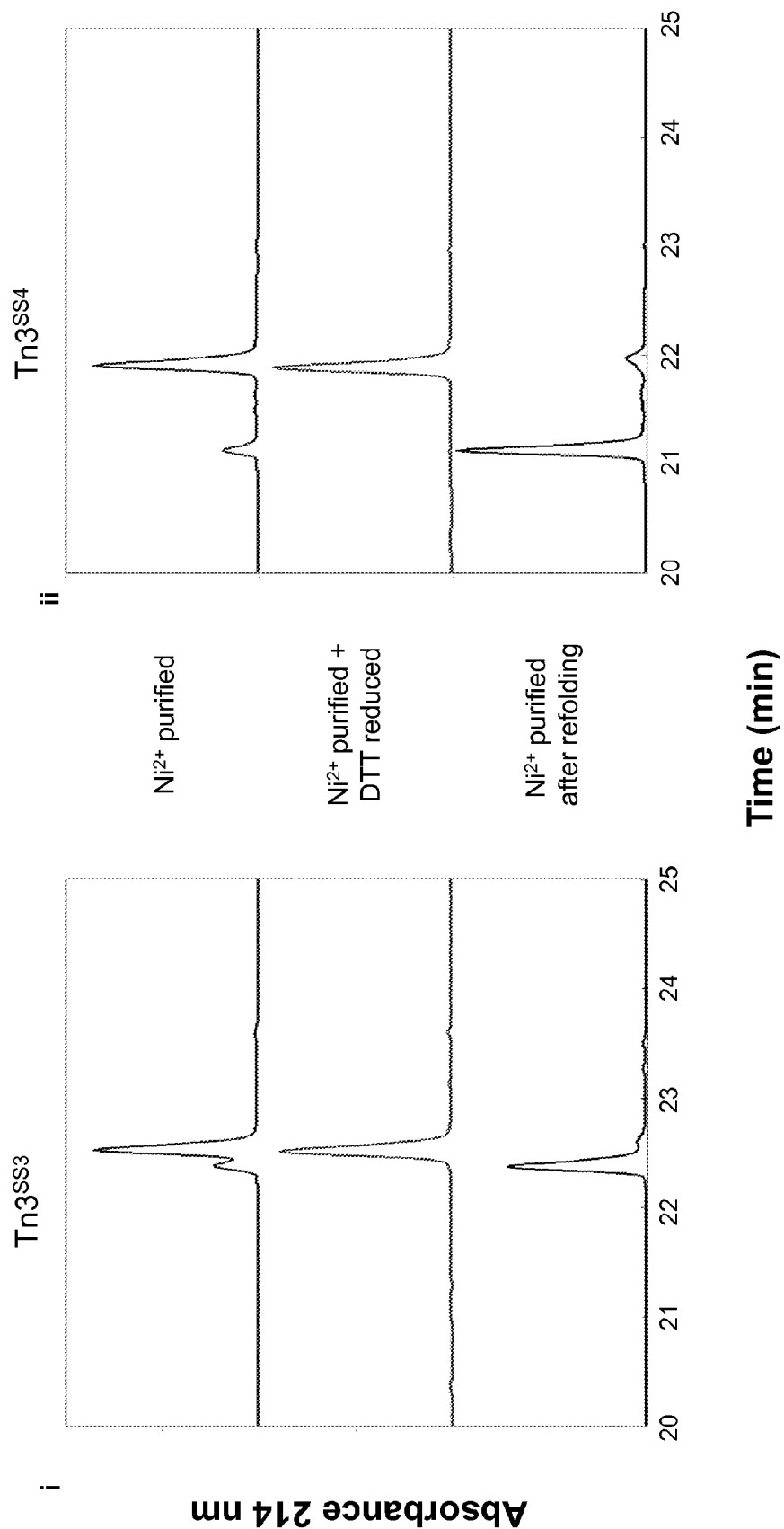

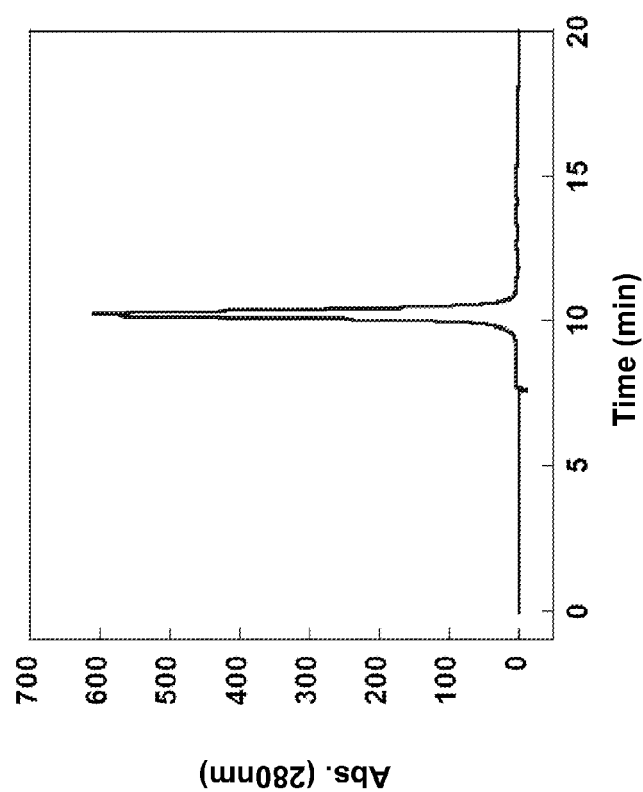
Fig. 10K SEC-MALS analysis of Tn3^{SS4}

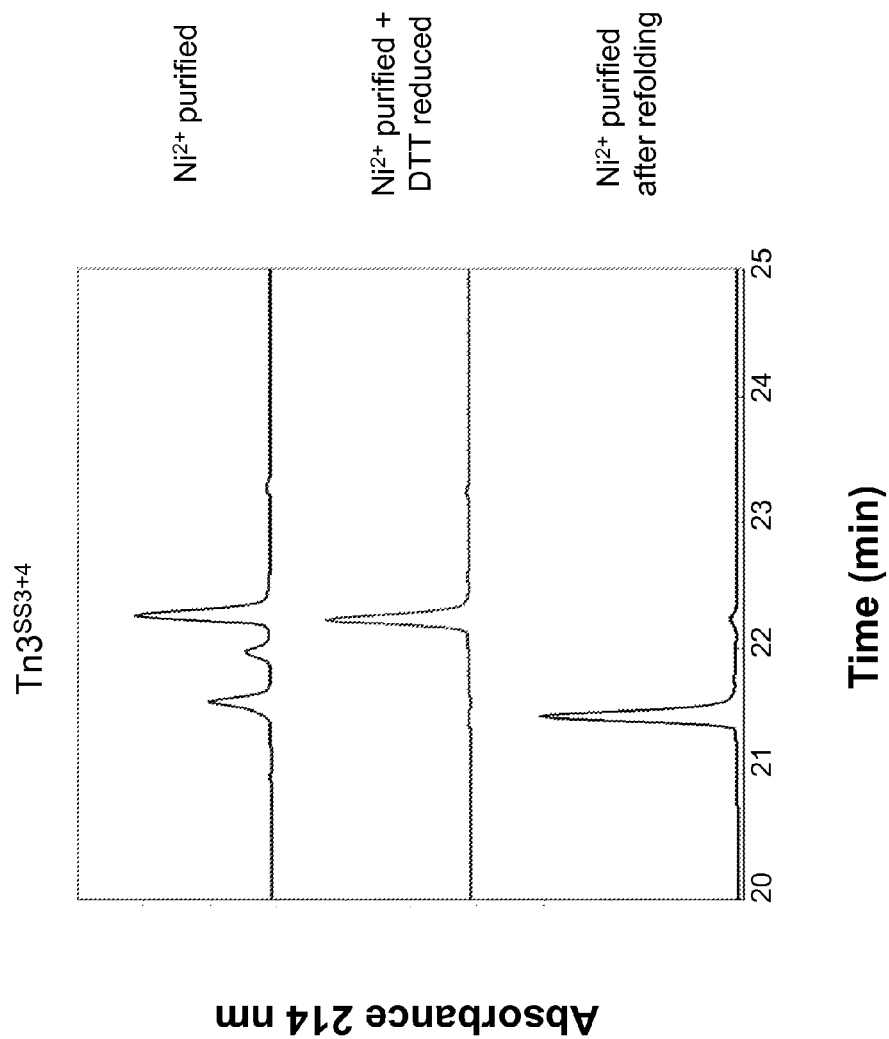

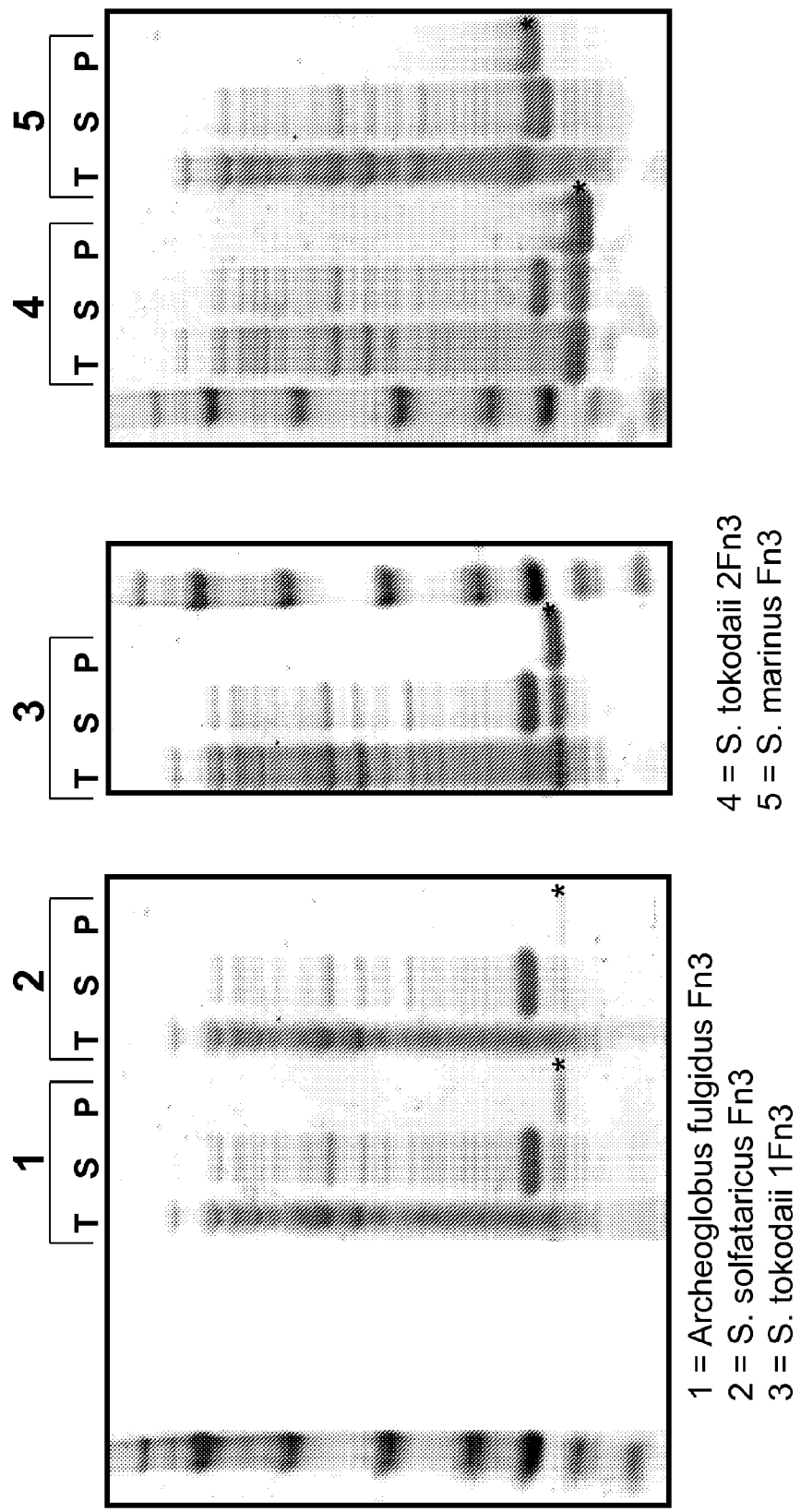

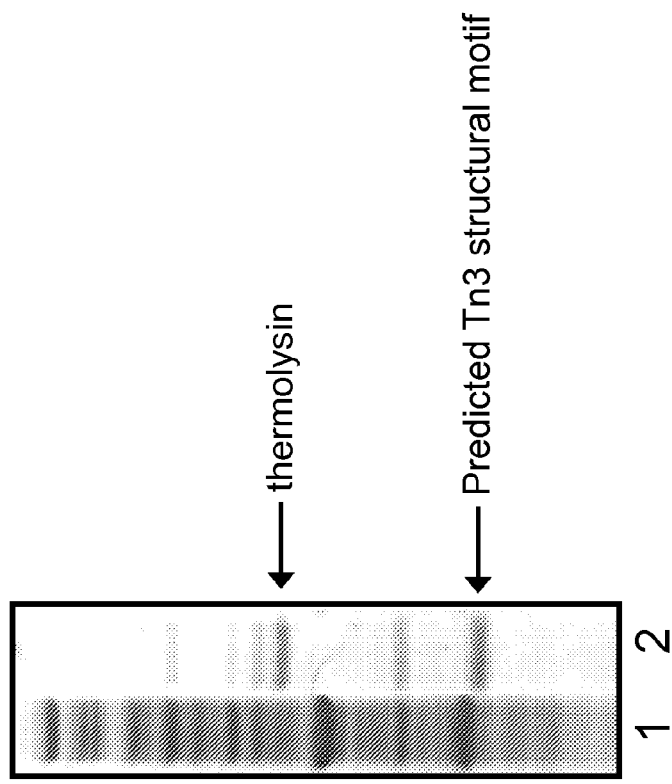

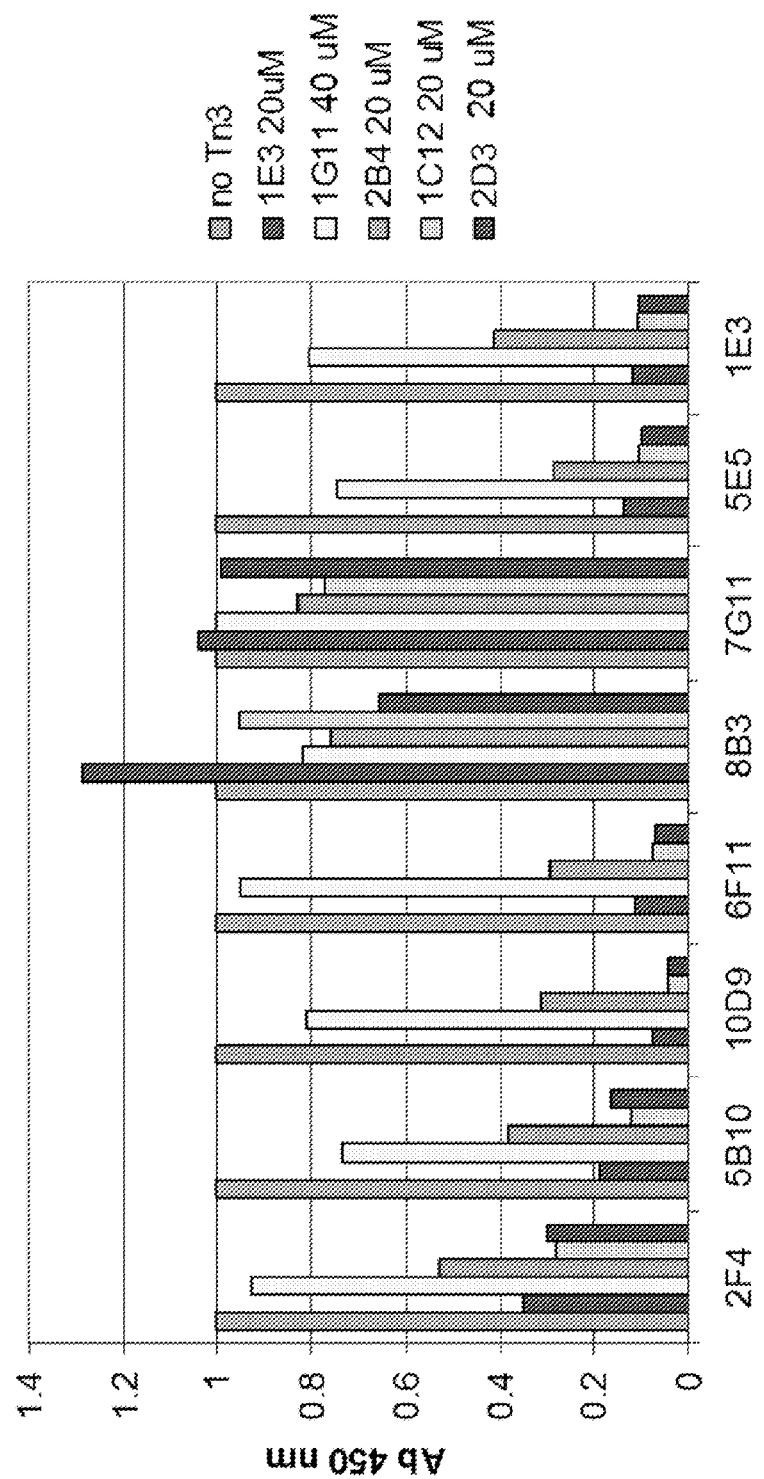

Fig. 17B
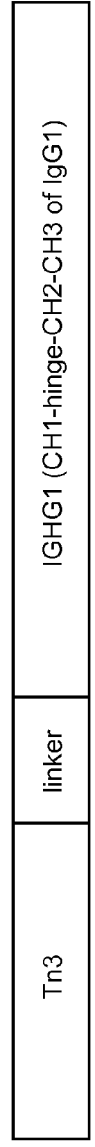
i) Tn3-Fc
ii) Tn3-Cκ
iii) Tn3-IGHG1

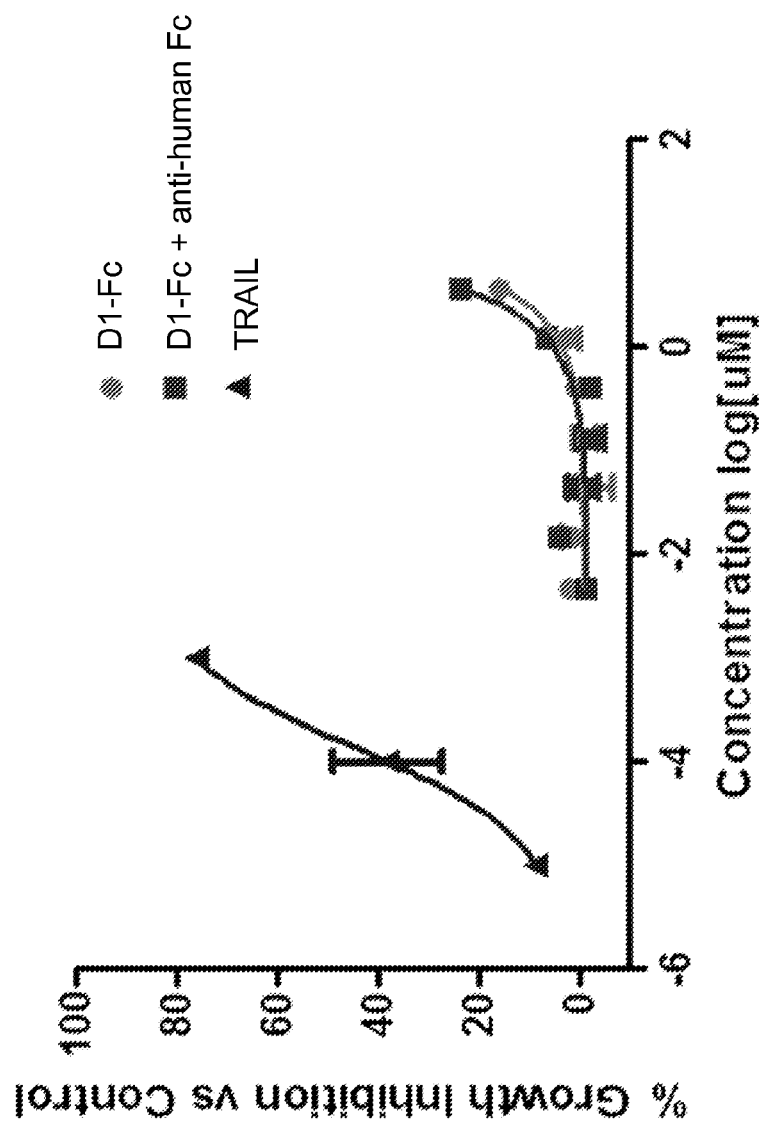

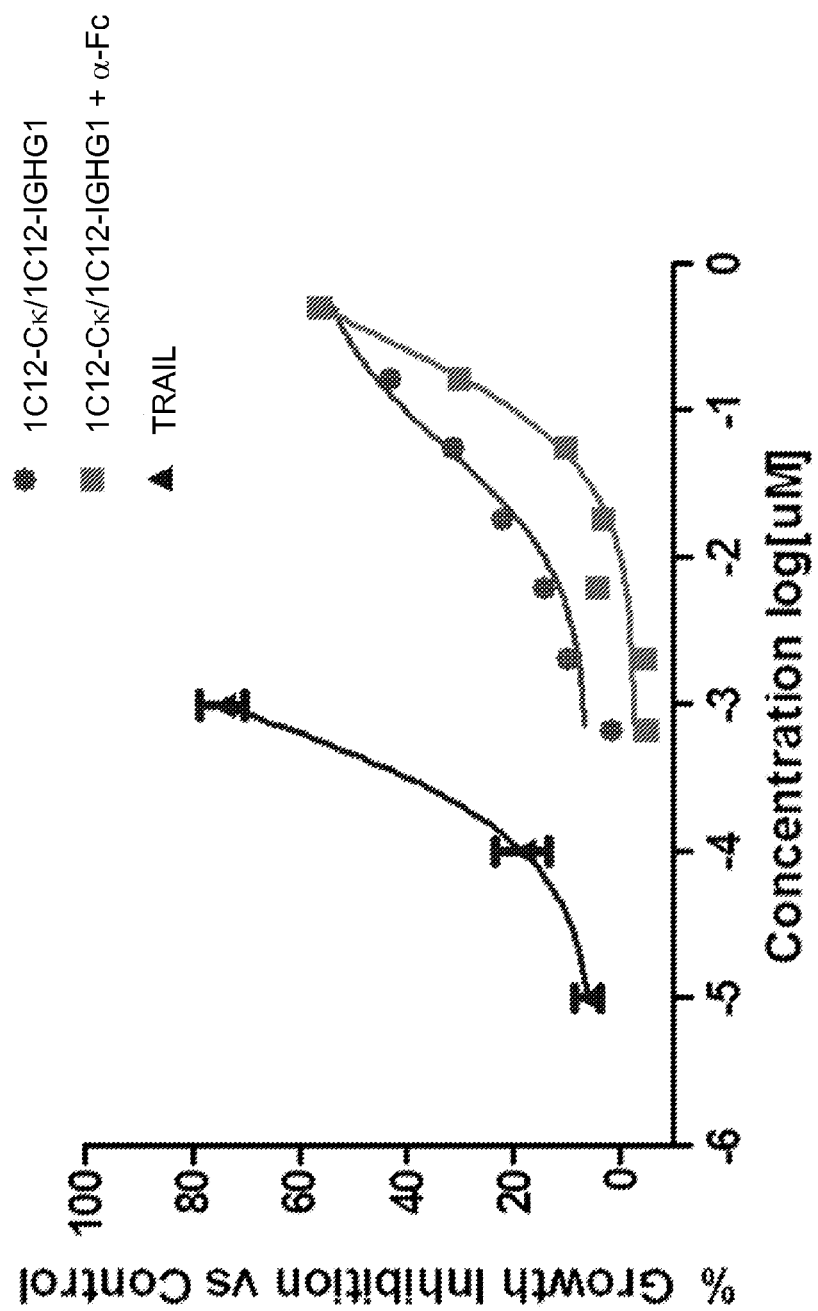

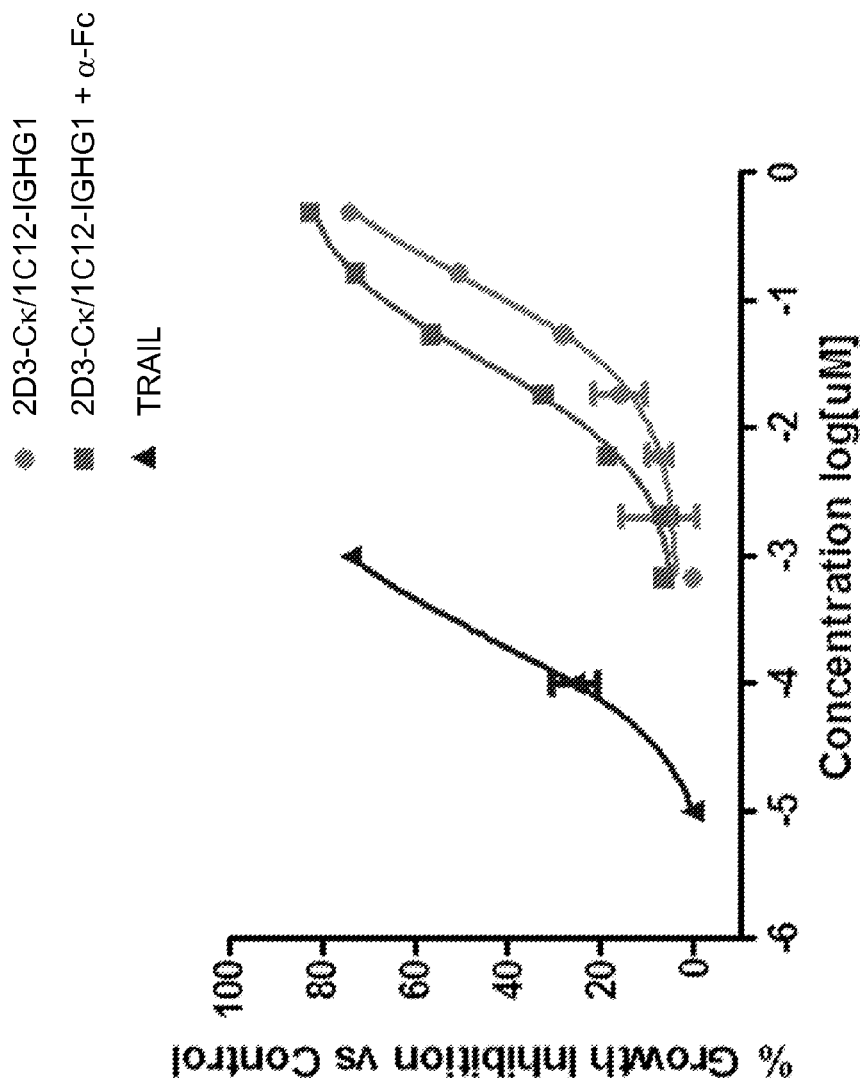

A
MTNITKRSLVAAGVLAALMAGNVALAAIEVKDVTDTTALITWFKPLAEID
GCELTYGIKDVPGDRTTIDLTEDENQYSIGNLKPDTEYEVSLICRRGDM
SSNPAKETFTTGGGTLGHHHHHHHH

B
pSec-oppA-Tn3:

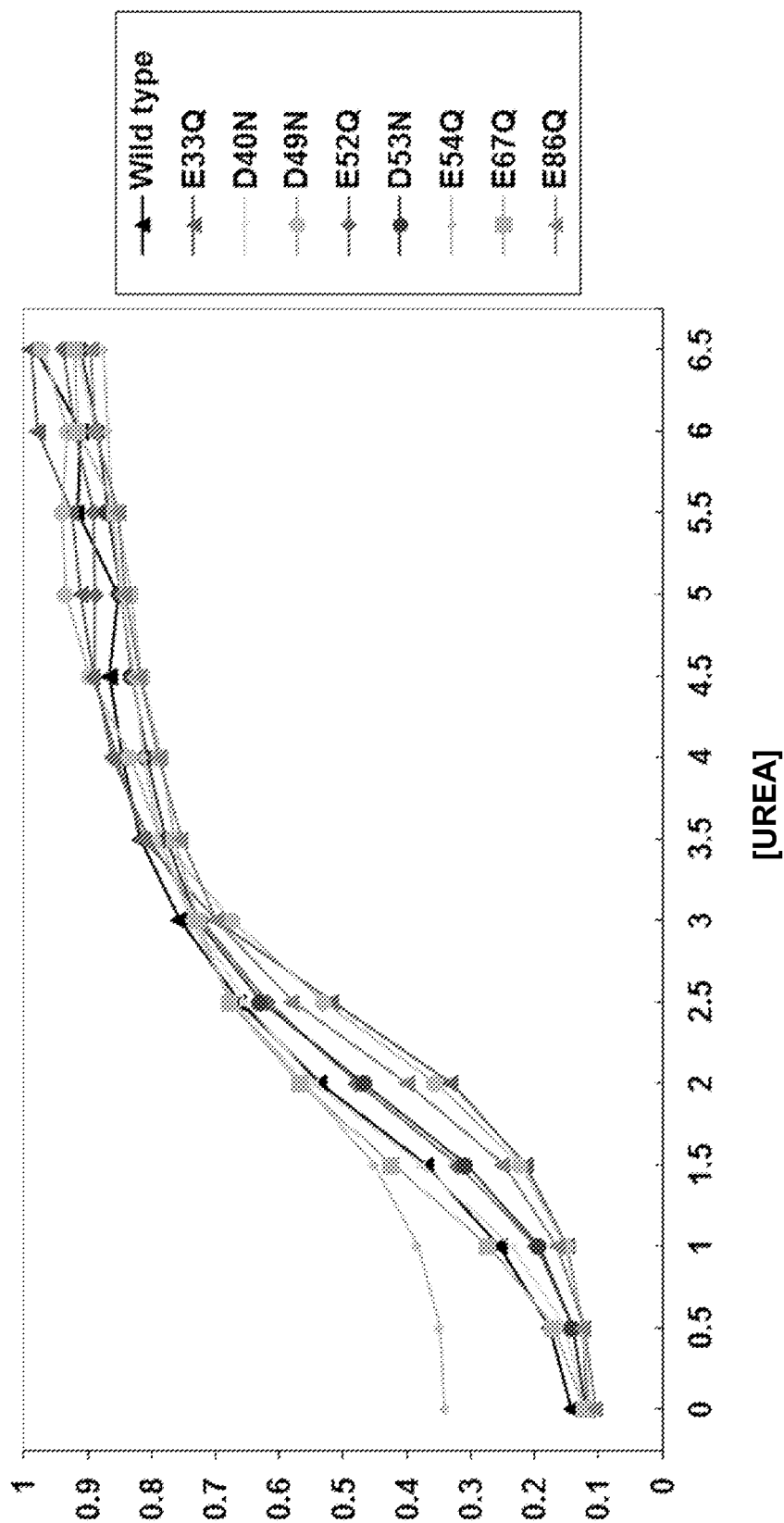

SEQUENCE LISTING

```
<160> NUMBER OF SEQ ID NOS: 289

<210> SEQ ID NO 1
<211> LENGTH: 90
<212> TYPE: PRT
<213> ORGANISM: Artificial Sequence
<220> FEATURE:
<223> OTHER INFORMATION: Synthetic construct

<400> SEQUENCE: 1

Arg Leu Asp Ala Pro Ser Gln Ile Glu Val Lys Asp Val Thr Asp Thr
1               5                   10                  15

Thr Ala Leu Ile Thr Trp Phe Lys Pro Leu Ala Glu Ile Asp Gly Ile
            20                  25                  30
```

```
Glu Leu Thr Tyr Gly Ile Lys Asp Val Pro Gly Asp Arg Thr Thr Ile
            35                  40                  45

Asp Leu Thr Glu Asp Glu Asn Gln Tyr Ser Ile Gly Asn Leu Lys Pro
 50                  55                  60

Asp Thr Glu Tyr Glu Val Ser Leu Ile Ser Arg Arg Gly Asp Met Ser
 65                  70                  75                  80

Ser Asn Pro Ala Lys Glu Thr Phe Thr Thr
                 85                  90
```

<210> SEQ ID NO 2
<211> LENGTH: 94
<212> TYPE: PRT
<213> ORGANISM: Artificial Sequence
<220> FEATURE:
<223> OTHER INFORMATION: Synthetic construct

<400> SEQUENCE: 2

```
Ser Glu Pro Gln Asn Leu Lys Ala Thr Ala Gly Asn Asn Ile Thr
 1               5                  10                  15

Leu Thr Trp Asp Pro Pro Ile Asp Asp Gly Gly Cys Arg Ile Val Glu
            20                  25                  30

Tyr Arg Ile Tyr Arg Gly Thr Asn Asn Asn Leu Glu Tyr Tyr Ala
            35                  40                  45

Ser Val Asn Gly Ser Thr Thr Thr Phe Ile Asp Lys Asn Ile Val Tyr
 50                  55                  60

Ser Gln Thr Tyr Tyr Lys Val Ser Ala Val Asn Asn Ile Val Glu
 65                  70                  75                  80

Gly Pro Lys Ser Asn Thr Ala Ser Ala Thr Pro Thr Ser Ser
                 85                  90
```

<210> SEQ ID NO 3
<211> LENGTH: 87
<212> TYPE: PRT
<213> ORGANISM: Artificial Sequence
<220> FEATURE:
<223> OTHER INFORMATION: Synthetic construct

<400> SEQUENCE: 3

```
Pro Pro Lys Pro Gln Ile Ala Ser Ile Ala Ser Gly Asn Glu Thr Ile
 1               5                  10                  15

Thr Val Lys Trp Tyr Asp Thr Asn Ala Ser Gly Tyr Tyr Ile Thr Tyr
            20                  25                  30

Trp Ser Asn Phe Ser Gln Lys Val Thr Ile Asn Val Gly Asn Val Thr
            35                  40                  45

Ser Tyr Thr Ile Lys His Leu Lys Asp Gly Val Thr Tyr Tyr Ile Gln
 50                  55                  60

Ile Val Pro Tyr Asn Ser Leu Gly Asn Gly Thr Pro Ser Asp Ile Ile
 65                  70                  75                  80

Ser Ala Thr Pro Ser Ser Val
                 85
```

<210> SEQ ID NO 4
<211> LENGTH: 86
<212> TYPE: PRT
<213> ORGANISM: Artificial Sequence
<220> FEATURE:
<223> OTHER INFORMATION: Synthetic construct

<400> SEQUENCE: 4

```
Pro Asn Pro Pro Ile Ile Lys Val Lys Ile Gly Asn Leu Asn Ala Thr
 1               5                  10                  15
```

```
Leu Thr Trp Tyr Asp Thr Phe Asn Gly Gly Tyr Pro Ile Glu Gly Tyr
            20                  25                  30

Tyr Leu Tyr Val Asn Gly Lys Gly Ile Asn Val Gly Asn Ile Thr Ser
            35                  40                  45

Tyr Val Leu Thr Asn Leu Thr Ala Gly Glu Leu Tyr Thr Ile Glu Leu
 50                  55                  60

Ile Ala Tyr Asn Lys Ile Gly Asn Ser Ser Ile Ser Ser Val Ser Phe
 65                  70                  75                  80

Ile Ala Ala Ser Lys Ala
                85

<210> SEQ ID NO 5
<211> LENGTH: 101
<212> TYPE: PRT
<213> ORGANISM: Artificial Sequence
<220> FEATURE:
<223> OTHER INFORMATION: Synthetic construct

<400> SEQUENCE: 5

Ala Ala Leu Glu Val Val Ala Ala Thr Pro Thr Ser Leu Leu Ile Ser
 1               5                  10                  15

Trp Asp Ala Pro Ala Val Thr Val Arg Tyr Tyr Arg Ile Thr Tyr Gly
            20                  25                  30

Glu Thr Gly Gly Asn Ser Pro Val Gln Glu Phe Thr Val Pro Gly Ser
            35                  40                  45

Lys Ser Thr Ala Thr Ile Ser Gly Leu Lys Pro Gly Val Asp Tyr Thr
 50                  55                  60

Ile Thr Val Tyr Ala Val Thr Gly Arg Gly Asp Ser Pro Ala Ser Ser
 65                  70                  75                  80

Lys Pro Ile Ser Ile Asn Tyr Arg Thr Gly Gly Thr Leu Glu His
                85                  90                  95

His His His His His
                100

<210> SEQ ID NO 6
<211> LENGTH: 87
<212> TYPE: PRT
<213> ORGANISM: Artificial Sequence
<220> FEATURE:
<223> OTHER INFORMATION: Synthetic construct

<400> SEQUENCE: 6

Leu Glu Val Val Ala Ala Thr Pro Thr Ser Leu Leu Ile Ser Trp Asp
 1               5                  10                  15

Ala Pro Ala Val Thr Val Arg Tyr Tyr Arg Ile Thr Tyr Gly Glu Thr
            20                  25                  30

Gly Gly Asn Ser Pro Val Gln Glu Phe Thr Val Pro Gly Ser Lys Ser
            35                  40                  45

Thr Ala Thr Ile Ser Gly Leu Lys Pro Gly Val Asp Tyr Thr Ile Thr
 50                  55                  60

Val Tyr Ala Val Thr Gly Arg Gly Asp Ser Pro Ala Ser Ser Lys Pro
 65                  70                  75                  80

Ile Ser Ile Asn Tyr Arg Thr
                85

<210> SEQ ID NO 7
<211> LENGTH: 96
<212> TYPE: PRT
<213> ORGANISM: Artificial Sequence
```

<220> FEATURE:
<223> OTHER INFORMATION: Synthetic construct

<400> SEQUENCE: 7

```
Ala Ala Pro Thr Val Asp Gln Val Asp Asp Thr Ser Ile Val Val Arg
1               5                   10                  15

Trp Ser Arg Pro Gln Ala Pro Ile Thr Gly Tyr Arg Ile Val Tyr Ser
                20                  25                  30

Pro Ser Val Glu Gly Ser Ser Thr Glu Leu Asn Leu Pro Glu Thr Ala
            35                  40                  45

Asn Ser Val Thr Leu Ser Asp Leu Gln Pro Gly Val Gln Tyr Asn Ile
        50                  55                  60

Thr Ile Tyr Ala Val Glu Glu Asn Gln Glu Ser Thr Pro Val Val Ile
65                  70                  75                  80

Gln Gln Glu Thr Gly Gly Thr Leu Glu His His His His His His
                85                  90                  95
```

<210> SEQ ID NO 8
<211> LENGTH: 82
<212> TYPE: PRT
<213> ORGANISM: Artificial Sequence
<220> FEATURE:
<223> OTHER INFORMATION: Synthetic construct

<400> SEQUENCE: 8

```
Pro Thr Val Asp Gln Val Asp Asp Thr Ser Ile Val Val Arg Trp Ser
1               5                   10                  15

Arg Pro Gln Ala Pro Ile Thr Gly Tyr Arg Ile Val Tyr Ser Pro Ser
                20                  25                  30

Val Glu Gly Ser Ser Thr Glu Leu Asn Leu Pro Glu Thr Ala Asn Ser
            35                  40                  45

Val Thr Leu Ser Asp Leu Gln Pro Gly Val Gln Tyr Asn Ile Thr Ile
        50                  55                  60

Tyr Ala Val Glu Glu Asn Gln Glu Ser Thr Pro Val Val Ile Gln Gln
65                  70                  75                  80

Glu Thr
```

<210> SEQ ID NO 9
<211> LENGTH: 94
<212> TYPE: PRT
<213> ORGANISM: Artificial Sequence
<220> FEATURE:
<223> OTHER INFORMATION: Synthetic construct

<400> SEQUENCE: 9

```
Ala Ala Pro Tyr Asn Thr Glu Val Thr Glu Thr Thr Ile Val Ile Thr
1               5                   10                  15

Trp Thr Pro Ala Pro Arg Ile Gly Phe Lys Leu Gly Val Arg Pro Ser
                20                  25                  30

Gln Gly Gly Glu Ala Pro Arg Glu Val Thr Ser Asp Ser Gly Ser Ile
            35                  40                  45

Val Val Ser Gly Leu Thr Pro Gly Val Glu Tyr Val Tyr Thr Ile Gln
        50                  55                  60

Val Leu Arg Asp Gly Gln Glu Arg Asp Ala Pro Ile Val Asn Lys Val
65                  70                  75                  80

Val Thr Gly Gly Gly Thr Leu Glu His His His His His His
                85                  90
```

<210> SEQ ID NO 10

```
<211> LENGTH: 80
<212> TYPE: PRT
<213> ORGANISM: Artificial Sequence
<220> FEATURE:
<223> OTHER INFORMATION: Synthetic construct

<400> SEQUENCE: 10

Pro Tyr Asn Thr Glu Val Thr Glu Thr Thr Ile Val Ile Thr Trp Thr
1               5                   10                  15

Pro Ala Pro Arg Ile Gly Phe Lys Leu Gly Val Arg Pro Ser Gln Gly
            20                  25                  30

Gly Glu Ala Pro Arg Glu Val Thr Ser Asp Ser Gly Ser Ile Val Val
        35                  40                  45

Ser Gly Leu Thr Pro Gly Val Glu Tyr Val Tyr Thr Ile Gln Val Leu
    50                  55                  60

Arg Asp Gly Gln Glu Arg Asp Ala Pro Ile Val Asn Lys Val Val Thr
65                  70                  75                  80

<210> SEQ ID NO 11
<211> LENGTH: 116
<212> TYPE: PRT
<213> ORGANISM: Artificial Sequence
<220> FEATURE:
<223> OTHER INFORMATION: Synthetic construct

<400> SEQUENCE: 11

Ala Ala Pro Pro Ile Ala Leu Asn Trp Thr Leu Leu Asn Val Ser Leu
1               5                   10                  15

Thr Gly Ile His Ala Asp Ile Gln Val Arg Trp Glu Ala Pro Arg Asn
            20                  25                  30

Ala Asp Ile Gln Lys Gly Trp Met Val Leu Glu Tyr Glu Leu Gln Tyr
        35                  40                  45

Lys Glu Val Asn Glu Thr Lys Trp Lys Met Met Asp Pro Ile Leu Thr
    50                  55                  60

Thr Ser Val Pro Val Tyr Ser Leu Lys Val Asp Lys Glu Tyr Glu Val
65                  70                  75                  80

Arg Val Arg Ser Lys Gln Arg Asn Ser Gly Asn Tyr Gly Glu Phe Ser
                85                  90                  95

Glu Val Leu Tyr Val Thr Leu Pro Gly Gly Gly Thr Leu Glu His His
            100                 105                 110

His His His His
        115

<210> SEQ ID NO 12
<211> LENGTH: 102
<212> TYPE: PRT
<213> ORGANISM: Artificial Sequence
<220> FEATURE:
<223> OTHER INFORMATION: Synthetic construct

<400> SEQUENCE: 12

Pro Pro Ile Ala Leu Asn Trp Thr Leu Leu Asn Val Ser Leu Thr Gly
1               5                   10                  15

Ile His Ala Asp Ile Gln Val Arg Trp Glu Ala Pro Arg Asn Ala Asp
            20                  25                  30

Ile Gln Lys Gly Trp Met Val Leu Glu Tyr Glu Leu Gln Tyr Lys Glu
        35                  40                  45

Val Asn Glu Thr Lys Trp Lys Met Met Asp Pro Ile Leu Thr Thr Ser
    50                  55                  60

Val Pro Val Tyr Ser Leu Lys Val Asp Lys Glu Tyr Glu Val Arg Val
```

```
                     65                  70                  75                  80
Arg Ser Lys Gln Arg Asn Ser Gly Asn Tyr Gly Glu Phe Ser Glu Val
                85                  90                  95

Leu Tyr Val Thr Leu Pro
            100

<210> SEQ ID NO 13
<211> LENGTH: 110
<212> TYPE: PRT
<213> ORGANISM: Artificial Sequence
<220> FEATURE:
<223> OTHER INFORMATION: Synthetic construct

<400> SEQUENCE: 13

Ala Ala Pro Pro Ser Leu Asn Val Thr Lys Asp Gly Asp Ser Tyr Ser
1               5                   10                  15

Leu Arg Trp Glu Thr Met Lys Met Arg Tyr Glu His Ile Asp His Thr
            20                  25                  30

Phe Glu Ile Gln Tyr Arg Lys Asp Thr Ala Thr Trp Lys Asp Ser Lys
        35                  40                  45

Thr Glu Thr Leu Gln Asn Ala His Ser Met Ala Leu Pro Ala Leu Glu
    50                  55                  60

Pro Ser Thr Arg Tyr Trp Ala Arg Val Arg Val Arg Thr Ser Arg Thr
65                  70                  75                  80

Gly Tyr Asn Gly Ile Trp Ser Glu Trp Ser Glu Ala Arg Ser Trp Asp
                85                  90                  95

Thr Glu Gly Gly Gly Thr Leu Glu His His His His His
            100                 105                 110

<210> SEQ ID NO 14
<211> LENGTH: 96
<212> TYPE: PRT
<213> ORGANISM: Artificial Sequence
<220> FEATURE:
<223> OTHER INFORMATION: Synthetic construct

<400> SEQUENCE: 14

Pro Pro Ser Leu Asn Val Thr Lys Asp Gly Asp Ser Tyr Ser Leu Arg
1               5                   10                  15

Trp Glu Thr Met Lys Met Arg Tyr Glu His Ile Asp His Thr Phe Glu
            20                  25                  30

Ile Gln Tyr Arg Lys Asp Thr Ala Thr Trp Lys Asp Ser Lys Thr Glu
        35                  40                  45

Thr Leu Gln Asn Ala His Ser Met Ala Leu Pro Ala Leu Glu Pro Ser
    50                  55                  60

Thr Arg Tyr Trp Ala Arg Val Arg Val Arg Thr Ser Arg Thr Gly Tyr
65                  70                  75                  80

Asn Gly Ile Trp Ser Glu Trp Ser Glu Ala Arg Ser Trp Asp Thr Glu
                85                  90                  95

<210> SEQ ID NO 15
<211> LENGTH: 103
<212> TYPE: PRT
<213> ORGANISM: Artificial Sequence
<220> FEATURE:
<223> OTHER INFORMATION: Synthetic construct

<400> SEQUENCE: 15

Ala Ala Pro Pro Val Asn Phe Thr Ile Lys Val Thr Gly Leu Ala Gln
1               5                   10                  15
```

-continued

```
Val Leu Leu Gln Trp Lys Pro Asn Pro Asp Gln Glu Gln Arg Asn Val
             20                  25                  30

Asn Leu Glu Tyr Gln Val Lys Ile Asn Ala Pro Lys Glu Asp Asp Tyr
         35                  40                  45

Glu Thr Arg Ile Thr Glu Ser Lys Leu Val Thr Ile Leu His Lys Gly
 50                  55                  60

Phe Ser Ala Ser Val Arg Thr Ile Leu Gln Asn Asp His Ser Leu Leu
 65                  70                  75                  80

Ala Ser Ser Trp Ala Ser Ala Glu Leu His Ala Gly Gly Gly Thr Leu
                 85                  90                  95

Glu His His His His His His
            100
```

<210> SEQ ID NO 16
<211> LENGTH: 89
<212> TYPE: PRT
<213> ORGANISM: Artificial Sequence
<220> FEATURE:
<223> OTHER INFORMATION: Synthetic construct

<400> SEQUENCE: 16

```
Pro Pro Val Asn Phe Thr Ile Lys Val Thr Gly Leu Ala Gln Val Leu
 1               5                  10                  15

Leu Gln Trp Lys Pro Asn Pro Asp Gln Glu Gln Arg Asn Val Asn Leu
             20                  25                  30

Glu Tyr Gln Val Lys Ile Asn Ala Pro Lys Glu Asp Asp Tyr Glu Thr
         35                  40                  45

Arg Ile Thr Glu Ser Lys Leu Val Thr Ile Leu His Lys Gly Phe Ser
 50                  55                  60

Ala Ser Val Arg Thr Ile Leu Gln Asn Asp His Ser Leu Leu Ala Ser
 65                  70                  75                  80

Ser Trp Ala Ser Ala Glu Leu His Ala
                 85
```

<210> SEQ ID NO 17
<211> LENGTH: 105
<212> TYPE: PRT
<213> ORGANISM: Artificial Sequence
<220> FEATURE:
<223> OTHER INFORMATION: Synthetic construct

<400> SEQUENCE: 17

```
Ala Ala Leu Ser Val Thr Asp Val Thr Thr Ser Ser Leu Arg Leu Asn
 1               5                  10                  15

Trp Glu Ala Pro Pro Gly Ala Phe Asp Ser Phe Leu Leu Arg Phe Gly
             20                  25                  30

Val Pro Ser Pro Ser Thr Leu Glu Pro His Pro Arg Pro Leu Leu Gln
         35                  40                  45

Arg Glu Leu Met Val Pro Gly Thr Arg His Ser Ala Val Leu Arg Asp
     50                  55                  60

Leu Arg Ser Gly Thr Leu Tyr Ser Leu Thr Leu Tyr Gly Leu Arg Gly
 65                  70                  75                  80

Pro His Lys Ala Asp Ser Ile Gln Gly Thr Ala Arg Thr Gly Gly Gly
                 85                  90                  95

Thr Leu Glu His His His His His
            100                 105
```

<210> SEQ ID NO 18
<211> LENGTH: 91

```
<212> TYPE: PRT
<213> ORGANISM: Artificial Sequence
<220> FEATURE:
<223> OTHER INFORMATION: Synthetic construct

<400> SEQUENCE: 18

Leu Ser Val Thr Asp Val Thr Thr Ser Ser Leu Arg Leu Asn Trp Glu
1               5                   10                  15

Ala Pro Pro Gly Ala Phe Asp Ser Phe Leu Leu Arg Phe Gly Val Pro
                20                  25                  30

Ser Pro Ser Thr Leu Glu Pro His Pro Arg Pro Leu Leu Gln Arg Glu
            35                  40                  45

Leu Met Val Pro Gly Thr Arg His Ser Ala Val Leu Arg Asp Leu Arg
        50                  55                  60

Ser Gly Thr Leu Tyr Ser Leu Thr Leu Tyr Gly Leu Arg Gly Pro His
65                  70                  75                  80

Lys Ala Asp Ser Ile Gln Gly Thr Ala Arg Thr
                85                  90

<210> SEQ ID NO 19
<211> LENGTH: 95
<212> TYPE: PRT
<213> ORGANISM: Artificial Sequence
<220> FEATURE:
<223> OTHER INFORMATION: Synthetic construct

<400> SEQUENCE: 19

Ala Ala Leu Arg Ala Leu Asn Leu Thr Glu Gly Phe Ala Val Leu His
1               5                   10                  15

Trp Lys Pro Pro Gln Asn Pro Val Asp Thr Tyr Asp Ile Gln Val Thr
                20                  25                  30

Ala Pro Gly Ala Pro Pro Leu Gln Ala Glu Thr Pro Gly Ser Ala Val
            35                  40                  45

Asp Tyr Pro Leu His Asp Leu Val Leu His Thr Asn Tyr Thr Ala Thr
        50                  55                  60

Val Arg Gly Leu Arg Gly Pro Asn Leu Thr Ser Pro Ala Ser Ile Thr
65                  70                  75                  80

Phe Thr Thr Gly Gly Gly Thr Leu Glu His His His His His His
                85                  90                  95

<210> SEQ ID NO 20
<211> LENGTH: 81
<212> TYPE: PRT
<213> ORGANISM: Artificial Sequence
<220> FEATURE:
<223> OTHER INFORMATION: Synthetic construct

<400> SEQUENCE: 20

Leu Arg Ala Leu Asn Leu Thr Glu Gly Phe Ala Val Leu His Trp Lys
1               5                   10                  15

Pro Pro Gln Asn Pro Val Asp Thr Tyr Asp Ile Gln Val Thr Ala Pro
                20                  25                  30

Gly Ala Pro Pro Leu Gln Ala Glu Thr Pro Gly Ser Ala Val Asp Tyr
            35                  40                  45

Pro Leu His Asp Leu Val Leu His Thr Asn Tyr Thr Ala Thr Val Arg
        50                  55                  60

Gly Leu Arg Gly Pro Asn Leu Thr Ser Pro Ala Ser Ile Thr Phe Thr
65                  70                  75                  80

Thr
```

```
<210> SEQ ID NO 21
<211> LENGTH: 95
<212> TYPE: PRT
<213> ORGANISM: Artificial Sequence
<220> FEATURE:
<223> OTHER INFORMATION: Synthetic consrtuct

<400> SEQUENCE: 21

Ala Ala Leu Glu Ala Lys Glu Val Thr Pro Arg Thr Ala Leu Leu Thr
1               5                   10                  15

Trp Thr Glu Pro Pro Val Arg Pro Ala Gly Tyr Leu Leu Ser Phe His
                20                  25                  30

Thr Pro Gly Gly Gln Thr Gln Glu Ile Leu Leu Pro Gly Gly Ile Thr
            35                  40                  45

Ser His Gln Leu Leu Gly Leu Phe Pro Ser Thr Ser Tyr Asn Ala Arg
    50                  55                  60

Leu Gln Ala Met Trp Gly Gln Ser Leu Leu Pro Pro Val Ser Thr Ser
65                  70                  75                  80

Phe Thr Thr Gly Gly Gly Thr Leu Glu His His His His His
                85                  90                  95

<210> SEQ ID NO 22
<211> LENGTH: 81
<212> TYPE: PRT
<213> ORGANISM: Artificial Sequence
<220> FEATURE:
<223> OTHER INFORMATION: Synthetic construct

<400> SEQUENCE: 22

Leu Glu Ala Lys Glu Val Thr Pro Arg Thr Ala Leu Leu Thr Trp Thr
1               5                   10                  15

Glu Pro Pro Val Arg Pro Ala Gly Tyr Leu Leu Ser Phe His Thr Pro
                20                  25                  30

Gly Gly Gln Thr Gln Glu Ile Leu Leu Pro Gly Gly Ile Thr Ser His
            35                  40                  45

Gln Leu Leu Gly Leu Phe Pro Ser Thr Ser Tyr Asn Ala Arg Leu Gln
    50                  55                  60

Ala Met Trp Gly Gln Ser Leu Leu Pro Pro Val Ser Thr Ser Phe Thr
65                  70                  75                  80

Thr

<210> SEQ ID NO 23
<211> LENGTH: 97
<212> TYPE: PRT
<213> ORGANISM: Artificial Sequence
<220> FEATURE:
<223> OTHER INFORMATION: Synthetic construct

<400> SEQUENCE: 23

Ala Ala Ile Glu Val Lys Asp Val Asp Thr Thr Ala Leu Ile Thr
1               5                   10                  15

Trp Phe Lys Pro Leu Ala Glu Ile Asp Gly Ile Glu Leu Thr Tyr Gly
                20                  25                  30

Ile Lys Asp Val Pro Gly Asp Arg Thr Thr Ile Asp Leu Thr Glu Asp
            35                  40                  45

Glu Asn Gln Tyr Ser Ile Gly Asn Leu Lys Pro Asp Thr Glu Tyr Glu
    50                  55                  60

Val Ser Leu Ile Ser Arg Arg Gly Asp Met Ser Ser Asn Pro Ala Lys
65                  70                  75                  80
```

```
Glu Thr Phe Thr Thr Gly Gly Gly Thr Leu Glu His His His His
                    85                  90                  95
His

<210> SEQ ID NO 24
<211> LENGTH: 83
<212> TYPE: PRT
<213> ORGANISM: Artificial Sequence
<220> FEATURE:
<223> OTHER INFORMATION: Synthetic construct

<400> SEQUENCE: 24

Ile Glu Val Lys Asp Val Thr Asp Thr Thr Ala Leu Ile Thr Trp Phe
1               5                   10                  15

Lys Pro Leu Ala Glu Ile Asp Gly Ile Glu Leu Thr Tyr Gly Ile Lys
            20                  25                  30

Asp Val Pro Gly Asp Arg Thr Thr Ile Asp Leu Thr Glu Asp Glu Asn
        35                  40                  45

Gln Tyr Ser Ile Gly Asn Leu Lys Pro Asp Thr Glu Tyr Glu Val Ser
    50                  55                  60

Leu Ile Ser Arg Arg Gly Asp Met Ser Ser Asn Pro Ala Lys Glu Thr
65                  70                  75                  80

Phe Thr Thr

<210> SEQ ID NO 25
<211> LENGTH: 107
<212> TYPE: PRT
<213> ORGANISM: Artificial Sequence
<220> FEATURE:
<223> OTHER INFORMATION: Synthetic construct

<400> SEQUENCE: 25

Ala Ala Pro Lys Phe Thr Lys Cys Arg Ser Pro Glu Arg Glu Thr Phe
1               5                   10                  15

Ser Cys His Trp Thr Asp Glu Val His His Gly Thr Lys Asn Leu Gly
            20                  25                  30

Pro Ile Gln Leu Phe Tyr Thr Arg Arg Asn Thr Gln Glu Trp Thr Gln
        35                  40                  45

Glu Trp Lys Glu Cys Pro Asp Tyr Val Ser Ala Gly Glu Asn Ser Cys
    50                  55                  60

Tyr Phe Asn Ser Ser Phe Thr Ser Ile Trp Ile Pro Tyr Cys Ile Lys
65                  70                  75                  80

Leu Thr Ser Asn Gly Gly Thr Val Asp Glu Lys Cys Phe Ser Val Gly
                    85                  90                  95

Gly Gly Thr Leu Glu His His His His His His
                100                 105

<210> SEQ ID NO 26
<211> LENGTH: 93
<212> TYPE: PRT
<213> ORGANISM: Artificial Sequence
<220> FEATURE:
<223> OTHER INFORMATION: Synthetic construct

<400> SEQUENCE: 26

Pro Lys Phe Thr Lys Cys Arg Ser Pro Glu Arg Glu Thr Phe Ser Cys
1               5                   10                  15

His Trp Thr Asp Glu Val His His Gly Thr Lys Asn Leu Gly Pro Ile
            20                  25                  30

Gln Leu Phe Tyr Thr Arg Arg Asn Thr Gln Glu Trp Thr Gln Glu Trp
```

```
                    35                  40                  45
Lys Glu Cys Pro Asp Tyr Val Ser Ala Gly Glu Asn Ser Cys Tyr Phe
 50                  55                  60

Asn Ser Ser Phe Thr Ser Ile Trp Ile Pro Tyr Cys Ile Lys Leu Thr
 65                  70                  75                  80

Ser Asn Gly Gly Thr Val Asp Glu Lys Cys Phe Ser Val
                 85                  90

<210> SEQ ID NO 27
<211> LENGTH: 111
<212> TYPE: PRT
<213> ORGANISM: Artificial Sequence
<220> FEATURE:
<223> OTHER INFORMATION: Synthetic construct

<400> SEQUENCE: 27

Ala Ala Pro Ser Gly Phe Pro Gln Asn Leu His Val Thr Gly Leu Thr
 1               5                  10                  15

Thr Ser Thr Thr Glu Leu Ala Trp Asp Pro Pro Val Leu Ala Glu Arg
                 20                  25                  30

Asn Gly Arg Ile Ile Ser Tyr Thr Val Val Phe Arg Asp Ile Asn Ser
             35                  40                  45

Gln Gln Glu Leu Gln Asn Ile Thr Thr Asp Thr Arg Phe Thr Leu Thr
 50                  55                  60

Gly Leu Lys Pro Asp Thr Thr Tyr Asp Ile Lys Val Arg Ala Trp Thr
 65                  70                  75                  80

Ser Lys Gly Ser Gly Pro Leu Ser Pro Ser Ile Gln Ser Arg Thr Met
                 85                  90                  95

Pro Val Glu Gly Gly Gly Thr Leu Glu His His His His His His
             100                 105                 110

<210> SEQ ID NO 28
<211> LENGTH: 97
<212> TYPE: PRT
<213> ORGANISM: Artificial Sequence
<220> FEATURE:
<223> OTHER INFORMATION: Synthetic construct

<400> SEQUENCE: 28

Pro Ser Gly Phe Pro Gln Asn Leu His Val Thr Gly Leu Thr Thr Ser
 1               5                  10                  15

Thr Thr Glu Leu Ala Trp Asp Pro Pro Val Leu Ala Glu Arg Asn Gly
                 20                  25                  30

Arg Ile Ile Ser Tyr Thr Val Val Phe Arg Asp Ile Asn Ser Gln Gln
             35                  40                  45

Glu Leu Gln Asn Ile Thr Thr Asp Thr Arg Phe Thr Leu Thr Gly Leu
 50                  55                  60

Lys Pro Asp Thr Thr Tyr Asp Ile Lys Val Arg Ala Trp Thr Ser Lys
 65                  70                  75                  80

Gly Ser Gly Pro Leu Ser Pro Ser Ile Gln Ser Arg Thr Met Pro Val
                 85                  90                  95

Glu

<210> SEQ ID NO 29
<211> LENGTH: 108
<212> TYPE: PRT
<213> ORGANISM: Artificial Sequence
<220> FEATURE:
<223> OTHER INFORMATION: Synthetic construct
```

```
<400> SEQUENCE: 29

Ala Ala Pro Lys Pro Ile Asp Leu Val Val Thr Glu Thr Ala
1               5                  10                  15

Thr Ser Val Thr Leu Thr Trp Asp Ser Gly Asn Ser Glu Pro Val Thr
            20                  25                  30

Tyr Tyr Gly Ile Gln Tyr Arg Ala Ala Gly Thr Glu Gly Pro Phe Gln
        35                  40                  45

Glu Val Asp Gly Val Ala Thr Thr Arg Tyr Ser Ile Gly Gly Leu Ser
    50                  55                  60

Pro Phe Ser Glu Tyr Ala Phe Arg Val Leu Ala Val Asn Ser Ile Gly
65                  70                  75                  80

Arg Gly Pro Pro Ser Glu Ala Val Arg Ala Arg Thr Gly Glu Gln Ala
                85                  90                  95

Gly Gly Gly Thr Leu Glu His His His His His His
            100                 105

<210> SEQ ID NO 30
<211> LENGTH: 92
<212> TYPE: PRT
<213> ORGANISM: Artificial Sequence
<220> FEATURE:
<223> OTHER INFORMATION: Synthetic construct

<400> SEQUENCE: 30

Pro Lys Pro Pro Ile Asp Leu Val Val Thr Glu Thr Ala Thr Ser
1               5                  10                  15

Val Thr Leu Thr Trp Asp Ser Gly Asn Ser Glu Pro Val Thr Tyr Tyr
            20                  25                  30

Gly Ile Gln Tyr Arg Ala Ala Gly Thr Glu Gly Pro Phe Gln Glu Val
        35                  40                  45

Asp Gly Val Ala Thr Thr Arg Tyr Ser Ile Gly Gly Leu Ser Pro Phe
    50                  55                  60

Ser Glu Tyr Ala Phe Arg Val Leu Ala Val Asn Ser Ile Gly Arg Gly
65                  70                  75                  80

Pro Pro Ser Glu Ala Val Arg Ala Arg Thr Gly Glu
                85                  90

<210> SEQ ID NO 31
<211> LENGTH: 101
<212> TYPE: PRT
<213> ORGANISM: Artificial Sequence
<220> FEATURE:
<223> OTHER INFORMATION: Synthetic construct

<400> SEQUENCE: 31

Ala Ala Leu Ser Pro Pro Arg Asn Leu Arg Ile Ser Asn Val Gly Ser
1               5                  10                  15

Asn Ser Ala Arg Leu Thr Trp Asp Pro Thr Ser Arg Gln Ile Asn Gly
            20                  25                  30

Tyr Arg Ile Val Tyr Asn Asn Ala Asp Gly Thr Glu Ile Asn Glu Val
        35                  40                  45

Glu Val Asp Pro Ile Thr Thr Thr Phe Pro Leu Lys Gly Leu Thr Pro Leu
    50                  55                  60

Thr Glu Tyr Thr Ile Ala Ile Phe Ser Ile Tyr Asp Glu Gly Gln Ser
65                  70                  75                  80

Glu Pro Leu Thr Gly Val Phe Thr Thr Gly Gly Gly Thr Leu Glu His
                85                  90                  95

His His His His His
```

<210> SEQ ID NO 32
<211> LENGTH: 87
<212> TYPE: PRT
<213> ORGANISM: Artificial Sequence
<220> FEATURE:
<223> OTHER INFORMATION: Sythetic construct

<400> SEQUENCE: 32

Leu Ser Pro Pro Arg Asn Leu Arg Ile Ser Asn Val Gly Ser Asn Ser
1               5                   10                  15

Ala Arg Leu Thr Trp Asp Pro Thr Ser Arg Gln Ile Asn Gly Tyr Arg
            20                  25                  30

Ile Val Tyr Asn Asn Ala Asp Gly Thr Glu Ile Asn Glu Val Glu Val
        35                  40                  45

Asp Pro Ile Thr Thr Phe Pro Leu Lys Gly Leu Thr Pro Leu Thr Glu
    50                  55                  60

Tyr Thr Ile Ala Ile Phe Ser Ile Tyr Asp Glu Gly Gln Ser Glu Pro
65                  70                  75                  80

Leu Thr Gly Val Phe Thr Thr
                85

<210> SEQ ID NO 33
<211> LENGTH: 285
<212> TYPE: DNA
<213> ORGANISM: Artificial Sequence
<220> FEATURE:
<223> OTHER INFORMATION: Synthetic construct

<400> SEQUENCE: 33
gccatggccg ccctggaagt ggtggcggcg accccgacca gcctgctgat tagctgggat     60
gcgccggcgg tgaccgtgcg ctattatcgt attacctatg gcgaaaccgg cggcaatagc    120
ccggtgcagg aatttaccgt gccgggcagc aaaagcaccg cgaccattag cggcctgaaa    180
ccgggcgtgg attataccat taccgtgtat gcggtgaccg gcgtggcga tagcccggcg     240 agcagcaaac cgattagcat taactatcgt accggtggcg gtacc                    285

<210> SEQ ID NO 34
<211> LENGTH: 261
<212> TYPE: DNA
<213> ORGANISM: Artificial Sequence
<220> FEATURE:
<223> OTHER INFORMATION: Synthetic construct

<400> SEQUENCE: 34
ctggaagtgg tggcggcgac cccgaccagc ctgctgatta gctgggatgc gccggcggtg     60
accgtgcgct attatcgtat tacctatggc gaaaccggcg gcaatagccc ggtgcaggaa    120
tttaccgtgc cgggcagcaa aagcaccgcg accattagcg gcctgaaacc gggcgtggat    180
tataccatta ccgtgtatgc ggtgaccggc cgtggcgata gcccggcgag cagcaaaccg    240
attagcatta actatcgtac c                                              261

<210> SEQ ID NO 35
<211> LENGTH: 270
<212> TYPE: DNA
<213> ORGANISM: Artificial Sequence
<220> FEATURE:
<223> OTHER INFORMATION: Synthetic construct

<400> SEQUENCE: 35

```
gccatggccg ccccgaccgt ggatcaggtg gatgatacca gcattgtggt gcgctggagc    60
cgtccgcagg cgccgattac cggctatcgt attgtgtata gcccgagcgt ggaaggcagc   120
agcaccgaac tgaacctgcc ggaaaccgcg aatagcgtga ccctgagcga tctgcagccg   180
ggcgtgcagt ataacattac catttatgcg gtggaagaaa accaggaaag caccccggtg   240
gtgattcagc aggaaaccgg tggcggtacc                                    270
```

<210> SEQ ID NO 36
<211> LENGTH: 246
<212> TYPE: DNA
<213> ORGANISM: Artificial Sequence
<220> FEATURE:
<223> OTHER INFORMATION: Synthetic construct

<400> SEQUENCE: 36

```
ccgaccgtgg atcaggtgga tgataccagc attgtggtgc gctggagccg tccgcaggcg    60
ccgattaccg gctatcgtat tgtgtatagc ccgagcgtgg aaggcagcag caccgaactg   120
aacctgccgg aaaccgcgaa tagcgtgacc ctgagcgatc tgcagccggg cgtgcagtat   180
aacattacca tttatgcggt ggaagaaaac caggaaagca ccccggtggt gattcagcag   240
gaaacc                                                              246
```

<210> SEQ ID NO 37
<211> LENGTH: 264
<212> TYPE: DNA
<213> ORGANISM: Artificial Sequence
<220> FEATURE:
<223> OTHER INFORMATION: Synthetic construct

<400> SEQUENCE: 37

```
gccatggccg ccccgtataa caccgaagtg accgaaacca ccattgtgat tacctggacc    60
ccggcgccgc gtattggctt taaactgggc gtgcgtccga gccagggcgg tgaagcgccg   120
cgcgaagtga ccagcgatag cggcagcatt gtggtgagcg gctgaccccc gggcgtggaa   180
tatgtgtata ccattcaggt gctgcgtgat ggccaggaac gtgatgcgcc gattgtgaac   240
aaagtggtga ccggtggcgg tacc                                          264
```

<210> SEQ ID NO 38
<211> LENGTH: 240
<212> TYPE: DNA
<213> ORGANISM: Artificial Sequence
<220> FEATURE:
<223> OTHER INFORMATION: Synthetic construct

<400> SEQUENCE: 38

```
ccgtataaca ccgaagtgac cgaaaccacc attgtgatta cctggacccc ggcgccgcgt    60
attggcttta aactgggcgt gcgtccgagc cagggcggtg aagcgccgcg cgaagtgacc   120
agcgatagcg gcagcattgt ggtgagcggc ctgaccccgg gcgtggaata tgtgtatacc   180
attcaggtgc tgcgtgatgg ccaggaacgt gatgcgccga ttgtgaacaa agtggtgacc   240
```

<210> SEQ ID NO 39
<211> LENGTH: 330
<212> TYPE: DNA
<213> ORGANISM: Artificial Sequence
<220> FEATURE:
<223> OTHER INFORMATION: Synthetic construct

<400> SEQUENCE: 39

```
gccatggccg ccccgccgat cgctctgaat tggaccctgc tgaatgtttc gctgaccggt    60
```

```
attcatgccg atattcaggt gcgttgggaa gcgccgcgta acgccgatat tcagaaaggc    120
tggatggtgc tggaatatga actgcagtat aaagaagtga atgaaaccaa atggaaaatg    180
atggacccga ttctgaccac cagcgtgccg gtgtacagcc tgaaagtgga taagaatac     240 gaagtccgtg tgcgttctaa acagcgtaat agcggcaatt atggtgaatt tagtgaagtc    300
ctgtatgtta ccctgccggg tggcggtacc                                    330

<210> SEQ ID NO 40
<211> LENGTH: 306
<212> TYPE: DNA
<213> ORGANISM: Artificial Sequence
<220> FEATURE:
<223> OTHER INFORMATION: Synthetic construct

<400> SEQUENCE: 40
ccgccgatcg ctctgaattg gaccctgctg aatgtttcgc tgaccggtat tcatgccgat     60
attcaggtgc gttgggaagc gccgcgtaac gccgatattc agaaaggctg atggtgctg    120 gaatatgaac tgcagtataa agaagtgaat gaaaccaaat ggaaaatgat ggacccgatt   180
ctgaccacca gcgtgccggt gtacagcctg aaagtggata agaatacga agtccgtgtg    240 cgttctaaac agcgtaatag cggcaattat ggtgaattta gtgaagtcct gtatgttacc   300
ctgccg                                                              306

<210> SEQ ID NO 41
<211> LENGTH: 312
<212> TYPE: DNA
<213> ORGANISM: Artificial Sequence
<220> FEATURE:
<223> OTHER INFORMATION: Synthetic construct

<400> SEQUENCE: 41
gccatggccg ccccgccgag cctgaacgtg accaaagatg gcgatagcta tagcctgcgc     60
tgggaaacca tgaaaatgcg ctatgaacat attgatcata cctttgaaat tcagtatcgc   120
aaagataccg cgacctggaa agatagcaaa accgaaaccc tgcagaacgc gcatagcatg   180
gcgctgccgg cgctggaacc gagcacccgt tattgggcgc gtgtgcgtgt gcgtaccagc   240
cgtaccggct ataatggcat ttggagcgaa tggagcgaag cgcgtagctg ggataccgaa   300
ggtggcggta cc                                                       312

<210> SEQ ID NO 42
<211> LENGTH: 291
<212> TYPE: DNA
<213> ORGANISM: Artificial Sequence
<220> FEATURE:
<223> OTHER INFORMATION: Synthetic construct

<400> SEQUENCE: 42
gccatggccg ccccgccggt gaactttacc attaaagtga ccggcctggc gcaggtgctg     60
ctgcagtgga aaccgaaccc ggatcaggaa cagcgtaacg tgaacctgga atatcaggtg   120
aaaattaacg cgccgaaaga agatgattat gaaacccgca ttaccgaaag caaactggtg   180
accattctgc ataaaggctt tagcgcgagc gtgcgtacca ttctgcagaa cgatcatagc   240
ctgctggcga gcagctgggc gagcgcggaa ctgcatgcgg gtggcggtac c             291

<210> SEQ ID NO 43
<211> LENGTH: 267
<212> TYPE: DNA
<213> ORGANISM: Artificial Sequence
<220> FEATURE:
```

-continued

<223> OTHER INFORMATION: Synthetic construct

<400> SEQUENCE: 43

```
ccgccggtga actttaccat taaagtgacc ggcctggcgc aggtgctgct gcagtggaaa      60
ccgaacccgg atcaggaaca gcgtaacgtg aacctggaat atcaggtgaa aattaacgcg     120
ccgaaagaag atgattatga aacccgcatt accgaaagca aactggtgac cattctgcat     180
aaaggcttta gcgcgagcgt gcgtaccatt ctgcagaacg atcatagcct gctggcgagc     240
agctgggcga gcgcggaact gcatgcg                                         267
```

<210> SEQ ID NO 44
<211> LENGTH: 297
<212> TYPE: DNA
<213> ORGANISM: Artificial Sequence
<220> FEATURE:
<223> OTHER INFORMATION: Synthetic construct

<400> SEQUENCE: 44

```
gccatggccg ccctgagcgt gaccgatgtg accaccagca gcctgcgtct gaactgggaa      60
gcgccgccgg gcgcgtttga tagctttctg ctgcgttttg gcgtgccgag cccgagcacc     120
ctggaaccgc atccgcgtcc gctgctgcag cgtgaactga tggtgccggg cacccgtcat     180
agcgcggtgc tgcgtgatct gcgtagcggc accctgtata gcctgaccct gtatggcctg     240
cgtggcccgc ataaagcgga tagcattcag ggcaccgcgc gtaccggtgg cggtacc        297
```

<210> SEQ ID NO 45
<211> LENGTH: 273
<212> TYPE: DNA
<213> ORGANISM: Artificial Sequence
<220> FEATURE:
<223> OTHER INFORMATION: Synthetic construct

<400> SEQUENCE: 45

```
ctgagcgtga ccgatgtgac caccagcagc ctgcgtctga actgggaagc gccgccgggc      60
gcgtttgata gctttctgct gcgttttggc gtgccgagcc cgagcaccct ggaaccgcat     120
ccgcgtccgc tgctgcagcg tgaactgatg gtgccgggca cccgtcatag cgcggtgctg     180
cgtgatctgc gtagcggcac cctgtatagc ctgaccctgt atggcctgcg tggcccgcat     240
aaagcggata gcattcaggg caccgcgcgt acc                                   273
```

<210> SEQ ID NO 46
<211> LENGTH: 267
<212> TYPE: DNA
<213> ORGANISM: Artificial Sequence
<220> FEATURE:
<223> OTHER INFORMATION: Synthetic construct

<400> SEQUENCE: 46

```
gccatggccg ccctgcgcgc gctgaacctg accgaaggct tgcggtgct gcattggaaa       60
ccgccgcaga acccggtgga tacctatgat attcaggtga ccgcgccggg cgcgccgccg     120
ctgcaggcgg aaaccccggg cagcgcggtg gattatccgc tgcatgatct ggtgctgcat     180
accaactata ccgcgaccgt gcgtggcctg cgcggcccga atctgaccag cccggcgagc     240
attacccttta ccaccggtgg cggtacc                                        267
```

<210> SEQ ID NO 47
<211> LENGTH: 243
<212> TYPE: DNA
<213> ORGANISM: Artificial Sequence
<220> FEATURE:
```

<223> OTHER INFORMATION: Synthetic construct

<400> SEQUENCE: 47

```
ctgcgcgcgc tgaacctgac cgaaggcttt gcggtgctgc attggaaacc gccgcagaac    60
ccggtggata cctatgatat tcaggtgacc gcgccgggcg cgccgccgct gcaggcggaa   120
accccgggca gcgcggtgga ttatccgctg catgatctgg tgctgcatac caactatacc   180
gcgaccgtgc gtggcctgcg cggcccgaat ctgaccagcc cggcgagcat tacctttacc   240
acc                                                                 243
```

<210> SEQ ID NO 48
<211> LENGTH: 267
<212> TYPE: DNA
<213> ORGANISM: Artificial Sequence
<220> FEATURE:
<223> OTHER INFORMATION: Synthetic construct

<400> SEQUENCE: 48

```
gccatggccg ccctggaagc gaaagaagtg accccgcgta ccgcgctgct gacctggacc    60
gaaccgccgg tgcgcccggc gggttatctg ctgagctttc ataccccggg cggccagacc   120
caggaaattc tgctgccggg cggcattacc agccatcagc tgctgggcct gtttccgagc   180
accagctata cgcgcgtcct gcaggcgatg tggggccaga gcctgctgcc gccggtgagc   240
accagcttta ccaccggtgg cggtacc                                       267
```

<210> SEQ ID NO 49
<211> LENGTH: 243
<212> TYPE: DNA
<213> ORGANISM: Artificial Sequence
<220> FEATURE:
<223> OTHER INFORMATION: Synthetic construct

<400> SEQUENCE: 49

```
ctggaagcga aagaagtgac cccgcgtacc gcgctgctga cctggaccga accgccggtg    60
cgcccggcgg gttatctgct gagctttcat accccgggcg gccagaccca ggaaattctg   120
ctgccgggcg gcattaccag ccatcagctg ctgggcctgt ttccgagcac cagctataac   180
gcgcgtctgc aggcgatgtg gggccagagc ctgctgccgc cggtgagcac cagctttacc   240
acc                                                                 243
```

<210> SEQ ID NO 50
<211> LENGTH: 273
<212> TYPE: DNA
<213> ORGANISM: Artificial Sequence
<220> FEATURE:
<223> OTHER INFORMATION: Synthetic construct

<400> SEQUENCE: 50

```
gccatggccg ccattgaagt gaaagatgtg accgatacca ccgcgctgat tacctggttt    60
aaaccgctgg cggaaattga tggcattgaa ctgacctatg cattaaaga tgtgccgggc   120 gatcgcacca ccattgatct gaccgaagat gaaaaccagt atagcattgg caacctgaaa   180
ccggataccg aatatgaagt gagcctgatt agccgtcgtg gcgatatgag cagcaacccg   240
gcgaaagaaa cctttaccac cggtggcggt acc                                273
```

<210> SEQ ID NO 51
<211> LENGTH: 249
<212> TYPE: DNA
<213> ORGANISM: Artificial Sequence
<220> FEATURE:

<223> OTHER INFORMATION: Synthetic construct

<400> SEQUENCE: 51

```
attgaagtga aagatgtgac cgataccacc gcgctgatta cctggtttaa accgctggcg    60
gaaattgatg gcattgaact gacctatggc attaaagatg tgccgggcga tcgcaccacc   120
attgatctga ccgaagatga aaaccagtat agcattggca acctgaaacc ggataccgaa   180
tatgaagtga gcctgattag ccgtcgtggc gatatgagca gcaacccggc gaaagaaacc   240
tttaccacc                                                            249
```

<210> SEQ ID NO 52
<211> LENGTH: 303
<212> TYPE: DNA
<213> ORGANISM: Artificial Sequence
<220> FEATURE:
<223> OTHER INFORMATION: Synthetic construct

<400> SEQUENCE: 52

```
gccatggccg ccccgaaatt taccaaatgc cgtagcccgg aacgcgaaac ctttagctgc    60
cattggaccg atgaagttca tcatggcacc aaaaatctgg gcccgattca gctgttttat   120
acccgccgta atacccagga atggacccag gaatggaaag aatgcccgga ttatgttagc   180
gcgggcgaaa acagctgcta tttttaacagc agctttacca gcatttggat tccgtattgc   240
attaaactga ccagcaacgg tggcaccgtt gatgaaaaat gctttagcgt gggtggcggt   300
acc                                                                  303
```

<210> SEQ ID NO 53
<211> LENGTH: 279
<212> TYPE: DNA
<213> ORGANISM: Artificial Sequence
<220> FEATURE:
<223> OTHER INFORMATION: Synthetic construct

<400> SEQUENCE: 53

```
ccgaaattta ccaaatgccg tagcccggaa cgcgaaacct ttagctgcca ttggaccgat    60
gaagttcatc atggcaccaa aaatctgggc ccgattcagc tgttttatac ccgccgtaat   120
acccaggaat ggacccagga atggaaagaa tgcccggatt atgttagcgc gggcgaaaac   180
agctgctatt ttaacagcag ctttaccagc atttggattc cgtattgcat taaactgacc   240
agcaacggtg gcaccgttga tgaaaaatgc tttagcgtg                           279
```

<210> SEQ ID NO 54
<211> LENGTH: 315
<212> TYPE: DNA
<213> ORGANISM: Artificial Sequence
<220> FEATURE:
<223> OTHER INFORMATION: Synthetic construct

<400> SEQUENCE: 54

```
gccatggcag ccccgtctgg ttttccgcag aatctgcatg tgaccggcct gaccaccagc    60
accaccgaac tggcgtggga tccgccggtg ctggcggaac gcaacggccg tattattagc   120
tataccgtgg tgtttcgtga tattaacagc cagcaggaac tgcagaacat taccaccgat   180
acccgcttta ccctgaccgg tctgaaaccg gataccacct atgatattaa agtgcgcgcc   240
tggaccagca aaggcagcgg cccgctgagc ccgagcattc agagccgcac catgccggtg   300
gaaggtggcg gtacc                                                     315
```

<210> SEQ ID NO 55

```
<211> LENGTH: 291
<212> TYPE: DNA
<213> ORGANISM: Artificial Sequence
<220> FEATURE:
<223> OTHER INFORMATION: Synthetic construct

<400> SEQUENCE: 55
ccgtctggtt ttccgcagaa tctgcatgtg accggcctga ccaccagcac caccgaactg      60
gcgtgggatc cgccggtgct ggcggaacgc aacggccgta ttattagcta taccgtggtg     120
tttcgtgata ttaacagcca gcaggaactg cagaacatta ccaccgatac ccgctttacc     180
ctgaccggtc tgaaaccgga taccacctat gatattaaag tgcgcgcctg gaccagcaaa     240
ggcagcggcc cgctgagccc gagcattcag agccgcacca tgccggtgga a              291

<210> SEQ ID NO 56
<211> LENGTH: 306
<212> TYPE: DNA
<213> ORGANISM: Artificial Sequence
<220> FEATURE:
<223> OTHER INFORMATION: Synthetic construct

<400> SEQUENCE: 56
gccatggccg ccccgaaacc gccgattgat ctggtggtta ccgaaaccac cgcgaccagc      60
gtgaccctga cctgggatag cggcaatagc gaaccggtga cctattatgg tattcagtat     120
cgcgcggcgg gcaccgaagg tccgtttcag gaagtggatg gcgtggcgac cacccgttat     180
agcattggcg gtctgagccc gtttagcgaa tatgcgtttc gcgtgctggc ggttaatagc     240
attggccgcg gtccgccgag cgaagcggtg cgtgcgcgca ccggcgaaca ggcgggtggc     300
ggtacc                                                               306

<210> SEQ ID NO 57
<211> LENGTH: 282
<212> TYPE: DNA
<213> ORGANISM: Artificial Sequence
<220> FEATURE:
<223> OTHER INFORMATION: Synthetic construct

<400> SEQUENCE: 57
ccgaaaccgc cgattgatct ggtggttacc gaaaccaccg cgaccagcgt gaccctgacc      60
tgggatagcg gcaatagcga accggtgacc tattatggta ttcagtatcg cgcggcgggc     120
accgaaggtc cgtttcagga agtggatggc gtggcgacca cccgttatag cattggcggt     180
ctgagcccgt ttagcgaata tgcgtttcgc gtgctggcgg ttaatagcat tggccgcggt     240
ccgccgagcg aagcggtgcg tgcgcgcacc ggcgaacagg cg                        282

<210> SEQ ID NO 58
<211> LENGTH: 285
<212> TYPE: DNA
<213> ORGANISM: Artificial Sequence
<220> FEATURE:
<223> OTHER INFORMATION: Synthetic construct

<400> SEQUENCE: 58
gccatggccg ccctgagccc gccgcgtaac ctgcgcatta gcaacgtggg tagcaatagc      60
gcgcgcctga cctgggatcc gaccagccgc cagattaatg ctatcgcat tgtgtataac     120 aacgccgatg gcaccgaaat taacgaagtg gaagtggatc cgattaccac ctttccgctg     180
aaaggcctga ccccgctgac cgaatatacc attgcgattt ttagcattta tgatgaaggt     240
cagagcgaac cgctgaccgg tgtgtttacc accggtggcg gtacc                     285
```

<210> SEQ ID NO 59
<211> LENGTH: 261
<212> TYPE: DNA
<213> ORGANISM: Artificial Sequence
<220> FEATURE:
<223> OTHER INFORMATION: Synthetic construct

<400> SEQUENCE: 59

```
ctgagcccgc cgcgtaacct gcgcattagc aacgtgggta gcaatagcgc gcgcctgacc      60
tgggatccga ccagccgcca gattaatggc tatcgcattg tgtataacaa cgccgatggc     120
accgaaatta acgaagtgga agtggatccg attaccacct ttccgctgaa aggcctgacc     180
ccgctgaccg aatataccat tgcgattttt agcatttatg atgaaggtca gagcgaaccg     240
ctgaccggtg tgtttaccac c                                               261
```

<210> SEQ ID NO 60
<211> LENGTH: 97
<212> TYPE: PRT
<213> ORGANISM: Artificial Sequence
<220> FEATURE:
<223> OTHER INFORMATION: Synthetic construct

<400> SEQUENCE: 60

```
Ala Ala Ile Glu Val Lys Asp Val Thr Asp Thr Thr Ala Leu Ile Thr
1               5                   10                  15

Trp Phe Lys Pro Leu Ala Glu Ile Asp Gly Ile Glu Leu Thr Tyr Gly
                20                  25                  30

Ile Lys Asp Val Pro Gly Asp Arg Thr Thr Ile Asp Leu Thr Glu Asp
            35                  40                  45

Glu Asn Gln Tyr Ser Ile Gly Asn Leu Lys Pro Asp Thr Glu Tyr Glu
        50                  55                  60

Val Ser Leu Ile Ser Arg Arg Gly Asp Met Ser Ser Asn Pro Ala Lys
65                  70                  75                  80

Glu Thr Phe Thr Thr Gly Gly Gly Thr Leu Glu His His His His His
                85                  90                  95

His
```

<210> SEQ ID NO 61
<211> LENGTH: 83
<212> TYPE: PRT
<213> ORGANISM: Artificial Sequence
<220> FEATURE:
<223> OTHER INFORMATION: Synthetic construct

<400> SEQUENCE: 61

```
Ile Glu Val Lys Asp Val Thr Asp Thr Thr Ala Leu Ile Thr Trp Phe
1               5                   10                  15

Lys Pro Leu Ala Glu Ile Asp Gly Ile Glu Leu Thr Tyr Gly Ile Lys
                20                  25                  30

Asp Val Pro Gly Asp Arg Thr Thr Ile Asp Leu Thr Glu Asp Glu Asn
            35                  40                  45

Gln Tyr Ser Ile Gly Asn Leu Lys Pro Asp Thr Glu Tyr Glu Val Ser
        50                  55                  60

Leu Ile Ser Arg Arg Gly Asp Met Ser Ser Asn Pro Ala Lys Glu Thr
65                  70                  75                  80

Phe Thr Thr
```

<210> SEQ ID NO 62
<211> LENGTH: 97

```
<212> TYPE: PRT
<213> ORGANISM: Artificial Sequence
<220> FEATURE:
<223> OTHER INFORMATION: Synthetic construct

<400> SEQUENCE: 62

Ala Ala Ile Glu Val Lys Asp Val Thr Asp Thr Thr Ala Leu Ile Thr
1               5                   10                  15

Trp Ser Pro Pro Ser Val Leu Val Gly Tyr Thr Ile Glu Leu Thr Tyr
            20                  25                  30

Gly Ile Lys Asp Val Pro Gly Asp Arg Thr Thr Ile Asp Leu Thr Glu
        35                  40                  45

Asp Glu Asn Gln Tyr Ser Ile Gly Asn Leu Lys Pro Asp Thr Glu Tyr
    50                  55                  60

Glu Val Ser Leu Ile Ser Val Thr Glu Phe Gly Arg Arg Arg Ser Lys
65                  70                  75                  80

Glu Thr Phe Thr Thr Gly Gly Gly Thr Leu Glu His His His His
                85                  90                  95

His

<210> SEQ ID NO 63
<211> LENGTH: 83
<212> TYPE: PRT
<213> ORGANISM: Artificial Sequence
<220> FEATURE:
<223> OTHER INFORMATION: Synthetic construct

<400> SEQUENCE: 63

Ile Glu Val Lys Asp Val Thr Asp Thr Thr Ala Leu Ile Thr Trp Ser
1               5                   10                  15

Pro Pro Ser Val Leu Val Gly Tyr Thr Ile Glu Leu Thr Tyr Gly Ile
            20                  25                  30

Lys Asp Val Pro Gly Asp Arg Thr Thr Ile Asp Leu Thr Glu Asp Glu
        35                  40                  45

Asn Gln Tyr Ser Ile Gly Asn Leu Lys Pro Asp Thr Glu Tyr Glu Val
    50                  55                  60

Ser Leu Ile Ser Val Thr Glu Phe Gly Arg Arg Arg Ser Lys Glu Thr
65                  70                  75                  80

Phe Thr Thr

<210> SEQ ID NO 64
<211> LENGTH: 83
<212> TYPE: PRT
<213> ORGANISM: Artificial Sequence
<220> FEATURE:
<223> OTHER INFORMATION: Synthetic construct

<400> SEQUENCE: 64

Ile Glu Cys Lys Asp Val Thr Asp Thr Thr Ala Leu Cys Thr Trp Phe
1               5                   10                  15

Lys Pro Leu Ala Glu Ile Asp Gly Ile Glu Leu Thr Tyr Gly Ile Lys
            20                  25                  30

Asp Val Pro Gly Asp Arg Thr Thr Ile Asp Leu Thr Glu Asp Glu Asn
        35                  40                  45

Gln Tyr Ser Ile Gly Asn Leu Lys Pro Asp Thr Glu Tyr Glu Val Ser
    50                  55                  60

Leu Ile Ser Arg Arg Gly Asp Met Ser Ser Asn Pro Ala Lys Glu Thr
65                  70                  75                  80

Phe Thr Thr
```

<210> SEQ ID NO 65
<211> LENGTH: 83
<212> TYPE: PRT
<213> ORGANISM: Artificial Sequence
<220> FEATURE:
<223> OTHER INFORMATION: Synthetic construct

<400> SEQUENCE: 65

```
Ile Glu Val Lys Asp Val Thr Asp Thr Thr Ala Leu Ile Thr Trp Phe
1               5                   10                  15

Lys Pro Leu Ala Glu Ile Asp Gly Ile Glu Leu Thr Tyr Gly Ile Lys
            20                  25                  30

Asp Val Pro Gly Asp Arg Thr Thr Ile Asp Leu Thr Glu Asp Glu Asn
        35                  40                  45

Gln Tyr Ser Ile Gly Asn Leu Lys Pro Asp Thr Glu Tyr Cys Val Ser
    50                  55                  60

Leu Ile Ser Arg Arg Gly Asp Met Ser Ser Asn Pro Ala Lys Glu Cys
65                  70                  75                  80

Phe Thr Thr
```

<210> SEQ ID NO 66
<211> LENGTH: 83
<212> TYPE: PRT
<213> ORGANISM: Artificial Sequence
<220> FEATURE:
<223> OTHER INFORMATION: Synthetic construct

<400> SEQUENCE: 66

```
Ile Glu Val Lys Asp Val Thr Asp Thr Thr Ala Leu Ile Thr Trp Phe
1               5                   10                  15

Lys Pro Leu Ala Glu Ile Asp Gly Cys Glu Leu Thr Tyr Gly Ile Lys
            20                  25                  30

Asp Val Pro Gly Asp Arg Thr Thr Ile Asp Leu Thr Glu Asp Glu Asn
        35                  40                  45

Gln Tyr Ser Ile Gly Asn Leu Lys Pro Asp Thr Glu Tyr Glu Val Ser
    50                  55                  60

Leu Ile Cys Arg Arg Gly Asp Met Ser Ser Asn Pro Ala Lys Glu Thr
65                  70                  75                  80

Phe Thr Thr
```

<210> SEQ ID NO 67
<211> LENGTH: 83
<212> TYPE: PRT
<213> ORGANISM: Artificial Sequence
<220> FEATURE:
<223> OTHER INFORMATION: Synthetic construct

<400> SEQUENCE: 67

```
Ile Glu Val Lys Asp Val Thr Asp Thr Thr Ala Leu Ile Thr Trp Phe
1               5                   10                  15

Lys Pro Leu Ala Glu Ile Asp Gly Cys Glu Leu Thr Tyr Gly Ile Lys
            20                  25                  30

Asp Val Pro Gly Asp Arg Thr Thr Ile Asp Leu Thr Glu Asp Glu Asn
        35                  40                  45

Gln Tyr Ser Ile Gly Asn Leu Lys Pro Asp Thr Glu Tyr Cys Val Ser
    50                  55                  60

Leu Ile Cys Arg Arg Gly Asp Met Ser Ser Asn Pro Ala Lys Glu Cys
65                  70                  75                  80
```

```
Phe Thr Thr

<210> SEQ ID NO 68
<211> LENGTH: 91
<212> TYPE: PRT
<213> ORGANISM: Artificial Sequence
<220> FEATURE:
<223> OTHER INFORMATION: Synthetic construct

<400> SEQUENCE: 68

Pro Ala Ile Ser Asn Val Arg Val Ser Asp Val Thr Asn Ser Ser Ala
1               5                   10                  15

Thr Ile Arg Trp Asp Val Ser Leu Ala Ala Asn Asn Arg Val Leu Phe
            20                  25                  30

Ser Thr Asn Ser Asp Leu Ser Ser Pro Gln Trp Ser Ala Trp Asp Asn
        35                  40                  45

Ser Thr Asp Ser Pro Met Ile Thr Leu Ser Gly Leu Ser Ala Gly Thr
    50                  55                  60

Ala Tyr Tyr Phe Ser Val Tyr Ser Phe Arg Pro Asp Asn Ala Ser Leu
65                  70                  75                  80

Tyr Ser Asn Ser Ser Ile Met Ser Phe Thr Thr
                85                  90

<210> SEQ ID NO 69
<211> LENGTH: 89
<212> TYPE: PRT
<213> ORGANISM: Artificial Sequence
<220> FEATURE:
<223> OTHER INFORMATION: Synthetic construct

<400> SEQUENCE: 69

Pro Pro Pro Lys Pro Val Ile Arg Phe Ala Gln Ala Gly Asn Asn Ser
1               5                   10                  15

Ile Ser Leu Ser Trp Tyr Asp Thr Asn Thr Ser Gly Tyr Tyr Ile Gln
            20                  25                  30

Trp Trp Ser Ser Ile Asp Asn Asn Lys Ser Thr Ile Asn Val Gly Asn
        35                  40                  45

Val Ser Ser Tyr Leu Phe Ile Asn Leu Thr Asn Gly Val Thr Tyr Tyr
    50                  55                  60

Phe Arg Ile Ile Pro Tyr Asn Gln Ala Gly Asn Gly Thr Ser Ser Asp
65                  70                  75                  80

Ile Ile Ser Leu Thr Pro Gly Ala Val
                85

<210> SEQ ID NO 70
<211> LENGTH: 89
<212> TYPE: PRT
<213> ORGANISM: Artificial Sequence
<220> FEATURE:
<223> OTHER INFORMATION: Synthetic construct

<400> SEQUENCE: 70

Pro Asp Ser Pro Ser Val Lys Val Ile Gly Asp Arg Asn Ala Thr
1               5                   10                  15

Val Ile Trp Ser Lys Pro Tyr Asn Gly Gly Phe Pro Ile Leu Gly Tyr
            20                  25                  30

Tyr Leu Thr Val Lys Thr Asp Asn Ser Ser Tyr Thr Ile Asn Val Gly
        35                  40                  45

Asn Val Ser Lys Tyr Thr Leu Thr Asn Leu Thr Pro Glu Val Leu Tyr
    50                  55                  60
```

```
Glu Val Met Val Val Ala Tyr Asn Lys Leu Gly Ser Ser Pro Gly
65                  70                  75                  80

Ile Val Asn Phe Val Ala Leu Thr Thr
                85

<210> SEQ ID NO 71
<211> LENGTH: 87
<212> TYPE: PRT
<213> ORGANISM: Artificial Sequence
<220> FEATURE:
<223> OTHER INFORMATION: Synthetic construct

<400> SEQUENCE: 71

Leu Thr Thr Ala Ser Ile Ser Val Ser Val Tyr Lys Lys Val Asn Gly
1               5                   10                  15

Val Leu Ile Ser Trp Asn Lys Thr Glu Asn Thr Thr Tyr Asn Leu Leu
            20                  25                  30

Ile Ser Asp Lys Lys Gly Lys Ile Ile Val Asn Ile Thr Thr Thr Asn
        35                  40                  45

Thr Ser Tyr Phe Ala Tyr Ile Pro Tyr Gly Ile Tyr Asn Val Thr Ile
    50                  55                  60

Arg Ala Thr Asn Gln Val Gly Thr Asn Ser Thr Ser Phe Pro Ile Val
65                  70                  75                  80

Phe Tyr Ile Pro Pro Phe Ile
                85

<210> SEQ ID NO 72
<211> LENGTH: 84
<212> TYPE: PRT
<213> ORGANISM: Artificial Sequence
<220> FEATURE:
<223> OTHER INFORMATION: Synthetic construct

<400> SEQUENCE: 72

Pro Leu Val Lys Phe Ser Ile Gly Asn Asn Ser Ile Leu Asn Leu Lys
1               5                   10                  15

Trp Asn Asn Val Thr Gly Ala Thr Phe Tyr Leu Val Tyr Val Asn Thr
            20                  25                  30

Thr Leu Ile Ala Asn Val Thr Thr Asp Ser Tyr Ser Leu Asn Leu Thr
        35                  40                  45

Pro Gly Phe His Val Ile Arg Val Val Ala Ala Pro Ile Tyr Asn
    50                  55                  60

Ser Ser Pro Ala Ser Leu Gly Ile Leu Ile Gln Gln His Ser Val Thr
65                  70                  75                  80

Ser Ser Ile Thr

<210> SEQ ID NO 73
<211> LENGTH: 88
<212> TYPE: PRT
<213> ORGANISM: Artificial Sequence
<220> FEATURE:
<223> OTHER INFORMATION: Synthetic construct

<400> SEQUENCE: 73

Pro Leu Pro Pro Lys Ile Thr Ser Tyr Ser Ala Gly Asn Glu Ser Val
1               5                   10                  15

Thr Leu Gly Trp Asn Pro Val Arg Leu Ser Ser Gly Tyr Glu Ile Ile
            20                  25                  30

Tyr Trp Asn Asn Met Gly Phe Asn Ser Ser Ile Asn Val Gly Asn Val
        35                  40                  45
```

-continued

Thr Ser Tyr Thr Val Thr Gly Leu Lys Asp Gly Ile Thr Tyr Tyr Phe
    50                  55                  60

Glu Val Leu Ala Tyr Asn Ser Ile Gly Tyr Ser Pro Ser Ser Ile
65                  70                  75                  80

Ile Ala Leu Thr Pro Ala Ser Val
                85

<210> SEQ ID NO 74
<211> LENGTH: 92
<212> TYPE: PRT
<213> ORGANISM: Artificial Sequence
<220> FEATURE:
<223> OTHER INFORMATION: Synthetic construct

<400> SEQUENCE: 74

Pro Asn Pro Pro Gln Leu Val Ser Val Lys Tyr Gly Asn Asp Asn Val
1               5                   10                  15

Thr Leu Asn Trp Leu Pro Pro Thr Phe Ser Gly Gly Tyr Leu Leu Leu
            20                  25                  30

Gly Tyr Tyr Val Ile Val Lys Asn Glu Asn Ser Met Val Ser Ser His
        35                  40                  45

Phe Val Asn Ser Thr Ser Leu Thr Ile Ser Asn Leu Thr Pro Asn Val
    50                  55                  60

Thr Tyr Asn Val Phe Ile Tyr Ala Val Asn Lys Leu Gly Asn Ser Ser
65                  70                  75                  80

Pro Leu Val Leu Thr Val Val Pro Ile Thr Lys Ala
                85                  90

<210> SEQ ID NO 75
<211> LENGTH: 86
<212> TYPE: PRT
<213> ORGANISM: Artificial Sequence
<220> FEATURE:
<223> OTHER INFORMATION: Synthetic construct

<400> SEQUENCE: 75

Pro Ile Thr Lys Ala Ser Val Phe Ala Phe Ile Thr Lys Leu Gly Asn
1               5                   10                  15

Gly Ile Leu Val Asn Trp Thr Thr Ser Phe Pro Ala Asn Ile Thr Leu
            20                  25                  30

Glu Leu Tyr Asn Pro Asn Gly Asn Leu Ile Ser Gln Ile Ala Ala Ile
        35                  40                  45

Lys Gly Asn Ser Ser Tyr Leu Phe Arg Val Pro Gln Gly Asn Tyr Thr
    50                  55                  60

Leu Val Ile Ile Ala Ser Asn Ser Ala Gly Val Ser Lys Tyr Val Tyr
65                  70                  75                  80

Gln Val Val Tyr Tyr Leu
                85

<210> SEQ ID NO 76
<211> LENGTH: 83
<212> TYPE: PRT
<213> ORGANISM: Artificial Sequence
<220> FEATURE:
<223> OTHER INFORMATION: Synthetic construct

<400> SEQUENCE: 76

Pro Pro Ala Ser Pro Gln Val Ser Leu Ile Gly Phe Gly Asn Asn Leu
1               5                   10                  15

Tyr Ile Ser Trp Asn Asn Glu Ala Asn Val Ile Thr Tyr Leu Val Tyr
            20                  25                  30

Val Asn Asn Ser Leu Val Tyr Glu Gly Pro Ser Asn Ser Ile Val Thr
         35                  40                  45

Asn Ile Ser Asn Gly Thr Tyr Leu Val Lys Val Ile Gly Val Asn Pro
     50                  55                  60

Ala Gly Ser Ser Ser Pro Gly Ile Ala Val Ile His Tyr Thr Gly Asp
 65                  70                  75                  80

Tyr Val Thr

<210> SEQ ID NO 77
<211> LENGTH: 83
<212> TYPE: PRT
<213> ORGANISM: Artificial Sequence
<220> FEATURE:
<223> OTHER INFORMATION: Synthetic construct

<400> SEQUENCE: 77

Ala Ser Lys Ala Asn Leu Thr Val Thr Val Tyr Lys Lys Ile Asn Gly
 1               5                  10                  15

Phe Leu Val Ser Trp Asn Ser Thr Ser Lys Ala Lys Tyr Ile Leu Thr
                 20                  25                  30

Val Ser Lys Glu Asn Val Val Leu Leu Asn Val Ser Thr Thr Asn Thr
         35                  40                  45

Ser Tyr Phe Val Lys Val Pro Phe Gly Val Tyr Asn Ile Ser Leu Glu
     50                  55                  60

Ala Val Asn Ile Val Gly Ile Thr Lys Tyr Ala Phe Ile Leu Ile Tyr
 65                  70                  75                  80

Tyr Ile Gln

<210> SEQ ID NO 78
<211> LENGTH: 81
<212> TYPE: PRT
<213> ORGANISM: Artificial Sequence
<220> FEATURE:
<223> OTHER INFORMATION: Synthetic construct

<400> SEQUENCE: 78

Pro Ala Ser Pro Thr Val Asn Trp Ser Ile Thr Leu Asn Thr Val Ser
 1               5                  10                  15

Leu Asn Trp Ser Lys Val Ser Gly Ala Glu Tyr Tyr Leu Ile Tyr Asp
                 20                  25                  30

Asn Gly Lys Leu Ile Thr Asn Thr Thr Asn Thr Ala Phe Thr Phe Asn
         35                  40                  45

Leu Thr Ile Gly Gln Asn Glu Ile Glu Val Tyr Ala Ala Asn Ala Tyr
     50                  55                  60

Tyr Lys Ser Ala Pro Tyr Ile Ile Asn Asp Val Arg Asn Tyr Ile Val
 65                  70                  75                  80

Val

<210> SEQ ID NO 79
<211> LENGTH: 105
<212> TYPE: PRT
<213> ORGANISM: Artificial Sequence
<220> FEATURE:
<223> OTHER INFORMATION: Synthetic construct

<400> SEQUENCE: 79

Ala Ala Pro Ala Ile Ser Asn Val Arg Val Ser Asp Val Thr Asn Ser
 1               5                  10                  15

Ser Ala Thr Ile Arg Trp Asp Val Ser Leu Ala Ala Asn Asn Arg Val

```
                20                  25                  30
Leu Phe Ser Thr Asn Ser Asp Leu Ser Ser Pro Gln Trp Ser Ala Trp
        35                  40                  45
Asp Asn Ser Thr Asp Ser Pro Met Ile Thr Leu Ser Gly Leu Ser Ala
 50                  55                  60
Gly Thr Ala Tyr Tyr Phe Ser Val Tyr Ser Phe Arg Pro Asp Asn Ala
 65                  70                  75                  80
Ser Leu Tyr Ser Asn Ser Ser Ile Met Ser Phe Thr Thr Gly Gly Gly
                85                  90                  95
Thr Leu Glu His His His His His His
            100                 105
```

<210> SEQ ID NO 80
<211> LENGTH: 91
<212> TYPE: PRT
<213> ORGANISM: Artificial Sequence
<220> FEATURE:
<223> OTHER INFORMATION: Synthetic construct

<400> SEQUENCE: 80

```
Pro Ala Ile Ser Asn Val Arg Val Ser Asp Val Thr Asn Ser Ser Ala
 1               5                  10                  15
Thr Ile Arg Trp Asp Val Ser Leu Ala Ala Asn Asn Arg Val Leu Phe
                20                  25                  30
Ser Thr Asn Ser Asp Leu Ser Ser Pro Gln Trp Ser Ala Trp Asp Asn
        35                  40                  45
Ser Thr Asp Ser Pro Met Ile Thr Leu Ser Gly Leu Ser Ala Gly Thr
 50                  55                  60
Ala Tyr Tyr Phe Ser Val Tyr Ser Phe Arg Pro Asp Asn Ala Ser Leu
 65                  70                  75                  80
Tyr Ser Asn Ser Ser Ile Met Ser Phe Thr Thr
                85                  90
```

<210> SEQ ID NO 81
<211> LENGTH: 108
<212> TYPE: PRT
<213> ORGANISM: Artificial Sequence
<220> FEATURE:
<223> OTHER INFORMATION: Synthetic construct

<400> SEQUENCE: 81

```
Ala Ala Ser Glu Pro Gln Asn Leu Lys Ala Thr Ala Gly Asn Asn Asn
 1               5                  10                  15
Ile Thr Leu Thr Trp Asp Pro Pro Ile Asp Asp Gly Gly Cys Arg Ile
                20                  25                  30
Val Glu Tyr Arg Ile Tyr Arg Gly Thr Asn Asn Asn Leu Glu Tyr
        35                  40                  45
Tyr Ala Ser Val Asn Gly Ser Thr Thr Thr Phe Ile Asp Lys Asn Ile
 50                  55                  60
Val Tyr Ser Gln Thr Tyr Tyr Tyr Lys Val Ser Ala Val Asn Asn Ile
 65                  70                  75                  80
Val Glu Gly Pro Lys Ser Asn Thr Ala Ser Ala Thr Pro Thr Ser Ser
                85                  90                  95
Gly Gly Gly Thr Leu Glu His His His His His
            100                 105
```

<210> SEQ ID NO 82
<211> LENGTH: 94
<212> TYPE: PRT

<213> ORGANISM: Artificial Sequence
<220> FEATURE:
<223> OTHER INFORMATION: Synthetic construct

<400> SEQUENCE: 82

```
Ser Glu Pro Gln Asn Leu Lys Ala Thr Ala Gly Asn Asn Ile Thr
1               5                   10                  15

Leu Thr Trp Asp Pro Pro Ile Asp Asp Gly Gly Cys Arg Ile Val Glu
            20                  25                  30

Tyr Arg Ile Tyr Arg Gly Thr Asn Asn Asn Leu Glu Tyr Tyr Ala
            35                  40                  45

Ser Val Asn Gly Ser Thr Thr Thr Phe Ile Asp Lys Asn Ile Val Tyr
50                  55                          60

Ser Gln Thr Tyr Tyr Lys Val Ser Ala Val Asn Asn Ile Val Glu
65                  70                  75                  80

Gly Pro Lys Ser Asn Thr Ala Ser Ala Thr Pro Thr Ser Ser
                85                  90
```

<210> SEQ ID NO 83
<211> LENGTH: 102
<212> TYPE: PRT
<213> ORGANISM: Artificial Sequence
<220> FEATURE:
<223> OTHER INFORMATION: Synthetic construct

<400> SEQUENCE: 83

```
Ala Ala Pro Leu Pro Pro Lys Ile Thr Ser Tyr Ser Ala Gly Asn Glu
1               5                   10                  15

Ser Val Thr Leu Gly Trp Asn Pro Val Arg Leu Ser Ser Gly Tyr Glu
            20                  25                  30

Ile Ile Tyr Trp Asn Asn Met Gly Phe Asn Ser Ser Ile Asn Val Gly
            35                  40                  45

Asn Val Thr Ser Tyr Thr Val Thr Gly Leu Lys Asp Gly Ile Thr Tyr
50                  55                  60

Tyr Phe Glu Val Leu Ala Tyr Asn Ser Ile Gly Tyr Ser Ser Pro Ser
65                  70                  75                  80

Ser Ile Ile Ala Leu Thr Pro Ala Ser Val Gly Gly Thr Leu Glu
                85                  90                  95

His His His His His His
            100
```

<210> SEQ ID NO 84
<211> LENGTH: 88
<212> TYPE: PRT
<213> ORGANISM: Artificial Sequence
<220> FEATURE:
<223> OTHER INFORMATION: Synthetic cosntruct

<400> SEQUENCE: 84

```
Pro Leu Pro Pro Lys Ile Thr Ser Tyr Ser Ala Gly Asn Glu Ser Val
1               5                   10                  15

Thr Leu Gly Trp Asn Pro Val Arg Leu Ser Ser Gly Tyr Glu Ile Ile
            20                  25                  30

Tyr Trp Asn Asn Met Gly Phe Asn Ser Ser Ile Asn Val Gly Asn Val
            35                  40                  45

Thr Ser Tyr Thr Val Thr Gly Leu Lys Asp Gly Ile Thr Tyr Tyr Phe
50                  55                  60

Glu Val Leu Ala Tyr Asn Ser Ile Gly Tyr Ser Ser Pro Ser Ser Ile
65                  70                  75                  80
```

```
Ile Ala Leu Thr Pro Ala Ser Val
                85
```

<210> SEQ ID NO 85
<211> LENGTH: 101
<212> TYPE: PRT
<213> ORGANISM: Artificial Sequence
<220> FEATURE:
<223> OTHER INFORMATION: Synthetic construct

<400> SEQUENCE: 85

```
Ala Ala Pro Pro Lys Pro Gln Ile Ala Ser Ile Ala Ser Gly Asn Glu
1               5                   10                  15

Thr Ile Thr Val Lys Trp Tyr Asp Thr Asn Ala Ser Gly Tyr Tyr Ile
            20                  25                  30

Thr Tyr Trp Ser Asn Phe Ser Gln Lys Val Thr Ile Asn Val Gly Asn
        35                  40                  45

Val Thr Ser Tyr Thr Ile Lys His Leu Lys Asp Gly Val Thr Tyr Tyr
    50                  55                  60

Ile Gln Ile Val Pro Tyr Asn Ser Leu Gly Asn Gly Thr Pro Ser Asp
65                  70                  75                  80

Ile Ile Ser Ala Thr Pro Ser Ser Val Gly Gly Gly Thr Leu Glu His
                85                  90                  95

His His His His His
            100
```

<210> SEQ ID NO 86
<211> LENGTH: 87
<212> TYPE: PRT
<213> ORGANISM: Artificial Sequence
<220> FEATURE:
<223> OTHER INFORMATION: Synthetic construct

<400> SEQUENCE: 86

```
Pro Pro Lys Pro Gln Ile Ala Ser Ile Ala Ser Gly Asn Glu Thr Ile
1               5                   10                  15

Thr Val Lys Trp Tyr Asp Thr Asn Ala Ser Gly Tyr Tyr Ile Thr Tyr
            20                  25                  30

Trp Ser Asn Phe Ser Gln Lys Val Thr Ile Asn Val Gly Asn Val Thr
        35                  40                  45

Ser Tyr Thr Ile Lys His Leu Lys Asp Gly Val Thr Tyr Tyr Ile Gln
    50                  55                  60

Ile Val Pro Tyr Asn Ser Leu Gly Asn Gly Thr Pro Ser Asp Ile Ile
65                  70                  75                  80

Ser Ala Thr Pro Ser Ser Val
                85
```

<210> SEQ ID NO 87
<211> LENGTH: 100
<212> TYPE: PRT
<213> ORGANISM: Artificial Sequence
<220> FEATURE:
<223> OTHER INFORMATION: Synthetic construct

<400> SEQUENCE: 87

```
Ala Ala Pro Asn Pro Ile Ile Lys Val Lys Ile Gly Asn Leu Asn
1               5                   10                  15

Ala Thr Leu Thr Trp Tyr Asp Thr Phe Asn Gly Gly Tyr Pro Ile Glu
            20                  25                  30

Gly Tyr Tyr Leu Tyr Val Asn Gly Lys Gly Ile Asn Val Gly Asn Ile
        35                  40                  45
```

Thr Ser Tyr Val Leu Thr Asn Leu Thr Ala Gly Glu Leu Tyr Thr Ile
         50                  55                  60

Glu Leu Ile Ala Tyr Asn Lys Ile Gly Asn Ser Ser Ile Ser Ser Val
 65                  70                  75                  80

Ser Phe Ile Ala Ala Ser Lys Ala Gly Gly Thr Leu Glu His His
                 85                  90                  95

His His His His
        100

<210> SEQ ID NO 88
<211> LENGTH: 86
<212> TYPE: PRT
<213> ORGANISM: Artificial Sequence
<220> FEATURE:
<223> OTHER INFORMATION: Synthetic construct

<400> SEQUENCE: 88

Pro Asn Pro Pro Ile Ile Lys Val Lys Ile Gly Asn Leu Asn Ala Thr
 1               5                   10                  15

Leu Thr Trp Tyr Asp Thr Phe Asn Gly Gly Tyr Pro Ile Glu Gly Tyr
             20                  25                  30

Tyr Leu Tyr Val Asn Gly Lys Gly Ile Asn Val Gly Asn Ile Thr Ser
         35                  40                  45

Tyr Val Leu Thr Asn Leu Thr Ala Gly Glu Leu Tyr Thr Ile Glu Leu
     50                  55                  60

Ile Ala Tyr Asn Lys Ile Gly Asn Ser Ser Ile Ser Ser Val Ser Phe
 65                  70                  75                  80

Ile Ala Ala Ser Lys Ala
                 85

<210> SEQ ID NO 89
<211> LENGTH: 297
<212> TYPE: DNA
<213> ORGANISM: Artificial Sequence
<220> FEATURE:
<223> OTHER INFORMATION: Synthetic construct

<400> SEQUENCE: 89
gccatggcag ccccggcgat tagcaatgtg cgcgttagcg atgtgaccaa cagcagcgcc      60
accattcgtt gggatgtgag cctggcggcg aataatcgcg tgctgtttag caccaacagc     120
gatctgagca gcccgcagtg gagcgcgtgg gataacagca ccgatagccc gatgattacc     180
ctgagcggtc tgagcgcggg caccgcgtat tattttagcg tgtatagctt tcgtccggat     240
aatgcgagcc tgtatagcaa cagcagcatt atgagcttta ccaccggtgg cggtacc       297

<210> SEQ ID NO 90
<211> LENGTH: 273
<212> TYPE: DNA
<213> ORGANISM: Artificial Sequence
<220> FEATURE:
<223> OTHER INFORMATION: Synthetic construct

<400> SEQUENCE: 90
ccggcgatta gcaatgtgcg cgttagcgat gtgaccaaca gcagcgccac cattcgttgg      60
gatgtgagcc tggcggcgaa taatcgcgtg ctgtttagca ccaacagcga tctgagcagc     120
ccgcagtgga gcgcgtggga taacagcacc gatagcccga tgattaccct gagcggtctg     180
agcgcgggca ccgcgtatta ttttagcgtg tatagctttc gtccggataa tgcgagcctg     240
tatagcaaca gcagcattat gagctttacc acc                                  273

<210> SEQ ID NO 91
<211> LENGTH: 306
<212> TYPE: DNA
<213> ORGANISM: Artificial Sequence
<220> FEATURE:
<223> OTHER INFORMATION: Synthetic construct

<400> SEQUENCE: 91

```
gccatggccg ccagcgaacc gcagaacctg aaagcgaccg cgggtaataa caatattacc      60
ctgacctggg atccgccgat tgatgatggt ggctgccgca ttgtggaata tcgtatttat     120
cgtggcacca ataataacaa cctggaatat tatgcgagcg ttaacggcag caccaccacc     180
tttattgata aaaatattgt gtatagccag acctattatt ataaagtgag cgcggtgaac     240
aatattgtgg aaggcccgaa aagcaacacc gcgagcgcga ccccgaccag cagcggtggc     300
ggtacc                                                                306
```

<210> SEQ ID NO 92
<211> LENGTH: 282
<212> TYPE: DNA
<213> ORGANISM: Artificial Sequence
<220> FEATURE:
<223> OTHER INFORMATION: Synthetic cosntruct

<400> SEQUENCE: 92

```
agcgaaccgc agaacctgaa agcgaccgcg gtaataaca atattaccct gacctgggat       60
ccgccgattg atgatggtgg ctgccgcatt gtggaatatc gtatttatcg tggcaccaat     120
aataacaacc tggaatatta tgcgagcgtt aacggcagca ccaccacctt tattgataaa     180
aatattgtgt atagccagac ctattattat aaagtgagcg cggtgaacaa tattgtggaa     240
ggcccgaaaa gcaacaccgc gagcgcgacc ccgaccagca gc                        282
```

<210> SEQ ID NO 93
<211> LENGTH: 288
<212> TYPE: DNA
<213> ORGANISM: Artificial Sequence
<220> FEATURE:
<223> OTHER INFORMATION: Synthetic cosntruct

<400> SEQUENCE: 93

```
gccatggccg ccccgctccc accgaaaatt accagctata gcgcgggcaa cgaaagcgtg      60
accctgggct ggaacccggt gcgtctgagc agcggctatg aaattattta ttggaacaat     120 atgggctttta acagcagcat taatgtgggt aatgtgacca gctataccgt gaccggcctg     180
aaagatggca ttacctatta ttttgaagtg ctggcctata acagcattgg ttatagcagc     240
ccgagcagca ttatcgcgct gaccccggcg agcgtgggtg gcggtacc                  288
```

<210> SEQ ID NO 94
<211> LENGTH: 264
<212> TYPE: DNA
<213> ORGANISM: Artificial Sequence
<220> FEATURE:
<223> OTHER INFORMATION: Synthetic construct

<400> SEQUENCE: 94

```
ccgctcccac cgaaaattac cagctatagc gcgggcaacg aaagcgtgac cctgggctgg      60
aacccggtgc gtctgagcag cggctatgaa attatttatt ggaacaatat gggctttaac     120
agcagcatta atgtgggtaa tgtgaccagc tataccgtga ccggcctgaa agatggcatt     180
acctattatt ttgaagtgct ggcctataac agcattggtt atagcagccc gagcagcatt     240
```

```
atcgcgctga ccccggcgag cgtg                                    264
```

<210> SEQ ID NO 95
<211> LENGTH: 285
<212> TYPE: DNA
<213> ORGANISM: Artificial Sequence
<220> FEATURE:
<223> OTHER INFORMATION: Synthetic construct

<400> SEQUENCE: 95

```
gccatggccg ccccgccgaa accgcagatt gccagcattg ccagcggtaa tgaaaccatt    60
accgtgaaat ggtatgatac caatgcgagc ggctattata ttacctattg gagcaatttt   120
agccagaaag tgaccattaa tgtgggtaac gtgaccagct ataccattaa acatctgaaa   180
gatggcgtga cctattatat tcagattgtg ccgtataaca gcctgggcaa tggcaccccg   240
agcgatatta ttagcgcgac cccgagcagc gttggtggcg gtacc                  285
```

<210> SEQ ID NO 96
<211> LENGTH: 261
<212> TYPE: DNA
<213> ORGANISM: Artificial Sequence
<220> FEATURE:
<223> OTHER INFORMATION: Synthetic construct

<400> SEQUENCE: 96

```
ccgccgaaac cgcagattgc cagcattgcc agcggtaatg aaaccattac cgtgaaatgg    60
tatgatacca atgcgagcgg ctattatatt acctattgga gcaattttag ccagaaagtg   120
accattaatg tgggtaacgt gaccagctat accattaaac atctgaaaga tggcgtgacc   180
tattatattc agattgtgcc gtataacagc ctgggcaatg gcaccccgag cgatattatt   240
agcgcgaccc cgagcagcgt t                                            261
```

<210> SEQ ID NO 97
<211> LENGTH: 282
<212> TYPE: DNA
<213> ORGANISM: Artificial Sequence
<220> FEATURE:
<223> OTHER INFORMATION: Synthetic construct

<400> SEQUENCE: 97

```
gccatggccg ccccgaatcc gccgattatt aaagtgaaaa ttggcaatct gaatgcgacc    60
ctgacctggt atgataccct taatggtggt tatccgattg aaggctatta tctgtatgtg   120
aacggtaaag gtattaacgt gggcaacatt accagctatg tgctgaccaa tctgaccgcc   180
ggtgaactgt ataccattga actgattgcg tataacaaaa tcggcaacag cagcattagc   240
agcgtgagct ttattgcggc gagcaaagcg ggtggcggta cc                     282
```

<210> SEQ ID NO 98
<211> LENGTH: 258
<212> TYPE: DNA
<213> ORGANISM: Artificial Sequence
<220> FEATURE:
<223> OTHER INFORMATION: Synthetic construct

<400> SEQUENCE: 98

```
ccgaatccgc cgattattaa agtgaaaatt ggcaatctga atgcgaccct gacctggtat    60
gataccttta tggtggtta tccgattgaa ggctattatc tgtatgtgaa cggtaaaggt   120
attaacgtgg gcaacattac cagctatgtg ctgaccaatc tgaccgccgg tgaactgtat   180
accattgaac tgattgcgta taacaaaatc ggcaacagca gcattagcag cgtgagcttt   240
```

```
attgcggcga gcaaagcg                                                    258

<210> SEQ ID NO 99
<211> LENGTH: 3994
<212> TYPE: DNA
<213> ORGANISM: Artificial Sequence
<220> FEATURE:
<223> OTHER INFORMATION: Synthetic construct

<400> SEQUENCE: 99
gacgaaaggg cctcgtgata cgcctatttt tataggttaa tgtcatgata ataatggttt      60
cttagacgtc aggtggcact tttcggggaa atgtgcgcgg aacccctatt tgtttatttt     120
tctaaataca ttcaaatatg tatccgctca tgagacaata accctgataa atgcttcaat     180
aatattgaaa aaggaagagt atgagtattc aacatttccg tgtcgccctt attccctttt     240
ttgcggcatt ttgccttcct gttttttgctc acccagaaac gctggtgaaa gtaaaagatg     300
ctgaagatca gttgggtgct cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga taggtgcc tcactgatta agcattggta actgtcagac caagtttact    1080
catatatact ttagattgat ttaaaacttc attttt aatt taaaaggatc taggtgaaga    1140
tccttttga taatctcatg accaaaatcc cttaacgtga gttttcgttc cactgagcgt    1200
cagacccgt agaaaagatc aaaggatctt cttgagatcc ttttttttctg cgcgtaatct    1260
gctgcttgca acaaaaaaa ccaccgctac cagcggtggt ttgtttgccg gatcaagagc    1320
taccaactct ttttccgaag gtaactggct tcagcagagc gcagatacca atactgtcc    1380
ttctagtgta gccgtagtta ggccaccact caagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg tcgggctga acgggggggtt    1560
cgtgcataca gcccagcttg gagcgaacga cctacaccga actgagatac ctacagcgtg    1620
agctatgaga aagcgccacg cttcccgaag ggagaaaggc ggacaggtat ccggtaagcg    1680
gcagggtcgg aacaggagag cgcacagggg agcttccagg gggaaacgcc tggtatcttt    1740
atagtcctgt cgggtttcgc cacctctgac ttgagcgtcg attttgtga tgctcgtcag    1800
gggggcggag cctatggaaa aacgccagca acgcggcctt tttacggttc ctggcctttt    1860
gctggccttt tgctcacatg ttcttttcctg cgttatcccc tgattctgtg ataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
```

```
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg gataacaatt tcacacagga aacagctatg    2220
accatgatta cgccaagctt tggagccttt ttttggaga ttttcaacgt gaaaaaatta     2280
ttattcgcaa ttcctttagt tgttcctttc tatgcggccc agccggccat ggccgccatt    2340
gaagtgaaag atgtgaccga taccaccgcg ctgattacct ggtttaaacc gctggcggaa    2400
attgatggct gtgaactgac ctatggcatt aaagatgtgc cgggcgatcg caccaccata    2460
gatctgaccg aagatgaaaa ccagtatagc attggtaacc tgaaaccgga taccgaatat    2520
gaagtgagcc tgatttgccg tcgtggcgat atgagcggcg cgccggcgaa agaaaccttt    2580
accaccggtg gcggtacccc aaccgacccg ccaaccactc caccaactga tagcccaggc    2640
ggtactggtg gctctggttc cggtgatttt gattatgaaa agatggcaaa cgctaataag    2700
ggggctatga ccgaaaatgc cgatgaaaac gcgctacagt ctgacgctaa aggcaaactt    2760
gattctgtcg ctactgatta cggtgctgct atcgatggtt tcattggtga cgtttccggc    2820
cttgctaatg gtaatggtgc tactggtgat tttgctggct ctaattccca aatggctcaa    2880
gtcggtgacg gtgataattc accttttaatg aataatttcc gtcaatattt accttccctc    2940
cctcaatcgg ttgaatgtcg ccctttttgtc tttagcgctg gtaaaccata tgaattttct    3000
attgattgtg acaaaataaa cttattccgt ggtgtctttg cgtttctttt atatgttgcc    3060
acctttatgt atgtattttc tacgtttgct aacatactgc gtaataagga gtcttaagaa    3120
ttcgacggtc acagcttgtc tgtaagcgga tgccgggagc agacaagccc gtcagggcgc    3180
gtcagcgggt gttggcgggt gtcggggctg gcttaactat gcggcatcag agcagattgt    3240
actgagactg caccataaaa ttgtaaacgt taatatttttg ttaaaattcg cgttaaattt    3300
ttgttaaatc agctcatttt ttaaccaata ggccgaaatc ggcaaaatcc cttataaatc    3360
aaaagaatag cccgagatag ggttgagtgt tgttccagtt tggaacaaga gtccactatt    3420
aaagaacgtg gactccaacg tcaaagggcg aaaaaccgtc tatcagggcg atggcccact    3480
acgtgaacca tcacccaaat caagtttttt ggggtcgagg tgccgtaaag cactaaatcg    3540
gaaccctaaa gggagccccc gatttagagc ttgacgggga agccggcgaa acgtggcgag    3600
aaaggaaggg aagaaagcga aaggagcggg cgctagggcg ctggcaagtg tagcggtcac    3660
gctgcgcgta accaccacac ccgccgcgct taatgcgccg ctacagggcg cgtactatgg    3720
ttgctttgac gtatgcggtg tgaaataccg cacagatgcg taaggagaaa ataccgcatc    3780
aggcgccatt cgccattcag gctgcgcaac tgttgggaag ggcgatcggt gcgggcctct    3840
tcgctattac gccagctggc gaaagggggga tgtgctgcaa ggcgattaag ttgggtaacg    3900
ccagggtttt cccagtcacg acgttgtaaa acgacggcca gttccgggag ctgcatgtgt    3960
cagaggtttt caccgtcatc accgaaacgc gcga                                3994
```

<210> SEQ ID NO 100
<211> LENGTH: 11
<212> TYPE: PRT
<213> ORGANISM: Artificial Sequence
<220> FEATURE:
<223> OTHER INFORMATION: Synthetic construct

<400> SEQUENCE: 100

Ser Pro Pro Ser Val Leu Val Gly Tyr Thr Gly
1               5                   10

```
<210> SEQ ID NO 101
<211> LENGTH: 9
<212> TYPE: PRT
<213> ORGANISM: Artificial Sequence
<220> FEATURE:
<223> OTHER INFORMATION: Synthetic construct

<400> SEQUENCE: 101

Val Thr Glu Phe Gly Arg Arg Arg Ser
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic cosntruct

<400> SEQUENCE: 102

Phe Lys Pro Leu Ala Glu Ile Asp Gly
1               5

<210> SEQ ID NO 103
<211> LENGTH: 11
<212> TYPE: PRT
<213> ORGANISM: Artificial Sequence
<220> FEATURE:
<223> OTHER INFORMATION: Synthetic construct

<400> SEQUENCE: 103

Arg Lys Ile Ile Gly Leu Leu Ser Asn Pro Ala
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic construct

<400> SEQUENCE: 104

Gly Thr Val Val Gly Gln Lys Ser Asn Pro Ala
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthetic construct

<400> SEQUENCE: 105

Ser Pro Gly Glu Arg Ile Trp Met Phe Thr Gly
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Synthetic construct

<400> SEQUENCE: 106

Pro Asn Tyr Glu Arg Ile Ser Asn Pro Ala
1               5                   10

<210> SEQ ID NO 107
```

```
<211> LENGTH: 11
<212> TYPE: PRT
<213> ORGANISM: Artificial Sequence
<220> FEATURE:
<223> OTHER INFORMATION: Synthetic construct

<400> SEQUENCE: 107

Ser Pro Ser Gly Arg Val Ile Leu Trp Thr Gly
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic construct

<400> SEQUENCE: 108

Asp Asn Leu Tyr Gly Arg Ile Ser Asn Pro Ala
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic construct

<400> SEQUENCE: 109

Ala Thr Pro Gly Cys Arg Asn Gly Lys Ile Val Gly
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic construct

<400> SEQUENCE: 110

Thr Thr Ser Val Gly Ala Thr Ser Asn Pro Ala
1               5                   10

<210> SEQ ID NO 111
<211> LENGTH: 9
<212> TYPE: PRT
<213> ORGANISM: Artificial Sequence
<220> FEATURE:
<223> OTHER INFORMATION: Synthetic construct

<400> SEQUENCE: 111

Phe Lys Pro Leu Ala Glu Ile Asp Gly
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic construct

<400> SEQUENCE: 112

Tyr Asn Arg Tyr Gly Leu Cys Pro Ser
1               5

<210> SEQ ID NO 113
<211> LENGTH: 9
<212> TYPE: PRT
```

```
<213> ORGANISM: Artificial Sequence
<220> FEATURE:
<223> OTHER INFORMATION: Synthetic construct

<400> SEQUENCE: 113

Ser Asn Arg Ile Gly Met Cys Pro Ser
1               5

<210> SEQ ID NO 114
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (11)..(11)
<223> OTHER INFORMATION: Xaa can be any naturally occurring amino acid

<400> SEQUENCE: 114

Ala Gln Pro Thr Ser Pro Asn Gly Ser Ile Xaa Gly
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Synthetic construct

<400> SEQUENCE: 115

Arg Arg Gly Asp Met Ser Ser Asn Pro Ala
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic construct

<400> SEQUENCE: 116

Asp Thr Val His Gly Arg Leu Ser Asn Pro Ala
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic construct

<400> SEQUENCE: 117

Arg Lys Val Leu Gly Arg Leu Ser Asn Pro Ala
1               5                   10

<210> SEQ ID NO 118
<211> LENGTH: 9
<212> TYPE: PRT
<213> ORGANISM: Artificial Sequence
<220> FEATURE:
<223> OTHER INFORMATION: Synthetic construct

<400> SEQUENCE: 118

Arg Lys Leu Val Gly Ala Leu Arg Ser
1               5

<210> SEQ ID NO 119
```

```
<211> LENGTH: 10
<212> TYPE: PRT
<213> ORGANISM: Artificial Sequence
<220> FEATURE:
<223> OTHER INFORMATION: Synthetic construct

<400> SEQUENCE: 119

Arg Lys Val Leu Arg Tyr Ser Asn Pro Ala
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Synthetic construct

<400> SEQUENCE: 120

Ser Pro Cys Asn Gly Gly Lys Arg Cys Thr Gly
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Synthetic construct

<400> SEQUENCE: 121

Arg Arg Gly Asp Met Ser Ser Asn Pro Ala
1               5                   10

<210> SEQ ID NO 122
<211> LENGTH: 9
<212> TYPE: PRT
<213> ORGANISM: Artificial Sequence
<220> FEATURE:
<223> OTHER INFORMATION: Synthetic construct

<400> SEQUENCE: 122

Phe Lys Trp Leu Gly Ala Ile Arg Ser
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic construct

<400> SEQUENCE: 123

Gly Asn Cys Val Gly Asn Leu Trp Ser
1               5

<210> SEQ ID NO 124
<211> LENGTH: 11
<212> TYPE: PRT
<213> ORGANISM: Artificial Sequence
<220> FEATURE:
<223> OTHER INFORMATION: Synthetic construct

<400> SEQUENCE: 124

Ser Pro Ala Trp Ile Thr Trp His Arg Thr Gly
1               5                   10

<210> SEQ ID NO 125
<211> LENGTH: 9
<212> TYPE: PRT
```

```
<213> ORGANISM: Artificial Sequence
<220> FEATURE:
<223> OTHER INFORMATION: Synthetic construct

<400> SEQUENCE: 125

His Thr Pro Leu Gly His Leu Arg Ser
1               5

<210> SEQ ID NO 126
<211> LENGTH: 11
<212> TYPE: PRT
<213> ORGANISM: Artificial Sequence
<220> FEATURE:
<223> OTHER INFORMATION: Synthetic construct

<400> SEQUENCE: 126

Ser Pro Cys Ile Met Val Cys Leu Arg Thr Gly
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Synthetic construct

<400> SEQUENCE: 127

Arg Arg Gly Asp Met Ser Gly Ala Pro Ala
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Synthetic construct

<400> SEQUENCE: 128

Ser Pro Cys Leu Phe Val Cys Leu Arg Thr Gly
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Synthetic construct

<400> SEQUENCE: 129

Arg Arg Gly Asp Met Ser Gly Ala Pro Ala
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic construct

<400> SEQUENCE: 130

Ser Pro Pro Leu Phe Cys Cys Gln Lys Thr Gly
1               5                   10

<210> SEQ ID NO 131
<211> LENGTH: 9
<212> TYPE: PRT
<213> ORGANISM: Artificial Sequence
<220> FEATURE:
```

<223> OTHER INFORMATION: Synthetic construct

<400> SEQUENCE: 131

Phe Lys Leu Thr Gly Phe Leu Tyr Ser
1               5

<210> SEQ ID NO 132
<211> LENGTH: 11
<212> TYPE: PRT
<213> ORGANISM: Artificial Sequence
<220> FEATURE:
<223> OTHER INFORMATION: Synthetic construct

<400> SEQUENCE: 132

Ser Pro Ser Val Ala Arg Met Leu Glu Thr Gly
1               5                   10

<210> SEQ ID NO 133
<211> LENGTH: 9
<212> TYPE: PRT
<213> ORGANISM: Artificial Sequence
<220> FEATURE:
<223> OTHER INFORMATION: Synthetic construct

<400> SEQUENCE: 133

Ile Thr Leu Cys Gly Arg Gly Val Ser
1               5

<210> SEQ ID NO 134
<211> LENGTH: 11
<212> TYPE: PRT
<213> ORGANISM: Artificial Sequence
<220> FEATURE:
<223> OTHER INFORMATION: Synthetic construct

<400> SEQUENCE: 134

Ser Pro Pro Glu Tyr Ala Phe Tyr Tyr Thr Gly
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Synthetic construct

<400> SEQUENCE: 135

Val Lys Asn Cys Gly Leu Phe Ser Asn Pro Ala
1               5                   10

<210> SEQ ID NO 136
<211> LENGTH: 9
<212> TYPE: PRT
<213> ORGANISM: Artificial Sequence
<220> FEATURE:
<223> OTHER INFORMATION: Synthetic construct

<400> SEQUENCE: 136

Ser Leu Ala Pro Gly Tyr Arg Leu Gly
1               5

<210> SEQ ID NO 137
<211> LENGTH: 10
<212> TYPE: PRT
<213> ORGANISM: Artificial Sequence
<220> FEATURE:
<223> OTHER INFORMATION: Synthetic construct

```
<400> SEQUENCE: 137

Val Lys Leu Cys Met Arg Gly Asn Pro Ala
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Synthetic construct

<400> SEQUENCE: 138

Ala Thr Pro Ser Val Phe Asp Ser His Ile Glu Gly
1               5                   10

<210> SEQ ID NO 139
<211> LENGTH: 9
<212> TYPE: PRT
<213> ORGANISM: Artificial Sequence
<220> FEATURE:
<223> OTHER INFORMATION: Synthetic construct

<400> SEQUENCE: 139

Trp Lys His His Gly Asp Ala Trp Ser
1               5

<210> SEQ ID NO 140
<211> LENGTH: 12
<212> TYPE: PRT
<213> ORGANISM: Artificial Sequence
<220> FEATURE:
<223> OTHER INFORMATION: Synthetic construct

<400> SEQUENCE: 140

Ala Lys Pro Ser Ile Val Asn Gly Phe Ile Ser Gly
1               5                   10

<210> SEQ ID NO 141
<211> LENGTH: 9
<212> TYPE: PRT
<213> ORGANISM: Artificial Sequence
<220> FEATURE:
<223> OTHER INFORMATION: Synthetic construct

<400> SEQUENCE: 141

Asp Lys Cys Phe Gly Ala Met Lys Ser
1               5

<210> SEQ ID NO 142
<211> LENGTH: 12
<212> TYPE: PRT
<213> ORGANISM: Artificial Sequence
<220> FEATURE:
<223> OTHER INFORMATION: Synthetic construct

<400> SEQUENCE: 142

Ala Lys Pro Met Ser Cys Ser Gly Tyr Ile Gln Gly
1               5                   10

<210> SEQ ID NO 143
<211> LENGTH: 9
<212> TYPE: PRT
<213> ORGANISM: Artificial Sequence
<220> FEATURE:
<223> OTHER INFORMATION: Synthetic construct

<400> SEQUENCE: 143
```

```
Ala Lys Leu Thr Gly Trp Leu Cys Ser
1               5
```

<210> SEQ ID NO 144
<211> LENGTH: 12
<212> TYPE: PRT
<213> ORGANISM: Artificial Sequence
<220> FEATURE:
<223> OTHER INFORMATION: Synthetic construct

<400> SEQUENCE: 144

```
Ala Ala Pro Phe Phe Gly Ser Ser Tyr Ile Ser Gly
1               5                   10
```

<210> SEQ ID NO 145
<211> LENGTH: 6
<212> TYPE: PRT
<213> ORGANISM: Artificial Sequence
<220> FEATURE:
<223> OTHER INFORMATION: Synthetic construct

<400> SEQUENCE: 145

```
His Tyr Tyr Val Thr Arg
1               5
```

<210> SEQ ID NO 146
<211> LENGTH: 9
<212> TYPE: PRT
<213> ORGANISM: Artificial Sequence
<220> FEATURE:
<223> OTHER INFORMATION: Synthetic construct

<400> SEQUENCE: 146

```
Val Asn Leu Ser Gly His Met Pro Ser
1               5
```

<210> SEQ ID NO 147
<211> LENGTH: 12
<212> TYPE: PRT
<213> ORGANISM: Artificial Sequence
<220> FEATURE:
<223> OTHER INFORMATION: Synthetic construct

<400> SEQUENCE: 147

```
Ala Pro Pro Met Leu Thr Asp Ser Glu Ile Asn Gly
1               5                   10
```

<210> SEQ ID NO 148
<211> LENGTH: 6
<212> TYPE: PRT
<213> ORGANISM: Artificial Sequence
<220> FEATURE:
<223> OTHER INFORMATION: Synthetic construct

<400> SEQUENCE: 148

```
Thr Ser Ser Tyr Trp Ser
1               5
```

<210> SEQ ID NO 149
<211> LENGTH: 9
<212> TYPE: PRT
<213> ORGANISM: Artificial Sequence
<220> FEATURE:
<223> OTHER INFORMATION: Synthetic construct

<400> SEQUENCE: 149

```
Ser Thr Leu Arg Arg Asn Ala Ile Ser
1               5
```

```
<210> SEQ ID NO 150
<211> LENGTH: 12
<212> TYPE: PRT
<213> ORGANISM: Artificial Sequence
<220> FEATURE:
<223> OTHER INFORMATION: Synthetic construct

<400> SEQUENCE: 150

Ala Lys Pro Glu Lys Trp Asp Gly Ser Ile Tyr Gly
1               5                   10

<210> SEQ ID NO 151
<211> LENGTH: 6
<212> TYPE: PRT
<213> ORGANISM: Artificial Sequence
<220> FEATURE:
<223> OTHER INFORMATION: Synthetic construct

<400> SEQUENCE: 151

Asn Ser Arg His Thr Ala
1               5

<210> SEQ ID NO 152
<211> LENGTH: 11
<212> TYPE: PRT
<213> ORGANISM: Artificial Sequence
<220> FEATURE:
<223> OTHER INFORMATION: Synthetic construct

<400> SEQUENCE: 152

Phe Thr Pro Tyr Gly Ala Lys Ser Asn Pro Ala
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Synthetic construct

<400> SEQUENCE: 153

Ala Pro Pro Pro Phe Ser Asn Ser Cys Ile Ile Gly
1               5                   10

<210> SEQ ID NO 154
<211> LENGTH: 6
<212> TYPE: PRT
<213> ORGANISM: Artificial Sequence
<220> FEATURE:
<223> OTHER INFORMATION: Synthetic construct

<400> SEQUENCE: 154

Arg Pro Gly Arg Ala Ser
1               5

<210> SEQ ID NO 155
<211> LENGTH: 11
<212> TYPE: PRT
<213> ORGANISM: Artificial Sequence
<220> FEATURE:
<223> OTHER INFORMATION: Synthetic construct

<400> SEQUENCE: 155

Ser Thr Gly Thr Gly Leu Pro Ser Asn Pro Ala
1               5                   10
```

```
<210> SEQ ID NO 156
<211> LENGTH: 11
<212> TYPE: PRT
<213> ORGANISM: Artificial Sequence
<220> FEATURE:
<223> OTHER INFORMATION: Synthetic construct

<400> SEQUENCE: 156

Ser Pro Cys Cys Pro Tyr Asp Arg Tyr Thr Gly
1               5                   10

<210> SEQ ID NO 157
<211> LENGTH: 6
<212> TYPE: PRT
<213> ORGANISM: Artificial Sequence
<220> FEATURE:
<223> OTHER INFORMATION: Synthetic construct

<400> SEQUENCE: 157

Gln Ser Ser Arg Ser His
1               5

<210> SEQ ID NO 158
<211> LENGTH: 11
<212> TYPE: PRT
<213> ORGANISM: Artificial Sequence
<220> FEATURE:
<223> OTHER INFORMATION: Synthetic construct

<400> SEQUENCE: 158

Ile Thr Thr Phe Gly His Val Ser Asn Pro Ala
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Synthetic construct

<400> SEQUENCE: 159

Ala Lys Pro Arg Gln Gly Gly Ser Asn Ile Ser Gly
1               5                   10

<210> SEQ ID NO 160
<211> LENGTH: 6
<212> TYPE: PRT
<213> ORGANISM: Artificial Sequence
<220> FEATURE:
<223> OTHER INFORMATION: Synthetic construct

<400> SEQUENCE: 160

Tyr His Lys Gly Leu His
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic construct

<400> SEQUENCE: 161

Pro Lys Met Thr Gly Tyr Thr Tyr Ser
1               5

<210> SEQ ID NO 162
<211> LENGTH: 11
```

```
<212> TYPE: PRT
<213> ORGANISM: Artificial Sequence
<220> FEATURE:
<223> OTHER INFORMATION: Synthetic construct

<400> SEQUENCE: 162

Ser Pro Gly Pro Leu Leu Arg His Thr Thr Gly
1               5                   10

<210> SEQ ID NO 163
<211> LENGTH: 6
<212> TYPE: PRT
<213> ORGANISM: Artificial Sequence
<220> FEATURE:
<223> OTHER INFORMATION: Synthetic construct

<400> SEQUENCE: 163

Arg Pro Ile Pro Arg Ala
1               5

<210> SEQ ID NO 164
<211> LENGTH: 10
<212> TYPE: PRT
<213> ORGANISM: Artificial Sequence
<220> FEATURE:
<223> OTHER INFORMATION: Synthetic construct

<400> SEQUENCE: 164

Arg Asn Arg Pro Gln Gln Ser Asn Pro Ala
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Synthetic construct

<400> SEQUENCE: 165

Ser Pro Gly Gly Phe Gln Lys Ile Thr Thr Gly
1               5                   10

<210> SEQ ID NO 166
<211> LENGTH: 6
<212> TYPE: PRT
<213> ORGANISM: Artificial Sequence
<220> FEATURE:
<223> OTHER INFORMATION: Synthetic construct

<400> SEQUENCE: 166

Val Asn Arg Arg Asn His
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic construct

<400> SEQUENCE: 167

Leu Thr Tyr Lys Ala Arg Ala Ile Ser
1               5

<210> SEQ ID NO 168
<211> LENGTH: 11
<212> TYPE: PRT
<213> ORGANISM: Artificial Sequence
```

```
<220> FEATURE:
<223> OTHER INFORMATION: Synthetic construct

<400> SEQUENCE: 168

Ser Pro Arg Met Tyr Thr Trp Ile Gln Thr Gly
1               5                   10

<210> SEQ ID NO 169
<211> LENGTH: 6
<212> TYPE: PRT
<213> ORGANISM: Artificial Sequence
<220> FEATURE:
<223> OTHER INFORMATION: Synthetic construct

<400> SEQUENCE: 169

Thr His Leu Ser Gly Ser
1               5

<210> SEQ ID NO 170
<211> LENGTH: 9
<212> TYPE: PRT
<213> ORGANISM: Artificial Sequence
<220> FEATURE:
<223> OTHER INFORMATION: Synthetic construct

<400> SEQUENCE: 170

Leu Lys Leu Thr Arg Thr His Ile Ser
1               5

<210> SEQ ID NO 171
<211> LENGTH: 9
<212> TYPE: PRT
<213> ORGANISM: Artificial Sequence
<220> FEATURE:
<223> OTHER INFORMATION: Synthetic construct

<400> SEQUENCE: 171

Ser His Ala Gly Gly Ile Arg Ile Gly
1               5

<210> SEQ ID NO 172
<211> LENGTH: 6
<212> TYPE: PRT
<213> ORGANISM: Artificial Sequence
<220> FEATURE:
<223> OTHER INFORMATION: Synthetic construct

<400> SEQUENCE: 172

His Val Trp Gln Val Tyr
1               5

<210> SEQ ID NO 173
<211> LENGTH: 10
<212> TYPE: PRT
<213> ORGANISM: Artificial Sequence
<220> FEATURE:
<223> OTHER INFORMATION: Synthetic construct

<400> SEQUENCE: 173

Met Thr Pro Tyr Leu Leu Gly Asn Pro Ala
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Synthetic construct
```

```
<400> SEQUENCE: 174

Ser Pro Ser His Gly Val Glu Ser Ser Thr Gly
1               5                   10

<210> SEQ ID NO 175
<211> LENGTH: 6
<212> TYPE: PRT
<213> ORGANISM: Artificial Sequence
<220> FEATURE:
<223> OTHER INFORMATION: Synthetic construct

<400> SEQUENCE: 175

His Gly Leu Gln Arg Val
1               5

<210> SEQ ID NO 176
<211> LENGTH: 9
<212> TYPE: PRT
<213> ORGANISM: Artificial Sequence
<220> FEATURE:
<223> OTHER INFORMATION: Synthetic construct

<400> SEQUENCE: 176

Ala Lys Ile Cys Gly His Leu Val Ser
1               5

<210> SEQ ID NO 177
<211> LENGTH: 11
<212> TYPE: PRT
<213> ORGANISM: Artificial Sequence
<220> FEATURE:
<223> OTHER INFORMATION: Synthetic construct

<400> SEQUENCE: 177

Ser Pro Cys Gln Leu Leu Ala Leu Ile Thr Gly
1               5                   10

<210> SEQ ID NO 178
<211> LENGTH: 6
<212> TYPE: PRT
<213> ORGANISM: Artificial Sequence
<220> FEATURE:
<223> OTHER INFORMATION: Synthetic construct

<400> SEQUENCE: 178

Asn Ser Arg His Tyr His
1               5

<210> SEQ ID NO 179
<211> LENGTH: 11
<212> TYPE: PRT
<213> ORGANISM: Artificial Sequence
<220> FEATURE:
<223> OTHER INFORMATION: Synthetic construct

<400> SEQUENCE: 179

Tyr Thr Ser Thr Gly Gln Arg Ser Asn Pro Ala
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Synthetic construct

<400> SEQUENCE: 180
```

Ser Pro Cys Gln Met Leu Ser Ser Leu Thr Gly
1               5                   10

<210> SEQ ID NO 181
<211> LENGTH: 6
<212> TYPE: PRT
<213> ORGANISM: Artificial Sequence
<220> FEATURE:
<223> OTHER INFORMATION: Synthetic construct

<400> SEQUENCE: 181

Asn Ile Glu Arg Pro Lys
1               5

<210> SEQ ID NO 182
<211> LENGTH: 11
<212> TYPE: PRT
<213> ORGANISM: Artificial Sequence
<220> FEATURE:
<223> OTHER INFORMATION: Synthetic construct

<400> SEQUENCE: 182

Phe Thr Met Thr Gly Tyr Arg Ser Asn Pro Ala
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Synthetic construct

<400> SEQUENCE: 183

Ser Pro Cys Cys Gln Glu Phe Thr Leu Thr Gly
1               5                   10

<210> SEQ ID NO 184
<211> LENGTH: 6
<212> TYPE: PRT
<213> ORGANISM: Artificial Sequence
<220> FEATURE:
<223> OTHER INFORMATION: Synthetic construct

<400> SEQUENCE: 184

His Asn His His His His
1               5

<210> SEQ ID NO 185
<211> LENGTH: 11
<212> TYPE: PRT
<213> ORGANISM: Artificial Sequence
<220> FEATURE:
<223> OTHER INFORMATION: Synthetic construct

<400> SEQUENCE: 185

Ile Thr Asp Ala Gly Asn Lys Ser Asn Pro Ala
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Synthetic construct

<400> SEQUENCE: 186

Ser Pro Cys Ser Pro Cys Gln Leu Val Thr Gly

```
1               5                   10

<210> SEQ ID NO 187
<211> LENGTH: 6
<212> TYPE: PRT
<213> ORGANISM: Artificial Sequence
<220> FEATURE:
<223> OTHER INFORMATION: Synthetic construct

<400> SEQUENCE: 187

Ser Cys Thr Arg Ala Lys
1               5

<210> SEQ ID NO 188
<211> LENGTH: 11
<212> TYPE: PRT
<213> ORGANISM: Artificial Sequence
<220> FEATURE:
<223> OTHER INFORMATION: Synthetic construct

<400> SEQUENCE: 188

Ile Asn Lys Leu Gly Asp Thr Ser Asn Pro Ala
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Synthetic construct

<400> SEQUENCE: 189

Ser Pro Ser Arg Gly Gly Thr Ser Leu Thr Gly
1               5                   10

<210> SEQ ID NO 190
<211> LENGTH: 6
<212> TYPE: PRT
<213> ORGANISM: Artificial Sequence
<220> FEATURE:
<223> OTHER INFORMATION: Synthetic construct

<400> SEQUENCE: 190

Asp Gln Val Arg Ala Thr
1               5

<210> SEQ ID NO 191
<211> LENGTH: 11
<212> TYPE: PRT
<213> ORGANISM: Artificial Sequence
<220> FEATURE:
<223> OTHER INFORMATION: Synthetic construct

<400> SEQUENCE: 191

His Thr Asn Ser Gly Gln Pro Ser Asn Pro Ala
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Synthetic construct

<400> SEQUENCE: 192

Ser Pro Gly Met Phe Asp Gln Val Arg Thr Gly
1               5                   10
```

<210> SEQ ID NO 193
<211> LENGTH: 6
<212> TYPE: PRT
<213> ORGANISM: Artificial Sequence
<220> FEATURE:
<223> OTHER INFORMATION: Synthetic construct

<400> SEQUENCE: 193

Gly Lys Tyr Trp Glu Arg
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic construct

<400> SEQUENCE: 194

Arg Asn Gln Tyr Gly Gln His Gln Ser
1               5

<210> SEQ ID NO 195
<211> LENGTH: 11
<212> TYPE: PRT
<213> ORGANISM: Artificial Sequence
<220> FEATURE:
<223> OTHER INFORMATION: Synthetic construct

<400> SEQUENCE: 195

Ser Pro Pro Phe Arg Ala Gly His Val Thr Gly
1               5                   10

<210> SEQ ID NO 196
<211> LENGTH: 6
<212> TYPE: PRT
<213> ORGANISM: Artificial Sequence
<220> FEATURE:
<223> OTHER INFORMATION: Synthetic construct

<400> SEQUENCE: 196

Val Thr Ala Arg Cys Gln
1               5

<210> SEQ ID NO 197
<211> LENGTH: 11
<212> TYPE: PRT
<213> ORGANISM: Artificial Sequence
<220> FEATURE:
<223> OTHER INFORMATION: Synthetic construct

<400> SEQUENCE: 197

Thr Thr Gly Asn Gly Leu Arg Ser Asn Pro Ala
1               5                   10

<210> SEQ ID NO 198
<211> LENGTH: 9
<212> TYPE: PRT
<213> ORGANISM: Artificial Sequence
<220> FEATURE:
<223> OTHER INFORMATION: Synthetic construct

<400> SEQUENCE: 198

Ser Trp Ala Gln Ala Asn Pro Gly Gly
1               5

<210> SEQ ID NO 199

```
<211> LENGTH: 6
<212> TYPE: PRT
<213> ORGANISM: Artificial Sequence
<220> FEATURE:
<223> OTHER INFORMATION: Synthetic construct

<400> SEQUENCE: 199

Trp His Ser Ile Thr Phe
1               5

<210> SEQ ID NO 200
<211> LENGTH: 10
<212> TYPE: PRT
<213> ORGANISM: Artificial Sequence
<220> FEATURE:
<223> OTHER INFORMATION: Synthetic construct

<400> SEQUENCE: 200

Lys Thr Lys Val Gln Ser Ser Asn Pro Ala
1               5                   10

<210> SEQ ID NO 201
<211> LENGTH: 6
<212> TYPE: PRT
<213> ORGANISM: Artificial Sequence
<220> FEATURE:
<223> OTHER INFORMATION: Synthetic construct

<400> SEQUENCE: 201

Asp Val Thr Asp Thr Thr
1               5

<210> SEQ ID NO 202
<211> LENGTH: 9
<212> TYPE: PRT
<213> ORGANISM: Artificial Sequence
<220> FEATURE:
<223> OTHER INFORMATION: Synthetic construct

<400> SEQUENCE: 202

Phe Lys Pro Leu Ala Glu Ile Asp Gly
1               5

<210> SEQ ID NO 203
<211> LENGTH: 7
<212> TYPE: PRT
<213> ORGANISM: Artificial Sequence
<220> FEATURE:
<223> OTHER INFORMATION: Synthetic construct

<400> SEQUENCE: 203

Lys Asp Val Pro Gly Asp Arg
1               5

<210> SEQ ID NO 204
<211> LENGTH: 7
<212> TYPE: PRT
<213> ORGANISM: Artificial Sequence
<220> FEATURE:
<223> OTHER INFORMATION: Synthetic construct

<400> SEQUENCE: 204

Leu Thr Glu Asp Glu Asn Gln
1               5

<210> SEQ ID NO 205
<211> LENGTH: 6
<212> TYPE: PRT
```

```
<213> ORGANISM: Artificial Sequence
<220> FEATURE:
<223> OTHER INFORMATION: Synthetic construct

<400> SEQUENCE: 205

Gly Asn Leu Lys Pro Asp
1               5

<210> SEQ ID NO 206
<211> LENGTH: 10
<212> TYPE: PRT
<213> ORGANISM: Artificial Sequence
<220> FEATURE:
<223> OTHER INFORMATION: Synthetic construct

<400> SEQUENCE: 206

Arg Arg Gly Asp Met Ser Ser Asn Pro Ala
1               5                   10

<210> SEQ ID NO 207
<211> LENGTH: 7
<212> TYPE: PRT
<213> ORGANISM: Artificial Sequence
<220> FEATURE:
<223> OTHER INFORMATION: Synthetic construct

<400> SEQUENCE: 207

Lys Asp Val Thr Asp Thr Thr
1               5

<210> SEQ ID NO 208
<211> LENGTH: 6
<212> TYPE: PRT
<213> ORGANISM: Artificial Sequence
<220> FEATURE:
<223> OTHER INFORMATION: Synthetic construct

<400> SEQUENCE: 208

Thr Glu Asp Glu Asn Gln
1               5

<210> SEQ ID NO 209
<211> LENGTH: 8
<212> TYPE: PRT
<213> ORGANISM: Artificial Sequence
<220> FEATURE:
<223> OTHER INFORMATION: Synthetic construct

<400> SEQUENCE: 209

Gly Asn Leu Lys Pro Asp Thr Glu
1               5

<210> SEQ ID NO 210
<211> LENGTH: 85
<212> TYPE: PRT
<213> ORGANISM: Artificial Sequence
<220> FEATURE:
<223> OTHER INFORMATION: Synthetic construct

<400> SEQUENCE: 210

Ile Glu Val Lys Asp Val Thr Asp Thr Thr Ala Leu Ile Thr Trp Phe
1               5                   10                  15

Lys Pro Leu Ala Glu Ile Asp Gly Ile Glu Leu Thr Tyr Gly Ile Lys
            20                  25                  30

Asp Val Pro Gly Asp Arg Thr Thr Cys Asp Leu Thr Gly Glu Asp Glu
        35                  40                  45
```

Gly Asn Gln Cys Ser Ile Gly Asn Leu Lys Pro Asp Thr Glu Tyr Glu
 50                  55                  60

Val Ser Leu Ile Ser Arg Arg Gly Asp Met Ser Ser Asn Pro Ala Lys
 65                  70                  75                  80

Glu Thr Phe Thr Thr
             85

<210> SEQ ID NO 211
<211> LENGTH: 63
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 211
accgcgctga ttacctggtc tnnkscgnnk gstnnknnkn nkggcattga actgacctat    60
ggc                                                                 63

<210> SEQ ID NO 212
<211> LENGTH: 72
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 212
accgcgctga ttacctgggc gvmaccgnnk nnknnkrrcr gcnnkattnn kggtattgaa    60
ctgacctatg gc                                                       72

<210> SEQ ID NO 213
<211> LENGTH: 69

```
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 213
accgcgctga ttacctggtc tccgbstnnk nnknnknnkn nknnkaccgg cattgaactg      60
acctatggc                                                             69

<210> SEQ ID NO 214
<211> LENGTH: 66
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 214
tatgaagtga gcctgattag cnnkamsnnk nnkggtnnkn knnkagcaa agaaaccttt       60 accacc                                                                66

<210> SEQ ID NO 215
<211> LENGTH: 69
<212> TYPE: DNA
<213> ORGANISM: Artificial Sequence
<220> FEATURE:
<223> OTHER INFORMATION: Synthetic construct
```

```
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 215
tatgaagtga gcctgattag cnnkamsnnk nnknnknnkr gcaacccggc gaaagaaacc    60
tttaccacc                                                            69

<210> SEQ ID NO 216
<211> LENGTH: 72
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 216
tatgaagtga gcctgattag cnnkamsnnk nnkggtnnkn nkagcaaccc ggcgaaagaa    60
acctttacca cc                                                        72

<210> SEQ ID NO 217
<211> LENGTH: 63
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
```

```
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 217
accgcgctga ttacctggtc tnnkscgnnk gstnnknnkn nkggctgtga actgacctat    60
ggc                                                                  63

<210> SEQ ID NO 218
<211> LENGTH: 69
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 218
accgcgctga ttacctggtc tccgbstnnk nnknnknnkn nknnkaccgg ctgtgaactg    60
acctatggc                                                            69

<210> SEQ ID NO 219
<211> LENGTH: 72
<212> TYPE: PRT
<213> ORGANISM: Artificial Sequence
<220> FEATURE:
<223> OTHER INFORMATION: Synthetic construct

<400> SEQUENCE: 219

Ala Cys Cys Gly Cys Gly Cys Thr Gly Ala Thr Thr Ala Cys Cys Thr
1               5                   10                  15

Gly Gly Gly Cys Gly Val Met Ala Cys Cys Gly Asn Asn Lys Asn Asn
                20                  25                  30

Lys Asn Asn Lys Arg Arg Cys Arg Gly Cys Asn Asn Lys Ala Thr Thr
                35                  40                  45

Asn Asn Lys Gly Gly Thr Thr Gly Thr Gly Ala Ala Cys Thr Gly Ala
        50                  55                  60

Cys Cys Thr Ala Thr Gly Gly Cys
65                  70

<210> SEQ ID NO 220
```

```
<211> LENGTH: 66
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 220
tatgaagtga gcctgatttg cnnkamsnnk nnkggtnnkn nknnkagcaa agaaaccttt      60
accacc                                                                66

<210> SEQ ID NO 221
<211> LENGTH: 69
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t

<400> SEQUENCE: 221
tatgaagtga gcctgatttg cnnkamsnnk nnknnknnkr gcaacccggc gaaagaaacc      60
tttaccacc                                                             69

<210> SEQ ID NO 222
<211> LENGTH: 72
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(23)
```

<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 222
tatgaagtga gcctgatttg cnnkamsnnk nnkggtnnkn nkagcaaccc ggcgaaagaa     60
acctttacca cc                                                        72

<210> SEQ ID NO 223
<211> LENGTH: 67
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t

<400> SEQUENCE: 223
ccggtttcag gttaccaatg ctatamnnmn nmnnmnnmnn mnncagatct atggtggtgc     60
gatcgcc                                                              67

<210> SEQ ID NO 224
<211> LENGTH: 79
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)

<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 224
ccgccaccgg tggtaaaggt ttctttgctm nnmnnmnnac cmnnmnnskt mnngcaaatc    60
aggctcactt catattcgg                                                79

<210> SEQ ID NO 225
<211> LENGTH: 81
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t

<400> SEQUENCE: 225
cgccaccggt ggtaaaggtt tctttcgccg ggttgcymnn mnnmnnmnns ktmnngcaaa    60
tcaggctcac ttcatattcg g                                             81

<210> SEQ ID NO 226
<211> LENGTH: 85
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (58)..(59)

<223> OTHER INFORMATION: n is a, c, g, or t

<400> SEQUENCE: 226
ccgccaccgg tggtaaaggt ttctttcgcc gggttgctmn nmnnaccmnn mnnsktmnng    60
caaatcaggc tcacttcata ttcgg    85

<210> SEQ ID NO 227
<211> LENGTH: 26
<212> TYPE: PRT
<213> ORGANISM: Artificial Sequence
<220> FEATURE:
<223> OTHER INFORMATION: Synthetic construct

<400> SEQUENCE: 227

Met Thr Asn Ile Thr Lys Arg Ser Leu Val Ala Ala Gly Val Leu Ala
1               5                   10                  15

Ala Leu Met Ala Gly Asn Val Ala Leu Ala
            20                  25

<210> SEQ ID NO 228
<211> LENGTH: 11
<212> TYPE: PRT
<213> ORGANISM: Artificial Sequence
<220> FEATURE:
<223> OTHER INFORMATION: Synthetic construct

<400> SEQUENCE: 228

Arg Leu Asp Ala Pro Ser Gln Ile Glu Val Lys
1               5                   10

<210> SEQ ID NO 229
<211> LENGTH: 5
<212> TYPE: PRT
<213> ORGANISM: Artificial Sequence
<220> FEATURE:
<223> OTHER INFORMATION: Synthetic construct

<400> SEQUENCE: 229

Ala Leu Ile Thr Trp
1               5

<210> SEQ ID NO 230
<211> LENGTH: 7
<212> TYPE: PRT
<213> ORGANISM: Artificial Sequence
<220> FEATURE:
<223> OTHER INFORMATION: Synthetic construct

<400> SEQUENCE: 230

Ile Glu Leu Thr Tyr Gly Ile
1               5

<210> SEQ ID NO 231
<211> LENGTH: 4
<212> TYPE: PRT
<213> ORGANISM: Artificial Sequence
<220> FEATURE:
<223> OTHER INFORMATION: Synthetic construct

<400> SEQUENCE: 231

Thr Thr Ile Asp
1

<210> SEQ ID NO 232
<211> LENGTH: 3
<212> TYPE: PRT

```
<213> ORGANISM: Artificial Sequence
<220> FEATURE:
<223> OTHER INFORMATION: Synthetic construct

<400> SEQUENCE: 232

Tyr Ser Ile
1

<210> SEQ ID NO 233
<211> LENGTH: 9
<212> TYPE: PRT
<213> ORGANISM: Artificial Sequence
<220> FEATURE:
<223> OTHER INFORMATION: Synthetic construct

<400> SEQUENCE: 233

Thr Glu Tyr Glu Val Ser Leu Ile Ser
1               5

<210> SEQ ID NO 234
<211> LENGTH: 6
<212> TYPE: PRT
<213> ORGANISM: Artificial Sequence
<220> FEATURE:
<223> OTHER INFORMATION: Synthetic construct

<400> SEQUENCE: 234

Lys Glu Thr Phe Thr Thr
1               5

<210> SEQ ID NO 235
<211> LENGTH: 10
<212> TYPE: PRT
<213> ORGANISM: Artificial Sequence
<220> FEATURE:
<223> OTHER INFORMATION: Synthetic construct

<400> SEQUENCE: 235

Arg Leu Asp Ala Pro Ser Gln Ile Glu Val
1               5                   10

<210> SEQ ID NO 236
<211> LENGTH: 5
<212> TYPE: PRT
<213> ORGANISM: Artificial Sequence
<220> FEATURE:
<223> OTHER INFORMATION: Synthetic construct

<400> SEQUENCE: 236

Thr Thr Ile Asp Leu
1               5

<210> SEQ ID NO 237
<211> LENGTH: 7
<212> TYPE: PRT
<213> ORGANISM: Artificial Sequence
<220> FEATURE:
<223> OTHER INFORMATION: Synthetic construct

<400> SEQUENCE: 237

Tyr Glu Val Ser Leu Ile Ser
1               5

<210> SEQ ID NO 238
<211> LENGTH: 288
<212> TYPE: DNA
<213> ORGANISM: Artificial Sequence
<220> FEATURE:
```

-continued

<223> OTHER INFORMATION: Synthetic construct

<400> SEQUENCE: 238

```
ccgccgagcc tgaacgtgac caaagatggc gatagctata gcctgcgctg ggaaaccatg      60
aaaatgcgct atgaacatat tgatcatacc tttgaaattc agtatcgcaa agataccgcg     120
acctggaaag atagcaaaac cgaaaccctg cagaacgcgc atagcatggc gctgccggcg     180
ctggaaccga gcacccgtta ttgggcgcgt gtgcgtgtgc gtaccagccg taccggctat     240
aatggcattt ggagcgaatg gagcgaagcg cgtagctggg ataccgaa                  288
```

<210> SEQ ID NO 239
<211> LENGTH: 3
<212> TYPE: PRT
<213> ORGANISM: Artificial Sequence
<220> FEATURE:
<223> OTHER INFORMATION: synthetic construct

<400> SEQUENCE: 239

Ile Glu Val
1

<210> SEQ ID NO 240
<211> LENGTH: 4
<212> TYPE: PRT
<213> ORGANISM: Artificial Sequence
<220> FEATURE:
<223> OTHER INFORMATION: synthetic construct

<400> SEQUENCE: 240

Ile Glu Val Lys
1

<210> SEQ ID NO 241
<211> LENGTH: 3
<212> TYPE: PRT
<213> ORGANISM: Artificial Sequence
<220> FEATURE:
<223> OTHER INFORMATION: synthetic construct

<400> SEQUENCE: 241

Ile Glu Cys
1

<210> SEQ ID NO 242
<211> LENGTH: 5
<212> TYPE: PRT
<213> ORGANISM: Artificial Sequence
<220> FEATURE:
<223> OTHER INFORMATION: synthetic construct

<400> SEQUENCE: 242

Ala Leu Cys Thr Trp
1               5

<210> SEQ ID NO 243
<211> LENGTH: 5
<212> TYPE: PRT
<213> ORGANISM: Artificial Sequence
<220> FEATURE:
<223> OTHER INFORMATION: Synthetic construct

<400> SEQUENCE: 243

Thr Thr Cys Asp Leu
1               5

```
<210> SEQ ID NO 244
<211> LENGTH: 3
<212> TYPE: PRT
<213> ORGANISM: Artificial Sequence
<220> FEATURE:
<223> OTHER INFORMATION: Synthetic construct

<400> SEQUENCE: 244

Cys Ser Ile
1

<210> SEQ ID NO 245
<211> LENGTH: 7
<212> TYPE: PRT
<213> ORGANISM: Artificial Sequence
<220> FEATURE:
<223> OTHER INFORMATION: synthetic construct

<400> SEQUENCE: 245

Tyr Cys Val Ser Leu Ile Ser
1               5

<210> SEQ ID NO 246
<211> LENGTH: 6
<212> TYPE: PRT
<213> ORGANISM: Artificial Sequence
<220> FEATURE:
<223> OTHER INFORMATION: synthetic construct

<400> SEQUENCE: 246

Lys Glu Cys Phe Thr Thr
1               5

<210> SEQ ID NO 247
<211> LENGTH: 7
<212> TYPE: PRT
<213> ORGANISM: Artificial Sequence
<220> FEATURE:
<223> OTHER INFORMATION: synthetic construct

<400> SEQUENCE: 247

Cys Glu Leu Thr Tyr Gly Ile
1               5

<210> SEQ ID NO 248
<211> LENGTH: 7
<212> TYPE: PRT
<213> ORGANISM: Artificial Sequence
<220> FEATURE:
<223> OTHER INFORMATION: synthetic construct

<400> SEQUENCE: 248

Tyr Glu Val Ser Leu Ile Cys
1               5

<210> SEQ ID NO 249
<211> LENGTH: 7
<212> TYPE: PRT
<213> ORGANISM: Artificial Sequence
<220> FEATURE:
<223> OTHER INFORMATION: synthetic construct

<400> SEQUENCE: 249

Tyr Cys Val Ser Leu Ile Cys
1               5

<210> SEQ ID NO 250
<211> LENGTH: 4
```

```
<212> TYPE: PRT
<213> ORGANISM: Artificial Sequence
<220> FEATURE:
<223> OTHER INFORMATION: synthetic construct

<400> SEQUENCE: 250

Ile Glu Cys Lys
1

<210> SEQ ID NO 251
<211> LENGTH: 4
<212> TYPE: PRT
<213> ORGANISM: Artificial Sequence
<220> FEATURE:
<223> OTHER INFORMATION: synthetic construct

<400> SEQUENCE: 251

Thr Thr Cys Asp
1

<210> SEQ ID NO 252
<211> LENGTH: 8
<212> TYPE: PRT
<213> ORGANISM: Artificial Sequence
<220> FEATURE:
<223> OTHER INFORMATION: synthetic construct

<400> SEQUENCE: 252

Glu Tyr Cys Val Ser Leu Ile Ser
1               5

<210> SEQ ID NO 253
<211> LENGTH: 8
<212> TYPE: PRT
<213> ORGANISM: Artificial Sequence
<220> FEATURE:
<223> OTHER INFORMATION: synthetic construct

<400> SEQUENCE: 253

Glu Tyr Glu Val Ser Leu Cys Ser
1               5

<210> SEQ ID NO 254
<211> LENGTH: 8
<212> TYPE: PRT
<213> ORGANISM: Artificial Sequence
<220> FEATURE:
<223> OTHER INFORMATION: synthetic construct

<400> SEQUENCE: 254

Glu Tyr Cys Val Ser Leu Cys Ser
1               5

<210> SEQ ID NO 255
<211> LENGTH: 7
<212> TYPE: PRT
<213> ORGANISM: Artificial Sequence
<220> FEATURE:
<223> OTHER INFORMATION: synthetic construct

<400> SEQUENCE: 255

Gly Asn Leu Lys Pro Asp Thr
1               5

<210> SEQ ID NO 256
<211> LENGTH: 8
<212> TYPE: PRT
<213> ORGANISM: Artificial Sequence
```

```
<220> FEATURE:
<223> OTHER INFORMATION: synthetic construct

<400> SEQUENCE: 256

Glu Tyr Glu Val Ser Leu Ile Ser
1               5

<210> SEQ ID NO 257
<211> LENGTH: 12
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (2)..(2)
<223> OTHER INFORMATION: Xaa = pro, glu or lys,
<220> FEATURE:
<221> NAME/KEY: MISC_FEATURE
<222> LOCATION: (4)..(6)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Asp or Gly
<220> FEATURE:
<221> NAME/KEY: MISC_FEATURE
<222> LOCATION: (8)..(8)
<223> OTHER INFORMATION: Xaa = Ser or Gly
<220> FEATURE:
<221> NAME/KEY: MISC_FEATURE
<222> LOCATION: (9)..(9)
<223> OTHER INFORMATION: Xaa = any amino acid
<220> FEATURE:
<221> NAME/KEY: MISC_FEATURE
<222> LOCATION: (11)..(11)
<223> OTHER INFORMATION: Xaa = any amino acid

<400> SEQUENCE: 257

Ala Xaa Pro Xaa Xaa Xaa Xaa Xaa Xaa Ile Xaa Gly
1               5                   10

<210> SEQ ID NO 258
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa = Pro, Ser, or Gly
<220> FEATURE:
<221> NAME/KEY: MISC_FEATURE
<222> LOCATION: (4)..(9)
<223> OTHER INFORMATION: each Xaa may be any amino acid

<400> SEQUENCE: 258

Ser Pro Xaa Xaa Xaa Xaa Xaa Xaa Xaa Thr Gly
1               5                   10

<210> SEQ ID NO 259
<211> LENGTH: 11
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (2)..(2)
```

```
<223> OTHER INFORMATION: Xaa = Asp, Thr, Lys,
<220> FEATURE:
<221> NAME/KEY: MISC_FEATURE
<222> LOCATION: (3)..(4)
<223> OTHER INFORMATION: Xaa = any amino acid
<220> FEATURE:
<221> NAME/KEY: MISC_FEATURE
<222> LOCATION: (6)..(7)
<223> OTHER INFORMATION: Xaa = any amino acid

<400> SEQUENCE: 259

Xaa Xaa Xaa Xaa Gly Xaa Xaa Ser Asn Pro Ala
1               5                   10

<210> SEQ ID NO 260
<211> LENGTH: 5
<212> TYPE: PRT
<213> ORGANISM: Artificial Sequence
<220> FEATURE:
<223> OTHER INFORMATION: synthetic construct

<400> SEQUENCE: 260

Gly Gly Gly Gly Ser
1               5

<210> SEQ ID NO 261
<211> LENGTH: 6
<212> TYPE: PRT
<213> ORGANISM: Artificial Sequence
<220> FEATURE:
<223> OTHER INFORMATION: synthetic construct

<400> SEQUENCE: 261

Gly Gly Gly Thr Pro Thr
1               5

<210> SEQ ID NO 262
<211> LENGTH: 21
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 262
aaanhtnhtn htnhtnhtrs t                                             21

<210> SEQ ID NO 263
<211> LENGTH: 27
<212> TYPE: DNA
<213> ORGANISM: Artificial Sequence
<220> FEATURE:
<223> OTHER INFORMATION: synthetic construct
```

```
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 263
aaanhtnhtn htnhtnhtnh tnhtrst                                       27

<210> SEQ ID NO 264
<211> LENGTH: 21
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 264
nhtnhtnhtn htnhtnhtnh t                                             21

<210> SEQ ID NO 265
<211> LENGTH: 27
<212> TYPE: DNA
<213> ORGANISM: Artificial Sequence
<220> FEATURE:
<223> OTHER INFORMATION: synthetic construct
```

```
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 265
nhtnhtnhtn htnhtnhtnh tnhtnht                                          27

<210> SEQ ID NO 266
<211> LENGTH: 24
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 266
nhtrrbctgn htccgnhtrb tnht                                             24

<210> SEQ ID NO 267
<211> LENGTH: 89
<212> TYPE: PRT
<213> ORGANISM: Homo sapiens

<400> SEQUENCE: 267

Leu Asp Ala Pro Ser Gln Ile Glu Val Lys Asp Val Thr Asp Thr Thr
1               5                   10                  15
```

```
Ala Leu Ile Thr Trp Phe Lys Pro Leu Ala Glu Ile Asp Gly Ile Glu
            20                  25                  30

Leu Thr Tyr Gly Ile Lys Asp Val Pro Gly Asp Arg Thr Ile Asp
        35                  40                  45

Leu Thr Glu Asp Glu Asn Gln Tyr Ser Ile Gly Asn Leu Lys Pro Asp
 50                  55                  60

Thr Glu Tyr Glu Val Ser Leu Ile Ser Arg Arg Gly Asp Met Ser Ser
 65                  70                  75                  80

Asn Pro Ala Lys Glu Thr Phe Thr Thr
                85

<210> SEQ ID NO 268
<211> LENGTH: 97
<212> TYPE: PRT
<213> ORGANISM: Homo sapiens

<400> SEQUENCE: 268

Thr Val Ala Ala Tyr Asn Leu Thr Trp Lys Ser Thr Asn Phe Lys Thr
 1               5                  10                  15

Ile Leu Glu Trp Glu Pro Lys Pro Val Asn Gln Val Tyr Thr Val Gln
            20                  25                  30

Ile Ser Thr Lys Ser Gly Asp Trp Lys Ser Lys Cys Phe Tyr Thr Thr
        35                  40                  45

Asp Thr Glu Cys Asp Leu Thr Asp Glu Ile Val Lys Asp Val Lys Gln
 50                  55                  60

Thr Tyr Leu Ala Arg Val Phe Ser Tyr Pro Ala Gly Asn Val Glu Ser
 65                  70                  75                  80

Thr Gly Ser Ala Gly Glu Pro Leu Tyr Glu Asn Ser Pro Glu Phe Thr
                85                  90                  95

Pro

<210> SEQ ID NO 269
<211> LENGTH: 105
<212> TYPE: PRT
<213> ORGANISM: Oryctolagus cuniculus

<400> SEQUENCE: 269

Ala Asp Thr Thr Gly Arg Ala Tyr Asn Leu Thr Trp Lys Ser Thr Asn
 1               5                  10                  15

Phe Lys Thr Ile Leu Glu Trp Glu Pro Lys Ser Ile Asp His Val Tyr
            20                  25                  30

Thr Val Gln Ile Ser Thr Arg Leu Glu Asn Trp Lys Ser Lys Cys Phe
        35                  40                  45

Leu Thr Ala Glu Thr Glu Cys Asp Leu Thr Asp Glu Val Val Lys Asp
 50                  55                  60

Val Gly Gln Thr Tyr Met Ala Arg Val Leu Ser Tyr Pro Ala Arg Asn
 65                  70                  75                  80

Gly Asn Thr Thr Gly Phe Pro Glu Glu Pro Phe Arg Asn Ser Pro
                85                  90                  95

Glu Phe Thr Pro Tyr Leu Asp Thr Asn
                100                 105

<210> SEQ ID NO 270
<211> LENGTH: 93
<212> TYPE: PRT
<213> ORGANISM: Homo sapiens

<400> SEQUENCE: 270
```

```
Val Pro Thr Pro Thr Asn Val Thr Ile Glu Ser Tyr Asn Met Asn Pro
1               5                   10                  15

Ile Val Tyr Trp Glu Tyr Gln Ile Met Pro Gln Val Pro Val Phe Thr
            20                  25                  30

Val Glu Val Lys Asn Tyr Gly Val Lys Asn Ser Glu Trp Ile Asp Ala
        35                  40                  45

Cys Ile Asn Ile Ser His His Tyr Cys Asn Ile Ser Asp His Val Gly
    50                  55                  60

Asp Pro Ser Asn Ser Leu Trp Val Arg Val Lys Ala Arg Val Gly Gln
65                  70                  75                  80

Lys Glu Ser Ala Tyr Ala Lys Ser Glu Glu Phe Ala Val
                85                  90
```

<210> SEQ ID NO 271
<211> LENGTH: 91
<212> TYPE: PRT
<213> ORGANISM: Homo sapiens

<400> SEQUENCE: 271

```
Pro Glu Lys Pro Lys Asn Leu Ser Cys Ile Val Asn Glu Gly Lys Lys
1               5                   10                  15

Met Arg Cys Glu Trp Asp Gly Gly Arg Glu Thr His Leu Glu Thr Asn
            20                  25                  30

Phe Thr Leu Lys Ser Glu Trp Ala Thr His Lys Phe Ala Asp Cys Lys
        35                  40                  45

Ala Lys Arg Asp Thr Pro Thr Ser Cys Thr Val Asp Tyr Ser Thr Val
    50                  55                  60

Tyr Phe Val Asn Ile Glu Val Trp Val Glu Ala Glu Asn Ala Leu Gly
65                  70                  75                  80

Lys Val Thr Ser Asp His Ile Asn Phe Asp Pro
                85                  90
```

<210> SEQ ID NO 272
<211> LENGTH: 99
<212> TYPE: PRT
<213> ORGANISM: Homo sapiens

<400> SEQUENCE: 272

```
Gly Pro Glu Glu Leu Leu Cys Phe Thr Glu Arg Leu Glu Asp Leu Val
1               5                   10                  15

Cys Phe Trp Glu Glu Ala Ala Ser Ala Gly Val Gly Pro Gly Gln Tyr
            20                  25                  30

Ser Phe Ser Tyr Gln Leu Glu Asp Glu Pro Trp Lys Leu Cys Arg Leu
        35                  40                  45

His Gln Ala Pro Thr Ala Arg Gly Ala Val Arg Phe Trp Cys Ser Leu
    50                  55                  60

Pro Thr Ala Asp Thr Ser Ser Phe Val Pro Leu Glu Leu Arg Val Thr
65                  70                  75                  80

Ala Ala Ser Gly Ala Pro Arg Tyr His Arg Val Ile His Ile Asn Glu
                85                  90                  95

Val Val Leu
```

<210> SEQ ID NO 273
<211> LENGTH: 97
<212> TYPE: PRT
<213> ORGANISM: Homo sapiens

<400> SEQUENCE: 273

Phe Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu
    50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
            85                  90                  95

Lys

<210> SEQ ID NO 274
<211> LENGTH: 97
<212> TYPE: PRT
<213> ORGANISM: Homo sapiens

<400> SEQUENCE: 274

Pro Glu Glu Pro Gln Leu Ser Cys Phe Arg Lys Ser Pro Leu Ser Asn
1               5                   10                  15

Val Val Cys Glu Trp Gly Pro Arg Ser Thr Pro Ser Leu Thr Thr Lys
            20                  25                  30

Ala Val Leu Leu Val Arg Lys Phe Gln Asn Ser Pro Ala Glu Asp Phe
        35                  40                  45

Gln Glu Pro Cys Gln Tyr Ser Gln Glu Ser Gln Lys Phe Ser Cys Gln
    50                  55                  60

Leu Ala Val Pro Glu Gly Asp Ser Ser Phe Tyr Ile Val Ser Met Cys
65                  70                  75                  80

Val Ala Ser Ser Val Gly Ser Lys Phe Ser Lys Thr Gln Thr Phe Gln
            85                  90                  95

Gly

<210> SEQ ID NO 275
<211> LENGTH: 99
<212> TYPE: PRT
<213> ORGANISM: Homo sapiens

<400> SEQUENCE: 275

Pro Gly Lys Pro Glu Ile Phe Lys Cys Arg Ser Pro Asn Lys Glu Thr
1               5                   10                  15

Phe Thr Cys Trp Trp Arg Pro Gly Thr Asp Gly Gly Leu Pro Thr Asn
            20                  25                  30

Tyr Ser Leu Thr Tyr His Arg Glu Gly Glu Thr Leu Met His Glu Cys
        35                  40                  45

Pro Asp Tyr Ile Thr Gly Gly Pro Asn Ser Cys His Phe Gly Lys Gln
    50                  55                  60

Tyr Thr Ser Met Trp Arg Thr Tyr Ile Met Met Val Asn Ala Thr Asn
65                  70                  75                  80

Gln Met Gly Ser Ser Phe Ser Asp Glu Leu Tyr Val Asp Val Thr Tyr
            85                  90                  95

Ile Val Gln

<210> SEQ ID NO 276
<211> LENGTH: 102
<212> TYPE: PRT

<213> ORGANISM: Mus musculus

<400> SEQUENCE: 276

Pro Ala Ser Pro Ser Asn Leu Ser Cys Leu Met His Leu Thr Thr Asn
1               5                   10                  15

Ser Leu Val Cys Gln Trp Glu Pro Gly Pro Glu Thr His Leu Pro Thr
            20                  25                  30

Ser Phe Ile Leu Lys Ser Phe Arg Ser Arg Ala Asp Cys Gln Tyr Gln
        35                  40                  45

Gly Asp Thr Ile Pro Asp Cys Val Ala Lys Lys Arg Gln Asn Asn Cys
    50                  55                  60

Ser Ile Pro Arg Lys Asn Leu Leu Leu Tyr Gln Tyr Met Ala Ile Trp
65                  70                  75                  80

Val Gln Ala Glu Asn Met Leu Gly Ser Ser Glu Ser Pro Lys Leu Cys
                85                  90                  95

Leu Asp Pro Met Asp Val
            100

<210> SEQ ID NO 277
<211> LENGTH: 99
<212> TYPE: PRT
<213> ORGANISM: Rattus norvegicus

<400> SEQUENCE: 277

Pro Gly Lys Pro Glu Ile His Lys Cys Arg Ser Pro Asp Lys Glu Thr
1               5                   10                  15

Phe Thr Cys Trp Trp Asn Pro Gly Thr Asp Gly Gly Leu Pro Thr Asn
            20                  25                  30

Tyr Ser Leu Thr Tyr Ser Lys Glu Gly Glu Lys Thr Thr Tyr Glu Cys
        35                  40                  45

Pro Asp Tyr Lys Thr Ser Gly Pro Asn Ser Cys Phe Phe Ser Lys Gln
    50                  55                  60

Tyr Thr Ser Ile Trp Lys Ile Tyr Ile Ile Thr Val Asn Ala Thr Asn
65                  70                  75                  80

Gln Met Gly Ser Ser Ser Ser Asp Pro Leu Tyr Val Asp Val Thr Tyr
                85                  90                  95

Ile Val Glu

<210> SEQ ID NO 278
<211> LENGTH: 97
<212> TYPE: PRT
<213> ORGANISM: Homo sapiens

<400> SEQUENCE: 278

Pro Lys Phe Thr Lys Cys Arg Ser Pro Glu Arg Glu Thr Phe Ser Cys
1               5                   10                  15

His Trp Thr Asp Glu Val His His Gly Thr Lys Asn Leu Gly Pro Ile
            20                  25                  30

Gln Leu Phe Tyr Thr Arg Arg Asn Thr Gln Glu Trp Thr Gln Glu Trp
        35                  40                  45

Lys Glu Cys Pro Asp Tyr Val Ser Ala Gly Glu Asn Ser Cys Tyr Phe
    50                  55                  60

Asn Ser Ser Phe Thr Ser Ile Trp Ile Pro Tyr Cys Ile Lys Leu Thr
65                  70                  75                  80

Ser Asn Gly Gly Thr Val Asp Glu Lys Cys Phe Ser Val Asp Glu Ile
                85                  90                  95

Val

<210> SEQ ID NO 279
<211> LENGTH: 112
<212> TYPE: PRT
<213> ORGANISM: Homo sapiens

<400> SEQUENCE: 279

Leu Gly Gln Pro Thr Ile Gln Ser Phe Glu Gln Val Gly Thr Lys Val
1               5                   10                  15

Asn Val Thr Val Glu Asp Glu Arg Thr Leu Val Arg Arg Asn Asn Thr
                20                  25                  30

Phe Leu Ser Leu Arg Asp Val Phe Gly Lys Asp Leu Ile Tyr Thr Leu
            35                  40                  45

Tyr Tyr Trp Lys Ser Ser Ser Gly Lys Lys Thr Ala Lys Thr Asn
50                  55                  60

Thr Asn Glu Phe Leu Ile Asp Val Asp Lys Gly Glu Asn Tyr Cys Phe
65                  70                  75                  80

Ser Val Gln Ala Val Ile Pro Ser Arg Thr Val Asn Arg Lys Ser Thr
                85                  90                  95

Asp Ser Pro Val Glu Cys Met Gly Gln Glu Lys Gly Glu Phe Arg Glu
            100                 105                 110

<210> SEQ ID NO 280
<211> LENGTH: 105
<212> TYPE: PRT
<213> ORGANISM: Oryctolagus cuniculus

<400> SEQUENCE: 280

Leu Gly Gln Pro Thr Ile Gln Ser Phe Glu Gln Val Gly Thr Lys Leu
1               5                   10                  15

Asn Val Thr Val Gln Asp Ala Arg Thr Leu Val Arg Arg Asn Gly Thr
                20                  25                  30

Phe Leu Ser Leu Arg Ala Val Phe Gly Lys Asp Leu Asn Tyr Thr Leu
            35                  40                  45

Tyr Tyr Trp Arg Ala Ser Ser Thr Gly Lys Lys Thr Ala Thr Thr Asn
50                  55                  60

Thr Asn Glu Phe Leu Ile Asp Val Asp Lys Gly Glu Asn Tyr Cys Phe
65                  70                  75                  80

Ser Val Gln Ala Val Ile Pro Ser Arg Lys Arg Lys Gln Arg Ser Pro
                85                  90                  95

Glu Ser Leu Thr Glu Cys Thr Ser Arg
            100                 105

<210> SEQ ID NO 281
<211> LENGTH: 115
<212> TYPE: PRT
<213> ORGANISM: Homo sapiens

<400> SEQUENCE: 281

Ile Gly Pro Pro Lys Leu Asp Ile Arg Lys Glu Glu Lys Gln Ile Met
1               5                   10                  15

Ile Asp Ile Phe His Pro Ser Val Phe Val Asn Gly Asp Glu Gln Glu
                20                  25                  30

Val Asp Tyr Asp Pro Glu Thr Thr Cys Tyr Ile Arg Val Tyr Asn Val
            35                  40                  45

Tyr Val Arg Met Asn Gly Ser Glu Ile Gln Tyr Lys Ile Leu Thr Gln
50                  55                  60

Lys Glu Asp Asp Cys Asp Glu Ile Gln Cys Gln Leu Ala Ile Pro Val

```
                        65                  70                  75                  80
Ser Ser Leu Asn Ser Gln Tyr Cys Val Ser Ala Glu Gly Val Leu His
                85                  90                  95

Val Trp Gly Val Thr Thr Glu Lys Ser Lys Glu Val Cys Ile Thr Ile
            100                 105                 110

Phe Asn Ser
        115

<210> SEQ ID NO 282
<211> LENGTH: 105
<212> TYPE: PRT
<213> ORGANISM: Homo sapiens

<400> SEQUENCE: 282

Val Thr Leu Thr Val Gly Ser Val Asn Leu Glu Ile His Asn Gly Phe
1               5                   10                  15

Ile Leu Gly Lys Ile Gln Leu Pro Arg Pro Lys Met Ala Pro Ala Gln
            20                  25                  30

Asp Thr Tyr Glu Ser Ile Phe Ser His Phe Arg Glu Tyr Glu Ile Ala
        35                  40                  45

Ile Arg Lys Val Pro Gly Gln Phe Thr Phe Thr His Lys Lys Val Lys
50                  55                  60

His Glu Gln Phe Ser Leu Leu Thr Ser Gly Glu Val Gly Glu Phe Cys
65                  70                  75                  80

Val Gln Val Lys Pro Ser Val Ala Ser Arg Ser Asn Lys Gly Met Trp
                85                  90                  95

Ser Lys Glu Glu Cys Ile Ser Leu Thr
            100                 105

<210> SEQ ID NO 283
<211> LENGTH: 103
<212> TYPE: PRT
<213> ORGANISM: Mus musculus

<400> SEQUENCE: 283

Leu Glu Pro Pro Met Leu Gln Ala Leu Asp Ile Gly Pro Asp Val Val
1               5                   10                  15

Ser His Gln Pro Gly Cys Leu Trp Leu Ser Trp Lys Pro Trp Lys Pro
            20                  25                  30

Ser Glu Tyr Met Glu Gln Glu Cys Glu Leu Arg Tyr Gln Pro Gln Leu
        35                  40                  45

Lys Gly Ala Asn Trp Thr Leu Val Phe His Leu Pro Ser Ser Lys Asp
50                  55                  60

Gln Phe Glu Leu Cys Gly Leu His Gln Ala Pro Val Tyr Thr Leu Gln
65                  70                  75                  80

Met Arg Cys Ile Arg Ser Ser Leu Pro Gly Phe Trp Ser Pro Trp Ser
                85                  90                  95

Pro Gly Leu Gln Leu Arg Pro
            100

<210> SEQ ID NO 284
<211> LENGTH: 93
<212> TYPE: PRT
<213> ORGANISM: Drosophila melanogaster

<400> SEQUENCE: 284

Pro Asn Ala Pro Lys Leu Thr Gly Ile Thr Cys Gln Ala Asp Lys Ala
1               5                   10                  15
```

Glu Ile His Trp Glu Gln Gln Gly Asp Asn Arg Ser Pro Ile Leu His
                20                  25                  30

Tyr Thr Ile Gln Phe Asn Thr Ser Phe Thr Pro Ala Ser Trp Asp Ala
            35                  40                  45

Ala Tyr Glu Lys Val Pro Asn Thr Asp Ser Ser Phe Val Val Gln Met
 50                  55                  60

Ser Pro Trp Ala Asn Tyr Thr Phe Arg Val Ile Ala Phe Asn Lys Ile
 65                  70                  75                  80

Gly Ala Ser Pro Pro Ser Ala His Ser Asp Ser Cys Thr
                85                  90

<210> SEQ ID NO 285
<211> LENGTH: 94
<212> TYPE: PRT
<213> ORGANISM: Homo sapiens

<400> SEQUENCE: 285

Pro Asp Pro Pro Lys Asn Leu Gln Leu Lys Pro Leu Lys Asn Ser Arg
 1               5                  10                  15

Gln Val Glu Val Ser Trp Glu Tyr Pro Asp Thr Trp Ser Thr Pro His
                20                  25                  30

Ser Tyr Phe Ser Leu Thr Phe Cys Val Gln Val Gln Gly Lys Ser Lys
            35                  40                  45

Arg Glu Lys Lys Asp Arg Val Phe Thr Asp Lys Thr Ser Ala Thr Val
 50                  55                  60

Ile Cys Arg Lys Asn Ala Ser Ile Ser Val Arg Ala Gln Asp Arg Tyr
 65                  70                  75                  80

Tyr Ser Ser Ser Trp Ser Glu Trp Ala Ser Val Pro Cys Ser
                85                  90

<210> SEQ ID NO 286
<211> LENGTH: 94
<212> TYPE: PRT
<213> ORGANISM: Homo sapiens

<400> SEQUENCE: 286

Pro Ser Pro Pro Ser Val Trp Phe Glu Ala Glu Phe Phe His His Ile
 1               5                  10                  15

Leu His Trp Thr Pro Ile Pro Gln Gln Ser Glu Ser Thr Cys Tyr Glu
                20                  25                  30

Val Ala Leu Leu Arg Tyr Gly Ile Glu Ser Trp Asn Ser Ile Ser Gln
            35                  40                  45

Cys Ser Gln Thr Leu Ser Tyr Asp Leu Thr Ala Val Thr Leu Asp Leu
 50                  55                  60

Tyr His Ser Asn Gly Tyr Arg Ala Arg Val Arg Ala Val Asp Gly Ser
 65                  70                  75                  80

Arg His Ser Gln Trp Thr Val Thr Asn Thr Arg Phe Ser Val
                85                  90

<210> SEQ ID NO 287
<211> LENGTH: 115
<212> TYPE: PRT
<213> ORGANISM: Homo sapiens

<400> SEQUENCE: 287

Gln Lys Glu Pro Lys Asn Lys Thr Phe Leu Arg Cys Glu Ala Lys Asn
 1               5                  10                  15

Tyr Ser Gly Arg Phe Thr Cys Trp Trp Leu Thr Thr Ile Ser Thr Asp
                20                  25                  30

Leu Thr Phe Ser Val Lys Ser Arg Gly Ser Ser Asp Pro Gln Gly
        35                  40                  45

Val Thr Cys Gly Ala Ala Thr Leu Ser Ala Glu Arg Val Arg Gly Asp
 50                  55                  60

Asn Lys Glu Tyr Glu Tyr Ser Val Glu Cys Gln Glu Asp Ser Ala Cys
 65                  70                  75                  80

Pro Ala Ala Glu Glu Ser Leu Pro Ile Glu Val Met Val Asp Ala Val
                85                  90                  95

His Lys Leu Lys Tyr Glu Asn Tyr Thr Ser Ser Phe Phe Ile Arg Asp
                100                 105                 110

Ile Ile Lys
        115

<210> SEQ ID NO 288
<211> LENGTH: 104
<212> TYPE: PRT
<213> ORGANISM: Homo sapiens

<400> SEQUENCE: 288

Pro Trp Ala Pro Glu Asn Leu Thr Leu His Lys Leu Ser Glu Ser Gln
1               5                   10                  15

Leu Glu Leu Asn Trp Asn Asn Arg Phe Leu Asn His Cys Leu Glu His
                20                  25                  30

Leu Val Gln Tyr Arg Thr Asp Trp Asp His Ser Trp Thr Glu Gln Ser
        35                  40                  45

Val Asp Tyr Arg His Lys Phe Ser Leu Pro Ser Val Asp Gly Gln Lys
 50                  55                  60

Arg Tyr Thr Phe Arg Val Arg Ser Arg Phe Asn Pro Leu Cys Gly Ser
 65                  70                  75                  80

Ala Gln His Trp Ser Glu Trp Ser His Pro Ile His Trp Gly Ser Asn
                85                  90                  95

Thr Ser Lys Glu Asn Pro Arg Thr
                100

<210> SEQ ID NO 289
<211> LENGTH: 124
<212> TYPE: PRT
<213> ORGANISM: Artificial Sequence
<220> FEATURE:
<223> OTHER INFORMATION: synthetic construct

<400> SEQUENCE: 289

Met Thr Asn Ile Thr Lys Arg Ser Leu Val Ala Ala Gly Val Leu Ala
1               5                   10                  15

Ala Leu Met Ala Gly Asn Val Ala Leu Ala Ala Ile Glu Val Lys Asp
                20                  25                  30

Val Thr Asp Thr Thr Ala Leu Ile Thr Trp Phe Lys Pro Leu Ala Glu
        35                  40                  45

Ile Asp Gly Cys Glu Leu Thr Tyr Gly Ile Lys Asp Val Pro Gly Asp
 50                  55                  60

Arg Thr Thr Ile Asp Leu Thr Glu Asp Glu Asn Gln Tyr Ser Ile Gly
 65                  70                  75                  80

Asn Leu Lys Pro Asp Thr Glu Tyr Glu Val Ser Leu Ile Cys Arg Arg
                85                  90                  95

```
Gly Asp Met Ser Ser Asn Pro Ala Lys Glu Thr Phe Thr Thr Gly Gly
            100                 105                 110

Gly Thr Leu Gly His His His His His His His
            115                 120
```

PROTEIN SCAFFOLDS

CROSS-REFERENCE TO RELATED APPLICATIONS

This application is a National Phase filing of International Application No. PCT/US2008/012398 filed on Oct. 31, 2008, said Application No. PCT/US2008/012398 claims benefit under 35 U.S.C. 119(e) of U.S. Provisional Application No. 60/984,209, filed Oct. 31, 2007, each of the above listed applications are incorporated by reference herein in their entireties for all purposes.

REFERENCE TO THE SEQUENCE LISTING

This application incorporates by reference a Sequence Listing submitted Mar. 31, 2013 as text file entitled "TN3100US1_substituteSL.txt" created on Mar. 29, 2013 and have a size of 144 kilobytes.

FIELD OF THE INVENTION

This invention relates to protein scaffolds that specifically bind a target and methods of making, screening and using such scaffolds.

BACKGROUND OF THE INVENTION

This invention relates to protein scaffolds useful, for example, for the generation of products having novel binding characteristics.

Proteins having relatively defined three-dimensional structures, commonly referred to as protein scaffolds, may be used as reagents for the design of engineered products. These scaffolds typically contain one or more regions which are amenable to specific or random sequence variation, and such sequence randomization is often carried out to produce libraries of proteins from which desired products may be selected. One particular area in which such scaffolds are useful is the field of antibody mimetic design.

While therapeutic antibodies are known with some successful examples on the market (HERCEPTIN®, AVASTIN®, SYNAGIS®), there is a growing interest in generating antibody fragments as therapeutic proteins. The advantages are the ease of manipulation by molecular biology techniques in order to obtain desired binding characteristics, the ability to express such fragments in microbial systems, and the expectation that antibody fragments will have better tissue penetration than full-length antibodies. One example is REOPRO®.

In addition, there have been efforts to develop small, non-antibody therapeutics, i.e., antibody mimetics, in order to capitalize on the advantages of antibodies and antibody fragments, such as high affinity binding of targets and low immunogenicity and toxicity, while avoiding some of the shortfalls, such as the requirement for intradomain disulfide bonds which require proper refolding, and the tendency for antibody fragments to aggregate and be less stable than full-length IgGs. One example is a "minibody" scaffold, which is related to the immunoglobulin fold, which is designed by deleting three beta strands from a heavy chain variable domain of a monoclonal antibody (Tramontano et al., J. Mol. Recognit. 7:9, 1994). This protein includes 61 residues and can be used to present two hypervariable loops, much like complementarity determining regions (CDRs) in antibodies. These two loops have been randomized and products selected for antigen binding, but thus far the framework appears to have somewhat limited utility due to solubility problems. Another framework used to display loops has been tendamistat, a small protein inhibitor of α-amylase, which contains a 74 residue, six-strand beta sheet sandwich held together by two disulfide bonds and forms 3 CDR-like loops (McConnell and Hoess, J. Mol. Biol. 250:460, 1995).

Other proteins have been tested as frameworks and have been used to display randomized residues on alpha helical surfaces (Nord et al., Nat. Biotechnol. 15:772, 1997; Nord et al., Protein Eng. 8:601, 1995), loops between alpha helices in alpha helix bundles (Ku and Schultz, Proc. Natl. Acad. Sci. USA 92:6552, 1995), and loops constrained by disulfide bridges, such as those of the small protease inhibitors (Markland et al., Biochemistry 35:8045, 1996; Markland et al., Biochemistry 35:8058, 1996; Rottgen and Collins, Gene 164: 243, 1995; Wang et al., J. Biol. Chem. 270:12250, 1995).

Thus, there is a need to develop small, stable, artificial antibody-like molecules for a variety of therapeutic and diagnostic applications.

Citation or discussion of a reference herein shall not be construed as an admission that such is prior art to the present invention.

SUMMARY OF THE INVENTION

The present invention provides a family of recombinant, non-naturally occurring protein scaffolds capable of binding any compound of interest. In particular, the proteins described herein may be used to display defined loops which are analogous to the complementarity-determining regions ("CDRs") of an antibody variable region. These loops maybe subjected to randomization or restricted evolution to generate diversity required to bind a multitude of target compounds. The proteins may be assembled into multispecific scaffolds capable of binding different targets.

The invention provides recombinant, non-naturally occurring polypeptide scaffolds (herein after known as "scaffolds of the invention") comprising, a plurality of beta strand domains linked to a plurality of loop region sequences derived from a naturally occurring protein sequence, wherein one or more of said loop region sequences vary by deletion, substitution or addition by at least one amino acid from the corresponding loop sequences in the naturally occurring protein sequence, and wherein the beta strand domains of the polypeptide scaffold have at least 50% homology to the corresponding domain sequences of a naturally occurring protein sequence. In some embodiments, the naturally occurring sequence is the protein sequence corresponding to human tenascin C. In particular, these scaffolds include, the third FnIII domain of tenascin C (also known as the "Tn3" domain). In specific embodiments, scaffolds of the invention comprise an amino acid sequence selected from the group consisting of SEQ ID NOs: 1, 5-32, 64-67, and 210. In other specific embodiments, scaffolds of the invention may be encoded by a nucleic acid comprising a sequence selected from the group consisting of SEQ ID NOs:33-59.

In other embodiments, the naturally occurring sequence corresponds to a predicted Tn3 structural motif, such as those derived from a thermophilic organism, for example but not limited to, *Archaeoglobus fulgidus, Staphylothermus marinus, Sulfolobus acidocaldarius, Sulfolobus solfataricus*, and *Sulfolobus tokodaii*.

In specific embodiments, scaffolds of the invention comprise an amino acid sequence selected from the group consisting of SEQ ID NOs: 2-4, 68-88, and 210. In other specific embodiments, scaffolds of the invention may be encoded by a nucleic acid comprising a sequence selected from the group consisting of SEQ ID NOs:89-98.

In another aspect of the invention, the scaffolds of the invention also include disulfide-stabilized scaffolds. The disulfide-stabilized scaffolds exhibit enhanced stability as measured by thermal tolerance, resistance to chaotropic denaturation and protease treatment.

The scaffolds of the invention are engineered to bind targets of interest, as described herein. Such binding may, for example, exhibit an affinity of at least 100 µM.

The invention also provides multimeric scaffolds comprising at least two scaffolds of the invention (hereinafter known as "multimeric scaffolds of the invention"). In some embodiments, the multimeric scaffolds of the invention comprise at least two scaffolds linked, for example, but not limited to, a dimerization domain, an amino acid linker, a disulfide bond, a chemical crosslink, and IgG molecule or fragment thereof, or an Fc region.

The invention also provides polypeptide display libraries (hereinafter referred to as "libraries of the invention") comprising a plurality of scaffolds of the invention. The libraries of the invention are useful for capturing and identifying target binding scaffolds to build multimeric scaffolds.

In another aspect the invention also provides isolated nucleic acid molecules encoding the scaffolds and libraries of the invention.

The invention also provides methods of making, using, screening, optimizing, and engineering the scaffolds and libraries of the invention.

In yet another aspect, the invention also provides pharmaceutical compositions comprising the scaffolds of the invention.

The invention also provides methods of treating, preventing, ameliorating, detecting, diagnosing, or monitoring a disease or symptoms thereof, as described herein, in a patient by administering therapeutically effective amounts of the scaffolds of the invention and/or pharmaceutical compositions comprising the scaffolds of the invention.

In specific embodiments, the invention provides TRAIL-R2 specific binders which are useful for preventing ameliorating, detecting, diagnosing, or monitoring diseases, such as but not limited to cancer. In other specific embodiments, TRAIL-R2 specific binding scaffolds of the invention are useful for the treatment of cancers in which cancer cells express TRAIL-R2. In some embodiments, cancers may include, but are not limited to, lung cancer, non-Hodgkin's lymphoma, gastrointestinal cancer, renal cancer, ovarian cancer, liver cancer, stomach cancer, bladder cancer, breast cancer, colon cancer, colorectal cancer, pancreatic cancer, liver cancer, prostate cancer, and melanoma.

BRIEF DESCRIPTION OF THE FIGURES

For the purpose of illustrating the invention, there are depicted in the drawings certain embodiments on the invention. However, the invention is not limited to the precise arrangements and instrumentalities of the embodiments depicted in the drawings.

FIG. 9C. The SYNAGIS® specific binding scaffold exhibits a similar stability to the base scaffold. A SYNAGIS® specific binding scaffold was identified from a library of scaffolds as prepared in Example 3. Presented here are the results from a Urea denaturation experiment in which the intrinsic fluorescence measures the unfolding of the proteins. In this experiment, the Tn3 scaffold (WT) and SYNAGIS® specific binding scaffold SynBP01 (A1) exhibited very similar denaturation profiles with increasing Urea concentrations.

FIG. 9D. Binding scaffolds engage the target antibody SYNAGIS®, bivalently. The tracing represents an experiment characterizing the engagement of two scaffolds on an immobilized molecule in a BIAcore assay format. In this experiment, immobilized SYNAGIS® is overlaid with a either a solution of 1 μM SYNAGIS® specific protein scaffold (blue tracing) or a solution of 1 μM SYNAGIS® specific protein scaffold+0.19 μM crosslinking mAb (red tracing). The graph depicts the differential binding characteristics exhibited by monomer scaffolds or crosslinked scaffolds.

Figure 10A:
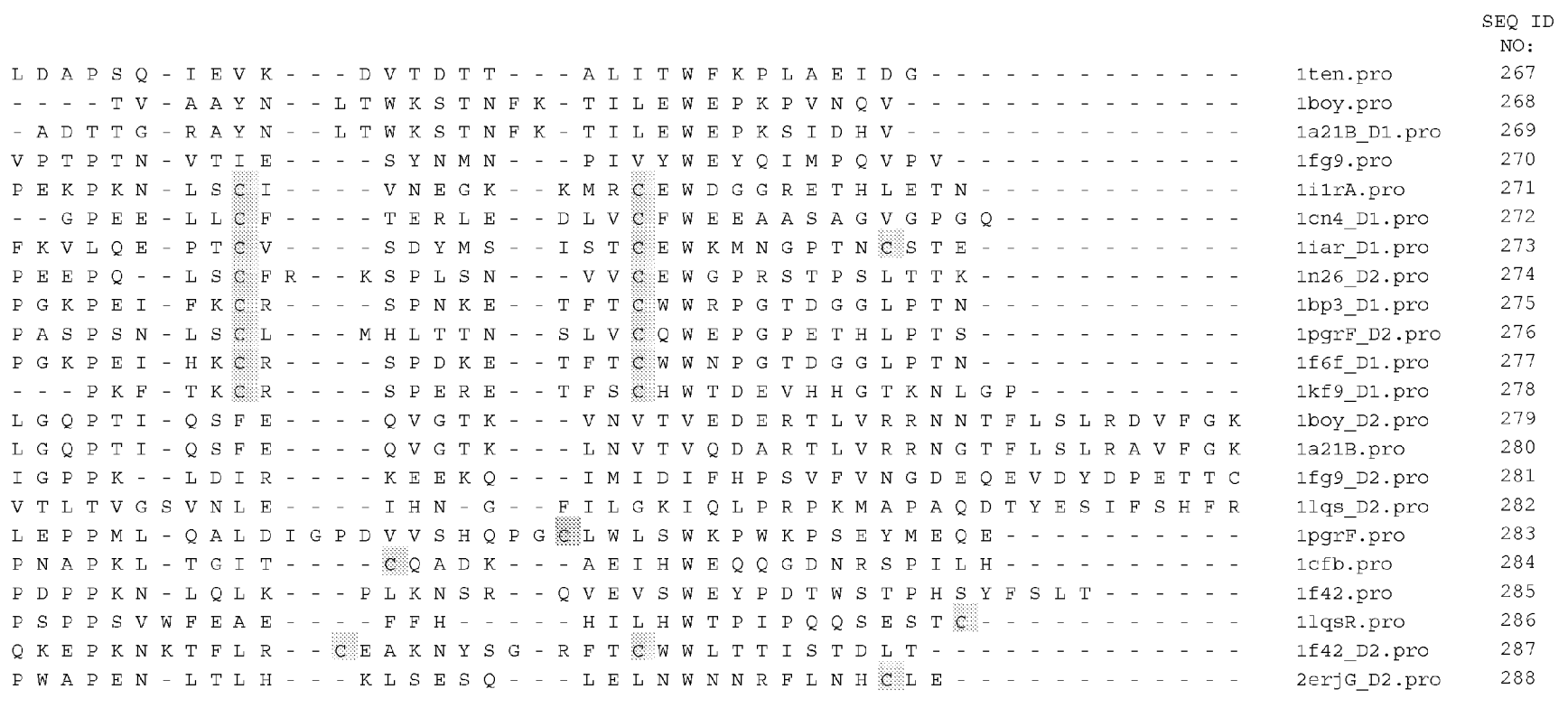
Figure 10B:
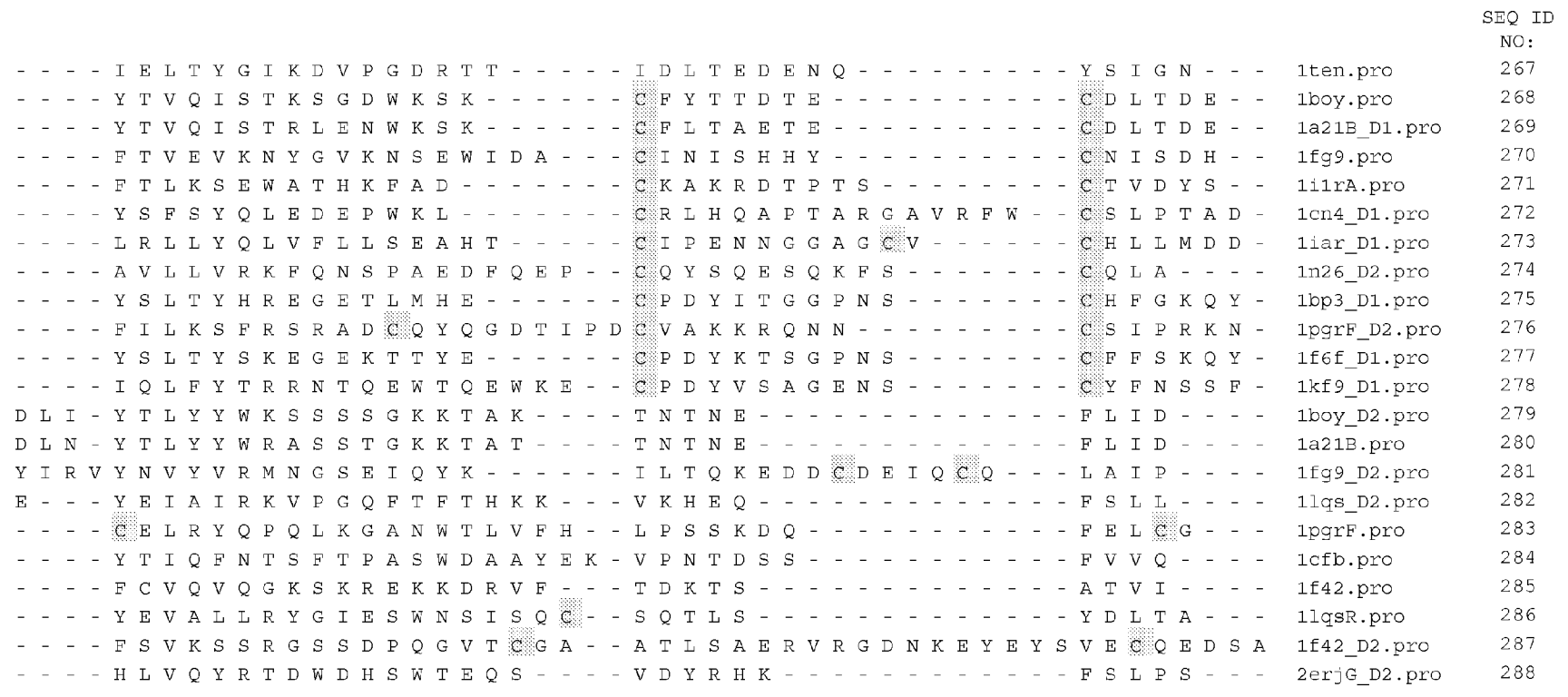
Figure 10C:
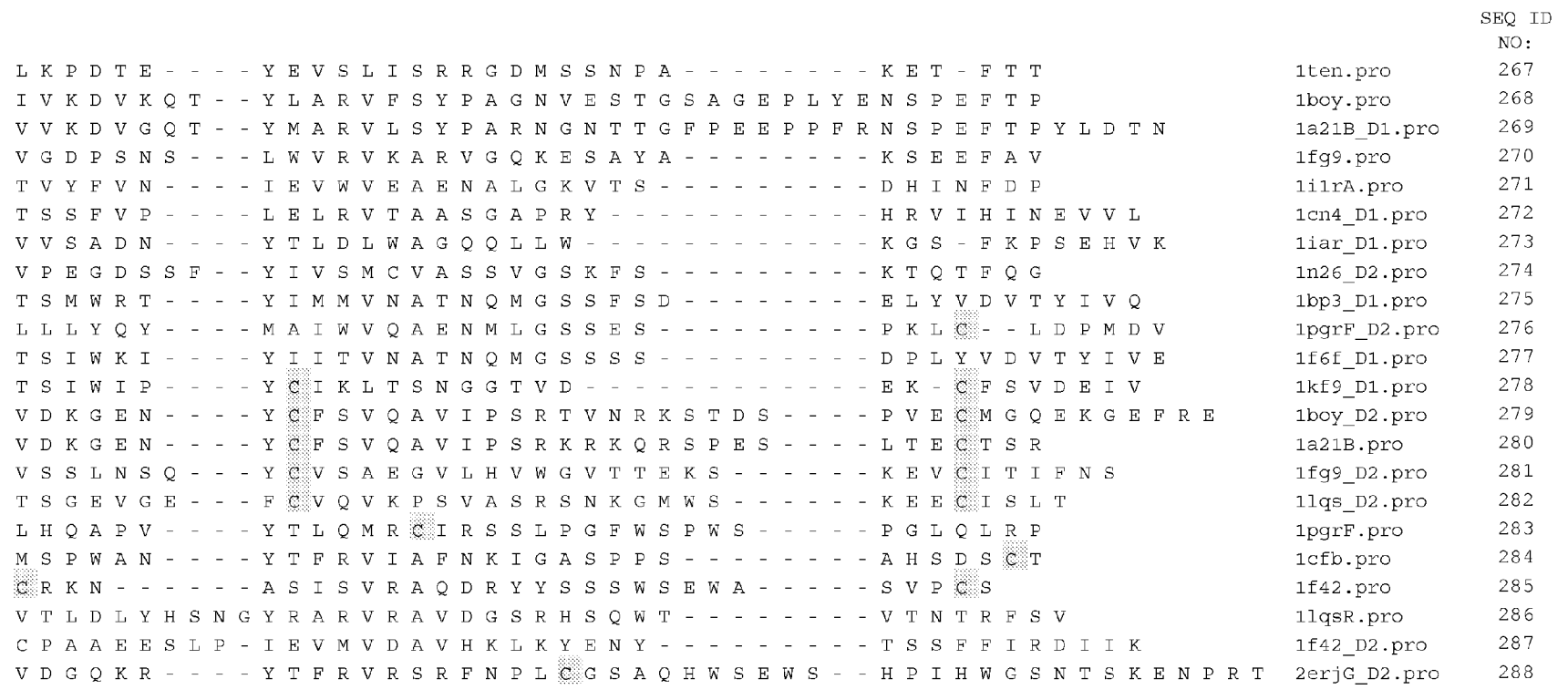

FIG. 10A-C. Sequence alignment of naturally occurring disulfide containing Tn3 structural motifs. The sequence alignment presented outlines the position of cysteine residues in 21 naturally occurring disulfide containing Tn3 related structural motifs in an effort to determine candidate positions for stability engineering. Like-colored Cys residues within individual Tn3 sequences are linked by a disulfide bond. The sequence of Tn3 (Iten.pro) is included in the alignment to facilitate the identification of residues and positions in Tn3 corresponding to cysteine residues in disulfide-containing scaffolds.

FIG. 10D. Targeted disulfide engineering to increase scaffold stability. The graphic depicts the potential disulfide locations to be engineered into the scaffold sequence. In an effort to increase stability, the four depicted disulfide locations were individually engineered into the scaffold. The resultant recombinant scaffolds were termed $Tn3^{SS1}$, $Tn3^{SS2}$, $Tn3^{SS3}$, and $Tn3^{SS4}$ respectfully.

FIG. 10E. RP-HPLC tracing of selected purified disulfide engineered scaffolds. Depicted in the graphic are the reverse-phase HPLC chromatograms of (i) $Tn3^{SS3}$ and (ii) $Tn3^{SS4}$ after purification, following reduction, and after refolding to form disulfide bonds. The chromatograms demonstrated that the cysteines contained within the scaffolds are only partially oxidized following protein purification (upper tracing) are completely reduced by treatment with DTT (middle tracing) and completely oxidized to disulfides after refolding (lower tracing).

FIG. 10F. Expression and characterization of disulfide engineered scaffolds. The figure depicts the results of a polyacrylamide gel electrophoresis analysis of 4 disulfide engineered scaffolds presented in FIG. 10D. Samples of purified and refolded constructs Tn3 (WT), $Tn3^{SS1}$ (1), $Tn3^{SS2}$ (2), $Tn3^{SS3}$ (3), $Tn3^{SS4}$ (4) were analyzed under reducing and non-reducing conditions to evaluate the predicted formation of disulfide bonds. As depicted, the $Tn3^{SS2}$ forms a disulfide linked dimer. The other constructs, (Tn3, $Tn3^{SS1}$, $Tn3^{SS3}$ and $Tn3^{SS4}$) do not form dimers in response to the incorporated cysteine residues as the purified and refolded disulfide containing scaffolds migrate similarly under reducing and non-reducing conditions.

FIG. 10G. Urea denaturation profile of the single disulfide engineered scaffolds. The graph depicts the results of a urea denaturation study of selected disulfide containing scaffolds outlined in panel A $Tn3^{SS1}$(SS1), $Tn3^{SS3}$(SS3), and $Tn3^{SS4}$ (SS4) as well as Tn3 (WT) scaffold. In this experiment the various purified and refolded scaffolds are exposed to increasing levels of urea. As a measure of unfolding, the relative fluorescence is monitored. As a protein unfolds or becomes less stable, the relative fluorescence increases. As presented in the panel, the $Tn3^{SS1}$ containing scaffold exhibits a higher sensitivity to urea compared to the Tn3 scaffold and is therefore less stable. Also, scaffolds $Tn3^{SS3}$ and $Tn3^{SS4}$ exhibit greater resistance to urea mediated denaturation as compared to Tn3 and are therefore more stable. The scaffold $Tn3^{SS4}$ exhibited the greatest resistance to urea mediated denaturation of the scaffolds tested in this experiment.

FIG. 10H. The $Tn3^{SS4}$ disulfide engineered scaffold exhibits increased stability as compared to the Tn3 scaffold. The graph depicts the results from a guanidine hydrochloride denaturation assay comparing the stability of the Tn3 scaffold (circles) to the disulfide containing scaffold, $Tn3^{SS4}$ (squares). As presented in the graph, the $Tn3^{SS4}$ scaffold exhibited a greater resistance to guanidine mediated denaturation, and therefore, was more stable, as compared to the Tn3 scaffold.

FIG. 10I. The $Tn3^{SS4}$ scaffold exhibits a high level of protease resistance compared to the Tn3 scaffold. The panel depicts the results from a protease sensitivity assay comparing the stability of the Tn3 scaffold to the $Tn3^{SS4}$ containing scaffold. In this experiment, the relative protease resistance correlates with the protein stability. For the Tn3 scaffold, incubation for as little as ten minutes with thermolysin results in degradation. After one hour of incubation in thermolysin, the Tn3 scaffold is completely degraded. The $Tn3^{SS4}$ containing scaffold exhibited thermolysin resistance over the entire 16 hour time course suggesting a greater stability than the Tn3 scaffold.

FIG. 10J. The $Tn3^{SS4}$ disulfide engineered scaffold exhibits a high melting temperature (Tm). The graph depicts the results from a thermal stability study comparing the Tn3 scaffold (dotted line) to the disulfide containing $Tn3^{SS4}$ scaffold (solid line). As presented in the melt curve, the $Tn3^{SS4}$ scaffold exhibited a higher melting temperature (about 71° C.) than the Tn3 scaffold (about 45° C., See also FIG. 3A).

FIG. 11A. Expression and purification of scaffolds from hyperthermophilic organisms. Presented here are Coomassie-stained PAGE gels documenting the expression and purification of predicted scaffolds (Tn3 structural motifs) from various hyperthermophilic bacteria. All of the predicted scaffolds were expressed and purified to homogeneity. In the figure, T represents total cell lysate, S represents soluble lysate fraction and P represents purified protein.

FIG. 11I. A scaffold from *Staphylothermus marinus* is purified from a host cell. The panel depicts one step in the purification of the *Staphylothermus marinus* scaffold. Due to the high level of stability exhibited by this scaffold, it is possible to treat the crude *E. coli* lysate containing the recombinant scaffold with thermolysin to degrade the bulk of the host cell proteins while retaining the scaffold. Lane 1 represents the crude lysate prior to protease treatment. Coomassie staining of a PAGE gel containing the crude lysate demonstrates that the scaffold is present. Protease treatment of the crude lysate at 55° C. for 45 minutes resulted in a loss of much of the host cell proteins while the scaffold remains intact (Lane 2).

These variants (designated BC only and FG only) were subjected to an ELISA based binding assay in which they did not exhibit binding to the plate bound SYNAGIS®. As a control, SynBP01 binding in the ELISA assay format is presented. In addition, the SS4 disulfide mutation was overlaid on SynBP01. This variant, designated SynBP01 SS4 did not exhibit any binding to plate bound SYNAGIS® in the ELISA format.

Figure 13:
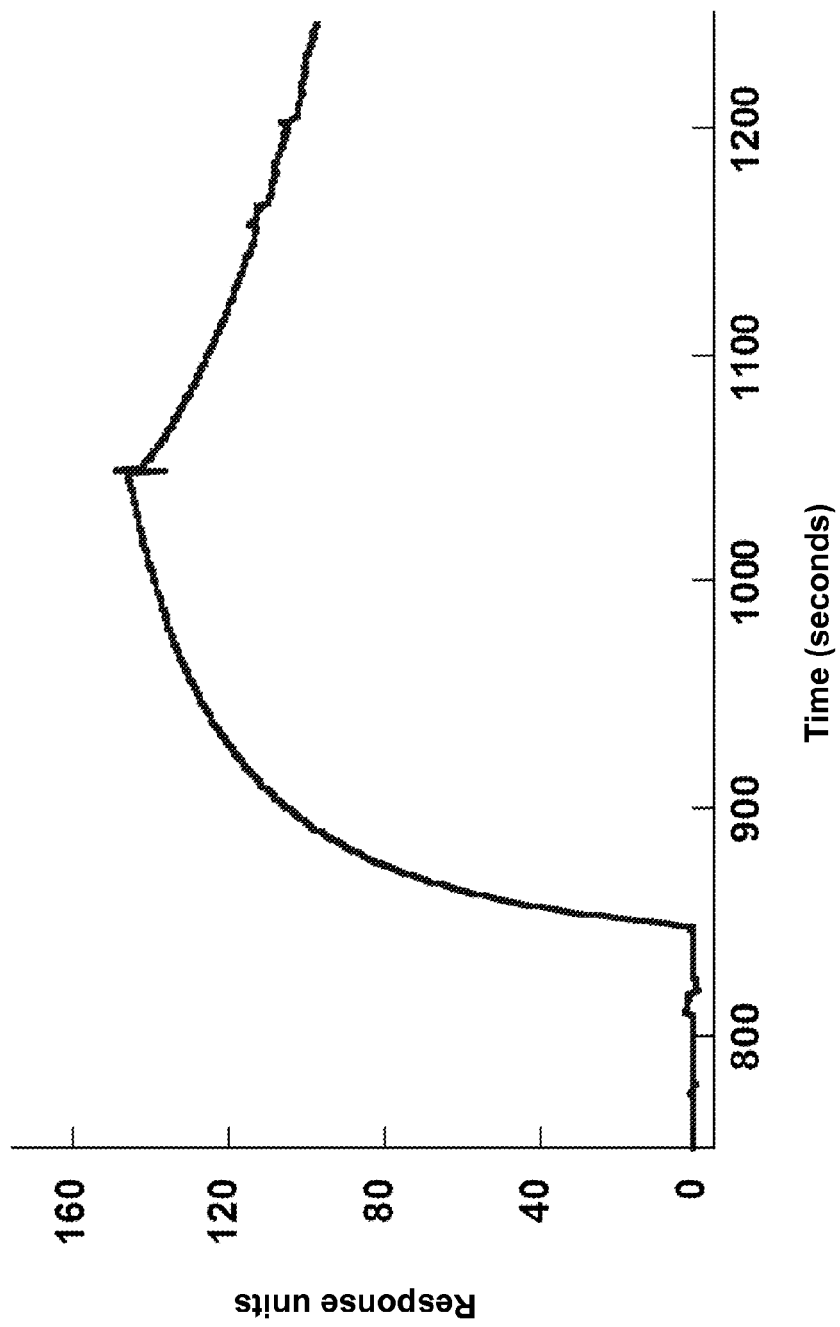

FIG. 13. Binding affinity determination of the TRAIL-R2 specific clone 5E5 as measured by BIAcore. This panel depicts an affinity determination of clone 5E5 for chip bound TRAIL-R2. The $K_d$ was estimated to be approximately 700 nM.

FIG. 14. Competitive binding exhibited by multiple TRAIL-R2 specific clones. Depicted in this panel are the results from a competitive binding experiment of various TRAIL-R2 specific scaffolds. Two TRAIL-R2 specific clones, 5E5 and 7G11 were tested for competitive binding against other TRAIL-R2 specific clones displayed on phage. 5E5 competes with itself and all other clones except 2H6 and 7G11. 7G11 only competes with itself and 2H6. This data indicates that there are two groups of clones recognizing two different epitopes on TRAIL-R2.

FIG. 15. Competition of various TRAIL-R2 specific clones. Depicted in this panel are the results from a competitive binding experiment of various TRAIL-R2 specific scaffolds. Five TRAIL-R2 specific clones, 1E3, 1G11, 2B4, 1C12 and 2D3 were tested for competitive binding against other TRAIL-R2 specific clones displayed on phage. 1E3, 1C12 and 2D3 competed with most of the phage displayed clones except for 8B3 and 7G11. Soluble 1G11 did not compete with any of the phage displayed clones, and 2B4 showed little to moderate inhibition in most cases. This data suggests that 1E3, 1C12 and 2D3 recognize the same epitope on TRAIL-R2.

FIG. 16. TRAIL-R2 binders inhibits cell viability. Depicted in panel is the sensitivity of the Colo-205 cell line to the treatment of 5E5, 7G11, 1C12, 2D3 and 1E3 when complexed with anti-HIS tag antibody and anti-mouse IgG in the molar ratio of 2:1:0.5. The percent viable cells was obtained by expressing the assay signal for treatment with TRAIL-R2 binding clones as a percentage of the signal obtained for cells treated with a control Tn3 which does not bind TRAIL-R2.

FIG. 17A. Diagram representing examples of Multivalent Tn3-fusion proteins. The bivalent construct represents a Tn3 fused to an antibody Fc region whereas the tetravalent construct fuses the Tn3 to heavy chain constant regions and/or the light chain Ckappa region.

FIG. 17B. Diagram showing linkage of protein modules in Multivalent Tn3-fusion proteins. i) In the Fc fusion construct, the N-terminal Tn3 module is linked to the Fc region of IgG1 via a peptide linker and hinge regions of IgG1. The linker sequence can vary in length and composition, but was a -GA- motif in Example 16. ii) In the Ckappa fusion construct, the N-terminal Tn3 module is linked to the constant region of an antibody kappa light chain via a peptide linker. The linker sequence can vary in length and composition, but was a -GGGTPT- motif in Example 16. iii) In the IGHG1 fusion construct, the N-terminal Tn3 module is linked to the constant region of an IgG1 heavy chain via a peptide linker. The linker sequence can vary in length and composition, but was a -GGGTPT- motif in Example 16.

FIG. 18. Expression of multivalent Tn3 constructs. Represented in the figure is a reducing SDS-PAGE showing the relative sizes of bivalent Tn3 constructs (samples 1-3), and tetravalent Tn3 constructs (samples 4-7) after protein A purification. Sample numbers correspond to those shown in Table 10. All constructs expressed exhibit the predicted sizes by this analysis.

FIG. 19. Binding affinity of Tn3 monomers and multimers. Depicted in this panel are sensorgrams from a Biosensor binding experiment using mono-, bi- and tetravalent 1C12 and D1 Tn3 constructs. TRAIL-R2-Fc fusion protein was immobilized on a sensor chip while sample proteins were injected over the chip. “tetra” refers to the tetravalent Cκ/IGHG1 fusion constructs. The 1C12 constructs show improved binding to TRAIL-R2 as a function of valency, while the control D1 contstructs do no exhibit binding.

FIG. 20. Effects of Bivalent Tn3 constructs targeting TRAIL-R2. Depicted in this panel are the growth inhibition curves of H2122 cells that were treated with (A) TRAIL-R2 specific Tn3 binder 1C12 in bivalent form or a (B) non-specific Tn3 binder in bivalent form with or without the addition of a crosslinking antibody (anti-human Fc). Relative to the control non-binder, the TRAIL-R2 specific binder exhibited mild activity in the assay, which decreased in the presence of the secondary antibody.

FIG. 21. Effects of Tetravalent Tn3 constructs targeting TRAIL-R2. Depicted in this panel are the growth inhibition curves of H2122 cells that were treated with (A) TRAIL-R2 specific Tn3 binder 1C12 in monospecific tetravalent form or a (B) non-specific Tn3 binder in monospecific tetravalent form with or without the addition of a crosslinking antibody (anti-human Fc). Relative to the control non-binder, the TRAIL-R2 specific binder exhibited activity in the assay, which decreased slightly in the presence of the secondary antibody.

FIG. 22. Effects of Multispecific Tetravalent Tn3 constructs targeting TRAIL-R2. Depicted in this panel are the growth inhibition curves of H2122 cells that were treated with (A) TRAIL-R2 specific Tn3 binder 1C12 and 2D3 in a bispecific tetravalent form (1C12 fused to the constant region of IgG1 heavy chain, 2D3 fused to the Ckappa domain) or a (B) TRAIL-R2 specific binder 2D3 and 1C12 in a bispecific tetravalent form (2D3 fused to the constant region of IgG1 heavy chain, 1C12 fused to the Ckappa domain) with or without the addition of a crosslinking antibody (anti-human Fc). Relative to the control non-binder (shown in FIG. 21), the TRAIL-R2 specific binders exhibited activity in the assay, which increased in the presence of the secondary antibody.

FIG. 23: Design of pSec constructs. (A) represents the amino acid sequence for the open reading frame in pSec-oppA-Tn3. The oppA signal peptide (underlined) SEQ ID NO:227 is cleaved after secretion into the periplasmic space. The penultimate residue within the oppA signal (italicized) was mutated to methionine in the pSec-oppA(L25M)-Tn3 derivative to introduce an Nco I cloning site. (B) depicts the pSec-oppA(L25M)-Tn3 construct showing the layout of the promoter, signal peptide, Tn3 and His tag modules within the construct.

FIG. 24. Preparation of secreted Tn3 constructs. (A) represents the SDS-PAGE analysis of crude media and periplasmic fractions from *E. coli* secreting Tn3. (B) represents the SDS-PAGE analysis of the Tn3 scaffold purified from the *E. coli* media. (C) represents the HPLC analysis of the Tn3 purified from the *E. coli* media. A shift in retention time following reduction by DTT is consistent with the presence of a disulfide bond.

FIG. 25. SDS-PAGE of a SYNAGIS®-Fc bivalent binder. Presented in this panel is the reducing (lane 1) and non-reducing (lane 2) SDS-PAGE analysis of the SynBP01 scaffold fused to an Fc region. These results demonstrate that the fusion is the correct size and may indicate dimerization.

Figure 26:
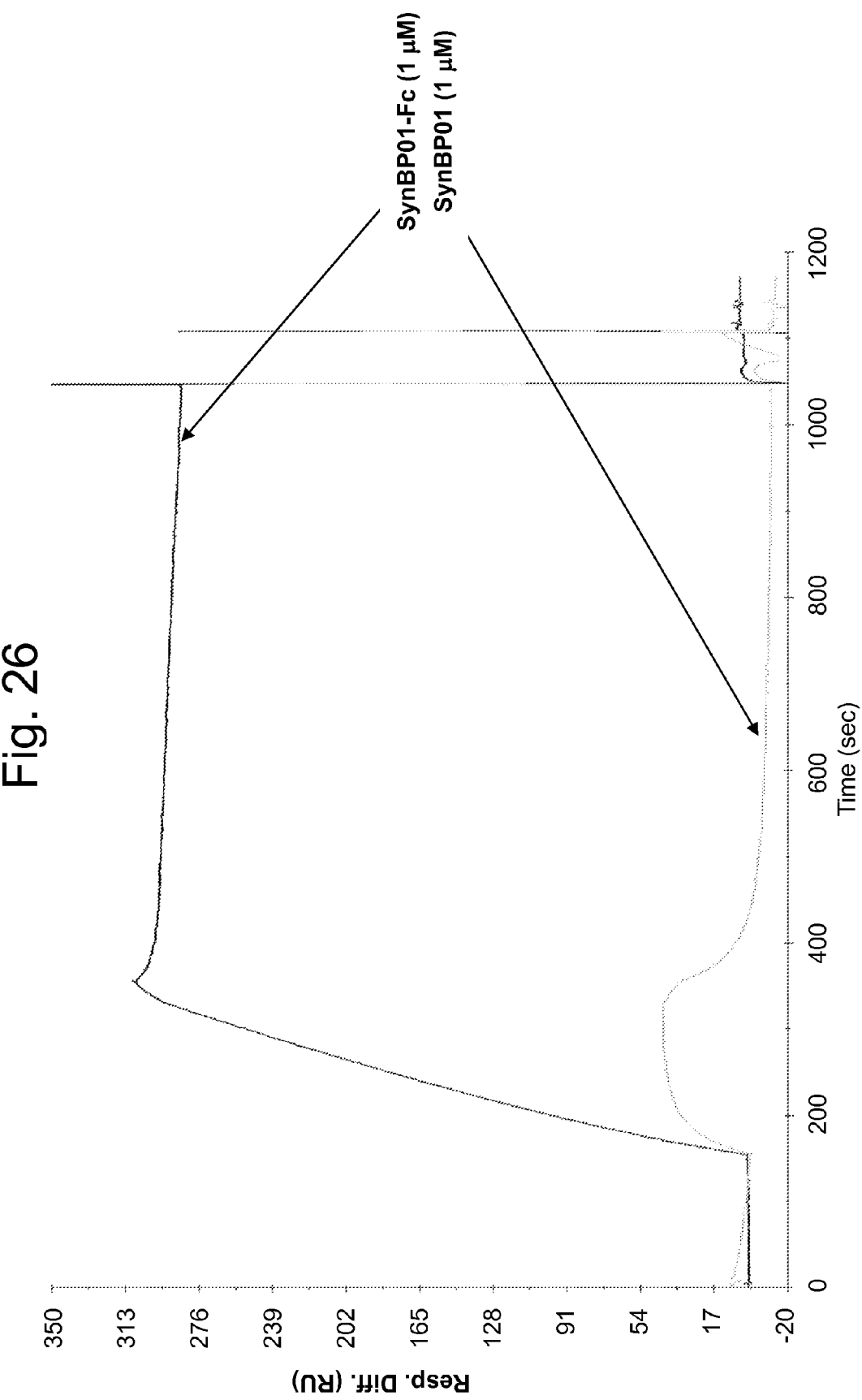

FIG. 26. Comparative binding analysis of a SYNAGIS®-Fc bivalent binder with SynBP01. Comparative BIAcore analysis of SynBP01 vs. SynBP01-Fc. Briefly, SYNAGIS® was immobilized on the surface of a CM5 sensor chip through amine coupling. SynBP01 or SynBP01-Fc, at a concentration of 1 µM, was injected at a flow rate of 75 µL/min. The bivalent SynBP01-Fc construct exhibits a higher affinity than the single domain binder.

Figure 27:
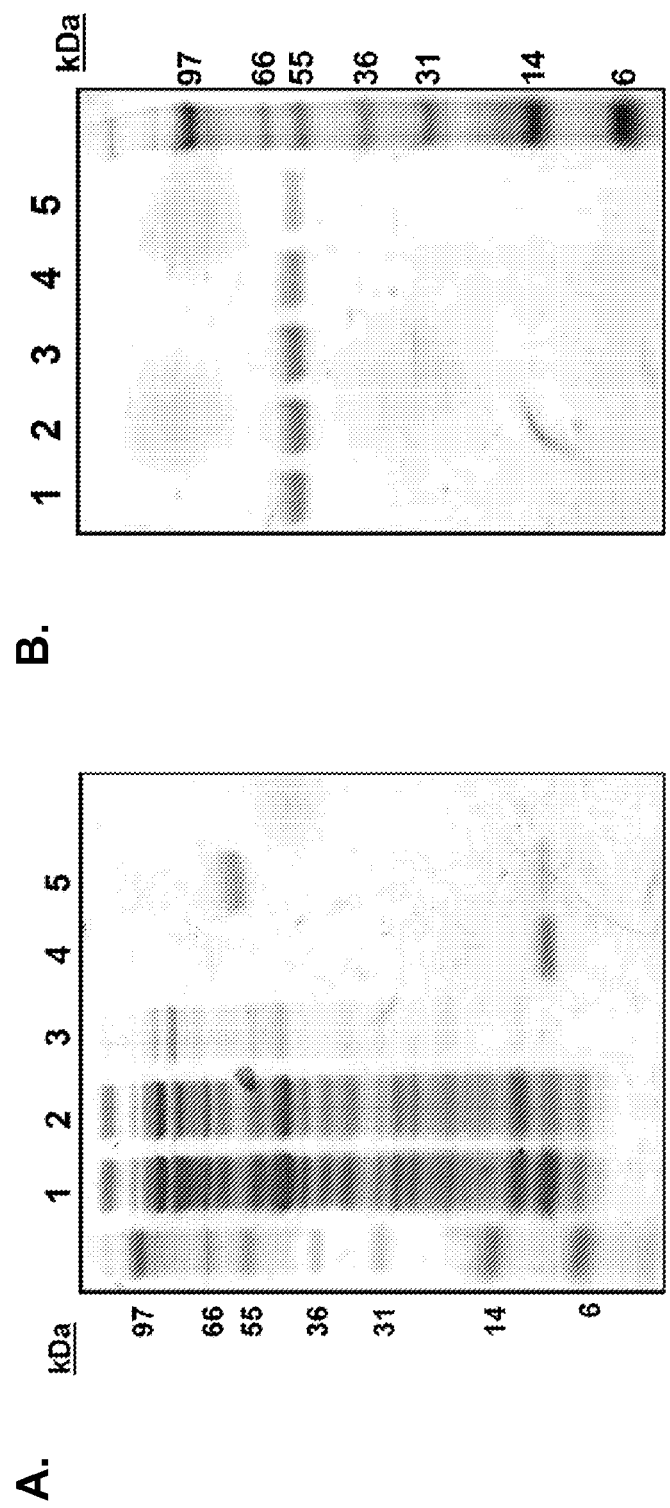

FIG. 27. Tn3 scaffolds may be conjugated to PEG. (A) SDS-PAGE analysis of immobilized metal-affinity column purification of STn3(CTC) (lanes 1-4), and of purified STn3 (CTC) after treatment with maleimide-derivatized PEG (prior to cation-exchange chromatography) (lane 5). Lane 1: Total cell lysate from STn3(CTC)-expressing cells; Lane 2: Flow-through from IMAC column; Lane 3: Wash fraction from IMAC column; Lane 4: STn3(CTC), unPEGylated; Lane 5: PEGylated STn3(CTC). (B) SDS-PAGE analysis of PEGylated STn3 (CTC), as purified from SP XL cation-exchange column. Peak gradient fractions are shown in lanes 1-5.

Figure 28:
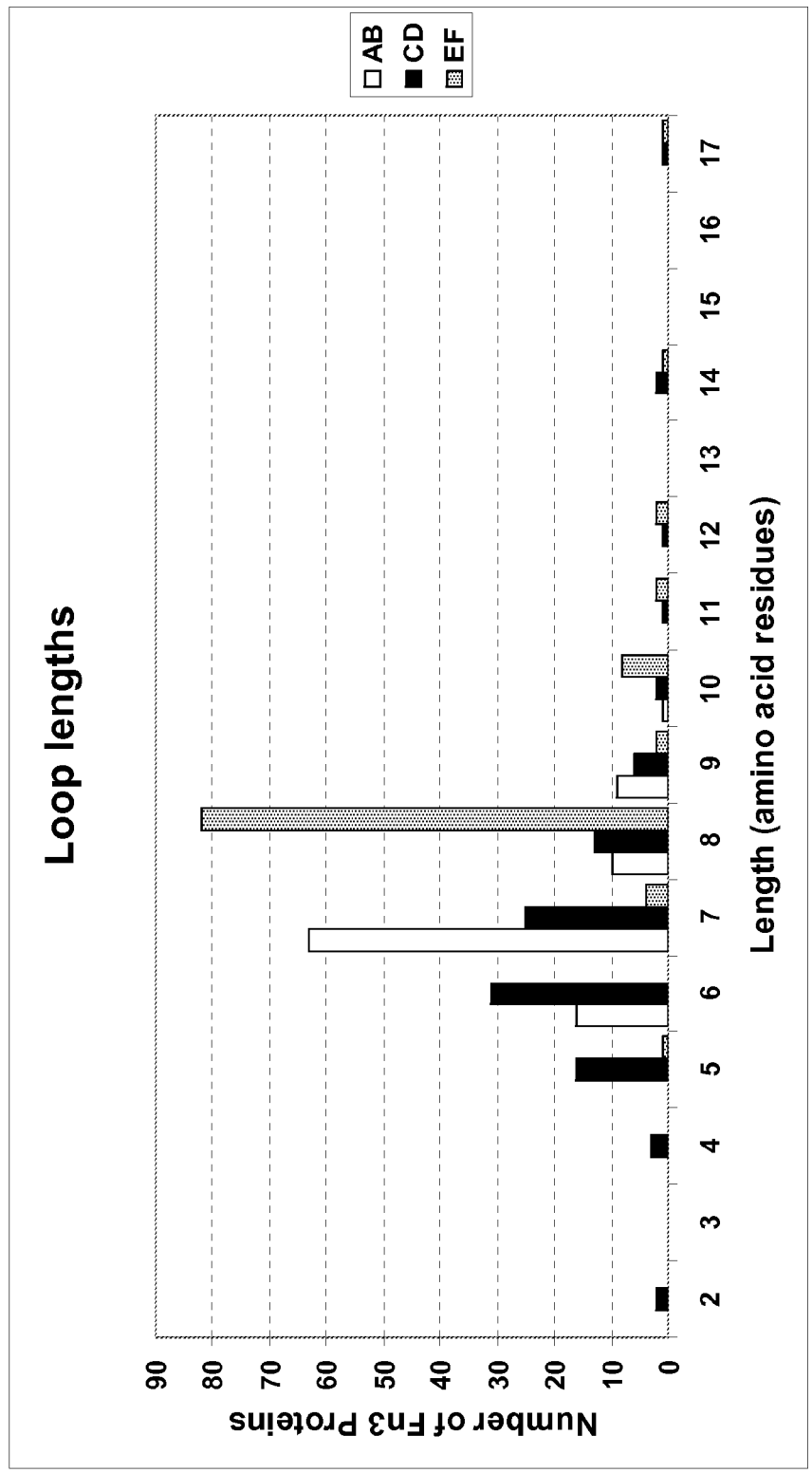

FIG. 28. The AB, CD, and EF loops demonstrate loop-length diversity. The length of AB, CD and EF loops was extracted for each of 103 Fn3 sequences and this data was used to produce the loop length frequency distribution shown. For any given loop, the sum of frequencies for all lengths is equal to 103, the number of sequences analyzed.

Figure 29:
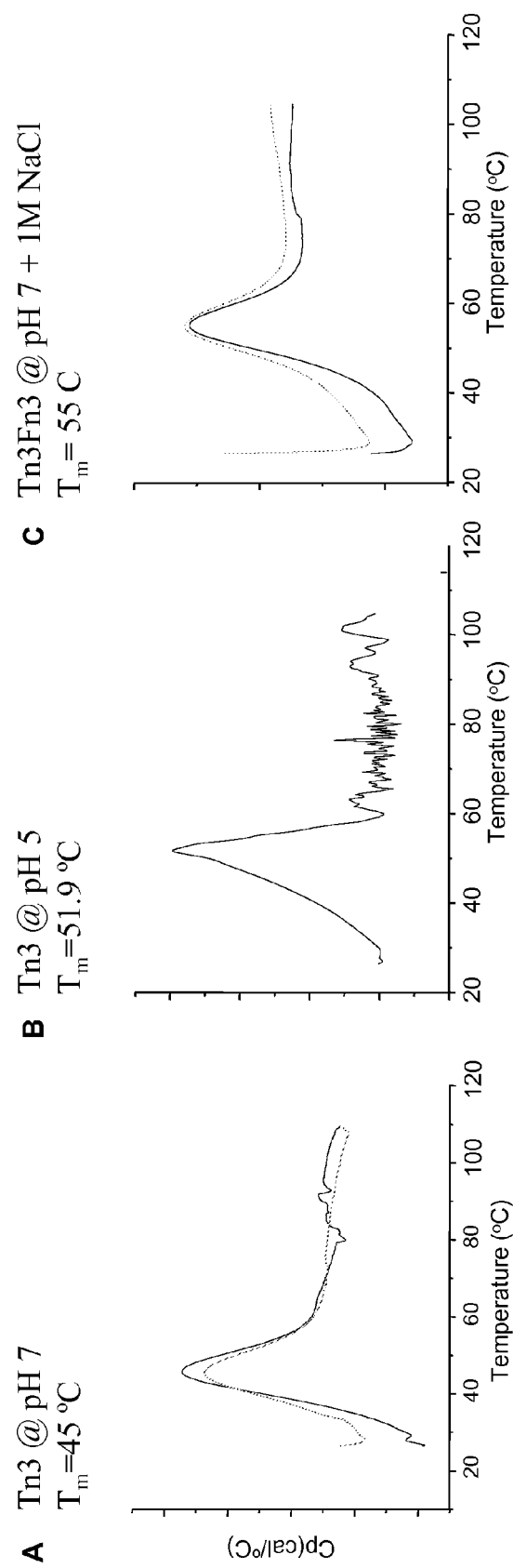

FIG. 29. Melting temperature determinations for Tn3 at different pH and ionic strength. The graphs show the thermal melting curve determinations, as measured by differential scanning calorimetry, for the Tn3 scaffold at pH 7.0 (in 20 mM sodium phosphate buffer) (A), at pH 5.0 (in 20 mM sodium acetate buffer)(B) and in high salt buffer at pH 7.0 (20 mM sodium phosphate buffer containing 1.0 M salt)(C). The $T_m$'s were determined to be about 45° C. for Tn3 at pH 7.0, 52° C. at pH 5.0, and 55° C. at pH 7.0 in the presence of high ionic strength. Repeat scans (in yellow) for the pH 7.0 samples show that thermal unfolding is reversible under these conditions. Thermal unfolding of Tn3 is irreversible at pH 5.0

Figure 30A:
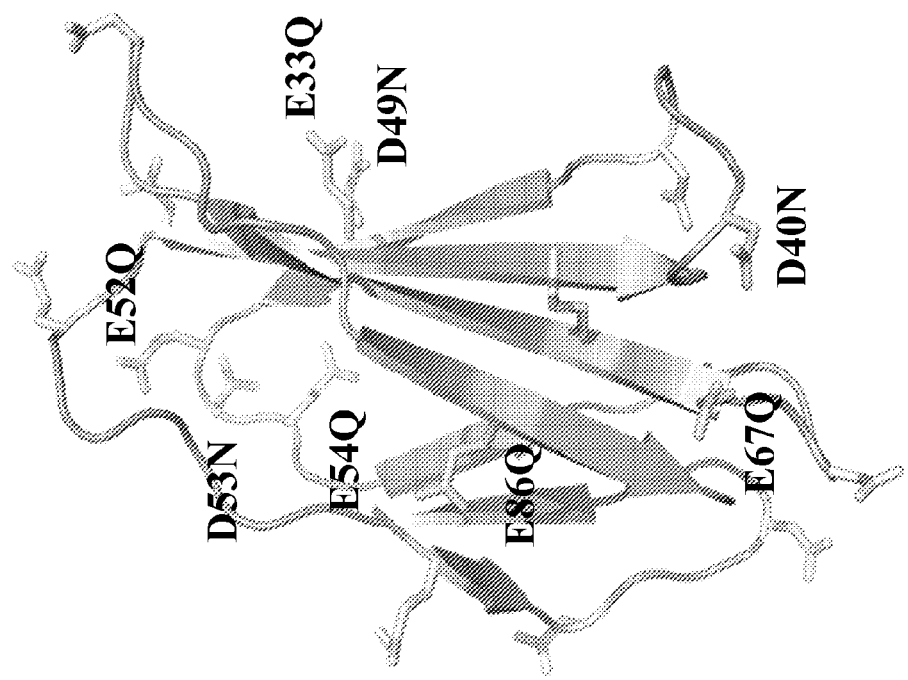

FIG. 30A. Design of charge mutants of Tn3. A cartoon representation of the three dimensional structure of Tn3 is shown (pdb code: 1ten). Residues 8-90 of SEQ ID 1 are shown, with the side chains of all Asp and Glu residues shown in yellow and white. A panel of 8 mutants were designed in which the Asp and Glu residues shown in yellow were replaced with Asn or Gln. Residue numbering is according to SEQ ID 1.

Figure 30B:
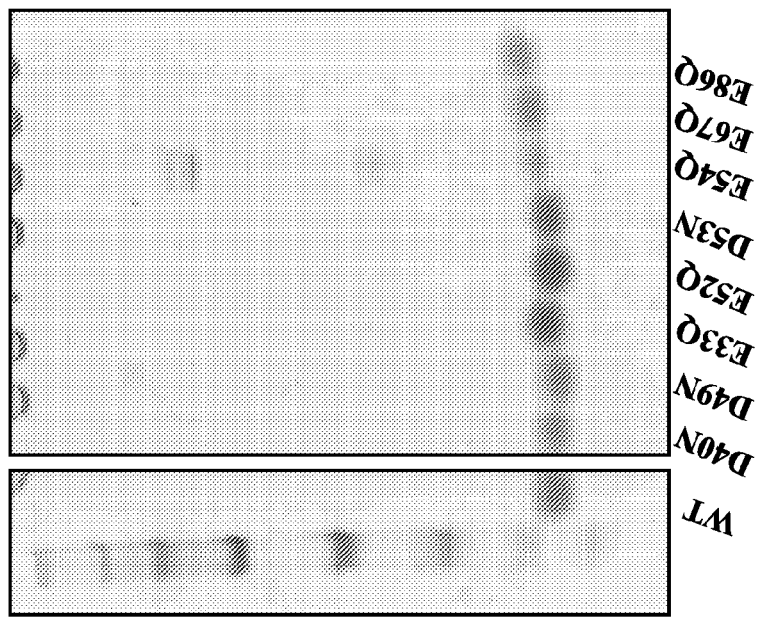

FIG. 30B. SDS-PAGE analysis of purified recombinant charge mutants of Tn3. Aliquots of each of the purified proteins was run on an SDS-PAGE gel. For comparison, the wild type protein was run in a separate lane of the same gel, and shows a similar migration rate to the various charge mutants.

FIG. 31A. Additivity of stabilizing Tn3 mutations.

A series of Tn3 point mutants were generated in which individual Asp or Glu residues were replaced with Asn or Gln. Presented here are the results from a urea denaturation experiment in which the intrinsic fluorescence measures the unfolding of the proteins. In this experiment, 5 of 8 charge mutants of the Tn3 scaffold (E33Q, D49N, E52Q, D53N, E86Q) required a higher concentration of urea to effect unfolding as compared to the wild type Tn3 scaffold.

Figure 31B:
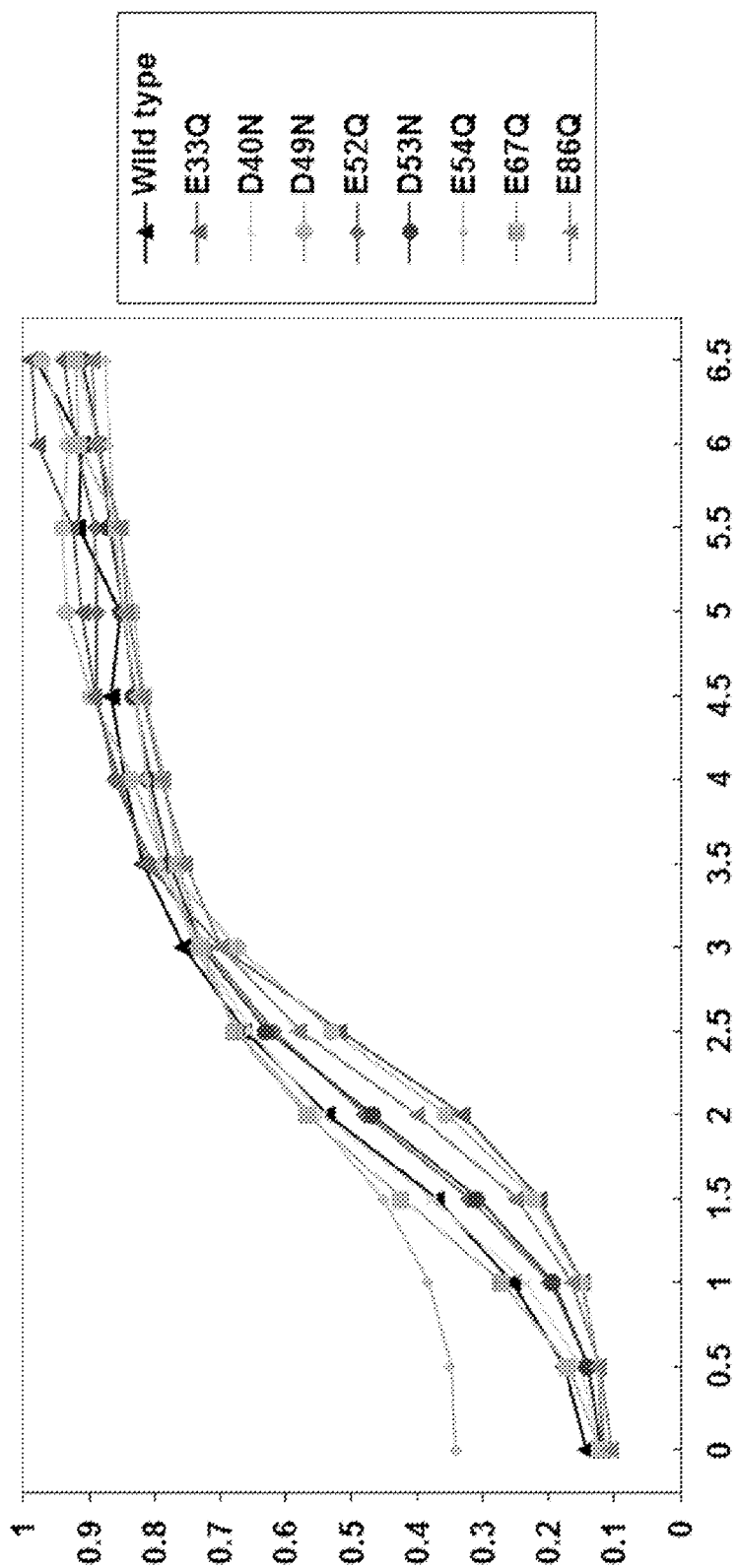

FIG. 31B. Combination of charge mutations leads to additive improvements in Tn3 stability.

Point mutations of Asp or Glu residues which enhanced the stability of wild type Tn3 were combined into double or triple mutations of Tn3. Each of the combined Tn3 mutants (E33Q/D49N, D49N/E86Q and E33Q/D49N/E86Q) exhibited greater stability than any of the corresponding point mutants or wild type Tn3.

Figure 32:
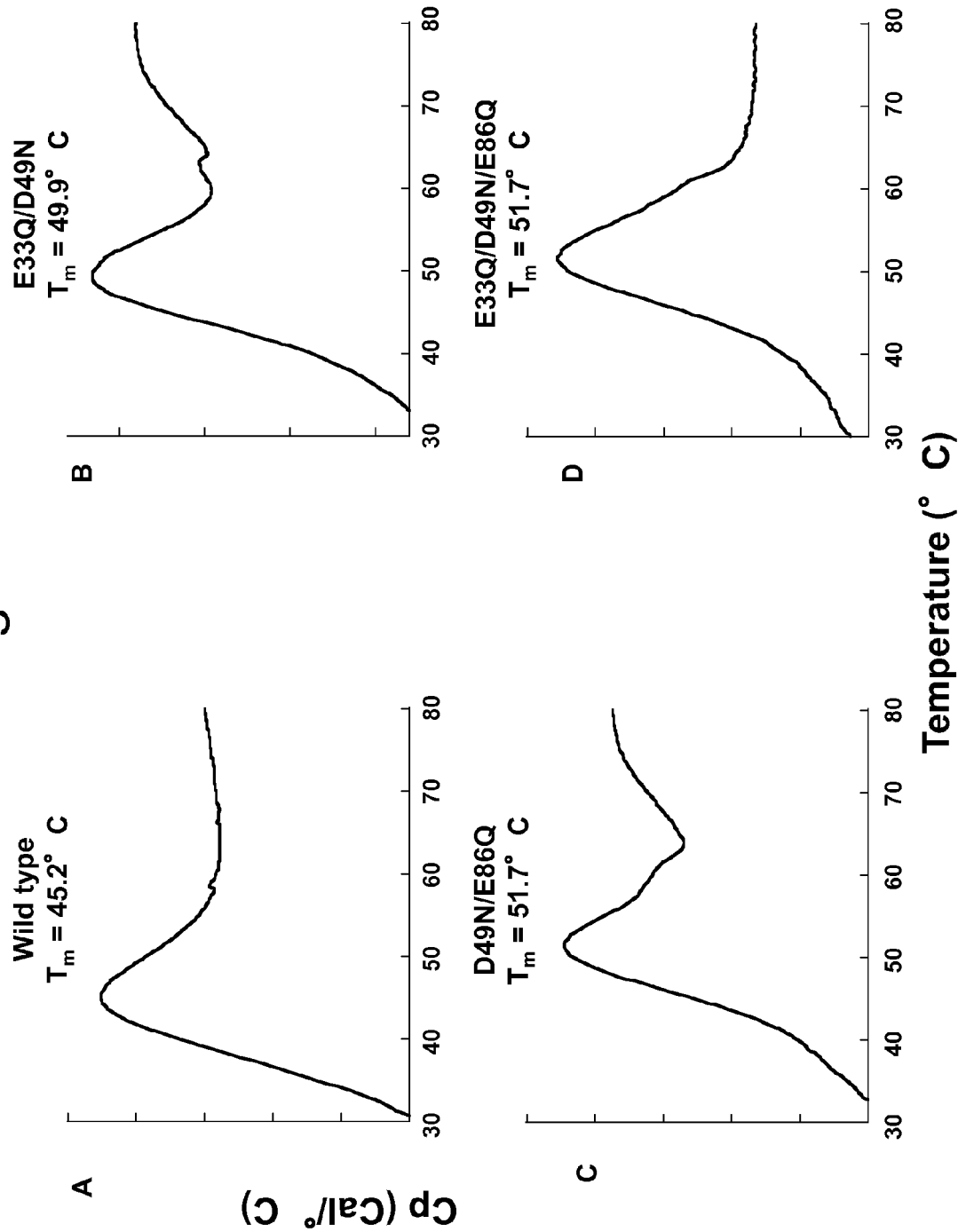

FIG. 32. Melting temperature determinations for wild type and charge engineered Tn3 scaffolds. The graph illustrates the thermal melting curve determinations of the Tn3 scaffold variants at pH 7.0 as measured by differential scanning calorimetry. The $T_m$'s were determined to be about 45° C. for wild type Tn3(A), 50° C. for E33Q/D49N Tn3 (B), 52° C. for D49N/E86Q Tn3 (C) and 52° C. for E33Q/D49N/E86Q Tn3 (D).

DETAILED DESCRIPTION

The protein scaffolds described herein have been designed to be superior both to antibody-derived fragments and to non-antibody frameworks. The major advantage of the scaffolds of the invention over antibody fragments is structural. These scaffolds are derived from whole, stable, and soluble structural modules found in human body fluid proteins and from other sources in nature (for example, but not limited to, thermophilic bacteria). Consequently, they exhibit better folding and thermostability properties than antibody fragments, whose creation involves the removal of parts of the antibody native fold, often exposing amino acid residues that, in an intact antibody, would be buried in a hydrophobic environment, such as an interface between variable and constant domains. Exposure of such hydrophobic residues to solvent increases the likelihood of aggregation.

Moreover, the scaffolds of the invention provide the functional advantages of antibody molecules. In particular, despite the fact that the scaffold is not an immunoglobulin, its overall fold is close to that of the variable region of the IgG heavy chain, making it possible to display its three loops in an analogous fashion to antibody CDRs in relative orientations. Because of this structure, the scaffolds of the invention possess antigen binding properties that are similar in nature and affinity to those of antibodies. As a result, loop randomization and shuffling strategies may be employed in vitro that are similar to the process of affinity maturation of antibodies in vivo.

The FnIII Structural Motif

The scaffolds of the present invention are based on the structure of a fibronectin module of type III (FnIII), a domain found in mammalian blood and structural proteins. This domain occurs often in the proteins sequenced to date, including fibronectins, tenascin, intracellular cytoskeletal proteins, cytokine receptors and prokaryotic enzymes (Bork and Doolittle, Proc. Natl. Acad. Sci. USA 89:8990, 1992; Bork et al., Nature Biotech. 15:553, 1997; Meinke et al., J. Bacteriol. 175:1910, 1993; Watanabe et al., J. Biol. Chem. 265:15659, 1990). Although the domain appears many times in nature, the amino acid sequences are quite divergent. In particular, these scaffolds include, the third FnIII domain of tenascin C (also known as the "Tn3" domain). The overall fold of this domain is closely related to that of the smallest functional antibody fragment, the variable region of the heavy chain, which comprises the entire antigen recognition unit in camel and llama IgG.

In addition, the Tn3 domain possesses exposed loop sequences tolerant of randomization, facilitating the generation of diverse pools of protein scaffolds capable of binding specific targets with high affinity.

These protein scaffolds may be utilized for the purpose of designing proteins which are capable of binding to virtually any compound (for example, any protein) of interest. In particular, the molecules based on the Tn3 structural motif described herein may be used as scaffolds which are subjected to directed evolution designed to randomize one or more of the loops which are analogous to the complementarity-determining regions (CDRs) of an antibody variable region. Such a directed evolution approach results in the production of antibody-like molecules with high affinities for antigens of interest. In addition, the scaffolds described herein may be used to display defined exposed loops (for example, loops previously randomized and selected on the basis of antigen binding) in order to direct the evolution of molecules that bind to such introduced loops. A selection of this type may be carried out to identify recognition molecules for any individual CDR-like loop or, alternatively, for the recognition of two or all three CDR-like loops combined into a non-linear epitope binding moiety.

A set of three loops of Tn3 corresponding to the antigen-binding loops of the IgG heavy chain run between amino acid residues 23-31 (BC), 50-56 (DE), and 75-84 (FG). The length of the BC, DE, and FG loops, 9, 6, and 10 residues, respectively, fall within the narrow range of the corresponding antigen-recognition loops found in antibody heavy chains, that is, 7-10, 4-8, and 4-28 residue lengths, respectively. Alternatively, in another embodiment, the BC, DE, and FG loops may run between amino acid residues 23 to 31, 51 to 56, and 75 to 84 respectively. Accordingly, once randomized and selected for high antigen affinity, these loops may make contacts with antigens equivalent to the contacts of the corresponding loops in antibodies. The AB, CD, and EF loops of the Tn3 domain also share this property and hence, also are available for randomization and selection for high affinity for antigens. This process may be accomplished in parallel or in series with the randomization of the BC, DE, and FG loops.

In a specific embodiment, one or more loop regions of the scaffold based on the Tn3 domain of human tenascin C comprise amino acid residues:
I. From 12 to 17 inclusive in an AB loop;
II. From 23 to 31 inclusive in a BC loop;
III. From 39 to 45 inclusive in a CD loop;
IV. From 50 to 56 inclusive in a DE loop;
V. From 60 to 66 inclusive in an EF loop; and
VI. From 75 to 84 inclusive in an FG loop.

In another specific embodiment, scaffolds of the invention comprise at least one, at least two, at least three, at least four, at least five, or at least six loops wherein a loop comprises an amino acid sequence of SEQ ID NOs: 201, 202, 203, 204, 205, or 206. In one embodiment, scaffolds of the invention comprise an AB loop having an amino acid sequence of SEQ ID NO:201. In another embodiment, scaffolds of the invention comprise a BC loop having an amino acid sequence of SEQ ID NO:202. In another embodiment, scaffolds of the invention comprise a CD loop having an amino acid sequence of SEQ ID NO:203. In another embodiment, scaffolds of the invention comprise a DE loop having an amino acid sequence of SEQ ID NO:204. In another embodiment, scaffolds of the invention comprise an EF loop having an amino acid sequence of SEQ ID NO:205. In another embodiment, scaffolds of the invention comprise a FG loop having an amino acid sequence of SEQ ID NO:206. In a specific embodiment, scaffolds of the invention comprise an AB loop having an amino acid sequence of SEQ ID NO:201, a BC loop having an amino acid sequence of SEQ ID NO:202, a CD loop having an amino acid sequence of SEQ ID NO:203, a DE loop having an amino acid sequence of SEQ ID NO:204, an EF loop having an amino acid sequence of SEQ ID NO:205, and an FG loop having an amino acid sequence of SEQ ID NO:206.

In another specific embodiment, one or more loop regions of the scaffold based on the Tn3 domain of human tenascin C comprise amino acid residues:
I. From 11 to 17 inclusive in an AB loop;
II. From 23 to 31 inclusive in a BC loop;
III. From 39 to 45 inclusive in a CD loop;
IV. From 51 to 56 inclusive in a DE loop;
V. From 60 to 67 inclusive in an EF loop; and
VI. From 75 to 84 inclusive in an FG loop.

In another specific embodiment, scaffolds of the invention comprise at least one, at least two, at least three, at least four, at least five, or at least six loops wherein a loop comprises an amino acid sequence of SEQ ID NOs: 207, 202, 203, 208, 209, or 206. In one embodiment, scaffolds of the invention comprise an AB loop having an amino acid sequence of SEQ ID NO:207. In another embodiment, scaffolds of the invention comprise a BC loop having an amino acid sequence of SEQ ID NO:202. In another embodiment, scaffolds of the invention comprise a CD loop having an amino acid sequence of SEQ ID NO:203. In another embodiment, scaffolds of the invention comprise a DE loop having an amino acid sequence of SEQ ID NO:208. In another embodiment, scaffolds of the invention comprise an EF loop having an amino acid sequence of SEQ ID NO:209. In another embodiment, scaffolds of the invention comprise a FG loop having an amino acid sequence of SEQ ID NO:206. In a specific embodiment, scaffolds of the invention comprise an AB loop having an amino acid sequence of SEQ ID NO:207, a BC loop having an amino acid sequence of SEQ ID NO:202, a CD loop having an amino acid sequence of SEQ ID NO:203, a DE loop having an amino acid sequence of SEQ ID NO:208, an EF loop having an amino acid sequence of SEQ ID NO:209, and an FG loop having an amino acid sequence of SEQ ID NO:206.

In other embodiments, scaffolds of the invention comprise loop regions that are variants of the cognate loop regions in any of SEQ ID NOs:1-32 or 68-88.

The invention provides recombinant, non-naturally occurring polypeptide scaffolds comprising, a plurality of beta strand domains linked to a plurality of loop region sequences derived from a naturally occurring protein sequence, wherein one or more of said loop region sequences vary by deletion, substitution or addition by at least one amino acid from the corresponding loop sequences in the naturally occurring protein sequence, and wherein the beta strand domains of the polypeptide scaffold have at least 50% homology to the corresponding domain sequences of a naturally occurring protein sequence. For example, such amino acid sequences may be, but are not limited to, any of SEQ ID NOs: 1-32, 60-88, and 210. In another specific embodiment, the scaffold of the invention comprises the sequence of the Tn3 domain of human tenascin C. In another embodiment, the scaffold of the invention comprises a sequence having at least 50% homology to the Tn3 domain of human tenascin C. In further embodiments, said homology to the Tn3 domain is at least 55%, at least 60%, at least 65%, at least 70%, at least 75%, at least 80%, at least 85%, at least 90%, at least 95%, at least 99%, or more. In other embodiments, the naturally occurring sequence is a protein sequence corresponding to an additional Tn3 structural motif from human tenascin C. In other embodiments, the naturally occurring sequence is a protein sequence corresponding to a Tn3 structural motif from another tenascin protein, or alternatively, a tenascin protein from another organism (such as, but not limited to, murine, porcine, bovine, or equine tenascins).

Although Tn3 represents a scaffold for the generation of antibody mimics, other molecules may be substituted for Tn3 in the molecules described herein. These include, without limitation, related Tn3 structural motifs from animals and prokaryotes. In addition, Tn3 structural motifs from other proteins may also be used. Modules from different organisms and parent proteins may be most appropriate for different applications; for example, in designing a scaffold stable at a low pH, it may be most desirable to generate that protein from organism that optimally grows at a low pH (such as, but not limited to *Sulfolobus tokodaii*). In another embodiment, related Tn3 structural motifs may be identified and utilized from hyperthermophillic bacteria such as, but not limited to *Archaeoglobus fulgidus* and *Staphylothermus marinus*, each of which exhibit optimal growth at greater than 70° C. In other embodiments, the naturally occurring sequence corresponds to a predicted Tn3 structural motif from a thermophilic organism, for example, but not limited to *Archaeoglobus fulgidus, Staphylothermus marinus, Sulfolobus acidocaldarius, Sulfolobus solfataricus*, and *Sulfolobus tokodaii*. In yet another embodiment, the scaffolds of the invention have a protein sequence having at least 30%, at least 35%, at least 40%, at least 45%, at least 50%, at least 55%, at least 60%, at least 65%, at least 70%, at least 75%, at least 80%, at least 85%, at least 90%, at least 95% or at least 99% homology to any of the sequences from a sequence corresponding to a Tn3 structural motif or a predicted Tn3 structural motif from a thermophillic organism as described above. In some embodiments, the Tn3 structural motifs from thermophillic organisms may be selected from the amino acid sequences of SEQ ID NOs.:2-4, and 68-88.

The invention also provides scaffolds of the invention with a plurality of beta strands of more than seven. In one embodiment, scaffolds of the invention comprise a plurality at least 7, at least 8, at least 9, at least 10, at least 11 or more beta strands.

The invention also provides scaffolds of the invention with a plurality of loop regions of more than six. In one embodiment, scaffolds of the invention comprise a plurality at least 7, at least 8, at least 9, at least 10, at least 11 or more loop regions.

In one embodiment, scaffolds of the invention comprise at least seven beta strands, wherein said beta strands are designated N-terminus to C-terminus A, B, C, D, E, F, and G strands. In another embodiment, the scaffolds of the invention comprise at least seven beta strands, each strand separated by a loop region wherein the loop regions are designated N-terminus to C-terminus, AB, BC, CD, DE, EF, and FG loops. In alternative embodiment, the scaffolds of the invention comprise less than seven beta strands, each strand separated by a loop region. In an alternate embodiment, the scaffolds of the invention comprise less than seven beta strands, each strand separated by a loop region.

In another specific embodiment, scaffolds of the invention comprise at least one, at least two, at least three, at least four, at least five, at least six, or at least seven beta strands, wherein said beta strands comprise amino acid sequences selected from SEQ ID NOs:228-234. In another specific embodiment, scaffolds of the invention comprise at least seven beta strands, designated N-terminus to C-Terminus A-G, wherein said A strand comprises the sequence of SEQ ID NO:228. In another specific embodiment, scaffolds of the invention comprise at least seven beta strands, designated N-terminus to C-Terminus A-G, wherein said B strand comprises the sequence of SEQ ID NO:229. In another specific embodiment, scaffolds of the invention comprise at least seven beta strands, designated N-terminus to C-Terminus A-G, wherein said C strand comprises the sequence of SEQ ID NO:230. In another specific embodiment, scaffolds of the invention comprise at least seven beta strands, designated N-terminus to C-Terminus A-G, wherein said D strand comprises the sequence of SEQ ID NO:231. In another specific embodiment, scaffolds of the invention comprise at least seven beta strands, designated N-terminus to C-Terminus A-G, wherein said E strand comprises the sequence of SEQ ID NO:232. In another specific embodiment, scaffolds of the invention comprise at least seven beta strands, designated N-terminus to C-Terminus A-G, wherein said F strand comprises the sequence of SEQ ID NO:233. In another specific embodiment, scaffolds of the invention comprise at least seven beta strands, designated N-terminus to C-Terminus A-G, wherein said G strand comprises the sequence of SEQ ID NO:234. In another specific embodiment, scaffolds of the invention comprise an A strand having the sequence of SEQ ID NO:228, a B strand having the sequence of SEQ ID NO:229, a C strand having the sequence of SEQ ID NO:230, a D strand having the sequence of SEQ ID NO:231, an E strand having the sequence of SEQ ID NO:232, an F strand having the sequence of SEQ ID NO:233 and a G strand having the sequence of SEQ ID NO:234.

In another specific embodiment, scaffolds of the invention comprise at least one, at least two, at least three, at least four, at least five, at least six, or at least seven beta strands, wherein said beta strands comprise amino acid sequences selected from SEQ ID NOs:235, 229, 230, 236, 232, 237, and 234. In another specific embodiment, scaffolds of the invention comprise at least seven beta strands, designated N-terminus to C-Terminus A-G, wherein said A strand comprises the sequence of SEQ ID NO:235. In another specific embodiment, scaffolds of the invention comprise at least seven beta strands, designated N-terminus to C-Terminus A-G, wherein said B strand comprises the sequence of SEQ ID NO:229. In another specific embodiment, scaffolds of the invention comprise at least seven beta strands, designated N-terminus to C-Terminus A-G, wherein said C strand comprises the sequence of SEQ ID NO:230. In another specific embodiment, scaffolds of the invention comprise at least seven beta strands, designated N-terminus to C-Terminus A-G, wherein said D strand comprises the sequence of SEQ ID NO:236. In another specific embodiment, scaffolds of the invention comprise at least seven beta strands, designated N-terminus to C-Terminus A-G, wherein said E strand comprises the sequence of SEQ ID NO:232. In another specific embodiment, scaffolds of the invention comprise at least seven beta strands, designated N-terminus to C-Terminus A-G, wherein said F strand comprises the sequence of SEQ ID NO:237. In another specific embodiment, scaffolds of the invention comprise at least seven beta strands, designated N-terminus to C-Terminus A-G, wherein said G strand comprises the sequence of SEQ ID NO:234. In another specific embodiment, scaffolds of the invention comprise an A strand having the sequence of SEQ ID NO:235, a B strand having the sequence of SEQ ID NO:229, a C strand having the sequence of SEQ ID NO:230, a D strand having the sequence of SEQ ID NO:236, an E strand having the sequence of SEQ ID NO:232, an F strand having the sequence of SEQ ID NO:237 and a G strand having the sequence of SEQ ID NO:234.

In another embodiment, scaffolds of the invention comprises beta strand sequences having at least 50% homology to the cognate beta strands of any of SEQ ID NOs:1-32 or 68-99. In further embodiments, said homology is at least 55%, at least 60%, at least 65%, at least 70%, at least 75%, at least 80%, at least 85%, at least 90%, at least 95%, at least 99%, or more.

The loops connecting the various strands of the protein scaffold may be randomized for length and/or sequence diversity. In one embodiment, the scaffolds of the invention have at least one loop is randomized for length and/or sequence diversity. In another embodiment, the scaffolds of the invention have at least one loop is kept constant while at least one additional loop is randomized for length and/or sequence diversity. In another embodiment, the libraries of the invention have scaffolds where at least one of loops AB, CD, and EF are kept constant while at least one of loops BC, DE, and FG are randomized for length or sequence diversity.

In a specific embodiment, the scaffolds of the invention comprise a BC loop which is randomized with the following consensus sequence: S-X-a-X-b-X-X-X-G, wherein X represents any amino acid, wherein (a) represents proline or alanine and wherein (b) represents alanine or glycine.

In another embodiment, the scaffolds of the invention have a BC loop which is randomized with the following consensus sequence: A-d-P-X-X-X-e-f-X-I-X-G (SEQ ID NO: 257), wherein X represents any amino acid and wherein (d) represents proline, glutamate or lysine, wherein (e) represents asparagine or glycine, and wherein (f) represents serine or glycine.

In another embodiment, the scaffolds of the invention have a BC loop which comprises 11 amino acids having a consensus sequence of S-P-c-X-X-X-X-X-X-T-G, (SEQ ID NO: 258), wherein X represents any amino acid and wherein (c) represents proline, serine or glycine.

In a specific embodiment, the scaffolds of the invention comprise an FG loop which is randomized with the following consensus sequence: X-a-X-X-G-X-X-X-S, wherein X represents any amino acid and wherein (a) represents asparagine, threonine or lysine.

In another specific embodiment, the scaffolds of the invention comprise an FG loop which is randomized with the following consensus sequence: X-a-X-X-X-X-b-N-P-A, wherein X represents any amino acid, wherein (a) represents asparagine, threonine or lysine and wherein (b) represents serine or glycine.

In another specific embodiment, the scaffolds of the invention comprise an FG loop which is randomized with the following consensus sequence: X-a-X-X-G-X-X-S-N-P-A, (SEQ ID NO: 259), wherein X represents any amino acid, and wherein (a) represents asparagine, threonine or lysine.

In a specific embodiment, the libraries of the invention comprise scaffolds with a DE loop, comprising 6 residues, which is randomized with the following consensus sequence: X-X-X-X-X-X, wherein X represents any amino acid.

In a specific embodiment, the scaffolds of the invention comprise an AB loop, comprising 7 residues, which is randomized with the following consensus sequence: K-X-X-X-X-X-a, wherein X represents asparagine, aspartic acid, histidine, tyrosine, isoleucine, valine, leucine, phenylalanine, threonine, alanine, proline, or serine, and wherein (a) represents serine, threonine, alanine, or glycine.

In a specific embodiment, the scaffolds of the invention comprise an AB loop, comprising 9 residues, which is randomized with the following consensus sequence: K-X-X-X-X-X-X-X-a, wherein X represents asparagine, aspartic acid, histidine, tyrosine, isoleucine, valine, leucine, phenylalanine, threonine, alanine, proline, or serine, and wherein (a) represents serine, threonine, alanine, or glycine.

In a specific embodiment, the scaffolds of the invention comprise a CD loop, comprising 7, 8, or 9 residues, wherein each residue in the CD loop is randomized and wherein X represents asparagine, aspartic acid, histidine, tyrosine, isoleucine, valine, leucine, phenylalanine, threonine, alanine, proline, or serine.

In a specific embodiment, the scaffolds of the invention comprise an EF loop comprising 8 residues, which is randomized with the following consensus sequence: X-b-L-X-P-X-c-X, wherein X represents asparagine, aspartic acid, histidine, tyrosine, isoleucine, valine, leucine, phenylalanine, threonine, alanine, proline, or serine, wherein (b) represents asparagine, lysine, arginine, aspartic acid, glutamic acid, or glycine, and wherein (c) represents isoleucine, threonine, serine, valine, alanine, or glycine.

In some embodiments, the scaffolds of the invention may comprise about 75 to about 500, about 75 to about 200, about 75 to about 100, about 75 to about 250, or about 75 to about 150 amino acids.

Disulfide-Engineered Scaffold-Based Proteins

In an effort to increase the stability of scaffolds of the invention, a bioinformatics approach was utilized to identify candidate positions suitable for engineering of a disulfide bond. However, disulfide design by manual inspection of protein structures to identify candidate residue pairs in close proximity is often unproductive due to the strict geometric constraints required by that type of bond (see Dombkowski, Bioinformatics Vol. 19 No. 14, 2003 1852-1853). Thus, the present invention provides scaffolds having disulfide bonds engineered at positions that exhibit enhanced stability as measured by thermal tolerance, resistance to chaotropic denaturation and protease treatment.

In one embodiment, the scaffolds of the invention comprise at least one, at least two, at least three, at least four, or at least five non-naturally occurring disulfide bonds. In one embodiment, the scaffolds of the invention comprise a least one non-naturally occurring disulfide bond, wherein said at least one non-naturally occurring disulfide bond stabilizes the scaffold. In another embodiment, the scaffolds of the invention comprise at least one non-naturally occurring disulfide bond located between two beta strands. For example, said at least one non-naturally occurring disulfide bond may form a link between the A strand and B strand, or between the D strand and E strand, or between the F strand and G strand, or between the C strand and F strand. In another embodiment, said at least one non-naturally occurring disulfide bond forms a first bond between the F strand and the G strand, and a second link between the C strand and F strand. In another embodiment, the scaffolds of the invention comprise at least one non-naturally occurring disulfide bond located between two loop regions. In another embodiment, the scaffolds of the invention comprise at least one non-naturally occurring disulfide bond located between a loop region and a beta strand. In another embodiment, scaffolds of the invention comprise at least one non-naturally occurring disulfide bond that is located within the same beta strand. In another embodiment, scaffolds of the invention comprise at least one non-naturally occurring disulfide bond that is located within the same loop region. In another embodiment, scaffolds of the invention comprise at least one non-naturally occurring disulfide bond, wherein the bond is located between two distinct scaffolds.

In another embodiment, the scaffolds of the invention comprise a disulfide bond that forms a multimeric scaffold (the term "multimeric" is defined as at least two or more scaffolds in association) of at least 2, at least 3, at least 4 or more scaffolds.

The increase in stability contributed by the engineering of disulfide bonds can be readily measured by techniques well known in the art, such as thermal ($T_m$) and chaotropic denaturation (such as urea, or guanidine), protease treatment (such as thermolysin) or another art accepted stability parameter. A comprehensive review of techniques used to measure protein stability can be found, for example in "Current Protocols in Molecular Biology" and "Current Protocols in Protein Science" by John Wiley and Sons. 2007.

In one embodiment the disulfide containing scaffolds of the invention exhibit an increase in stability of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% or more compared to the same scaffold prior to disulfide engineering, as measured by thermal tolerance, resistance to chaotropic denaturation, protease treatment or another stability parameter well-known in the art.

The stability of a protein may be measured by the level of fluorescence exhibited by the protein under varying conditions. There is a positive correlation between the relative unfoldedness of a protein and a change in the internal fluorescence the protein exhibits under stress. Suitable protein stability assays to measure thermal characteristics include Differential Scanning Calorimetry (DSC) and Circular Dichroism (CD). When the protein demonstrates a sizable shift in parameters measured by DSC or CD, it correlates to an unfolded structure, the temperature at which this shift is made is termed the melting temperature or ($T_m$). In one embodiment, the disulfide engineered scaffolds of the invention exhibit an increased melting temperature ($T_m$) of at least greater than 45° C., at least greater than 50° C., at least greater than 55° C., at least greater than 60° C., at least greater than 65° C., at least greater than 70° C., at least greater than 71° C., at least greater than 72° C., at least greater than 73° C., at least greater than 74° C., at least greater than 75° C., at least greater than 76° C., at least greater than 77° C., at least greater than 78° C., at least greater than 79° C., at least greater than 80° C., at least greater than 81° C., at least greater than 82° C., at least greater than 83° C., at least greater than 84° C., at least greater than 85° C., at least greater than 85° C., at least greater than 86° C., at least greater than 87° C., at least greater than 88° C., at least greater than 89° C., at least greater than 90° C., at least greater than 91° C., at least greater than 92° C., at least greater than 93° C., at least greater than 94° C., at least greater than 94° C., at least greater than, at least greater than 95° C., at least greater than 96° C., at least greater than 97° C. or at least greater than 98° C., or at least greater than 100° C., or at least greater than 105°, or at least greater than 110°, or at least greater than 120° than the melting temperature ($T_m$) exhibited by the same scaffold prior to engineering under the same experimental conditions.

In another embodiment, the disulfide engineered scaffolds of the invention exhibit an increased melting temperature ($T_m$) of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% or more compared to the same scaffold prior to disulfide engineering under the same experimental conditions.

Another assay for protein stability involves exposing a protein to a chaotropic agent, such as urea or guanidine (for example, guanidine-HCl or guanidine isothiocynate) which acts to destabilize interactions within the protein. Upon exposing the protein to increasing levels of urea or guanidine, the relative internal fluorescence is measured to asses a value in which 50% of the protein molecules are unfolded. This value is termed the $C_m$ value and represents a benchmark value for protein stability. The higher the $C_m$ value, the more stable the protein. In one embodiment, the disulfide engineered scaffolds of the invention exhibit an increased $C_m$ at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% or more compared to the same scaffold prior to disulfide engineering as measured in a urea denaturation experiment under similar conditions.

In another embodiment, the disulfide engineered scaffolds of the invention exhibit an increased $C_m$ at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% or more compared to the same scaffold prior to disulfide engineering as measured in a guanidine denaturation experiment under similar conditions.

Another assay used to assay protein stability is a protease resistance assay. In this assay, a relative level of protein stability is correlated with the resistance to protease degradation over time. The more resistant to protease treatment, the more stable the protein is. In one embodiment, the disulfide engineered scaffolds of the invention exhibit increased stability by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% or more compared to the same scaffold prior to disulfide engineering as measured in a protease resistance experiment under similar conditions.

In some instances it may be advantageous to utilize a scaffold of the invention with decreased stability, for example but not limited to, a scaffold conjugated to a cytotoxin, or a radionuclide. Such scaffolds may require faster clearance rates related to non-specific toxicity. In one embodiment, the scaffolds of the invention comprise a disulfide bond that de-stabilizes the scaffold as compared to the scaffold prior to engineering. In one embodiment the disulfide containing scaffolds of the invention exhibit a decrease in stability of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% or more compared to the same scaffold prior to disulfide engineering, as measured by thermal tolerance, resistance to chaotropic denaturation, protease treatment or another stability parameter well-known in the art under similar experimental conditions.

Scaffold Kinetics

The invention provides scaffolds that specifically bind a target (for example, a protein). In some embodiments, the target may be, for example, but not limited to, a cell-surface antigen, a soluble antigen, an immobilized antigen, an immunosilent antigen, an intracellular antigen, an intranuclear antigen, a self antigen, a non-self antigen, a cancer antigen, a bacterial antigen, or a viral antigen.

In some embodiments, scaffolds of the invention specifically bind a target with specific kinetics. In some embodiments, scaffolds of the invention may have an association rate constant or $k_{on}$ rate (scaffold(Sc)+antigen (Ag)($k_{on}$→Sc—Ag) of at least $10^5$ $M^{-1}$ $s^{-1}$, at least $1.5\times10^5 M^{-1}$ $s^{-1}$, at least $2\times10^5$ $M^{-1}$ $s^{-1}$, at least $2.5\times10^5$ $M^{-1}$ $s^{-1}$, at least $5\times10^5$ $M^{-1}$ $s^{-1}$, at least $10^6$ $M^{-1}$ $s^{-1}$, at least $5\times10^6$ $M^{-1}$ $s^{-1}$, at least $10^7$ $M^{-1}$ $s^{-1}$, at least $5\times10^7 M^{-1}$ $s^{-1}$, or at least $10^8$ $M^{-1}$ $s^{-1}$, or a $k_{on}$ rate of about $10^5$ to about $10^8 M^{-1}$ $S^{-1}$, a $k_{on}$ rate of about $1.5\times10^5$ $M^{-1}$ $s^{-1}$ to about $1\times10^7$ $M^{-1}$ $s^{-1}$, a $k_{on}$ rate of about $2\times10^5$ to about $1\times10^6 M^{-1}$ $s^{-1}$, or a $k_{on}$ rate of about $4.5\times10^5$ to about $5\times10^7$ $M^{-1}$ $s^{-1}$ as determined by a BIAcore® assay or by other assays known in the art.

In some embodiments, scaffolds of the invention may have a $k_{off}$ rate (Scaffold (Sc)+antigen (Ag $k_{off}$↔ Sc—Ag) of less than $10^{-3}$ $s^{-1}$, less than $5\times10^{-3}$ $s^{-1}$, less than $10^{-4} s^{-1}$, less than $2\times10^{-4}$ s$^{-1}$, less than $5\times10^{-4}$ s$^{-1}$, less than $10^{-5}$ s$^{-1}$, less than $5\times10^{-5}$ S$^{-1}$, less than $10^{-6}$ S$^{-1}$, less than $5\times10^{-6}$ s$^{-1}$, less than $10^{-7}$ s$^{-1}$, less than $5\times10^{-7}$ S$^{-1}$, less than $10^{-8}$ S$^{-1}$, less than $5\times10^{-8}$ s$^{-1}$, less than $10^{-9}$ s$^{-1}$, less than $5\times10^{-9}$ S$^{-1}$, or less than $10^{-10}$ s$^{-1}$, or $10^{-3}$-$10^{-10}$ s$^{-1}$, $10^{-4}$-$10^{-8}$ s$^{-1}$, or $10^{-5}$-$10^{-8}$ s$^{-1}$ as determined by a BIAcore® assay or by other assays known in the art.

In some embodiments, scaffolds of the invention may have an affinity constant or $K_a$ ($k_{on}/k_{off}$) of at least $10^2$ M$^{-1}$, at least $5\times10^2$ M$^{-1}$, at least $10^3$ M$^{-1}$, at least $5\times10^3$ M$^{-1}$, at least $10^4$ M$^{-1}$, at least $5\times10^4$ M$^{-1}$, at least $10^5$ M$^{-1}$, at least $5\times10^5$ M$^{-1}$, at least $10^6$ M$^{-1}$, at least $5\times10^6$ M$^{-1}$, at least $10^7$ M$^{-1}$, at least $5\times10^7$ M$^{-1}$, at least $10^8$ M$^{-1}$, at least $5\times10^8$ M$^{-1}$, at least $10^9$ M$^{-1}$, at least $5\times10^9$ M$^{-1}$, at least $10^{10}$ M$^{-1}$, at least $5\times10^{10}$ M$^{-1}$, at least $10^{11}$ M$^{-1}$, at least $5\times10^{11}$ M$^{-1}$, at least $10^{12}$M$^{-1}$, at least $5\times10^{12}$ M$^{-1}$, at least $10^{13}$ M$^{-1}$, at least $5\times10^{13}$ M$^{-1}$, at least $10^{14}$ M$^{-1}$, at least $5\times10^{14}$ M$^{-1}$, at least $10^{15}$ M$^{-1}$, or at least $5\times10^5$ M$^{-1}$, or $10^2$-$5\times10^5$ M$^{-1}$, $10^4$-$1\times10^{10}$ M$^{-1}$, or $10^5$-$1\times10^8$ M$^{-1}$. Scaffolds of the invention may have a $K_a$ of at most $10^{11}$M$^{-1}$, at most $5\times10^{11}$ M$^{-1}$, at most $10^{12}$ M$^{-1}$, at most $5\times10^{12}$ M$^{-1}$, at most $10^{13}$ M$^{-1}$, at most $5\times10^{13}$ M$^{-1}$, at most $10^{14}$M$^{-1}$, or at most $5\times10^{14}$ M$^{-1}$ as determined by a BIAcore® assay or by other assays known in the art.

In some embodiments, scaffolds of the invention may have a dissociation constant or $K_d$ ($k_{off}/k_{on}$) of less than $10^{-5}$ M, less than $5\times10^{-5}$M, less than $10^{-6}$M, less than $5\times10^{-6}$M, less than $10^{-7}$ M, less than $5\times10^{-7}$, less than $10^{-8}$ M, less than $5\times10^{-8}$ M, less than $10^{-9}$ M, less than $5\times10^{-9}$ M, less than $10^{-10}$ M, less than $5\times10^{-10}$ M, less than $10^{-11}$M, less than $5\times10^{-11}$ M, less than $10^{-12}$ M, less than $5\times10^{-12}$ M, less than $10^{-13}$ M, less than $5\times10^{-13}$ M, less than $10^{-14}$ M, less than $5\times10^{-14}$M, less than $10^{15}$ M, or less than $5\times10^{-15}$ M as determined by a BIAcore Assay® or by other assays known in the art.

Directed Evolution of Scaffold-Based Binding Proteins

The scaffolds described herein may be used in any technique for evolving new or improved target binding proteins. In one particular example, the target is immobilized on a solid support, such as a column resin or microtiter plate well, and the target contacted with a library of candidate scaffold-based binding proteins. Such a library may consist of clones constructed from the Tn3 motif based scaffold through randomization of the sequence and/or the length of the CDR-like loops. In one embodiment, the library may be a phage, phagemid, virus, bacterial or yeast display or a ribosome display library. If desired, this library may be an RNA-protein fusion library generated, for example, by the techniques described in Szostak et al., U.S. Pat. Nos. 6,258,558 B1, 6,261,804 B1; 5,643,768 and 5,658,754. Alternatively, it may be a DNA-protein library (for example, as described in Lohse, DNA-Protein Fusions and Uses Thereof, U.S. Ser. No. 60/110,549, filed Dec. 2, 1998, now abandoned, and U.S. Ser. No. 09/453,190, filed Dec. 2, 1999).

In this regard, bacteriophage (phage) display is one well known technique which allows one to screen large oligopeptide libraries to identify member(s) of those libraries which are capable of specifically binding to a target. Phage display is a technique by which variant polypeptides are displayed as fusion proteins to the coat protein on the surface of bacteriophage particles (Scott, J. K. and Smith, G. P. (1990) Science 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides or oligopeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments (see for example, U.S. Pat. Nos. 5,223,409, 5,403,484, 5,571,689, and 5,663,143).

Although most phage display methods have used filamentous phage, lambdoid phage display systems (WO 95/34683; U.S. Pat. No. 5,627,024), T4 phage display systems (Ren et al., Gene, 215: 439 (1998); Zhu et al., Cancer Research, 58(15): 3209-3214 (1998); Jiang et al., Infection & Immunity, 65(11): 4770-4777 (1997); Ren et al., Gene, 195(2):303-311 (1997); Ren, Protein Sci., 5: 1833 (1996); Efimov et al., Virus Genes, 10: 173 (1995)) and T7 phage display systems (Smith and Scott, Methods in Enzymology, 217: 228-257 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al. (1998) Mol. Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

For the present libraries of the invention, a bioinformatics approach was employed to determine the loop length and diversity preferences of naturally occurring Tn3 structural motifs (see Example 2). During this analysis, the preferences for loop length and sequence diversity were employed to develop a "restricted randomization" approach. In this restricted randomization, the relative loop length and sequence preferences were incorporated into the development of a library strategy. For example, it was determined, that one loop length preference for the BC loop was 9 residues. Upon further analysis of 9 residue containing BC loops it was determined whether there was a preference for a particular amino acid, or group of amino acids at that position or if the position was completely random. Integrating the loop length and sequence diversity analysis into library development resulted in a restricted randomization (i.e. certain positions within the randomized loop were limited in which amino acid could reside in that position). Examples of the restricted randomization approach are described in the Examples (see Example 2).

The invention also provides libraries (hereinafter referred to as "libraries of the invention") comprising scaffolds of the invention described herein. In one embodiment, the libraries of the invention comprise non-naturally occurring polypeptide scaffolds comprising, a plurality of beta strand domains linked to a plurality of loop region sequences derived from a naturally occurring protein sequence, wherein one or more of said loop region sequences vary by deletion, substitution or addition by at least one amino acid from the corresponding loop sequences in the naturally occurring protein sequence, and wherein the beta strand domains of the polypeptide scaffold have at least 50% homology to the corresponding domain sequences of a naturally occurring protein sequence. In some embodiments the naturally occurring sequence is the protein sequence corresponding to human tenascin Tn3. In other embodiments, the naturally occurring sequence is a protein sequence corresponding to an additional Tn3 structural motif from human tenascin C. In other embodiments, the naturally occurring sequence is a protein sequence corresponding to a Tn3 structural motif from another tenascin protein, or alternatively, a tenascin protein from another organism (such as, but not limited to, murine, porcine, bovine, or equine tenascins). In yet another embodiment, the naturally occurring sequence is a protein sequence corresponding to a Tn3 structural motif from any organism. In other embodiments, the naturally occurring sequence corresponds to a predicted Tn3 structural motif from a thermophilic organism, for example, but not limited to *Archaeoglobus fulgidus*, *Staphylothermus marinus*, *Sulfolobus acidocaldarius*, *Sulfolobus solfataricus*, and *Sulfolobus tokodaii*. In yet another embodiment, the scaffolds of the invention have a protein sequence having at least 30%, at least 35%, at least 40%, at least 45%, at least 50%, at least 55%, at least 60%, at least 65%, at least 70%, at least 75%, at least 80%, at least 85%, at least 90%, at least 95% or at least 99% homology to any of the sequences corresponding to a Tn3 structural motif or a predicted Tn3 structural motif as described above.

The library is incubated with the immobilized target, the support is washed to remove non-specific binders, and the tightest binders are eluted under very stringent conditions and subjected to PCR to recover the sequence information or to create a new library of binders which may be used to repeat the selection process, with or without further mutagenesis of the sequence. A number of rounds of selection may be performed until binders of sufficient affinity for the antigen are obtained.

In another embodiment, the libraries of the invention comprise scaffolds described herein. In one embodiment, libraries of the invention comprise scaffolds further comprising at least seven beta strands, wherein said beta strands are designated N-terminus to C-terminus A, B, C, D, E, F, and G strands. In another embodiment, the libraries of the invention comprise scaffolds which further comprise at least seven beta strands, each strand separated by a loop region wherein the loop regions are designated N-terminus to C-terminus, AB, BC, CD, DE, EF, and FG loops. In another embodiment, libraries of the invention comprise scaffolds further comprising at least seven beta strands, designated N-terminus to C-terminus A, B, C, D, E, F and G strands wherein each strand is connected by a loop region wherein the loop regions are designated N-terminus to C-terminus, AB, BC, CD, DE, EF, and FG.

In a specific embodiment, the libraries of the invention comprise scaffolds further comprising one or more loop regions of the scaffold based on the Tn3 domain of human tenascin C comprising amino acid residues:
 I. from 12 to 17 inclusive in an AB loop;
 II. from 23 to 31 inclusive in an BC loop;
 III. from 39 to 45 inclusive in an CD loop;
 IV. from 50 to 56 inclusive in an DE loop;
 V. from 60 to 66 inclusive in an EF loop; and
 VI. from 75 to 84 inclusive in an FG loop.

In another specific embodiment, libraries of the invention comprise scaffolds further comprising one or more loop regions of the scaffold based on the Tn3 domain of human tenascin C comprising amino acid residues:
 I. From 11 to 17 inclusive in an AB loop;
 II. From 23 to 31 inclusive in a BC loop;
 III. From 39 to 45 inclusive in a CD loop;
 IV. From 51 to 56 inclusive in a DE loop;
 V. From 60 to 67 inclusive in an EF loop; and
 VI. From 75 to 84 inclusive in an FG loop.

The invention also provides libraries comprising scaffolds comprising loop sequence diversity. In one embodiment, the libraries of the invention comprise scaffolds with at least one loop which contains at least one position that is randomized. In another embodiment, libraries of the invention comprise scaffolds with at least one loop which comprises at least one position that is randomized while further comprising at least one position that is held constant. In another embodiment, the libraries of the invention comprise scaffolds with a loop which comprises at least one position that is subjected to a restricted randomization. In another embodiment, the libraries of the invention comprise scaffolds with at least one loop which comprises at least one position that is subjected to a restricted randomization and further comprises at least one position that is held constant. In another embodiment, the libraries of the invention comprise scaffolds with at least one loop which comprises at least one position that is subjected to a restricted randomization and further comprises at least one position that is randomized and at least one position that is held constant.

The loops connecting the various strands of the protein scaffold may be randomized for length and/or sequence diversity. In one embodiment, the libraries of the invention have scaffolds with at least one loop is randomized for length and/or sequence diversity. In another embodiment, the libraries of the invention have scaffolds where at least one loop is kept constant while at least one additional loop is randomized for length and/or sequence diversity. In another embodiment, the libraries of the invention have scaffolds where at least one, at least two, or all three of loops AB, CD, and EF are kept constant while at least one, at least two, or all three of loops BC, DE, and FG are randomized for length or sequence diversity. In another embodiment, the libraries of the invention have scaffolds wherein at least one, at least two, or at least all three of loops AB, CD, and EF are randomized while at least one, at least two, or all three of loops BC, DE, and FG are randomized for length or sequence diversity.

In a specific embodiment, the libraries of the invention comprise scaffolds with a BC loop which is randomized with the following consensus sequence: S-X-a-X-b-X-X-X-G, wherein X represents any amino acid, wherein (a) represents proline or alanine and wherein (b) represents alanine or glycine.

In another specific embodiment the scaffolds of the invention comprise a BC loop which is randomized with the following consensus sequence: A-d-P-X-X-X-e-f-X-I-X-G (SEQ ID NO: 257), wherein X represents any amino acid and wherein (d) represents proline, glutamate or lysine, wherein (e) represents asparagine or glycine, and wherein (f) represents serine or glycine.

In another embodiment, the libraries of the invention have a BC loop which comprises 11 amino acids having a consensus sequence of S-P-c-X-X-X-X-X-X-T-G (SEQ ID NO: 258), wherein X represents any amino acid and wherein (c) represents proline, serine or glycine.

In a specific embodiment, the libraries of the invention comprise scaffolds with an FG loop which is randomized with the following consensus sequence: X-a-X-X-G-X-X-X-S, wherein X represents any amino acid and wherein (a) represents asparagine, threonine or lysine.

In another specific embodiment, the libraries of the invention comprise scaffolds with an FG loop which is randomized with the following consensus sequence: X-a-X-X-X-X-b-N-P-A, wherein X represents any amino acid, wherein (a) represents asparagine, threonine or lysine and wherein (b) represents serine or glycine.

In another specific embodiment, the libraries of the invention comprise a scaffold with an FG loop which is randomized with the following consensus sequence: X-a-X-X-G-X-X-S-N-P-A (SEQ ID NO: 259), wherein X represents any amino acid, and wherein (a) represents asparagine, threonine or lysine.

In a specific embodiment, the libraries of the invention comprise scaffolds with an AB loop, comprising 7 residues, which is randomized with the following consensus sequence: K-X-X-X-X-X-a, wherein X represents asparagine, aspartic acid, histidine, tyrosine, isoleucine, valine, leucine, phenylalanine, threonine, alanine, proline, or serine, and wherein (a) represents serine, threonine, alanine, or glycine.

In a specific embodiment, the libraries of the invention comprise scaffolds with an AB loop, comprising 9 residues, which is randomized with the following consensus sequence: K-X-X-X-X-X-X-X-a, wherein X represents asparagine, aspartic acid, histidine, tyrosine, isoleucine, valine, leucine, phenylalanine, threonine, alanine, proline, or serine, and wherein (a) represents serine, threonine, alanine, or glycine.

In a specific embodiment, the libraries of the invention comprise scaffolds with a CD loop, comprising 7, 8, or 9 residues, wherein each residue in the CD loop is randomized and wherein X represents asparagine, aspartic acid, histidine, tyrosine, isoleucine, valine, leucine, phenylalanine, threonine, alanine, proline, or serine.

In a specific embodiment, the libraries of the invention comprise scaffolds with an EF loop comprising 8 residues, which is randomized with the following consensus sequence: X-b-L-X-P-X-c-X, wherein X represents asparagine, aspartic acid, histidine, tyrosine, isoleucine, valine, leucine, phenylalanine, threonine, alanine, proline, or serine, and wherein (b) represents asparagine, lysine, serine, arginine, aspartic acid, glutamic acid, or glycine, and wherein (c) represents isoleucine, threonine, serine, valine, alanine, or glycine.

A further embodiment of the invention is a collection of isolated nucleic acid molecules encoding a library comprising the scaffolds of the invention and as described above.

A further practical consideration in the design of these Tn3 libraries was to identify an alternative to the "NNK" (N=A, G, T, C; K=G, T) mixed codon scheme typically used in degenerate oligonucleotides to code for any amino acid. Although the "NNK" mixture gives 32 different codons which code for all 20 amino acids, they are not encoded equally (Table 11). For instance, 3/32 codons in the "NNK" scheme code for Leu (CTG, CTT, TTG), but only 1/32 codes for Asp (GAT). In addition, the "NNK" mixture encodes one stop codon (TAG) and a Cys codon (TGT), neither of which is desirable when generating naive libraries. In considering an alternative scheme, we took note of the fact that synthetic antibody libraries have been described which encode CDR sequences composed of a small subset of amino acids. Antibody libraries with CDR's composed of just 4 amino acids (Tyr, Ala, Asp, Ser), or even a binary pair (Tyr, Ser) have been shown to yield specific high affinity mAbs to protein antigens (Fellouse et al, Proc Natl Acad Sci, 2004, 101:12467-72, Fellouse et al. J. Mol. Biol., 2005, 348:1153-62). Similarly, a library of 10Fn3 scaffold proteins with randomized loop sequences comprising just Tyr and Ser also yielded specific binders to a protein target (Koide et al. Proc Natl Acad, Sci, 2007, 104:66-32-7). Although libraries containing highly restricted sets of amino acids are able to produce specific binding proteins, it is likely that the diversity of binders that are obtained from a library will be limited. We therefore designed an alternate "NHT" mixed codon scheme for introducing diversity into a Tn3 library (H=A, T, C). "NHT" mixes code for a reasonable subset of the 20 amino acids, but avoid the disadvantages described with "NNK" mixed codons (Table 12). This scheme generates 12 codons that code for 12/20 amino acids, that is, each codon codes for a unique amino acid. Moreover, there are no stop or Cys codons. Accordingly, in some embodiments, scaffolds of the invention comprise codons encoded by the NHT codon scheme. In other embodiments, scaffolds of the invention comprise codons encoded by the NNK mixed codon scheme.

In other embodiments, the scaffolds of the invention may be subjected to affinity maturation. In this art-accepted process, a specific binding protein is subject to a scheme that selects for increased affinity for a specific target (see Wu et al. Proc Natl Aca Sci USA. May 1998 26; 95(11):6037-42). The resultant scaffolds of the invention may exhibit binding characteristics at least as high as compared to the scaffolds prior to affinity maturation.

In other embodiments, the scaffolds of the invention may be subjected to "loop grafting" analogous to CDR grafting for antibodies. In this art-accepted process, one or more CDRs from an antibody are "grafted" onto an acceptor antibody (or, in this example, a scaffold of the invention (see Ewert et al. Methods:2004 October; 34(2):184-99). In another embodiment, at least one loop from another scaffold may be grafted onto a scaffold of the invention.

The invention also provides methods of identifying the amino acid sequence of a protein scaffold capable of binding to target so as to form a scaffold:target complex. In one embodiment, the method comprises the steps of: a) providing a polypeptide display library of the invention; b) contacting the polypeptide display library of (a) with an immobilized or separable target; c) separating the scaffold:target complexes from the free scaffolds; d) causing the replication of the separated scaffolds of (c) so as to result in a new polypeptide display library distinguished from that in (a) by having a lowered diversity and by being enriched in displayed scaffolds capable of binding the target; e) optionally repeating steps (b), (c), and (d) with the new library of (d); and determining the nucleic acid sequence of the region encoding the displayed scaffold of a species from (d) and hence deducing the peptide sequence capable of binding to the target.

In another embodiment, the scaffolds of the invention may be further randomized after identification from a library screen. In one embodiment, methods of the invention comprise further randomizing at least one, at least two, at least three, at least four, at least five or at least six loops of a scaffold identified from a library using a method described herein. In another embodiment, the further randomized scaffold is subjected to a subsequent method of identifying a scaffold capable of binding a target, said method comprising (a) contacting said further randomized scaffold with an immobilized or separable target, (b) separating the further randomized scaffold:target complexes from the free scaffolds, (c) causing the replication of the separated scaffolds of (b), optionally repeating steps (a)-(c), and (d) determining the nucleic acid sequence of the region encoding said further randomized scaffold and hence, deducing the peptide sequence capable of binding to the target. In a further embodiment, the further randomized scaffolds comprise at least one, at least two, at least three, at least four, at least five, or at least six randomized loops which were previously randomized in the first library. In an alternate further embodiment, the further randomized scaffolds comprise at least one, at least two, at least three, at least four, at least five, or at least six randomized loops which were not previously randomized in the first library.

In another embodiment, the scaffolds of the invention may be further randomized after identification from a library screen. In one embodiment, methods of the invention comprise further randomizing at least one, at least two, at least three, at least four, at least five, at least six or at least seven strands of a scaffold identified from a library using a method described herein. In another embodiment, the further randomized scaffold is subjected to a subsequent method of identifying a scaffold capable of binding a target, said method comprising (a) contacting said further randomized scaffold with an immobilized or separable target, (b) separating the further randomized scaffold:target complexes from the free scaffolds, (c) causing the replication of the separated scaffolds of (b), optionally repeating steps (a)-(c), and (d) determining the nucleic acid sequence of the region encoding said further randomized scaffold and hence, deducing the peptide sequence capable of binding to the target. In a further embodiment, the further randomized scaffolds comprise at least one, at least two, at least three, at least four, at least five, at least six, or at least seven randomized strands which were previously randomized in the first library. In an alternate further embodiment, the further randomized scaffolds comprise at least one, at least two, at least three, at least four, at least five, at least six, or at least seven randomized strands which were not previously randomized in the first library.

In another embodiment, the scaffolds of the invention may be further randomized after identification from a library screen. In one embodiment, methods of the invention comprise further randomizing at least one, at least two, at least three, at least four, at least five, or at least six and at least one, at least two, at least three, at least four, at least five, at least six, or at least seven strands of a scaffold identified from a library using a method described herein. In another embodiment, the further randomized scaffold is subjected to a subsequent method of identifying a scaffold capable of binding a target, said method comprising (a) contacting said further randomized scaffold with an immobilized or separable target, (b) separating the further randomized scaffold:target complexes from the free scaffolds, (c) causing the replication of the separated scaffolds of (b), optionally repeating steps (a)-(c), and (d) determining the nucleic acid sequence of the region encoding said further randomized scaffold and hence, deducing the peptide sequence capable of binding to the target. In a further embodiment, the further randomized scaffolds comprise at least one, at least two, at least three, at least four, at least five, or at least six randomized loops and at least one, at least two, at least three, at least four, at least five, at least six, or at least seven strands which were previously randomized in the first library. In an alternate further embodiment, the further randomized scaffolds comprise at least one, at least two, at least three, at least four, at least five, or at least six randomized loops and at least one, at least two, at least three, at least four, at least five, at least six, or at least seven strands which were not previously randomized in the first library.

In another embodiment, one method of obtaining a scaffold of the invention involves a first randomized loop selected from the group consisting of BC, DE, and FG loops and a second loop not randomized in said library selected from the group consisting of AB, CD, and EF loops. In yet another embodiment, another method of obtaining a scaffold of the invention involves a first randomized loop selected from the group consisting of AB, CD, EF loops and a second loop not randomized in said library selected from the group consisting of BC, DE, and FG loops.

The invention also provides a method obtaining at least two scaffolds that bind to at least one or more targets. This method allows for the screening of agents that act cooperatively to elicit a particular response. It may be advantageous to use such a screen when an agonistic activity requiring the cooperation of more than one scaffold is required (for example, but not limited to, agonism of a receptor tyrosine kinase). This method allows for the screening of cooperative agents without the reformatting of the library to form multimeric complexes. In one embodiment, the method of the invention comprises contacting a target ligand with a library of the invention under conditions that allow a scaffold:target ligand complex to form, engaging said scaffolds with a crosslinking agent (defined as an agent that brings together, in close proximity, at least two identical or distinct scaffolds) wherein the crosslinking of the scaffolds elicits a detectable response and obtaining from the complex, said scaffolds that bind the target. In a further embodiment, the crosslinking agent is a scaffold specific antibody, or fragment thereof, an epitope tag specific antibody of a fragment thereof, a dimerization domain, such as Fc region, a leucine zipper motif, a chemical crosslinker, or another dimerization domain known in the art.

The invention also provides methods of detecting a compound utilizing the scaffolds of the invention. Based on the binding specificities of the scaffolds obtained by library screening, it is possible to use such scaffolds in assays to detect the specific target in a sample, such as for diagnostic methods. In one embodiment, the method of detecting a compound comprises contacting said compound in a sample with a scaffold of the invention, under conditions that allow a compound:scaffold complex to form and detecting said scaffold, thereby detecting said compound in a sample. In further embodiments, the scaffold is labeled (i.e. radiolabel, fluorescent, enzyme-linked or colorimetric label) to facilitate the detection of said compound.

The invention also provides methods of capturing a compound utilizing the scaffolds of the invention. Based on the binding specificities of the scaffolds obtained by library screening, it is possible to use such scaffolds in assays to capture the specific target in a sample, such as for purification methods. In one embodiment, the method of capturing a compound in a sample comprises contacting said compound in a sample with a scaffold of the invention under conditions that allow the formation of a compound:scaffold complex and removing said complex from the sample, thereby capturing said compound in said sample. In further embodiments, the scaffold is immobilized to facilitate the removing of the compound:scaffold complex.

In some embodiments, scaffolds isolated from libraries of the invention comprise at least one, at least two, at least four, at least five, at least six, or more randomized loop regions. In some embodiments, isolated scaffold loop sequences may be swapped from a donor scaffold to any loop in a receiver scaffold (for example, an AB loop sequence from a donor scaffold may be transferred to an y loop region in a receiver scaffold). In specific embodiments, an isolated loop sequences may be transferred to the cognate loop in the receiving scaffold (for example, an AB loop sequence from a donor scaffold may be transferred to a receiver scaffold in the AB loop position). In some embodiments, isolated loop sequences may be "mix and matched" randomly with various receiver scaffolds.

In other embodiments, isolated scaffolds sequences may be identified by the loop sequence. For example, a library is used to pan against a particular target and an collection of specific binders are isolated. The randomized loop sequences may be characterized as specific sequences independently of the scaffold background (i.e., The scaffold that binds target X wherein said scaffold comprises an AB loop sequence of SEQ ID NO:x). In alternative embodiments, where a scaffold exhibits two loop sequences that bind target X, the loop sequences may be characterized as binding target X in the absence of the scaffold sequence. In other words, it is contemplated that scaffolds isolated from a library that bind a particular target may be expressed as the variable loop sequences that bind that target independent of the scaffold backbone. This process would be analogous to the concept of CDRs in variable regions of antibodies.

In some embodiments, the invention provides scaffolds comprising sequences that specifically bind SYNAGIS®. In such embodiments, scaffolds of the invention that specifically bind SYNAGIS® may comprise an BC loop sequence selected from SEQ ID NOs:100, 102, 105, 107, and 109. In other embodiments, scaffolds of the invention that specifically bind SYNAGIS® may comprise an FG loop sequence selected from SEQ ID NOs:101, 103, 104, 106, 108, or 110. In further embodiments, scaffolds of the invention that specifically bind SYNAGIS® may comprise at least one BC loop sequence selected from SEQ ID NOs:100, 102, 105, 107, and 109; and may comprise at least one FG loop sequence selected from SEQ ID NOs:101, 103, 104, 106, 108, or 110. In other embodiments, the invention may also comprise scaffolds which compete for binding with scaffolds that specifically bind SYNAGIS®, said SYNAGIS® binders comprising one BC loop sequence selected from SEQ ID NOs:100, 102, 105, 107, and 109; and comprising an FG loop sequence selected from SEQ ID NOs:101, 103, 104, 106, 108, or 110. Competition assays may be performed as presented herein in Examples 11 and/or 14, or by other assays known in the art.

In some embodiments, the invention provides scaffolds comprising sequences that specifically bind lysozyme. In such embodiments, scaffolds of the invention that specifically bind lysozyme may comprise at least one BC loop sequence selected from SED ID NOs:111, 114, 102, 120, and 124. In other embodiments, scaffolds of the invention that specifically bind lysozyme may comprise at least one FG loop sequence selected from SEQ ID NOs: 112, 113, 115, 116, 117, 118, 119, 121, 122, or 125. In further embodiments, scaffolds of the invention that specifically bind lysozyme may comprise at least one BC loop sequence selected from SED ID NOs:111, 114, 102, 120, and 124; and may comprise at least one FG loop sequence selected from SEQ ID NOs: 112, 113, 115, 116, 117, 118, 119, 121, 122, or 125. In other embodiments, the invention may also comprise scaffolds which compete for binding with scaffolds that bind lysozyme, said lysozyme binders comprising at least one BC loop sequence selected from SED ID NOs:111, 114, 102, 120, or 124; and at least one FG loop sequence selected from SEQ ID NOs: 112, 113, 115, 116, 117, 118, 119, 121, 122, or 125. Competition assays may be performed as presented herein in Examples 11 and/or 14, or by other assays known in the art.

Multimeric Scaffolds

In addition to scaffold monomers, any of the scaffold constructs described herein may be generated as dimers or multimers of scaffolds as a means to increase the valency and thus the avidity of antigen binding. Also, any of the scaffold constructs described herein may be generated as dimers or multimers of scaffolds as a means to increase the specificity of antigen binding (for example, scaffolds may be generated that bind distinct antigens). Such multimers (multimeric scaffolds or also known herein as multivalent scaffolds) may be generated through covalent binding between individual scaffold modules, for example, by the inclusion of an amino acid linker. In other methods, the multimeric scaffolds may be assembled through use of dimerization domains known in the art. In particular examples, covalently bonded scaffolds may be generated by constructing fusion genes that encode the monomeric scaffolds or, alternatively, by engineering codons for cysteine residues into monomer sequences and allowing disulfide bond formation to occur between the expression products.

Non-covalently bonded multimeric scaffolds may also be generated by a variety of techniques. These include the introduction, into monomer sequences, of codons corresponding to positively and/or negatively charged residues and allowing interactions between these residues in the expression products (and therefore between the monomers) to occur. This approach may be simplified by taking advantage of charged residues naturally present in a monomer subunit. Another means for generating non-covalently bonded scaffolds is to introduce, into the monomer scaffold gene (for example, at the amino- or carboxy-termini), the coding sequences for proteins or protein domains known to interact. Such proteins or protein domains include coil-coil motifs, leucine zipper motifs, and any of the numerous protein subunits (or fragments thereof) known to direct formation of dimers or higher order multimers.

In some embodiments, multimeric scaffolds of the invention comprise at least one scaffold fused to any domain (or fragment) of an antibody. In some embodiments, at least one scaffold is fused to an antibody variable domain, a CH1 domain, a Ckappa domain, a Clambda domain, a CH2, or a CH3 domain. In other embodiments, at least one scaffold is fused to the CH2 domain of an antibody Fc. In such embodiments, the resulting protein, when expressed will be bivalent for a particular target through the dimerization of the CH2 and CH3 regions of the antibody Fc fragment. In further embodiments, the scaffold of the invention replaces the antibody variable region connected to the Fc fragment. In alternative embodiments, the scaffold of the invention does not replace the antibody variable region connected to the CH1-Fc fragment, Ckappa or Clambda domains.

In further embodiments, multimeric scaffolds are constructed by fusing scaffolds to the CH1 and the Ckappa or Clamdba regions of an antibody. In some embodiments, the scaffolds of the invention replace the antibody variable regions fused to the CH1 and the Ckappa or Clambda regions of an antibody. In further embodiments, scaffolds of the invention may be fused to the C-terminus of the light chain or heavy chain of an antibody. In other embodiments, scaffolds of the invention may be fused to the N-terminus of the light chain or heavy chain of an antibody.

In some embodiments, multimeric scaffolds of the invention comprise scaffolds that are specific for the same epitope. In other embodiments, multimeric scaffolds of the invention comprise scaffolds that are specific for different epitopes otherwise known as an epitope binding domain. Multimeric scaffolds of the invention may be assembled and utilized as shown in "Multispecific epitope binding proteins and uses thereof" U.S. application Ser. No. 12/182,975, filed Jul. 30, 2008 which is hereby incorporated by reference in its entirety for all purposes. Such epitope binding domains may be selected from an antibody, an antibody fragment, a diabody, an scFv, a Fab, a Fv, or a binding peptide.

In other embodiments, the epitope binding domain will be specific for the same target as that of the scaffold of the invention.

In another embodiment, the epitope binding domain will be specific for a different target as that of the scaffold of the invention.

Choosing a suitable linker for a specific case where two or more scaffolds are to be connected may depend on a variety of parameters including, e.g. the nature of the monomer domains, and/or the stability of the peptide linker towards proteolysis and oxidation.

The linker polypeptide may predominantly include amino acid residues selected from the group consisting of Gly, Ser, Ala and Thr. For example, the peptide linker may contain at least 75% (calculated on the basis of the total number of residues present in the peptide linker), such as at least 80%, e.g. at least 85% or at least 90% of amino acid residues selected from the group consisting of Gly, Ser, Ala and Thr. The peptide linker may also consist of Gly, Ser, Ala and/or Thr residues only. The linker polypeptide should have a length, which is adequate to link two or more monomer domains of the invention or two or more multimeric scaffolds of the invention in such a way that they assume the correct conformation relative to one another so that they retain the desired activity.

A suitable length for this purpose is a length of at least one and typically fewer than about 50 amino acid residues, such as 2-25 amino acid residues, 5-20 amino acid residues, 5-15 amino acid residues, 8-12 amino acid residues or 11 residues. Similarly, the polypeptide encoding a linker can range in size, e.g., from about 2 to about 15 amino acids, from about 3 to about 15, from about 4 to about 12, about 10, about 8, or about 6 amino acids. In methods and compositions involving nucleic acids, such as DNA, RNA, or combinations of both, the polynucleotide containing the linker sequence can be, e.g., between about 6 nucleotides and about 45 nucleotides, between about 9 nucleotides and about 45 nucleotides, between about 12 nucleotides and about 36 nucleotides, about 30 nucleotides, about 24 nucleotides, or about 18 nucleotides. Likewise, the amino acid residues selected for inclusion in the linker polypeptide should exhibit properties that do not interfere significantly with the activity or function of the polypeptide multimer. Thus, the peptide linker should on the whole not exhibit a charge which would be inconsistent with the activity or function of the polypeptide multimer, or interfere with internal folding, or form bonds or other interactions with amino acid residues in one or more of the monomer domains which would seriously impede the binding of the polypeptide multimer to specific targets.

The peptide linker may also be selected from a library where the amino acid residues in the peptide linker are randomized for a specific set of monomer domains in a particular polypeptide multimer. A flexible linker could be used to find suitable combinations of monomer domains, which is then optimized using this random library of variable linkers to obtain linkers with optimal length and geometry. The optimal linkers may contain the minimal number of amino acid residues of the right type that participate in the binding to the target and restrict the movement of the monomer domains relative to each other in the polypeptide multimer when not bound to specific targets.

The use of naturally occurring as well as artificial peptide linkers to connect polypeptides into novel linked fusion polypeptides is well known in the literature (Hallewell et al. (1989), J. Biol. Chem. 264, 5260-5268; Alfthan et al. (1995), Protein Eng. 8, 725-731; Robinson & Sauer (1996), Biochemistry 35, 109-116; Khandekar et al. (1997), J. Biol. Chem. 272, 32190-32197; Fares et al. (1998), Endocrinology 139, 2459-2464; Smallshaw et al. (1999), Protein Eng. 12, 623-630; U.S. Pat. No. 5,856,456).

As mentioned above, it is generally preferred that the peptide linker possess at least some flexibility. Accordingly, in some embodiments, the peptide linker contains 1-25 glycine residues, 5-20 glycine residues, 5-15 glycine residues or 8-12 glycine residues. The peptide linker will typically contain at least 50% glycine residues, such as at least 75% glycine residues. In some embodiments of the invention, the peptide linker comprises glycine residues only. In specific embodiments, linker sequences may comprise a sequence of (G-G-G-G-S)$_x$ (SEQ ID NO: 260) where x is a positive integer. In another specific embodiment, linker sequences may comprise a sequence of (G-A)$_x$ where x is a positive integer. In another specific embodiment, linker sequences may comprise a sequence of (G-G-G-T-P-T)$_x$ (SEQ ID NO: 261) where x is a positive integer.

In some cases it may be desirable or necessary to provide some rigidity into the peptide linker. This may be accomplished by including proline residues in the amino acid sequence of the peptide linker. Thus, in another embodiment of the invention, the peptide linker may comprise at least one proline residue in the amino acid sequence of the peptide linker. For example, the peptide linker has an amino acid sequence, wherein at least 25%, such as at least 50%, e.g. at least 75%, of the amino acid residues are proline residues. In one particular embodiment of the invention, the peptide linker comprises proline residues only.

In some embodiments of the invention, the peptide linker is modified in such a way that an amino acid residue comprising an attachment group for a non-polypeptide moiety is introduced. Examples of such amino acid residues may be a cysteine residue (to which the non-polypeptide moiety is then subsequently attached) or the amino acid sequence may include an in vivo N-glycosylation site (thereby attaching a sugar moiety (in vivo) to the peptide linker). An additional option is to genetically incorporate non-natural amino acids using evolved tRNAs and tRNA synthetases (see, e.g., U.S. patent application Publication Ser. No. 2003/0082575) into the monomer domains or linkers. For example, insertion of keto-tyrosine allows for site-specific coupling to expressed monomer domains or multimers.

Sometimes, the amino acid sequences of all peptide linkers present in the polypeptide multimer will be identical. Alternatively, the amino acid sequences of all peptide linkers present in the polypeptide multimer may be different.

Fusions

The scaffolds described herein may be fused to other protein domains. For example, these scaffolds may be integrated with the human immune response by fusing the constant region of an IgG (Fc) with a scaffold, through the N or C-terminus The Fc fusion molecule activates the complement component of the immune response and increases the therapeutic value of the protein scaffold. Similarly, a fusion between a scaffold and a complement protein, such as C1q, may be used to target cells, and a fusion between scaffold and a toxin may be used to specifically destroy cells that carry a particular antigen.

Additionally, various publications describe methods for obtaining physiologically active molecules whose half-lives are modified either by introducing an FcRn-binding polypeptide into the molecules (WO 97/43316; U.S. Pat. Nos. 5,869, 046; 5,747,035; WO 96/32478; WO 91/14438) or by fusing the molecules with antibodies whose FcRn-binding affinities are preserved but affinities for other Fc receptors have been greatly reduced (WO 99/43713) or fusing with FcRn binding domains of antibodies (WO 00/09560; U.S. Pat. No. 4,703, 039). Specific techniques and methods of increasing half-life of physiologically active molecules can also be found in U.S. Pat. No. 7,083,784 granted Aug. 1, 2006 entitled "Antibodies with Increased Half-lives" which is hereby incorporated by reference for all purposes. Specifically, it is contemplated that the scaffolds of the invention can be fused to an Fc region from an IgG, wherein said Fc region comprises amino acid residue mutations (as numbered by the EU index in Kabat): M252Y/S254T/T256E or H433K/N434F/Y436H.

In addition, the scaffolds of the invention may be fused with molecules that increases or extends in vivo or serum half life. In some embodiments, the scaffolds of the invention associate with albumin, such as human serum albumin (HSA), polyethylene glycol (PEG), polysaccharides, immunoglobulin molecules (IgG), complement, hemoglobin, a binding peptide, lipoproteins and other factors to increase its half-life in the bloodstream and/or its tissue penetration. Any of these fusions may be generated by standard techniques, for example, by expression of the fusion protein from a recombinant fusion gene constructed using publicly available gene sequences.

Also, the scaffolds of the invention may bind or associate with molecules that increases or extends in vivo or serum half life. In some embodiments, the scaffolds of the invention associate with albumin, polyethylene glycol (PEG), polysaccharides, immunoglobulin molecules or immunoglobulin molecules having Fc mutations that increase serum half life, complement, hemoglobin, lipoproteins and other factors to increase serum half life. Any of these fusions may be generated by standard techniques, for example, by expression of the fusion protein from a recombinant fusion gene constructed using publicly available gene sequences.

The term "polyethylene glycol" or "PEG" means a polyethylene glycol compound or a derivative thereof, with or without coupling agents, coupling or activating moieties (e.g., with thiol, triflate, tresylate, azirdine, oxirane, N-hydroxysuccinimide or a maleimide moiety). The term "PEG" is intended to indicate polyethylene glycol of a molecular weight between 500 and 150,000 Da, including analogues thereof, wherein for instance the terminal OH-group has been replaced by a methoxy group (referred to as mPEG).

In one embodiment, the scaffolds are derivatized with polyethylene glycol (PEG). PEG is a linear, water-soluble polymer of ethylene oxide repeating units with two terminal hydroxyl groups. PEGs are classified by their molecular weights which typically range from about 500 daltons to about 40,000 daltons. In a presently preferred embodiment, the PEGs employed have molecular weights ranging from 5,000 daltons to about 20,000 daltons. PEGs coupled to the scaffolds of the invention can be either branched or unbranched. (See, for example, Monfardini, C. et al. 1995 Bioconjugate Chem 6:62-69). PEGs are commercially available from Nektar Inc., Sigma Chemical Co. and other companies. Such PEGs include, but are not limited to, monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), and monomethoxypolyethylene glycol-imidazolyl-carbonyl (MePEG-IM).

Briefly, in one embodiment, the hydrophilic polymer which is employed, for example, PEG, is capped at one end by an unreactive group such as a methoxy or ethoxy group. Thereafter, the polymer is activated at the other end by reaction with a suitable activating agent, such as cyanuric halides (for example, cyanuric chloride, bromide or fluoride), diimadozle, an anhydride reagent (for example, a dihalosuccinic anhydride, such as dibromosuccinic anhydride), acyl azide, p-diazoiumbenzyl ether, 3-(p-diazoniumphenoxy)-2-hydroxypropylether) and the like. The activated polymer is then reacted with a polypeptide as described herein to produce a polypeptide derivatized with a polymer. Alternatively, a functional group in the scaffolds of the invention can be activated for reaction with the polymer, or the two groups can be joined in a concerted coupling reaction using known coupling methods. It will be readily appreciated that the polypeptides of the invention can be derivatized with PEG using a myriad of other reaction schemes known to and used by those of skill in the art.

In some embodiments, scaffolds of the invention are engineered to provide reactive groups for conjugation. In such scaffolds, the N-terminus and/or C-terminus may also serve to provide reactive groups for conjugation. In other embodiments, the N-terminus may be conjugated to one moiety (such as, but not limited to PEG) while the C-terminus is conjugated to another moiety (such as, but not limited to biotin), or vice versa.

The term "in vivo half-life" is used in its normal meaning, i.e., the time at which 50% of the biological activity of the polypeptide is still present in the body/target organ, or the time at which the activity of the polypeptide is 50% of its initial value. As an alternative to determining functional in vivo half-life, "serum half-life" may be determined, i.e., the time at which 50% of the polypeptide molecules circulate in the plasma or bloodstream prior to being cleared. Determination of serum-half-life is often more simple than determining functional half-life and the magnitude of serum-half-life is usually a good indication of the magnitude of functional in vivo half-life. Alternative terms to serum half-life include plasma half-life, circulating half-life, circulatory half-life, serum clearance, plasma clearance, and clearance half-life. The functionality to be retained is normally selected from procoagulant, proteolytic, co-factor binding, receptor binding activity, or other type of biological activity associated with the particular protein.

The term "increased" with respect to the functional in vivo half-life or plasma half-life is used to indicate that the relevant half-life of the polypeptide is statistically significantly increased relative to that of a reference molecule (for example an unmodified polypeptide), as determined under comparable conditions. For instance the relevant half-life may be increased by at least about 25%, such as by at least about 50%, e.g., by at least about 100%, at least about 150%, at least about 200%, at least about 250%, or at least about 500% compared to an unmodified reference molecule. In other embodiments, the half-life may be increased by about at least 1 fold, at least 2 fold, at least 3 fold, at least 4 fold, at least 5 fold, at least 10 fold, at least 20 fold, or at least 50 fold as compared to an unmodified reference molecule.

Randomization Embodiments

In one aspect, the invention provides randomized scaffolds. In another embodiment, the invention also provides multimeric randomized scaffolds. In another embodiment, the invention also provides disulfide engineered randomized scaffolds. In yet another embodiment, the invention provides libraries comprising randomized scaffolds. The randomization scheme of the scaffolds of the invention and the display libraries comprising said scaffolds, collectively referred to in this section as "the present invention" is provided below.

In one embodiment, scaffolds of the invention comprise at least 1, at least 2, at least 3, at least 4, at least 5, or at least 6 randomized loops. In another embodiment, the present invention comprise at least one randomized loop wherein, at least the AB, or at least the BC, or at least the CD, or at least the DE, or at least the EF, or at least the FG loop is randomized.

In one embodiment, the present invention comprise one randomized loop. For example, the present invention comprise a randomized AB loop. In another embodiment, the present invention comprise a randomized BC loop. In another embodiment, the present invention comprise a randomized CD loop. In another embodiment, the present invention comprise a randomized DE loop. In another embodiment, the present invention comprise a randomized EF loop. In another embodiment, the present invention comprise a randomized FG loop.

In one embodiment, the present invention comprise two randomized loops. For example, the present invention comprise randomized AB and BC loops. In another embodiment, the present invention comprise randomized AB and CD loops. In another embodiment, the present invention comprise randomized AB and DE loops. In another embodiment, the present invention comprise randomized AB and EF loops. In another embodiment, the present invention comprise randomized AB and FG loops. In another embodiment, the present invention comprise randomized BC and CD loops. In another embodiment, the present invention comprise randomized BC and DE loops. In another embodiment, the present invention comprise randomized BC and EF loops. In another embodiment, the present invention comprise randomized BC and FG loops. In another embodiment, the present invention comprise randomized CD and DE loops. In another embodiment, the present invention comprise randomized CD and EF loops. In another embodiment, the present invention comprise randomized CD and FG loops. In another embodiment, the present invention comprise randomized DE and EF loops. In another embodiment, the present invention comprise randomized DE and FG loops. In another embodiment, the present invention comprise randomized EF and FG loops.

In another embodiment, the present invention comprise three randomized loops. For example, in one embodiment, the present invention comprise randomized AB, BC and CD loops. In another embodiment, the present invention comprise randomized AB, BC and DE loops. In another embodiment, the present invention comprise randomized AB, BC and EF loops. In another embodiment, the present invention comprise randomized AB, BC and FG loops. In another embodiment, the present invention comprise randomized AB, CD and DE loops. In another embodiment, the present invention comprise randomized AB, CD and EF loops. In another embodiment, the present invention comprise randomized AB, CD and FG loops. In another embodiment, the present invention comprise randomized AB, DE and EF loops. In another embodiment, the present invention comprise randomized AB, DE and FG loops. In another embodiment, the present invention comprise randomized AB, EF and FG loops. In another embodiment, the present invention comprise randomized BC, CD and DE loops. In another embodiment, the present invention comprise randomized BC, CD and EF loops. In another embodiment, the present invention comprise randomized BC, CD and FG loops. In another embodiment, the present invention comprise randomized BC, DE and EF loops. In another embodiment, the present invention comprise randomized BC, DE and FG loops. In another embodiment, the present invention comprise randomized BC, EF and FG loops. In another embodiment, the present invention comprise randomized CD, DE and EF loops. In another embodiment, the present invention comprise randomized CD, DE and FG loops. In another embodiment, the present invention comprise randomized CD, EF and FG loops. In another embodiment, the present invention comprise randomized DE, EF and FG loops.

In another embodiment, the present invention comprise four randomized loops. In another embodiment, the present invention comprise randomized AB, BC, CD and DE loops. In another embodiment, the present invention comprise randomized AB, BC, CD and EF loops. In another embodiment, the present invention comprise randomized AB, BC, CD and FG loops. In another embodiment, the present invention comprise randomized AB, CD, DE and EF loops. In another embodiment, the present invention comprise randomized AB, CD, DE and FG loops. In another embodiment, the present invention comprise randomized AB, CD, EF and FG loops. In another embodiment, the present invention comprise randomized AB, DE, EF and FG loops. In another embodiment, the present invention comprise randomized BC, CD, DE and EF loops. In another embodiment, the present invention comprise randomized BC, CD, DE and FG loops. In another embodiment, the present invention comprise randomized BC, DE, EF and FG loops. In another embodiment, the present invention comprise randomized CD, DE, EF and FG loops.

In another embodiment, the present invention comprise five randomized loops. In another embodiment, the present invention comprise randomized AB, BC, CD, DE, and EF loops. In another embodiment, the present invention comprise randomized AB, BC, CD, DE, and FG loops. In another embodiment, the present invention comprise randomized AB, CD, DE, EF and FG loops. In another embodiment, the present invention comprise randomized AB, BC, DE, EF and FG loops. In another embodiment, the present invention comprise randomized AB, BC, CD, EF, and FG loops. In another embodiment, the present invention comprise randomized BC, CD, DE, EF and FG loops.

In another embodiment, the present invention comprise 6 randomized loops. In one embodiment, the present invention comprise randomized AB, BC, CD, DE, EF, and FG loops.

In a specific embodiment, the present invention comprise 3 randomized loops wherein the BC, DE, and FG loops are all randomized. In another embodiment, protein the present invention comprise at least one randomized loop wherein, at least the AB, at least the CD, at least the EF loops are randomized. In a specific embodiment, the present invention comprise 3 randomized loops wherein the AB, CD, and EF loops are all randomized. In another specific embodiment, the present invention comprise randomized loops, wherein the AB, BC, CD, DE, EF, and FG loops are all randomized.

In another embodiment, the present invention comprise randomized loops wherein at least one, or at least two, or at least three, or at least four, or at least five, or at least six loops are not randomized.

In one embodiment, the present invention comprise at least one randomized loop, wherein one loop is not randomized. In one embodiment, the present invention comprise at least one randomized loop, wherein the AB loop is not randomized. In another embodiment, the present invention comprise at least one randomized loop, wherein the BC loop is not randomized. In another embodiment, the present invention comprise at least one randomized loop, wherein the CD loop is not randomized. In another embodiment, the present invention comprise at least one randomized loop, wherein the DE loop is not randomized. In another embodiment, the present invention comprise at least one randomized loop, wherein the EF loop is not randomized. In another embodiment, the present invention comprise at least one randomized loop, wherein the FG loop is not randomized.

In another embodiment, the present invention comprise at least one randomized loop wherein two loops are not randomized. In one embodiment, the present invention comprise at least one randomized loop wherein at least the AB and BC loops are not randomized. In another embodiment, the present invention comprise at least one randomized loop wherein at least the AB and CD loops are not randomized. In another embodiment, the present invention comprise at least one randomized loop wherein at least the AB and DE loops are not randomized. In another embodiment, the present invention comprise at least one randomized loop wherein at least the AB and EF loops are not randomized. In another embodiment, the present invention comprise at least one randomized loop wherein at least the AB and FG loops are not randomized. In another embodiment, the present invention comprise at least one randomized loop wherein at least the BC and CD loops are not randomized. In another embodiment, the present invention comprise at least one randomized loop wherein at least the BC and DE loops are not randomized. In another embodiment, the present invention comprise at least one randomized loop wherein at least the BC and EF loops are not randomized. In another embodiment, the present invention comprise at least one randomized loop wherein at least the BC and FG loops are not randomized. In another embodiment, the present invention comprise at least one randomized loop wherein at least the CD and DE loops are not randomized. In another embodiment, the present invention comprise at least one randomized loop wherein at least the CD and EF loops are not randomized. In another embodiment, the present invention comprise at least one randomized loop wherein at least the CD and FG loops are not randomized. In another embodiment, the present invention comprise at least one randomized loop wherein at least the DE and EF loops are not randomized. In another embodiment, the present invention comprise at least one randomized loop wherein at least the DE and FG loops are not randomized. In another embodiment, the present invention comprise at least one randomized loop wherein at least the EF and FG loops are not randomized.

In another embodiment, the present invention comprise at least one randomized loop wherein three loops are not randomized. In another embodiment, the present invention comprise at least one randomized loop wherein at least the AB, BC, and CD loops are not randomized. In another embodiment, the present invention comprise at least one randomized loop wherein at least the AB, BC, and DE loops are not randomized. In another embodiment, the present invention comprise at least one randomized loop wherein at least the AB, BC, and EF loops are not randomized. In another embodiment, the present invention comprise at least one randomized loop wherein at least the AB, BC, and FG loops are not randomized. In another embodiment, the present invention comprise at least one randomized loop wherein at least the AB, CD, and DE loops are not randomized. In another embodiment, the present invention comprise at least one randomized loop wherein at least the AB, CD, and EF loops are not randomized. In another embodiment, the present invention comprise at least one randomized loop wherein at least the AB, CD, and FG loops are not randomized. In another embodiment, the present invention comprise at least one randomized loop wherein at least the AB, DE, and EF loops are not randomized. In another embodiment, the present invention comprise at least one randomized loop wherein at least the AB, EF, and FG loops are not randomized. In another embodiment, the present invention comprise at least one randomized loop wherein at least the BC, CD, and DE loops are not randomized. In another embodiment, the present invention comprise at least one randomized loop wherein at least the BC, CD, and EF loops are not randomized. In another embodiment, the present invention comprise at least one randomized loop wherein at least the BC, CD, and FG loops are not randomized. In another embodiment, the present invention comprise at least one randomized loop wherein at least the BC, DE, and EF loops are not randomized. In another embodiment, the present invention comprise at least one randomized loop wherein at least the BC, EF, and FG loops are not randomized. In another embodiment, the present invention comprise at least one randomized loop wherein at least the CD, DE, and EF loops are not randomized. In another embodiment, the present invention comprise at least one randomized loop wherein at least the CD, DE, and FG loops are not randomized. In another embodiment, the present invention comprise at least one randomized loop wherein at least the CD, EF, and FG loops are not randomized. In another embodiment, the present invention comprise at least one randomized loop wherein at least the DE, EF, and FG loops are not randomized.

In another embodiment, the present invention comprise at least one randomized loop, wherein four loops are not randomized. In another embodiment, the present invention comprise at least one randomized loop wherein at least the AB, BC, CD, and DE loops are not randomized. In another embodiment, the present invention comprise at least one randomized loop wherein at least the AB, BC, CD, and EF loops are not randomized. In another embodiment, the present invention comprise at least one randomized loop wherein at least the AB, BC, CD, and FG loops are not randomized. In another embodiment, the present invention comprise at least one randomized loop wherein at least the AB, CD, DE, and EF loops are not randomized. In another embodiment, the present invention comprise at least one randomized loop wherein at least the AB, CD, DE, and FG loops are not randomized. In another embodiment, the present invention comprise at least one randomized loop wherein at least the AB, CD, EF, and FG loops are not randomized. In another embodiment, the present invention comprise at least one randomized loop wherein at least the AB, DE, EF, and FG loops are not randomized. In another embodiment, the present invention comprise at least one randomized loop wherein at least the BC, CD, DE and EF loops are not randomized. In another embodiment, the present invention comprise at least one randomized loop wherein at least the BC, CD, DE and FG loops are not randomized. In another embodiment, the present invention comprise at least one randomized loop wherein at least the BC, DE, EF, and FG loops are not randomized. In another embodiment, the present invention comprise at least one randomized loop wherein at least the CD, DE, EF and FG loops are not randomized.

In another embodiment, the present invention comprise at least one randomized loop, wherein five loops are not randomized. In another embodiment, the present invention comprise at least one randomized loop wherein at least the AB, BC, CD, DE and EF loops are not randomized. In another embodiment, the present invention comprise at least one randomized loop wherein at least the AB, BC, CD, DE and FG loops are not randomized. In another embodiment, the present invention comprise at least one randomized loop wherein at least the AB, CD, DE, EF and FG loops are not randomized. In another embodiment, the present invention comprise at least one randomized loop wherein at least the AB, BC, DE, EF and FG loops are not randomized. In another embodiment, the present invention comprise at least one randomized loop wherein at least the AB, BC, CD, EF and FG loops are not randomized. In another embodiment, the present invention comprise at least one randomized loop wherein at least the BC, CD, DE, EF and FG loops are not randomized.

In another embodiment, the present invention comprise at least one randomized loop, wherein six loops are not randomized. In another embodiment, the present invention comprise at least one randomized loop wherein at least the AB, BC, CD, DE, EF and FG loops are not randomized.

The invention also provides scaffolds wherein the beta strand regions are randomized wherein said beta strand randomized scaffold exhibits a stability and specific target affinity at least as high as the same scaffold prior to beta strand randomization measured under similar conditions. In one embodiment, the present invention comprise at least one, at least two, at least three, at least four, at least five, or at least size beta strands are randomized. In another embodiment, the present invention comprise at least the A strand, or at least the B strand, or at least the C strand, or at least the D strand, or at least the E strand, or at least the F strand is randomized.

In another embodiment, the present invention comprise two beta strands that are randomized. In another embodiment, the present invention comprise a randomized A strand and B strand. In another embodiment, the present invention comprise a randomized A strand and C strand. In another embodiment, the present invention comprise a randomized A strand and D strand. In another embodiment, the present invention comprise a randomized A strand and E strand. In another embodiment, the present invention comprise a randomized A strand and F strand. In another embodiment, the present invention comprise a randomized A strand and G strand. In another embodiment, the present invention comprise a randomized B strand and C strand. In another embodiment, the present invention comprise a randomized B strand and D strand. In another embodiment, the present invention comprise a randomized B strand and E strand. In another embodiment, the present invention comprise a randomized B strand and F strand. In another embodiment, the present invention comprise a randomized B strand and G strand. In another embodiment, the present invention comprise a randomized C strand and D strand. In another embodiment, the present invention comprise a randomized C strand and E strand. In another embodiment, the present invention comprise a randomized C strand and F strand. In another embodiment, the present invention comprise a randomized C strand and G strand. In another embodiment, the present invention comprise a randomized D strand and E strand. In another embodiment, the present invention comprise a randomized D strand and F strand. In another embodiment, the present invention comprise a randomized D strand and G strand. In another embodiment, the present invention comprise a randomized E strand and F strand. In another embodiment, the present invention comprise a randomized E strand and G strand. In another embodiment, the present invention comprise a randomized F strand and G strand.

In another embodiment, the present invention comprise three beta strands that are randomized. In one embodiment, the present invention comprise a randomized A, B, and C strand. In another embodiment, the present invention comprise a randomized A, B, and D strand. In another embodiment, the present invention comprise a randomized A, B, and E strand. In another embodiment, the present invention comprise a randomized A, B, and F strand. In another embodiment, the present invention comprise a randomized A, B, and G strand. In another embodiment, the present invention comprise a randomized A, C, and D strand. In another embodiment, the present invention comprise a randomized A, C, and E strand. In another embodiment, the present invention comprise a randomized A, C, and F strand. In another embodiment, the present invention comprise a randomized A, C, and G strand. In another embodiment, the present invention comprise a randomized A, D, and E strand. In another embodiment, the present invention comprise a randomized A, D, and F strand. In another embodiment, the present invention comprise a randomized A, D, and G strand. In another embodiment, the present invention comprise a randomized B, C, and D strand. In another embodiment, the present invention comprise a randomized B, C, and E strand. In another embodiment, the present invention comprise a randomized B, C, and F strand. In another embodiment, the present invention comprise a randomized B, C, and G strand. In another embodiment, the present invention comprise a randomized B, D, and E strand. In another embodiment, the present invention comprise a randomized B, D, and F strand. In another embodiment, the present invention comprise a randomized B, D, and G strand. In another embodiment, the present invention comprise a randomized C, D, and E strand. In another embodiment, the present invention comprise a randomized C, D, and F strand. In another embodiment, the present invention comprise a randomized C, D, and G strand. In another embodiment, the present invention comprise a randomized C, E, and F strand. In another embodiment, the present invention comprise a randomized C, E, and G strand. In another embodiment, the present invention comprise a randomized C, F, and G strand. In another embodiment, the present invention comprise a randomized D, E, and F strand. In another embodiment, the present invention comprise a randomized D, F, and G strand. In another embodiment, the present invention comprise a randomized E, F, and G strand.

In one embodiment the present invention comprise four beta strands that are randomized. In another embodiment, the present invention comprise a randomized A, B, C, and D strand. In another embodiment, the present invention comprise a randomized A, B, C, and E strand. In another embodiment, the present invention comprise a randomized A, B, C, and F strand. In another embodiment, the present invention comprise a randomized A, B, C, and G strand. In another embodiment, the present invention comprise a randomized A, C, D, and E strand. In another embodiment, the present invention comprise a randomized A, C, D, and F strand. In another embodiment, the present invention comprise a randomized A, C, D, and G strand. In another embodiment, the present invention comprise a randomized A, D, E, and F strand. In another embodiment, the present invention comprise a randomized A, D, E, and G strand. In another embodiment, the present invention comprise a randomized A, E, F, and G strand. In another embodiment, the present invention comprise a randomized B, C, D, and E strand. In another embodiment, the present invention comprise a randomized B, C, D, and F strand. In another embodiment, the present invention comprise a randomized B, C, D, and G strand. In another embodiment, the present invention comprise a randomized B, D, E, and F strand. In another embodiment, the present invention comprise a randomized B, D, E, and G strand. In another embodiment, the present invention comprise a randomized B, E, F, and G strand. In another embodiment, the present invention comprise a randomized C, D, E and F strand. In another embodiment, the present invention comprise a randomized C, D, E, and G strand. In another embodiment, the present invention comprise a randomized D, E, F, and G strand.

In one embodiment, the present invention comprise five beta strands that are randomized. In another embodiment, the present invention comprise a randomized A, B, C, D, and E strand. In another embodiment, the present invention comprise a randomized A, B, C, D, and F strand. In another embodiment, the present invention comprise a randomized A, B, C, D, and G strand. In another embodiment, the present invention comprise a randomized A, C, D, E and F strand. In another embodiment, the present invention comprise a randomized A, C, D, E and G strand. In another embodiment, the present invention comprise a randomized A, C, D, E and F strand. In another embodiment, the present invention comprise a randomized A, C, D, E, and G strand. In another embodiment, the present invention comprise a randomized A, B, C, E and F strand. In another embodiment, the present invention comprise a randomized A, B, C, E and G strand. In another embodiment, the present invention comprise a randomized A, B, C, D and F strand. In another embodiment, the present invention comprise a randomized A, B, C, D and G strand. In another embodiment, the present invention comprise a randomized B, C, D, E, and F strand. In another embodiment, the present invention comprise a randomized B, C, D, E, and G strand. In another embodiment, the present invention comprise a randomized B, D, E, F and G strand. In another embodiment, the present invention comprise a randomized B, C, E, F and G strand. In another embodiment, the present invention comprise a randomized B, C, D, F and G strand. In another embodiment, the present invention comprise a randomized C, D, E, F, and G strand.

In one embodiment, the present invention comprise six randomized beta strands. In one embodiment, the present invention comprise a randomized A, B, C, D, E, and F strand. In another embodiment, the present invention comprise a randomized A, B, C, D, E, and G strand. In another embodiment, the present invention comprise a randomized A, C, D, E, F and G strand. In another embodiment, the present invention comprise a randomized A, B, D, E, F and G strand. In another embodiment, the present invention comprise a randomized A, B, C, E, F and G strand. In another embodiment, the present invention comprise a randomized A, B, C, D, F and G strand. In another embodiment, the present invention comprise a randomized A, B, C, D, E and G strand. In another embodiment, the present invention comprise a randomized B, C, D, E, F and G strand.

In one embodiment, the present invention comprise six randomized beta strands. In one embodiment, the present invention comprise a randomized A, B, C, D, E, F, and G strand.

The invention also provides protein scaffolds with loop length diversity. In one embodiment, the present invention comprise at least one loop comprising at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 amino acid residues. In another embodiment, protein the present invention may comprise at least one loop comprising 1, 2, 4, 5, 6, 7, 8, 9, 10, 11, 12, 13, 14, 15, 16, 17, 18, 19, 20, 21, 22, 23, 24, 25, 26, 27, 28, 29, or 30 amino acid residues.

In another embodiment, the present invention may comprise at least two, at least three, at least four, at least five or at least six loops of the same length. In another embodiment, the present invention may comprise at least two loops, at least three, at least four, at least five or at least six loops of the different lengths.

In another embodiment, the present invention vary from a naturally occurring protein sequence by a deletion, substitution or addition of at least one amino acid from the corresponding loop sequences in the naturally occurring protein sequence. In one embodiment, the present invention comprise a deletion, substitution or addition of at least one amino acid in at least one, or at least two, or at least three, or at least four, or at least five, or at least six loop sequences from the corresponding naturally occurring protein sequence. In one embodiment, the present invention comprise a deletion, substitution or addition of at least 1, or at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids in at least one, or at least two, or at least three, or at least four, or at least five, or at least six loop sequences from the corresponding naturally occurring protein sequence. In another embodiment, the present invention comprise a deletion, substitution or addition of at least 1, at least 2, at least 3, at least 4 to about at least 8, at least, at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids in at least one, or at least two, or at least three, or at least four, or at least five, or at least six loop sequences from the corresponding naturally occurring protein sequence.

In one embodiment, the present invention comprise a deletion, substitution or addition of at least one amino acid in loop AB. In another embodiment the present invention comprise a deletion, substitution or addition of at least 1, or at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids in loop AB. In another embodiment the present invention comprise a deletion, substitution or addition of at least 1, at least 2, at least 3, at least 4 to about at least 8, at least, at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids amino acids in loop AB.

In one embodiment, the present invention comprise a deletion, substitution or addition of at least one amino acid in loop BC. In another embodiment the present invention comprise a deletion, substitution or addition of at least 1, or at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids in loop BC. In another embodiment the present invention comprise a deletion, substitution or addition of at least 1, at least 2, at least 3, at least 4 to about at least 8, at least, at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids amino acids in loop BC.

In one embodiment, the present invention comprise a deletion, substitution or addition of at least one amino acid in loop CD. In another embodiment the present invention comprise a deletion, substitution or addition of at least 1, or at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids in loop CD. In another embodiment the present invention comprise a deletion, substitution or addition of at least 1, at least 2, at least 3, at least 4 to about at least 8, at least, at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids amino acids in loop CD.

In one embodiment, the present invention comprise a deletion, substitution or addition of at least one amino acid in loop DE. In another embodiment the present invention comprise a deletion, substitution or addition of at least 1, or at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids in loop DE. In another embodiment the present invention comprise a deletion, substitution or addition of at least 1, at least 2, at least 3, at least 4 to about at least 8, at least, at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids amino acids in loop DE.

In one embodiment, the present invention comprise a deletion, substitution or addition of at least one amino acid in loop EF. In another embodiment the present invention comprise a deletion, substitution or addition of at least 1, or at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids in loop EF. In another embodiment the present invention comprise a deletion, substitution or addition of at least 1, at least 2, at least 3, at least 4 to about at least 8, at least, at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids in loop EF.

In one embodiment, the present invention comprise a deletion, substitution or addition of at least one amino acid in loop FG. In another embodiment the present invention comprise a deletion, substitution or addition of at least 1, or at least 2, or at least 3, or at least 4, or at least 5, or at least 6, or at least 7, or at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids in loop FG. In another embodiment the present invention comprise a deletion, substitution or addition of at least 1, at least 2, at least 3, at least 4 to about at least 8, at least, at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30 amino acids amino acids in loop FG.

The invention also provides scaffolds comprising loop sequence diversity. In one embodiment, the present invention comprise at least 1, at least 2, at least 3, at least 4, at least 5 or at least 6 loops which comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 positions that are randomized. In another embodiment, the present invention comprise at least 1, at least 2, at least 3, at least 4, at least 5 or at least 6 loops which comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 positions that are randomized while further comprising at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 positions that is held constant. In another embodiment, the present invention comprise at least 1, at least 2, at least 3, at least 4, at least 5 or at least 6 loops which comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 positions that is subjected to a restricted randomization. In another embodiment, the present invention comprise at least 1, at least 2, at least 3, at least 4, at least 5 or at least 6 loops which comprise at least 1, at least 2, at least 3, at least 4, at least 5 or at least 6 loops which comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 positions that is subjected to a restricted randomization and further comprises at least 1, at least 2, at least 3, at least 4, at least 5 or at least 6 loops which comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 positions that are held constant.

In another embodiment, the present invention comprise at least 1, at least 2, at least 3, at least 4, at least 5 or at least 6 loops which comprise at least 1, at least 2, at least 3, at least 4, at least 5 or at least 6 loops which comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 positions that are subjected to a restricted randomization and further comprises at least 1, at least 2, at least 3, at least 4, at least 5 or at least 6 loops which comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 positions that are randomized and at least 1, at least 2, at least 3, at least 4, at least 5 or at least 6 loops which comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 positions that are held constant.

The invention also provides scaffolds comprising loop sequence diversity. In one embodiment, the present invention comprise at least one loop which contains at least one position that is randomized. In another embodiment, the present invention comprise at least one loop which comprises at least one position that is randomized while further comprising at least one position that is held constant. In another embodiment, the present invention comprise a loop which comprises at least one position that is subjected to a restricted randomization. In another embodiment, the present invention comprise at least one loop which comprises at least one position that is subjected to a restricted randomization and further comprises at least one position that is held constant. In another embodiment, the present invention comprise at least one loop which comprises at least one position that is subjected to a restricted randomization and further comprises at least one position that is randomized and at least one position that is held constant.

In one embodiment, the present invention comprise at least one, at least two, at least three, at least four, at least five, or at least six loops randomized for length and diversity. In one embodiment, the present invention comprise an AB loop randomized for sequence length and diversity. In another embodiment, the present invention comprise a BC loop randomized for sequence length and diversity. the present invention comprise a CD loop randomized for sequence length and diversity. the present invention comprise a DE loop randomized for sequence length and diversity. the present invention comprise an EF loop randomized for sequence length and diversity. the present invention comprise a FG loop randomized for sequence length and diversity.

In another embodiment, the present invention comprise AB and BC loops randomized for sequence length and diversity. In another embodiment, the present invention comprise AB and CD loops randomized for sequence length and diversity. In another embodiment, the present invention comprise AB and DE loops randomized for sequence length and diversity. In another embodiment, the present invention comprise AB and EF loops randomized for sequence length and diversity. In another embodiment, the present invention comprise AB and FG loops randomized for sequence length and diversity. In another embodiment, the present invention comprise BC and CD loops randomized for sequence length and diversity. In another embodiment, the present invention comprise BC and DE loops randomized for sequence length and diversity. In another embodiment, the present invention comprise BC and EF loops randomized for sequence length and diversity. In another embodiment, the present invention comprise BC and FG loops randomized for sequence length and diversity. In another embodiment, the present invention comprise CD and DE loops randomized for sequence length and diversity. In another embodiment, the present invention comprise CD and EF loops randomized for sequence length and diversity. In another embodiment, the present invention comprise CD and FG loops randomized for sequence length and diversity. In another embodiment, the present invention comprise DE and EF loops randomized for sequence length and diversity. In another embodiment, the present invention comprise DE and FG loops randomized for sequence length and diversity. In another embodiment, the present invention comprise EF and FG loops randomized for sequence length and diversity.

In another embodiment, the present invention comprise AB, BC and CD loops randomized for sequence length and diversity. In another embodiment, the present invention comprise AB, BC and DE loops randomized for sequence length and diversity. In another embodiment, the present invention comprise AB, BC and EF loops randomized for sequence length and diversity. In another embodiment, the present invention comprise AB, BC and FG loops randomized for sequence length and diversity. In another embodiment, the present invention comprise AB, CD and DE loops randomized for sequence length and diversity. In another embodiment, the present invention comprise AB, CD and EF loops randomized for sequence length and diversity. In another embodiment, the present invention comprise AB, CD and FG loops randomized for sequence length and diversity. In another embodiment, the present invention comprise AB, DE and EF loops randomized for sequence length and diversity. In another embodiment, the present invention comprise AB, DE and FG loops randomized for sequence length and diversity. In another embodiment, the present invention comprise AB, EF and FG loops randomized for sequence length and diversity. In another embodiment, the present invention comprise BC, CD and DE loops randomized for sequence length and diversity. In another embodiment, the present invention comprise BC, CD and EF loops randomized for sequence length and diversity. In another embodiment, the present invention comprise BC, CD and FG loops randomized for sequence length and diversity. In another embodiment, the present invention comprise BC, DE and EF loops randomized for sequence length and diversity. In another embodiment, the present invention comprise BC, DE and FG loops randomized for sequence length and diversity. In another embodiment, the present invention comprise BC, EF and FG loops randomized for sequence length and diversity. In another embodiment, the present invention comprise CD, DE and EF loops randomized for sequence length and diversity. In another embodiment, the present invention comprise CD, DE and FG loops randomized for sequence length and diversity. In another embodiment, the present invention comprise CD, EF and FG loops randomized for sequence length and diversity. In another embodiment, the present invention comprise DE, EF and FG loops randomized for sequence length and diversity.

In another embodiment, the present invention comprise AB, BC, CD, and DE loops randomized for sequence length and diversity. In another embodiment, the present invention comprise AB, BC, CD, and EF loops randomized for sequence length and diversity. In another embodiment, the present invention comprise AB, BC, CD, and FG loops randomized for sequence length and diversity. In another embodiment, the present invention comprise AB, CD, DE, and EF loops randomized for sequence length and diversity. In another embodiment, the present invention comprise AB, CD, DE, and FG loops randomized for sequence length and diversity. In another embodiment, the present invention comprise AB, CD, EF, and FG loops randomized for sequence length and diversity. In another embodiment, the present invention comprise AB, DE, EF, and FG loops randomized for sequence length and diversity. In another embodiment, the present invention comprise BC, CD, DE and EF loops randomized for sequence length and diversity. In another embodiment, the present invention comprise BC, CD, DE and FG loops randomized for sequence length and diversity. In another embodiment, the present invention comprise BC, CD, EF and FG loops randomized for sequence length and diversity. In another embodiment, the present invention comprise BC, DE, EF and FG loops randomized for sequence length and diversity. In another embodiment, the present invention comprise CD, DE, EF, and FG loops randomized for sequence length and diversity.

In another embodiment, the present invention comprise AB, BC, CD, DE, and EF loops randomized for sequence length and diversity. In another embodiment, the present invention comprise AB, BC, CD, DE, and FG loops randomized for sequence length and diversity. In another embodiment, the present invention comprise AB, CD, DE, EF and FG loops randomized for sequence length and diversity. In another embodiment, the present invention comprise AB, BC, DE, EF and FG loops randomized for sequence length and diversity. In another embodiment, the present invention comprise AB, BC, CD, EF and FG loops randomized for sequence length and diversity. In another embodiment, the present invention comprise AB, BC, CD, EF, and FG loops randomized for sequence length and diversity. In another embodiment, the present invention comprise AB, BC, CD, DE, and EF loops randomized for sequence length and diversity. In another embodiment, the present invention comprise BC, CD, DE, EF and FG loops randomized for sequence length and diversity.

Scaffold Conjugates

The present invention encompasses the use of scaffolds conjugated or fused to one or more moieties, including but not limited to, peptides, polypeptides, proteins, fusion proteins, nucleic acid molecules, small molecules, mimetic agents, synthetic drugs, inorganic molecules, and organic molecules. The present invention encompasses the use of scaffolds recombinantly fused or chemically conjugated (including both covalent and non-covalent conjugations) to a heterologous protein or polypeptide (or fragment thereof, to a polypeptide of at least 10, at least 20, at least 30, at least 40, at least 50, at least 60, at least 70, at least 80, at least 90 or at least 100 amino acids) to generate fusion proteins. The fusion does not necessarily need to be direct, but may occur through linker sequences described herein. For example, scaffolds may be used to target heterologous polypeptides to particular cell types, either in vitro or in vivo, by fusing or conjugating the scaffolds to antibodies specific for particular cell surface receptors. Scaffolds fused or conjugated to heterologous polypeptides may also be used in in vitro immunoassays and purification methods using methods known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452, which are incorporated by reference in their entireties.

Additional fusion proteins comprising scaffolds of the invention may be generated through the techniques of gene-shuffling, motif-shuffling, exon-shuffling, and/or codon-shuffling (collectively referred to as "DNA shuffling"). DNA shuffling may be employed to alter the activities of scaffolds of the invention (e.g., scaffolds with higher affinities and lower dissociation rates). See, generally, U.S. Pat. Nos. 5,605, 793; 5,811,238; 5,830,721; 5,834,252; and 5,837,458, and Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Scaffolds, or the encoded scaffolds thereof, may be altered by being subjected to random mutagenesis by error-prone PCR, random nucleotide insertion or other methods prior to recombination. One or more portions of a polynucleotide encoding a scaffold, which bind to a specific target may be recombined with one or more components, motifs, sections, parts, domains, fragments, etc. of one or more heterologous molecules.

Moreover, the scaffolds of the invention can be fused to marker sequences, such as a peptide to facilitate purification. In some embodiments, the marker amino acid sequence is a hexa-histidine peptide (his-tag), such as the tag provided in a pQE vector (QIAGEN, Inc., 9259 Eton Avenue, Chatsworth, Calif, 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

In other embodiments, scaffolds of the invention, analogs or derivatives thereof may be conjugated to a diagnostic or detectable agent. Such scaffolds can be useful for monitoring or prognosing the development or progression of a disease as part of a clinical testing procedure, such as determining the efficacy of a particular therapy. Such diagnosis and detection can be accomplished by coupling the scaffold to detectable substances including, but not limited to various enzymes, such as but not limited to horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C) sulfur ($^{35}$S), tritium (3H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tn; positron emitting metals using various positron emission tomographies, nonradioactive paramagnetic metal ions, and molecules that are radiolabelled or conjugated to specific radioisotopes.

The present invention further encompasses uses of scaffolds conjugated to a therapeutic moiety. A scaffold may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), Auristatin molecules (e.g., auristatin PHE, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference), hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)), cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, procaine, tetracaine, lidocaine, propranolol, and puromycin and analogs or homologs thereof) and those compounds disclosed in U.S. Pat. Nos. 6,245,759, 6,399,633, 6,383,790, 6,335,156, 6,271,242, 6,242,196, 6,218,410, 6,218,372, 6,057,300 6,034,053, 5,985,877, 5,958,769, 5,925,376, 5,922,844, 5,911,995, 5,872,223, 5,863,904, 5,840,745, 5,728,868, 5,648,239, 5,587,459), farnesyl transferase inhibitors (e.g., R115777, BMS-214662 and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305), topoisomerase inhibitors (e.g., camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN-1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin) and pharmaceutically acceptable salts, solvates, clathrates, and prodrugs thereof. See, e.g., Rothenberg, M. L., Annals of Oncology 8:837-855 (1997); and Moreau, P., et al., J. Med. Chem. 41:1631-1640 (1998)), antisense oligonucleotides (e.g., those disclosed in the U.S. Pat. Nos. 6,277,832, 5,998,596, 5,885,834, 5,734,033, and 5,618,709), immunomodulators (e.g., antibodies and cytokines), antibodies, and adenosine deaminase inhibitors (e.g., Fludarabine phosphate and 2-Chlorodeoxyadenosine). Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclophosphamide, busulfan, dibromomannitol, streptozotocin, mitomycin C and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), Auristatin molecules (e.g., auristatin PHE, bryostatin 1, solastatin 10, see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference), anti-mitotic agents (e.g., vincristine and vinblastine), hormones (e.g., glucocorticoids, progestatins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)), and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459), farnesyl transferase inhibitors (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305), topoisomerase inhibitors (e.g., camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN-1518B; KT6006; KT6528; ED-110; NB-506; ED-110; NB-506; and rebeccamycin; bulgarein; DNA minor groove binders such as Hoescht dye 33342 and Hoechst dye 33258; nitidine; fagaronine; epiberberine; coralyne; beta-lapachone; BC-4-1; and pharmaceutically acceptable salts, solvates, clathrates, and prodrugs thereof. See, e.g., Rothenberg, M. L., Annals of Oncology 8:837-855 (1997); and Moreau, P., et al., J. Med. Chem. 41:1631-1640 (1998)), antisense oligonucleotides (e.g., those disclosed in the U.S. Pat. Nos. 6,277,832, 5,998,596, 5,885,834, 5,734,033, and 5,618,709), immunomodulators (e.g., antibodies and cytokines), antibodies (e.g., rituximab (Rituxan®), calicheamycin (Mylotarg®, ibritumomab tiuxetan (Zevalin®), and tositumomab (Bexxar®)), and adenosine deaminase inhibitors (e.g., Fludarabine phosphate and 2-Chlorodeoxyadenosine).

Further, a scaffold may be conjugated to a therapeutic moiety or drug moiety that modifies a given biological response. Therapeutic moieties or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International publication No. WO 97/33899), AIM II (see, International Publication No. WO 97/34911), Fas Ligand (Takahashi et al., 1994, J. Immunol., 6:1567-1574), and VEGI (see, International publication No. WO 99/23105), a thrombotic agent or an anti-angiogenic agent, e.g., angiostatin, endostatin or a component of the coagulation pathway (e.g., tissue factor); or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid. fibrinopeptides A and B from the α and β chains of fibrinogen, fibrin monomer).

Moreover, a scaffold can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7,10-tetraazacyclododecane-N,N',N'',N'''-tetraa-cetic acid (DOTA) which can be attached to the scaffold via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56. (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58. Similar approaches may be adapted for use with scaffolds of the invention.

The therapeutic moiety or drug conjugated to a scaffold of the invention should be chosen to achieve the desired prophylactic or therapeutic effect(s) for a particular disorder in a subject. A clinician or other medical personnel should consider the following when deciding on which therapeutic moiety or drug to conjugate to a scaffold: the nature of the disease, the severity of the disease, and the condition of the subject.

Scaffolds of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Production

Recombinant expression of a scaffold of the invention requires construction of an expression vector containing a polynucleotide that encodes the scaffold. Once a polynucleotide encoding a scaffold has been obtained, the vector for the production of scaffold may be produced by recombinant DNA technology using techniques well known in the art. Thus, methods for preparing a protein by expressing a polynucleotide containing a scaffold encoding nucleotide sequence are described herein. Methods that are well known to those skilled in the art can be used to construct expression vectors containing scaffold polypeptide coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding a scaffold of the invention, operably linked to a promoter.

The expression vector is transferred to a host cell by conventional techniques and the transfected cells are then cultured by conventional techniques to produce a scaffold of the invention. Thus, the invention includes host cells containing a polynucleotide encoding a scaffold of the invention, operably linked to a heterologous promoter. Suitable host cells include, but are not limited to, microorganisms such as bacteria (e.g., *E. coli* and *B. subtilis*).

A variety of host-expression vector systems may be utilized to express the scaffolds of the invention. Such host-expression systems represent vehicles by which the coding sequences of interest may be produced and subsequently purified, but also represent cells which may, when transformed or transfected with the appropriate nucleotide coding sequences, express a scaffold of the invention in situ. These include but are not limited to microorganisms such as bacteria (e.g., *E. coli* and *B. subtilis*) transformed with recombinant bacteriophage DNA, plasmid DNA or cosmid DNA expression vectors containing scaffold coding sequences; yeast (e.g., *Saccharomyces, Pichia*) transformed with recombinant yeast expression vectors containing scaffold coding sequences; insect cell systems infected with recombinant virus expression vectors (e.g., baculovirus) containing scaffold coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing scaffold coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

Expression vectors containing inserts of a gene encoding a scaffold of the invention can be identified by three general approaches: (a) nucleic acid hybridization, (b) presence or absence of "marker" gene functions, and (c) expression of inserted sequences. In the first approach, the presence of a gene encoding a peptide, polypeptide, protein or a fusion protein in an expression vector can be detected by nucleic acid hybridization using probes comprising sequences that are homologous to an inserted gene encoding the peptide, polypeptide, protein or the fusion protein, respectively. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding an antibody or fusion protein in the vector. For example, if the nucleotide sequence encoding the scaffold is inserted within the marker gene sequence of the vector, recombinants containing the gene encoding the scaffold insert can be identified by the absence of the marker gene function. In the third approach, recombinant expression vectors can be identified by assaying the gene product (e.g., scaffold or multimer thereof) expressed by the recombinant. Such assays can be based, for example, on the physical or functional properties of the protein in in vitro assay systems, e.g., binding, agonistic or antagonistic properties of the scaffold.

In some embodiments the scaffolds of the invention may be chemically synthesized at least partially. In other embodiments, the scaffolds of the invention may be produced semi-synthetically.

Scaffold Purification

Once a scaffold of the invention has been produced by recombinant expression, it may be purified by any method known in the art for purification of a protein, for example, by chromatography (e.g., metal-chelate chromatography, ion exchange, affinity, and sizing column chromatography), centrifugation, differential solubility, or by any other standard technique for the purification of proteins.

The highly stable nature of the scaffolds of the invention allow for variations on purification schemes. For example, the thermal stability exhibited by the scaffolds of the invention allow for the heating of the crude lysate comprising the scaffolds to remove the bulk of the host cell proteins by denaturation. In another embodiment, the high protease resistance exhibited by the scaffolds of the invention allow for the rapid degradation of host cell proteins in crude lysates prior to any purification steps. Also, the pH tolerance exhibited by the scaffolds of the invention allow for the selective precipitation of host cell proteins in the crude lysate by lowering or raising the pH prior to any purification steps. In some embodiments, the purification of the scaffolds of the invention are facilitated by a high temperature shift, a protease treatment, a pH shift up or down, or a combination of any of the above in an effort to remove bulk host cell proteins from the crude lysate. In some embodiments, the protein remaining after the heat denaturation, protease treatment, of pH shift is at least 50%, at least 55%, at least 60%, at least 65%, at least 70%, at least 75%, at least 80%, at least 85%, at least 90%, or at least 95% specific scaffold protein.

In some embodiments, methods of purifying the scaffolds comprise lowering the pH of the crude lysate containing said scaffold to about 6.5, or to about 6.0, or to about 5.5, or to about 5.0, or to about 4.5 or to about 4.0, or to about 3.5, or to about 3.0 or to about 2.5, or to about 2.0 in an effort to precipitate the host cell protein. In other embodiments, methods of purification comprise raising the pH of the crude lysate containing said scaffold to about 8.0, or to about 8.5, or to about 9.0, or to about 9.5, or to about 10.0, or to about 10.5, or to about 11.0, or to about 11.5, or to about 12.0, or to about 12.5 in an effort to precipitate the host cell protein.

Scalable Production of Scaffolds

In an effort to obtain large quantities, scaffolds of the invention may be produced by a scalable process (hereinafter referred to as "scalable process of the invention"). In some embodiments, scaffolds may be produced by a scalable process of the invention in the research laboratory that may be scaled up to produce the scaffolds of the invention in analytical scale bioreactors (for example, but not limited to 5 L, 10 L, 15 L, 30 L, or 50 L bioreactors). In other embodiments, the scaffolds may be produced by a scalable process of the invention in the research laboratory that may be scaled up to produce the scaffolds of the invention in production scale bioreactors (for example, but not limited to 75 L, 100 L, 150 L, 300 L, or 500 L). In some embodiments, the scalable process of the invention results in little or no reduction in production efficiency as compared to the production process performed in the research laboratory.

In some embodiments, the scalable process of the invention produces scaffolds at production efficiency of about 1 g/L, about 2 g/L, about 3 g/L, about 5 g/L, about 7.5 g/L, about 10 g/L, about 12.5 g/L, about 15.0 g/L, about 17.5 g/L, about 20 g/L, about 25 g/L, about 30 g/L, or higher.

In other embodiments, the scalable process of the invention produces scaffolds at a production efficiency of at least about 1 g/L, at least about 2 g/L, at least about 3 g/L, at least about 5 g/L, at least about 7.5 g/L, at least about 10 g/L, at least about 12.5 g/L, at least about 15 g/L, at least about 17.5 g/L, at least about 20 g/L, at least about 25 g/L, at least about 30 g/L, or higher.

In other embodiments, the scalable process of the invention produces scaffolds at a production efficiency from about 10 g/L to about 300 g/L, from about 10 g/L to about 250 g/L, from about 10 g/L to about 200 g/L, from about 10 g/L to about 175 g/L, from about 10 g/L to about 150 g/L, from about 10 g/L to about 100 g/L, from about 20 g/L to about 300 g/L, from about 20 g/L to about 250 g/L, from about 20 g/L to about 200 g/L, from 20 g/L to about 175 g/L, from about 20 g/L to about 150 g/L, from about 20 g/L to about 125 g/L, from about 20 g/L to about 100 g/L, from about 30 g/L to about 300 g/L, from about 30 g/L to about 250 g/L, from about 30 g/L to about 200 g/L, from about 30 g/L to about 175 g/L, from about 30 g/L to about 150 g/L, from about 30 g/L to about 125 g/L, from about 30 g/L to about 100 g/L, from about 50 g/L to about 300 g/L, from about 50 g/L to about 250 g/L, from about 50 g/L to about 200 g/L, from 50 g/L to about 175 g/L, from about 50 g/L to about 150 g/L, from about 50 g/L to about 125 g/L, or from about 50 g/L to about 100 g/L.

In some embodiments, the scalable process of the invention produces multimeric scaffolds at production efficiency of about 10 mg/L, about 20 m/L, about 30 mg/L, about 50 mg/L, about 75 mg/L, about 100 mg/L, about 125 mg/L, about 150 mg/L, about 175 mg/L, about 200 mg/L, about 250 mg/L, about 300 mg/L or higher.

In other embodiments, the scalable process of the invention produces multimeric scaffolds at a production efficiency of at least about 10 mg/L, at least about 20 m/L, at least about 30 mg/L, at least about 50 mg/L, at least about 75 mg/L, at least about 100 mg/L, at least about 125 mg/L, at least about 150 mg/L, at least about 175 mg/L, at least about 200 mg/L, at least about 250 mg/L, at least about 300 mg/L or higher.

In other embodiments, the scalable process of the invention produces multimeric scaffolds at a production efficiency from about 10 mg/L to about 300 mg/L, from about 10 mg/L to about 250 mg/L, from about 10 mg/L to about 200 mg/L, from about 10 mg/L to about 175 mg/L, from about 10 mg/L to about 150 mg/L, from about 10 mg/L to about 100 mg/L, from about 20 mg/L to about 300 mg/L, from about 20 mg/L to about 250 mg/L, from about 20 mg/L to about 200 mg/L, from 20 mg/L to about 175 mg/L, from about 20 mg/L to about 150 mg/L, from about 20 mg/L to about 125 mg/L, from about 20 mg/L to about 100 mg/L, from about 30 mg/L to about 300 mg/L, from about 30 mg/L to about 250 mg/L, from about 30 mg/L to about 200 mg/L, from about 30 mg/L to about 175 mg/L, from about 30 mg/L to about 150 mg/L, from about 30 mg/L to about 125 mg/L, from about 30 mg/L to about 100 mg/L, from about 50 mg/L to about 300 mg/L, from about 50 mg/L to about 250 mg/L, from about 50 mg/L to about 200 mg/L, from 50 mg/L to about 175 mg/L, from about 50 mg/L to about 150 mg/L, from about 50 mg/L to about 125 mg/L, or from about 50 mg/L to about 100 mg/L.

Production of Secreted Scaffolds

The invention also provides methods for the production of scaffolds intracellularly or as a secreted form. In some embodiments, the secreted scaffold is produced at levels described herein. In other embodiments, secreted scaffolds are properly folded and fully functional. In other embodiments, the production of secreted scaffolds comprises the use of a Ptac promoter. In other embodiments, the production of secreted scaffolds comprises the use of a oppA signal. In yet other embodiments, the secreted scaffold is expressed in a prokaryotic host cell. In further embodiments, the scaffold is secreted into the periplasmic space of a prokaryotic host cell. In yet other embodiments, the scaffold is secreted directly into the media. In yet further embodiments, scaffolds may be screened from crude cell culture media or periplasm extracts.

The invention also provides methods for the secretion of tandem proteins or fusions using protein scaffolds. In some embodiments, scaffolds of the invention may act as carrier molecules for the secretion of peptides and/or proteins into the cell culture media or periplasmic space of a prokaryotic cell.

In another embodiment, methods of purifying scaffolds of the invention comprise heating the crude lysate comprising said scaffold to 70° C. for 15 min and subsequently removing aggregated compounds by centrifugation. In other embodiments, methods of purifying scaffolds of the invention comprise heating the crude lysate comprising said scaffold to about 50° C., about 55° C., about 60° C., about 65° C., about 70° C., about 75° C., about 80° C., about 85° C., or about 90° C. and subsequently removing aggregated compounds by centrifugation. In other embodiments, methods of purifying scaffolds of the invention comprise heating the crude lysate for at least about 1 min, about 2 min, about 3 min, about 4 min, about 5 min, about 6 min, about 7 min, about 8 min, about 9 min, about 10 min, about 11 min, about 12 min, about 13 min, about 14 min, about 15 min, about 20 min, or about 30 min and subsequently removing aggregated compounds by centrifugation.

In another specific embodiment, methods of purifying scaffolds of the invention comprise shifting the pH of the crude lysate to 3.0 and heating the crude lysate to comprising said scaffold 70° C. for 15 min and subsequently removing aggregated compounds by centrifugation.

Assaying Scaffolds

The scaffolds of the invention may be assayed for specific binding to a target by any method known in the art. Representative assays which can be used, include but are not limited to, competitive and non-competitive assay systems using techniques such as western blots, radioimmunoassays, ELISA (enzyme linked immunosorbent assay), "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, to name but a few. Such assays are routine and known in the art (see, e.g., Ausubel et al, eds, 1994, Current Protocols in Molecular Biology, Vol. 1, John Wiley & Sons, Inc., New York).

ELISAs comprise preparing antigen (e.g. a scaffold), coating the well of a 96 well microtiter plate with the antigen, adding the epitope binding protein of interest (e.g. a scaffold specific antibody) conjugated to a detectable compound such as an enzymatic substrate (e.g., horseradish peroxidase or alkaline phosphatase) to the well and incubating for a period of time, and detecting the presence of the antigen. In ELISAs the epitope binding protein of interest does not have to be conjugated to a detectable compound; instead, a second antibody (which recognizes the protein of interest) conjugated to a detectable compound may be added to the well. Further, instead of coating the well with the antigen, the protein of interest may be coated to the well. In this case, a second antibody conjugated to a detectable compound may be added following the addition of the antigen of interest to the coated well.

One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity and other binding properties of a scaffold to an antigen may be determined by a variety of in vitro assay methods known in the art including for example, equilibrium methods (e.g., enzyme-linked immunoabsorbent assay (ELISA; or radioimmunoassay (RIA)), or kinetics (e.g., BIACORE® analysis), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999).

The stability of scaffolds of the invention may be increased by many different approaches. In one embodiment, the scaffolds of the invention comprise a non-naturally occurring disulfide bond, as described herein. In another embodiment, the scaffolds of the invention comprise an elongation of the N and/or C terminal regions. In another embodiment, the scaffolds of the invention comprise an addition, deletion or substitution of at least one amino acid residue to adjust the surface charge of the scaffold. In another embodiment, the scaffolds of the invention comprise an alteration to increase serum half-life, as described herein. In yet another embodiment, the scaffolds of the invention comprise an addition, deletion or substitution of at least one amino acid residue to stabilize the hydrophobic core of the scaffold.

The stability of scaffolds of the invention may be assessed by many different techniques. A selection of techniques know in the art include melting temperature, Differential scanning calorimetry (DSC), Circular Dichroism (CD), Polyacrylamide gel electrophoresis (PAGE), protease resistance, Isothermal calorimetry (ITC), nuclear magnetic resonance (NMR), internal fluorescence, and biological activity. In one embodiment, engineered scaffolds of the invention exhibit increased stability compared to the same scaffold prior to engineering.

Pharmaceutical Compositions

In another aspect, the present invention provides a composition, for example, but not limited to, a pharmaceutical composition, containing one or a combination of scaffolds or target binding proteins of the present invention, formulated together with a pharmaceutically acceptable carrier. Such compositions may include one or a combination of, for example, but not limited to two or more different scaffolds of the invention. For example, a pharmaceutical composition of the invention may comprise a combination of scaffolds that bind to different epitopes on the target antigen or that have complementary activities.

Pharmaceutical compositions of the invention also can be administered in combination therapy, such as, combined with other agents. For example, the combination therapy can include a scaffold of the present invention combined with at least one other therapy wherein the therapy may be immunotherapy, chemotherapy, radiation treatment, or drug therapy.

The pharmaceutical compounds of the invention may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

In one embodiment the compositions (e.g., liquid formulations) of the invention are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1): 223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg. In another embodiment, endotoxin and pyrogen levels in the composition are less then about 10 EU/mg, or less then about 5 EU/mg, or less then about 1 EU/mg, or less then about 0.1 EU/mg, or less then about 0.01 EU/mg, or less then about 0.001 EU/mg.

Dosing/Administration

To prepare pharmaceutical or sterile compositions including a scaffold of the invention, scaffold is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert, et al. (2003) New Engl. J. Med. 348:601-608; Milgrom, et al. (1999) New Engl. J. Med. 341:1966-1973; Slamon, et al. (2001) New Engl. J. Med. 344:783-792; Beniaminovitz, et al. (2000) New Engl. J. Med. 342:613-619; Ghosh, et al. (2003) New Engl. J. Med. 348: 24-32; Lipsky, et al. (2000) New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Scaffolds of the invention can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 25 mg/kg, or at least 50 mg/kg (see, e.g., Yang, et al. (2003) New Engl. J. Med. 349: 427-434; Herold, et al. (2002) New Engl. J. Med. 346:1692-1698; Liu, et al. (1999) J. Neurol. Neurosurg. Psych. 67:451-456; Portielji, et al. (2003) Cancer Immunol. Immunother. 52:133-144). The desired dose of a small molecule therapeutic, e.g., a peptide mimetic, protein scaffold, natural product, or organic chemical, is about the same as for an antibody or polypeptide, on a moles/kg body weight basis. The desired plasma concentration of a small molecule or scaffold therapeutic is about the same as for an antibody, on a moles/kg body weight basis. The dose may be at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more.

For scaffolds of the invention, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the scaffolds of the invention may be calculated using the patient's weight in kilograms (kg) multiplied by the dose to be administered in mg/kg. The dosage of the scaffolds of the invention may be 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of a patient's body weight.

Unit dose of the scaffolds of the invention may be 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the scaffolds of the invention may achieve a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in a subject. Alternatively, the dosage of the scaffolds of the invention may achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in the subject.

Doses of scaffolds of the invention may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side affects (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al. (1983) Biopolymers 22:547-556; Langer, et al. (1981) J. Biomed. Mater. Res. 15:167-277; Langer (1982) Chem. Tech. 12:98-105; Epstein, et al. (1985) Proc. Natl. Acad. Sci. USA 82:3688-3692; Hwang, et al. (1980) Proc. Natl. Acad. Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In one embodiment, an antibody, combination therapy, or a composition of the invention is administered using Alkermes AIR™ pulmonary drug delivery technology (Alkermes, Inc., Cambridge, Mass.).

A composition of the present invention may also be administered via one or more routes of administration using one or more of a variety of methods known in the art. As will be appreciated by the skilled artisan, the route and/or mode of administration will vary depending upon the desired results. Selected routes of administration for scaffolds of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the invention can be administered via a non-parenteral route, such as a topical, epidermal or mucosal route of administration, for example, intranasally, orally, vaginally, rectally, sublingually or topically.

If the scaffolds of the invention are administered in a controlled release or sustained release system, a pump may be used to achieve controlled or sustained release (see Langer, supra; Sefton, 1987, CRC Crit. Ref Biomed. Eng. 14:20; Buchwald et al., 1980, Surgery 88:507; Saudek et al., 1989, N. Engl. J. Med. 321:574). Polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more scaffolds of the invention. See, e.g., U.S. Pat. No. 4,526,938, PCT publication WO 91/05548, PCT publication WO 96/20698, Ning et al., 1996, "Intratumoral Radioimmunotheraphy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

If the scaffold of the invention is administered topically, it can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the scaffolds of the invention are administered intranasally, it can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice:A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the scaffolds of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the scaffolds of the invention. The two or more therapies may be administered within one same patient visit.

The scaffolds of the invention and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the scaffolds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V.V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The invention provides protocols for the administration of pharmaceutical composition comprising scaffolds of the invention alone or in combination with other therapies to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the invention can be administered to a subject concurrently. The term "concurrently" is not limited to the administration of therapies (e.g., prophylactic or therapeutic agents) at exactly the same time, but rather it is meant that a pharmaceutical composition comprising scaffolds of the invention are administered to a subject in a sequence and within a time interval such that the scaffolds of the invention can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

Methods of Using Scaffolds

The scaffolds of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders.

The invention also provides methods of using the scaffolds of the invention. The present invention also encompasses the use of the scaffolds of the invention for the prevention, diagnosis, management, treatment or amelioration of one or more symptoms associated with diseases, disorders of diseases or disorders, including but not limited to cancer, inflammatory and autoimmune diseases, infectious diseases either alone or in combination with other therapies. The invention also encompasses the use of the scaffolds of the invention conjugated or fused to a moiety (e.g., therapeutic agent or drug) for prevention, management, treatment or amelioration of one or more symptoms associated with diseases, disorders or infections, including but not limited to cancer, inflammatory and autoimmune diseases, infectious diseases either alone or in combination with other therapies.

Also, many cell surface receptors activate or deactivate as a consequence of crosslinking of subunits. The proteins of the invention may be used to stimulate or inhibit a response in a target cell by crosslinking of cell surface receptors. In another embodiment, the scaffolds of the invention of the invention may be used to block the interaction of multiple cell surface receptors with antigens. In another embodiment, the scaffolds of the invention may be used to strengthen the interaction of multiple cell surface receptors with antigens. In another embodiment, it may be possible to crosslink homo- or heterodimers of a cell surface receptor using the scaffolds of the invention containing binding domains that share specificity for the same antigen, or bind two different antigens. In another embodiment, the proteins of the invention could be used to deliver a ligand, or ligand analogue to a specific cell surface receptor.

The invention also provides methods of targeting epitopes not easily accomplished with traditional antibodies. For example, in one embodiment, the scaffolds and of the invention may be used to first target an adjacent antigen and while binding, another binding domain may engage the cryptic antigen.

The invention also provides methods of using the scaffolds to bring together distinct cell types. In one embodiment, the proteins of the invention may bind a target cell with one binding domain and recruit another cell via another binding domain. In another embodiment, the first cell may be a cancer cell and the second cell is an immune effector cell such as an NK cell. In another embodiment, the scaffolds of the invention may be used to strengthen the interaction between two distinct cells, such as an antigen presenting cell and a T cell to possibly boost the immune response.

The invention also provides methods of using the scaffolds proteins to ameliorate, treat, or prevent cancer or symptoms thereof. In one embodiment, methods of the invention are useful in the treatment of cancers of the head, neck, eye, mouth, throat, esophagus, chest, skin, bone, lung, colon, rectum, colorectal, stomach, spleen, kidney, skeletal muscle, subcutaneous tissue, metastatic melanoma, endometrial, prostate, breast, ovaries, testicles, thyroid, blood, lymph nodes, kidney, liver, pancreas, brain, or central nervous system.

The invention also provides methods of using the scaffolds to deplete a cell population. In one embodiment, methods of the invention are useful in the depletion of the following cell types: eosinophil, basophil, neutrophil, T cell, B cell, mast cell, monocytes and tumor cell.

TRAIL-R2 Specific Scaffolds

The TRAIL-R2 protein is encoded by a member of the TNF-receptor superfamily gene, and contains an intracellular death domain. In some instances, it may also be known as TNFRSF10B; CD262, DR5, KILLER<KILLER/DR5, TRAILR2, TRICK2, TRICK2A, TRICK2B, TRICKB, or ZTNFR9. This receptor can be activated by tumor necrosis factor-related apoptosis inducing ligand (TNFSF10/TRAIL/APO-2L), and transduces an apoptotic signal. Further, TRAIL-R2 induced apoptosis involves caspases and the intracellular adapter molecule FADD/MORT1 (Walczak et al. EMBOJ, (1997), 16, 5386-97).

In some embodiments, the invention also provides scaffolds that specifically bind to TRAIL-R2. In specific embodiments, scaffolds of the invention specifically bind to human TRAIL-R2. In other specific embodiments, scaffolds of the invention bind to TRAIL-R2 homologs from mouse, chicken, Rheses, cynomolgus, rat, or rabbit. In some embodiments, scaffolds of the invention bind to an exposed epitope of TRAIL-R2. Such embodiments include TRAIL-R2 endogenously expressed on cells and/or cells transfected to ectopically express the receptor. In other embodiments, scaffolds of the invention recognize epitopes displayed on a monomeric TRAIL-R2. In other embodiments, scaffolds of the invention recognize epitopes displayed on a homodimeric form of TRAIL-R2. In yet other embodiments, scaffolds of the invention bind monomeric TRAIL-R2 and facilitate dimerization or oligomerization of 2 or more TRAIL-R2 molecules (for example, but not limited to multimeric scaffolds). In yet other embodiments, scaffolds of the invention reduce or inhibit interaction of TRAIL-R2 with TRAIL ligand. In other embodiments, scaffolds of the invention mimic the interaction of TRAIL ligand with TRAIL-R2. In further embodiments, scaffolds of the invention agonize cellular signaling by TRAIL-R2.

The invention also provides methods of modulating TRAIL-R2 activity using the scaffolds described herein. In some embodiments, methods of the invention comprise contacting a cell expressing TRAIL-R2 with TRAIL-R2 specific scaffolds and blocking interaction with TRAIL ligand. In other embodiments, methods of the invention comprise contacting a cell expressing TRAIL-R2 with a TRAIL-R2 specific scaffold and mimicking the interaction of TRAIL ligand with TRAIL-R2. In other embodiments, methods of the invention comprise agonizing TRAIL-R2 by contacting with a TRAIL-R2 specific scaffold. In other embodiments, methods of the invention comprise dimerizing or oligomerize TRAIL-R2 by contacting a monomer of TRAIL-R2 expressed on cells with a TRAIL-R2 specific scaffold and facilitating dimerization or oligomerization. In further embodiments, dimerization of TRAIL-R2 may be achieved through the use of, for example, but not limited to, multimeric scaffolds, scaffolds that mimic TRAIL-R2 dimers, scaffolds that stabilize TRAIL-R2 dimer formation, scaffolds that destabilize TRAIL-R2 monomers or scaffolds that only recognize TRAIL-R2 dimers displayed on cells.

In other embodiments, dimerization or oligomerization of TRAIL-R2 may be achieved through the use of monomeric scaffolds coupled with a scaffold dimerization or oligomerization agent. Such scaffolds dimerization or oligomerization agents may include, for example, but not limited to, an anti-scaffold antibody, use of scaffolds with epitope tags coupled with antibodies to epitope tag, or the incorporation of various protein dimerization or oligomerization motifs described herein and known in the art. In a further embodiment, TRAIL-R2 dimers or oligomers may be induced by the administration of monomeric scaffolds followed by the administration of a scaffold dimerization or oligomerization agent.

In some embodiments, methods of the invention comprise the administration of a TRAIL-R2 specific scaffold that reduces cell viability as measured by routine assays known in the art. In further embodiments, the reduction in cell viability is activation of apoptosis as measured by known assays in the art. In other embodiments, reduction in cell viability is the inhibition of cell division as measured by art accepted methods. In some embodiments, cell viability is reduced by at least 10%, at least 20%, at least 30%, at least 40%, at least 50%, at least 60%, at least 70%, at least 80%, at least 90%, or more as compared to cell viability in the absence of treatment. In some embodiments, cell viability is measured using the procedure outlined in Example 15 and/or 17 herein or other known methods in the art.

In some embodiments, TRAIL-R2 binding scaffolds of the invention agonize TRAIL-R2 with similar activity as the ligand for TRAIL-R2, known as TRAIL (Apo-2 ligand). In other embodiments, TRAIL-R2 binding scaffolds of the invention are capable of sufficiently activating TRAIL-R2 to result in the activation of one or more intracellular signaling pathways, including the activation of caspase 3, caspase 8, caspase 10, or FADD. In other embodiments, TRAIL-R2 binding scaffolds of the invention activate apoptosis in at least one cancer cell type. In further embodiments, TRAIL-R2 binding scaffolds of the invention demonstrate an enhanced activation of apoptosis in at least one cell type as compared to TRAIL. In other embodiments, the TRAIL-R2 binding scaffolds of the invention may bind or compete with binding for the same epitope on TRAIL-R2 as TRAIL (ligand). In such embodiments, the TRAIL-R2 binding scaffolds are capable of blocking of inhibiting the interaction of TRAIL-R2 with TRAIL by at least 50%, at least 60%, at least 70%, at least 80%, at least 90%, or more which may be determined in an in vitro competitive assay using the soluble TRAIL ligand (such as the 114-281 fragment of TRAIL ligand), crystallographic studies, or other known in vivo or in vitro studies.

Methods of Using TRAIL-R2 Binders in Therapy

TRAIL-R2 is known to mediate apoptosis signaling. Although several types of normal cells express TRAIL-R2, apoptosis signaling through this receptor appears to be restricted primarily to tumor cells, which become more susceptible to death receptor-mediated apoptosis in the context of their transformation by oncogenes such as Myc or Ras (Wang et al., Cancer Cell 5:501-12 (2004); Nesterov et al., Cancer Res. 64:3922-7 (2004)). TRAIL-R2 is frequently expressed by human cancer cell lines as well as primary tumors.

The TRAIL-R2 specific scaffolds of the invention may be useful in the prevention, treatment, maintenance or amelioration of cancer. In some embodiments, cancer may involve cancer cells that express TRAIL-R2. In other embodiments, cancer cells overexpress TRAIL-R2 as compared to non-cancerous cells. In some embodiments, the cancer is, for example, carcinoma, lymphoma, blastoma, sarcoma, or leukemia. In other embodiments, cancer may include squamous cell cancer, small-cell lung cancer, non-small cell lung cancer (NSCLC), non-Hodgkin's lymphoma, blastoma, gastrointestinal cancer, renal cancer, ovarian cancer, liver cancer, stomach cancer, bladder cancer, hepatoma, breast cancer, colon cancer, colorectal cancer, pancreatic cancer, endometrial carcinoma, salivary gland carcinoma, kidney cancer, liver cancer, prostate cancer, vulval cancer, thyroid cancer, hepatic carcinoma, head and neck cancer, lung cancer, adenocarcinoma, renal cell carcinoma, hepatocellular carcinoma, or other cancers described herein.

In some embodiments, TRAIL-R2 specific scaffolds of the invention are administered to a subject in need of treatment (i.e. a patient with cancer). In such embodiments, a sterile, pyrogen-free composition comprising a TRAIL-R2 specific scaffold is administered to a subject in need thereof. The efficiency of treatment may be measured using a variety of in vitro and in vivo assays well known in the art, such as, but not limited to apoptotic activity, using caspase activation of Annexin V binding, as well as a reduction in tumor burden or volume.

In other embodiments, TRAIL-R2 specific scaffolds of the invention are useful for the diagnosis and detection of cancer or other TRAIL-R2 associated diseases. In such embodiments, TRAIL-R2 specific scaffolds of the invention are linked to a detection agent, such as, but not limited to a radioisotope, fluorescent or chemiluminescent label. Such linked binders are useful in methods that detect or diagnose cancer or TRAIL-R2 associated diseases in a subject, or a sample taken from said subject. In addition, TRAIL-R2 specific scaffolds are useful in the diagnosis and treatment of other TRAIL-R2 associated pathological conditions, such as immune-related diseases in mammals, including humans.

Specific TRAIL-R2 Binding Sequences

In an effort to identify TRAIL-R2 specific scaffolds, a two-loop library and a three loop library were screened. A number of clones were identified as specifically binding to TRAIL-R2.

In some embodiments TRAIL-R2 specific scaffolds of the invention comprise at least one, at least two, at least three, at least four, at least five, or at least six loop sequences that bind TRAIL-R2. In some embodiments, TRAIL-R2 specific scaffolds comprise at least one, at least two, at least three, at least four, at least five, or at least six loop sequences of TRAIL-R2 binding scaffold clones selected from 2F4, 5B10, 10D9, 6F11, 8B3, 5E5, 2H6, 7G11, or 6C7. In other embodiments, TRAIL-R2 specific scaffolds comprise at least one loop sequence selected from SEQ ID NOs:126-143. In other embodiments, TRAIL-R2 specific scaffolds comprise at least one BC loop sequence selected from SEQ ID NOs: 126, 128, 130, 132, 134, 136, 138, 140, or 142. In other embodiments, TRAIL-R2 specific scaffolds comprise at least one FG loop sequence selected from SEQ ID NOs: 127, 129, 131, 133, 135, 137, 139, 141, or 143. In other embodiments, TRAIL-R2 specific scaffolds comprise a BC loop sequence selected from SEQ ID NOs:126, 128, 130, 132, 134, 136, 138, 140, or 142; and an FG loop sequence selected from SEQ ID NOs:127, 129, 131, 133, 135, 137, 139, 141, or 143. In a specific embodiment, TRAIL-R2 specific scaffolds comprise a BC loop sequence of SEQ ID NO:126 and an FG loop sequence of 127. In a specific embodiment, TRAIL-R2 specific scaffolds comprise a BC loop sequence of SEQ ID NO: 128 and a FG loop sequence of SEQ ID NO: 129. In a specific embodiment, TRAIL-R2 specific scaffolds comprise a BC loop sequence of SEQ ID NO:130 and a FG loop sequence of SEQ ID NO:131. In a specific embodiment, TRAIL-R2 specific scaffolds comprise a BC loop sequence of SEQ ID NO:132 and a FG loop sequence of SEQ ID NO:133. In a specific embodiment, TRAIL-R2 specific scaffolds comprise a BC loop sequence of SEQ ID NO: 134 and a FG loop sequence of SEQ ID NO:135. In a specific embodiment, TRAIL-R2 specific scaffolds comprise a BC loop sequence of SEQ ID NO:136 and a FG loop sequence of SEQ ID NO:137. In another specific embodiment, TRAIL-R2 specific scaffolds comprise a BC loop sequence of SEQ ID NO:140 and an FC loop sequence of SEQ ID NO:141. In yet another specific embodiment, TRAIL-R2 specific scaffolds comprise a BC loop sequence of SEQ ID NO:138 and an FC loop sequence of SEQ ID NO:139.

In other embodiments, the invention may also comprise scaffolds which compete for binding with scaffolds that specifically bind TRAIL-R2, said TRAIL-R2 binders, selected from the group consisting of 2F4, 5B10, 10D9, 6F11, 8B3, 5E5, 2Hb, 7G11, or 6C7. In other embodiments, the invention may also comprise scaffolds which compete for binding with scaffolds that specifically bind TRAIL-R2, said TRAIL-R2 binders comprising one BC loop sequence selected from SEQ ID NOs: 126, 128, 130, 132, 134, 136, 138, 140, or 142; and one FG loop sequence selected from SEQ ID NOs: 127, 129, 131, 133, 135, 137, 139, 141, or 143. Competition assays may be performed as presented herein in Examples 11 and/or 14, or by other assays known in the art.

In other embodiments, TRAIL-R2 specific scaffolds comprise at least one, at least two, at least three, at least four, at least five, or at least six loop sequences of TRAIL-R2 binding scaffold clones selected from 1E03, 2B04, 1C12, 1A03, 1C10, 1B12, 2G03, 2D3, 1C06, 2F08, 1B04, 3B11, 1D8, 2A12, 1E05, 2F02, 1H05, 2A11, or 1G11. In other embodiments, TRAIL-R2 specific scaffolds comprise at least one loop from SEQ ID NOs:144-200. In other embodiments, TRAIL-R2 specific scaffolds comprise at least one BC loop sequence selected from SEQ ID NO:144, 147, 150, 153, 156, 159, 162, 165, 168, 171, 174, 177, 180, 183, 186, 189, 192, 195, or 198. In other embodiments, TRAIL-R2 specific scaffolds comprise at least one DE loop sequence selected from SEQ ID NO:145, 148, 151, 154, 157, 160, 163, 166, 169, 172, 175, 178, 181, 194, 187, 190, 193, 196, or 199. In other embodiments, TRAIL-R2 specific scaffolds comprise at least one FG loop sequence selected from SEQ ID NO:146, 149, 152, 155, 158, 161, 164, 167, 170, 173, 179, 182, 185, 188, 191, 194, 197, or 200. In further embodiments, TRAIL-R2 specific scaffolds comprise at least one BC loop sequence selected from SEQ ID NO:144, 147, 150, 153, 156, 159, 162, 165, 168, 171, 174, 177, 180, 183, 186, 189, 192, 195, or 198; at least one DE loop sequence selected from SEQ ID NO:145, 148, 151, 154, 157, 160, 163, 166, 169, 172, 175, 178, 181, 194, 187, 190, 193, 196, or 199; and at least one FG loop sequence selected from SEQ ID NO:146, 149, 152, 155, 158, 161, 164, 167, 170, 173, 179, 182, 185, 188, 191, 194, 197, or 200.

In a specific embodiment, TRAIL-R2 specific scaffolds comprise a BC loop sequence of SEQ ID NO:144, a DE loop sequence of SEQ ID NO:145, and an FG loop sequence of SEQ ID NO:146. In a specific embodiment, TRAIL-R2 specific scaffolds comprise a BC loop sequence of SEQ ID NO:147, a DE loop sequence of SEQ ID NO:148, and an FG loop sequence of SEQ ID NO:149. In a specific embodiment, TRAIL-R2 specific scaffolds comprise a BC loop sequence of SEQ ID NO:150, a DE loop sequence of SEQ ID NO:151, and an FG loop sequence of SEQ ID NO:152. In a specific embodiment, TRAIL-R2 specific scaffolds comprise a BC loop sequence of SEQ ID NO:153, a DE loop sequence of SEQ ID NO:154, and an FG loop sequence of SEQ ID NO:155. In a specific embodiment, TRAIL-R2 specific scaffolds comprise a BC loop sequence of SEQ ID NO:165, a DE loop sequence of SEQ ID NO:166, and an FG loop sequence of SEQ ID NO:167. In a specific embodiment, TRAIL-R2 specific scaffolds comprise a BC loop sequence of SEQ ID NO:198, a DE loop sequence of SEQ ID NO:199, and an FG loop sequence of SEQ ID NO:200.

In other embodiments, the invention may also comprise scaffolds which compete for binding with scaffolds that specifically bind TRAIL-R2, said TRAIL-R2 binders, selected from the group consisting of 1E03, 2B04, 1C12, 1A03, 1C10, 1B12, 2G03, 2D3, 1C06, 2F08, 1B04, 3B11, 1D8, 2A12, 1E05, 2F02, 1H05, 2A11, or 1G11. In other embodiments, the invention may also comprise scaffolds which compete for binding with scaffolds that specifically bind TRAIL-R2, said TRAIL-R2 binders comprising one BC loop sequence selected from SEQ ID NO:144, 147, 150, 153, 156, 159, 162, 165, 168, 171, 174, 177, 180, 183, 186, 189, 192, 195, or 198; at least one DE loop sequence selected from SEQ ID NO:145, 148, 151, 154, 157, 160, 163, 166, 169, 172, 175, 178, 181, 194, 187, 190, 193, 196, or 199; and at least one FG loop sequence selected from SEQ ID NO:146, 149, 152, 155, 158, 161, 164, 167, 170, 173, 179, 182, 185, 188, 191, 194, 197, or 200. Competition assays may be performed as presented herein in Examples 11 and/or 14, or by other assays known in the art.

Methods of Use for Scaffolds

The invention also provides methods of using scaffolds to inactivate, inhibit, or deplete cytokines. In one embodiment, methods of the invention are useful in the inactivation, inhibition, or depletion of at least one of the following cytokines: TNF-α, TGF-β, C5a, fMLP, Interferon alpha (including subtypes 1, 2a, 2b, 4, 4b, 5, 6, 7, 8, 10, 14, 16, 17 and 21), Interferon beta, Interferon omega, Interferon gamma, interleukins CCL 1-28, CXCL 1-17, and CX3CL1.

The invention also provides methods of using the scaffolds to inactivate various infections agents such as viruses, fungi, eukaryotic microbes, and bacteria. In some embodiments the scaffolds of the invention may be used to inactivate RSV, hMPV, PIV, or influenza viruses. In other embodiments, the scaffolds of the invention may be used to inactivate fungal pathogens, such as, but not limited to members of *Naegleria, Aspergillus, Blastomyces, Histoplasma, Candida* or *Tinea* genera. In other embodiments, the scaffolds of the invention may be used to inactivate eukaryotic microbes, such as, but not limited to members of *Giardia, Toxoplasma, Plasmodium, Trypanosoma*, and *Entamoeba* genera. In other embodiments, the scaffolds of the invention may be used to inactivate bacterial pathogens, such as but not limited to members of *Staphylococcus, Streptococcus, Pseudomonas, Clostridium, Borrelia, Vibro* and *Neiserria* genera.

The invention also provides methods of using scaffolds proteins as diagnostic reagents. The proteins of the invention may be useful in kits or reagents where different antigens need to be efficiently captured concurrently.

The proteins of the invention and compositions comprising the same are useful for many purposes, for example, as therapeutics against a wide range of chronic and acute diseases and disorders including, but not limited to, cancer. Examples of cancers that can be prevented, managed, treated or ameliorated in accordance with the methods of the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myclocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple mycloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungaling (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or ureter); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., inc., United States of America). It is also contemplated that cancers caused by aberrations in apoptosis can also be treated by the methods and compositions of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

The proteins of the invention and compositions comprising the same are useful for many purposes, for example, as therapeutics against a wide range of chronic and acute diseases and disorders including, but not limited to, autoimmune and/or inflammatory diseases. The compositions and methods of the invention described herein are useful for the prevention or treatment of autoimmune disorders and/or inflammatory disorders. Examples of autoimmune and/or inflammatory disorders include, but are not limited to, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, Sjogren's syndrome, psoriasis, atherosclerosis, diabetic and other retinopathies, retrolental fibroplasia, age-related macular degeneration, neovascular glaucoma, hemangiomas, thyroid hyperplasias (including Grave's disease), corneal and other tissue transplantation, and chronic inflammation, sepsis, rheumatoid arthritis, peritonitis, Crohn's disease, reperfusion injury, septicemia, endotoxic shock, cystic fibrosis, endocarditis, psoriasis, arthritis (e.g., psoriatic arthritis), anaphylactic shock, organ ischemia, reperfusion injury, spinal cord injury and allograft rejection. autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erythematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. The compositions and methods of the invention can be used with one or more conventional therapies that are used to prevent, manage or treat the above diseases.

The proteins of the invention and compositions comprising the same are useful for many purposes, for example, as therapeutics against a wide range of chronic and acute diseases and disorders including, but not limited to, infectious disease, including viral, bacterial and fungal diseases. Examples of viral pathogens include but are not limited to: adenovirdiae (e.g., mastadenovirus and aviadenovirus), herpesviridae (e.g., herpes simplex virus 1, herpes simplex virus 2, herpes simplex virus 5, and herpes simplex virus 6), leviviridae (e.g., levivirus, enterobacteria phase MS2, allolevirus), poxyiridae (e.g., chordopoxyirinae, parapoxvirus, avipoxvirus, capripoxvirus, leporiipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory synctial virus), and metapneumovirus (e.g., avian pneumovirus and human metapneumovirus)), picornaviridae (e.g., enterovirus, rhinovirus, hepatovirus (e.g., human hepatits A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus 1 and human immunodeficiency virus 2), spumavirus), flaviviridae (e.g., hepatitis C virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus). Examples of bacterial pathogens include but are not limited to: but not limited to, the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *clostridium*, Enterobacteriaceae family (e.g., *Citrobacter* species, *Edwardsiella, Enterobacter aerogenes, Erwinia* species, *Escherichia coli, Hafnia* species, *Klebsiella* species, *Morganella* species, *Proteus vulgaris, Providencia, Salmonella* species, *Serratia marcescens*, and *Shigella flexneri*), Gardinella family, Haemophilus influenzae, Halobacteriaceae family, Helicobacter family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcuss* (e.g., methicillin resistant *Staphylococcus aureus* and *Staphylococcus pyrogenes*), Streptococcus (e.g., *Streptococcus enteritidis, Streptococcus fasciae*, and *Streptococcus pneumoniae*), Vampirovibrio Helicobacter family, and Vampirovibrio family. Examples of fungal pathogens include, but are not limited to: *Absidia* species (e.g., *Absidia corymbifera* and *Absidia ramosa*), *Aspergillus* species, (e.g., *Aspergillus flavus, Aspergillus fumigatus, Aspergillus nidulans, Aspergillus niger*, and *Aspergillus terreus*), *Basidiobolus ranarum*, *Blastomyces dermatitidis, Candida* species (e.g., *Candida albicans, Candida glabrata, Candida kerr, Candida krusei, Candida parapsilosis, Candida pseudotropicalis, Candida quillermondii, Candida rugosa, Candida stellatoidea*, and *Candida tropicalis*), *Coccidioides immitis, Conidiobolus* species, *Cryptococcus neoforms, Cunninghamella* species, dermatophytes, *Histoplasma capsulatum, Microsporum gypseum, Mucor pusillus, Paracoccidioides brasiliensis, Pseudallescheria boydii, Rhinosporidium seeberi, Pneumocystis carinii, Rhizopus* species (e.g., *Rhizopus arrhizus, Rhizopus oryzae*, and *Rhizopus microsporus*), *Saccharomyces* species, *Sporothrix schenckii, zygomycetes*, and classes such as Zygomycetes, Ascomycetes, the Basidiomycetes, Deuteromycetes, and Oomycetes.

In another embodiment, the invention provides methods for preventing, managing, treating or ameliorating cancer, autoimmune, inflammatory or infectious diseases or one or more symptoms thereof, said methods comprising administering to a subject in need thereof a dose of a prophylactically or therapeutically effective amount of one or more scaffolds of the invention in combination with surgery, alone or in further combination with the administration of a standard or experimental chemotherapy, a hormonal therapy, a biological therapy/immunotherapy and/or a radiation therapy. In accordance with these embodiments, the scaffolds of the invention utilized to prevent, manage, treat or ameliorate cancer, autoimmune, inflammatory or infectious diseases or one or more symptoms or one or more symptoms thereof may or may not be conjugated or fused to a moiety (e.g., therapeutic agent or drug).

The invention provides methods for preventing, managing, treating or ameliorating cancer, autoimmune, inflammatory or infectious diseases or one or more symptoms or one or more symptoms thereof, said methods comprising administering to a subject in need thereof one or more scaffolds of the invention in combination with one or more of therapeutic agents that are not cancer therapeutics (a.k.a., non-cancer therapies). Examples of such agents include, but are not limited to, anti-emetic agents, anti-fungal agents, anti-bacterial agents, such as antibiotics, anti-inflammatory agents, and anti-viral agents. Non-limiting examples of anti-emetic agents include metopimazin and metochlopramide. Non-limiting examples of antifungal agents include azole drugs, imidazole, triazoles, polyene, amphotericin and ryrimidine. Non-limiting examples of anti-bacterial agents include dactinomycin, bleomycin, erythromycin, penicillin, mithramycin, cephalosporin, imipenem, axtreonam, vancomycin, cycloserine, bacitracin, chloramphenicol, clindamycin, tetracycline, streptomycin, tobramycin, gentamicin, amikacin, kanamycin, neomycin, spectinomycin, trimethoprim, norfloxacin, refampin, polymyxin, amphotericin B, nystatin, ketocanazole, isoniazid, metronidazole and pentamidine. Non-limiting examples of antiviral agents include nucleoside analogs (e.g., zidovudine, acyclivir, gangcyclivir, vidarbine, idoxuridine, trifluridine and ribavirin), foscaret, amantadine, rimantadine, saquinavir, indinavir, ritonavir, interferon ("IFN")-α,β or γ and AZT. Non-limiting examples of anti-inflammatory agents include non-steroidal anti-inflammatory drugs ("NSAIDs"), steroidal anti-inflammatory drugs, beta-agonists, anti-cholingenic agents and methylxanthines.

In another embodiment, the invention comprises compositions capable of inhibiting a cancer cell phenotype. In one embodiment, the cancer cell phenotype is cell growth, cell attachment, loss of cell attachment, decreased receptor expression (such as, for example, but not limited to Eph receptors), increased receptor expression (such as, for example, but not limited to Eph receptors), metastatic potential, cell cycle inhibition, receptor tyrosine kinase activation/inhibition or others.

In one embodiment, the invention comprises compositions capable of treating chronic inflammation. In one embodiment, the compositions are useful in the targeting of immune cells for destruction or deactivation. In one embodiment, the compositions are useful in targeting activated T cells, dormant T cells, B cells, neutrophils, eosiniphils, basophils, mast cells, or dendritic cells. In another embodiment, the invention comprises compositions capable of decreasing immune cell function. In another embodiment, the compositions are capable of ablating immune cell function.

In another embodiment, the invention comprises compositions capable of inhibiting or reducing angiogenesis. In another embodiment, the angiogenesis is related to tumor growth, rheumatoid arthritis, SLE, Sjogren's syndrome or others.

In another embodiment, the invention comprises compositions useful for treatment of diseases of the gastrointestinal tract. The scaffolds of the invention exhibit a high level of stability under low pH conditions. The stability at low pH suggests that the composition will be suitable for oral administration for a variety of gastrointestinal disorders, such as irritable bowel syndrome, gastroesophageal reflux, intestinal pseudo-obstructions, dumping syndrome, intractable nausea, peptic ulcer, appendicitis, ischemic colitis, ulcerative colitis, gastritis, *Helico pylori* disease, Crohn's disease, Whipple's disease, celiac sprue, diverticulitis, diverticulosis, dysphagia, hiatus hernia, infections esophageal disorders, hiccups, rumination and others.

The invention further provides combinatorial compositions and methods of using such compositions in the prevention, treatment, reduction, or amelioration of disease or symptoms thereof. The scaffolds of the invention may be combined with conventional therapies suitable for the prevention, treatment, reduction or amelioration of disease or symptoms thereof. Exemplary conventional therapies can be found in the Physician's Desk Reference (56th ed., 2002 and 57th ed., 2003). In some embodiments, scaffolds of the invention may be combined with chemotherapy, radiation therapy, surgery, immunotherapy with a biologic (antibody or peptide), small molecules, or another therapy known in the art. In some embodiments, the combinatorial therapy is administered together. In other embodiments, the combinatorial therapy is administered separately.

The invention also provides methods of diagnosing diseases. The scaffolds of the invention which bind a specific target associated with a disease may be implemented in a method used to diagnose said disease. In one embodiment, the scaffolds of the invention are used in a method to diagnose a disease in a subject, said method comprising obtaining a sample from the subject, contacting the target with the scaffold in said sample under conditions that allow the target:scaffold interaction to form, identifying the target:scaffold complex and thereby detecting the target in the sample. In some embodiments, the target is an antigen associated with disease. In another embodiment, the target is a cytokine, inflammatory mediator, and intracellular antigen, a self antigen, a non-self antigen, an intranuclear antigen, a cell-surface antigen, a bacterial antigen, a viral antigen or a fungal antigen. In other embodiments, the disease to be diagnosed is described herein.

The invention also provides methods of imaging specific targets. In one embodiment, scaffolds of the invention conjugated to imaging agents such as green-fluorescent proteins, other fluorescent tags (Cy3, Cy5, Rhodamine and others), biotin, or radionuclides may be used in methods to image the presence, location, or progression of a specific target. In some embodiments, the method of imaging a target comprising a scaffold of the invention is performed in vitro. In other embodiments, the method of imaging a target comprising a scaffold of the invention is performed in vivo. In other embodiments, the method of imaging a target comprising a scaffold of the invention is performed by MM, PET scanning, X-ray, fluorescence detection or by other detection methods known in the art.

The invention also provides methods of monitoring disease progression, relapse, treatment, or amelioration using the scaffolds of the invention. In one embodiment, methods of monitoring disease progression, relapse, treatment, or amelioration is accomplished by the methods of imaging, diagnosing, or contacting a compound/target with a scaffold of the invention as presented herein.

Kits

Also within the scope of the invention are kits comprising the compositions (e.g. scaffolds) of the invention and instructions for use. The kit can further contain a least one additional reagent, or one or more additional scaffolds of the invention. Kits typically include a label indicating the intended use of the contents of the kit. The term label includes any writing, or recorded material supplied on or with the kit, or which otherwise accompanies the kit.

Equivalents

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference. Additionally, U.S. Provisional Application No.: 60/984,209 filed Oct. 31, 2007 is hereby incorporated by reference herein in its entirety for all purposes.

Exemplary Embodiments:

1. A recombinant, non-naturally occurring polypeptide scaffold comprising,
   I. a plurality of beta strand domains linked to a plurality of loop region sequences derived from a naturally occurring protein sequence,
   II. wherein one or more of said loop region sequences vary by deletion, substitution or addition by at least one amino acid from the corresponding loop sequences in the naturally occurring protein sequence, and;
   III. wherein the beta strand domains of the polypeptide scaffold have at least 50%, at least 60%, at least 70%, at least 80%, or at least 90% homology to the corresponding domain sequences of the naturally occurring protein sequence of SEQ ID NO. 1

2. The scaffold of embodiment 1, wherein said plurality of beta strands is at least seven strands.

3. The scaffold of embodiment 1, wherein said plurality of loop regions is at least six regions.

4. The scaffold of embodiment 1, wherein said scaffold comprises seven beta strands wherein each is designated A, B, C, D, E, and F, and six loop regions, wherein a loop region connects each beta strand and is designated AB, BC, CD, DE, EF, and FG loops.

5. The scaffold of embodiment 4, wherein said scaffold comprises an AB loop sequence of SEQ ID NO:201, a BC loop sequence of SEQ ID NO:202, a CD loop sequence of SEQ ID NO:203, a DE loop sequence of SEQ ID NO:204, an EF loop sequence of SEQ ID NO:205 and an FG loop sequence of SEQ ID NO:206.
6. The scaffold of embodiment 4, wherein said scaffold comprises an AB loop sequence of SEQ ID NO:207, a BC loop sequence of SEQ ID NO:202, a CD loop sequence of SEQ ID NO:203, a DE loop sequence of SEQ ID NO:208, an EF loop sequence of SEQ ID NO:209 and an FG loop sequence of SEQ ID NO:206.
7. The scaffold of embodiment 1, wherein said beta strand domain comprises the polypeptide sequence encoded by SEQ ID NO.1
8. The scaffold of embodiment 5 or 6, wherein said loop region sequences comprise the BC and FG loops.
9. The scaffold of embodiment 8, wherein said BC loop comprises 9 amino acids having a consensus sequence of S-X-a-X-b-X-X-X-G, wherein X represents any amino acid, wherein (a) represents proline or alanine and wherein (b) represents alanine or glycine.
10. The scaffold of embodiment 8, wherein said BC loop comprises 11 amino acids having a consensus sequence of S-P-c-X-X-X-X-X-X-T-G (SEQ ID NO: 258), wherein X represents any amino acid and wherein (c) represents proline, serine or glycine.
11. The scaffold of embodiment 8, wherein said BC loop comprises 12 amino acids having a consensus sequence of A-d-P-X-X-X-e-f-X-I-X-G (SEQ ID NO: 257), wherein X represents any amino acid, wherein (d) represents proline, glutamate or lysine, wherein (e) represents asparagine or glycine, and wherein (f) represents serine or glycine.
12. The scaffold of embodiment 8, wherein said FG loop comprises 9 amino acids having a consensus sequence of X-a-X-X-G-X-X-X-S, wherein X represents any amino acid and wherein (a) represents asparagine, threonine or lysine.
13. The scaffold of embodiment 8, wherein said FG loop comprises 10 amino acids having a consensus sequence of X-a-X-X-X-X-b-N-P-A, wherein X represents any amino acid, wherein (a) represents asparagine, threonine or lysine and wherein (b) represents serine or glycine.
14. The scaffold of embodiment 8, wherein said FG loop comprises 11 amino acids having a consensus sequence of X-a-X-X-G-X-X-S-N-P-A (SEQ ID NO: 259), wherein X represents any amino acid, and wherein (a) represents asparagine, threonine or lysine.
15. The scaffold of any of embodiments 4-14, wherein said loop region sequences further comprise the DE loop.
16. The scaffold of embodiment 15, wherein said DE loop comprises 6 amino acids having a consensus sequence of X-X-X-X-X-X, wherein X represents any amino acid.
17. The scaffold of any of embodiments 4-14, wherein said loop region sequences further comprise the AB loop.
18. The scaffold of embodiment 7 wherein said AB loop comprises 7 residues having the consensus sequence: K-X-X-X-X-X-a, wherein X represents asparagine, aspartic acid, histidine, tyrosine, isoleucine, valine, leucine, phenylalanine, threonine, alanine, proline, or serine, and wherein (a) represents serine, threonine, alanine, or glycine.
19. The scaffold of embodiment 18 wherein said AB loop comprises 9 residues having the consensus sequence: K-X-X-X-X-X-X-X-a, wherein X represents asparagine, aspartic acid, histidine, tyrosine, isoleucine, valine, leucine, phenylalanine, threonine, alanine, proline, or serine, and wherein (a) represents serine, threonine, alanine, or glycine.
20. The scaffold of any of embodiments 4-14, wherein said loop region sequences further comprise the CD loop.
21. The scaffold of embodiment 20, wherein said CD loop comprises 7, 8, or 9 residues wherein each residue in the CD loop is randomized and wherein each residue may be asparagine, aspartic acid, histidine, tyrosine, isoleucine, valine, leucine, phenylalanine, threonine, alanine, proline, or serine.
22. The scaffold of any of embodiments 4-14, wherein said loop region sequences further comprise the EF loop.
23. The scaffold of embodiment 22, wherein said EF loop comprises 8 having the consensus sequence X-b-L-X-P-X-c-X, wherein X represents asparagine, aspartic acid, histidine, tyrosine, isoleucine, valine, leucine, phenylalanine, threonine, alanine, proline, or serine, wherein (b) represents asparagine, lysine, arginine, aspartic acid, glutamic acid, or glycine, and wherein (c) represents isoleucine, threonine, serine, valine, alanine, or glycine.
24. The scaffold of any of embodiments 1 to 14, wherein said scaffold further comprises at least one disulfide bond.
25. The scaffold of embodiment 24, wherein said disulfide bond forms a link between the A strand and B strand.
26. The scaffold of embodiment 24, wherein said disulfide bond forms a link between the D strand and E strand.
27. The scaffold of embodiment 24, wherein said disulfide bond forms a link between the F strand and G strand.
28. The scaffold of embodiment 24, wherein said disulfide bond forms a link between the C strand and F strand.
29. The scaffold of any of embodiments 1 to 28, wherein said scaffold further comprises at least two disulfide bonds.
30. The scaffold of embodiment 29, wherein said disulfide bonds form a first link between the F strand and the G strand, and a second link between the C strand and F strand.
31. The scaffold of embodiment 24 or 29, wherein said at least one disulfide bond is in a beta strand domain.
32. The scaffold of embodiment 24 or 29, wherein said at least one disulfide bond is in a loop region.
33. The scaffold of embodiment 15, wherein said scaffold comprises the sequence corresponding to Tn3$^{SS1}$(SEQ ID NO:64), Tn3$^{SS2}$(SEQ ID NO:210), Tn3$^{SS3}$(SEQ ID NO:65), or Tn3$^{SS4}$(SEQ ID NO:66),
34. The scaffold of embodiment 17, wherein said scaffold comprises the sequence corresponding to Tn3$^{SS3+4}$ (SEQ ID NO:67),
35. The scaffold of any of embodiments 1-34, wherein said scaffold binds a target.
36. The scaffold of embodiment 35 wherein said scaffold binds said target with an affinity ($K_D$) of at least 100 μM.
37. The scaffold of embodiment 36, wherein said target is a cell-surface antigen, a soluble antigen, an immobilized antigen, an immunosilent antigen, an intracellular antigen, an intranuclear antigen, a self antigen, a non-self antigen, a cancer antigen, a bacterial antigen, or a viral antigen.
38. The scaffold of embodiment 36, wherein said scaffold exhibits a thermal melting temperature (Tm) of at least 40° C. as measured by Differential scanning calorimetry (DSC) in 20 mM sodium phosphate, pH 7.0.
39. The scaffold of embodiment 36, wherein said scaffold exhibits an increased Cm of at least 10% as measured in a urea denaturation experiment compared to the same scaffold prior to engineering, under similar experimental conditions.
40. The scaffold of embodiment 36, wherein said scaffold exhibits an increased Cm of at least 10% as measured in a guanidine denaturation experiment compared to the same scaffold prior to engineering, under similar experimental conditions.
41. The scaffold of embodiment 36, wherein said scaffold exhibits an increased resistance to protease degradation by at least 10% as compared to the same scaffold prior to engineering under similar experimental conditions.

42. The scaffold of embodiment 36, wherein said scaffold is conjugated to a heterologous agent, wherein said agent is selected from the group consisting of another scaffold, Polyethylene glycol (PEG), human serum albumin (HSA), an Fc region of an antibody, an IgG molecule, a binding peptide, cytotoxic drug, radiolabel, imaging agent, His-Tag, Biotin, Flag-tag, nucleic acid, or a cytokine.

43. A multimeric scaffold comprising at least two scaffolds of embodiment 36.

44. The multimeric scaffold of embodiment 43, wherein said multimeric scaffolds further comprises an epitope binding domain, wherein said epitope binding domain is selected from the group consisting of an antibody, antibody fragment, diabody, scFv, Fab, Fv, a binding peptide.

45. The multimeric scaffold of embodiment 43, wherein said epitope binding domain is specific for a different target than said scaffold.

46. The multimeric scaffold of embodiment 43, wherein said epitope binding domain is specific for the same target as that of said scaffold.

47. The multimeric scaffold of any of embodiments 43-46, wherein said scaffolds are linked by another scaffold, an IgG molecule or fragment thereof, an Fc region, a dimerization domain, a chemical crosslink, a disulfide bond, or an amino acid linker.

48. An isolated nucleic acid molecule encoding the multimeric scaffold of any of embodiments 1-47.

49. An expression vector operably linked to the nucleic acid of embodiment 48.

50. A host cell comprising the vector of embodiment 49.

51. A polypeptide display library comprising the scaffold of embodiment 36, each scaffold comprising a plurality of beta strand domains linked to a plurality of loop region sequences derived from a naturally occurring protein sequence, wherein one or more of said loop region sequences vary by deletion, substitution or addition by at least one amino acid from the corresponding loop sequences in the naturally occurring protein sequence and wherein the beta strand domains of the polypeptide scaffold have at least 50% homology to the corresponding domain sequences of the naturally occurring protein sequence of SEQ ID No:1.

52. The library of embodiment 51, wherein said scaffold comprises at least two loop region sequences that vary by deletion, substitution or addition by at least one amino acid from the corresponding loop sequences in the naturally occurring protein sequence.

53. The library of embodiment 52, wherein said two loop region sequences are selected from the group consisting of BC/DE, BC/FG, DE/FG, AB/CD, AB/EF, and CD/ED loops.

54. The library of embodiment 53, wherein said loop region sequences comprise the BC and FG loops.

55. The library of embodiment 53 wherein said BC loop comprises 9 amino acids having a consensus sequence of S-X-a-X-b-X-X-X-G, wherein X represents any amino acid, wherein (a) represents proline or alanine and wherein (b) represents alanine or glycine.

56. The library of embodiment 53, wherein said BC loop comprises 11 amino acids having a consensus sequence of S-P-c-X-X-X-X-X-T-G (SEQ ID NO: 258), wherein X represents any amino acid and wherein (c) represents proline, serine or glycine.

57. The library of embodiment 53, wherein said BC loop comprises 12 amino acids having a consensus sequence of A-d-P-X-X-X-e-f-X-I-X-G (SEQ ID NO: 257), wherein X represents any amino acid, wherein (d) represents proline, glutamate or lysine, wherein (e) represents asparagine or glycine, and wherein (f) represents serine or glycine.

58. The library of embodiment 53, wherein said FG loop comprises 9 amino acids having a consensus sequence of X-a-X-X-G-X-X-X-S, wherein X represents any amino acid and wherein (a) represents asparagine, threonine or lysine.

59. The library of embodiment 53, wherein said FG loop comprises 10 amino acids having a consensus sequence of X-a-X-X-X-b-N-P-A, wherein X represents any amino acid, wherein (a) represents asparagine, threonine or lysine and wherein (b) represents serine or glycine.

60. The library of embodiment 53, wherein said FG loop comprises 11 amino acids having a consensus sequence of X-a-X-X-G-X-X-S-N-P-A SEQ ID NO: 259), wherein X represents any amino acid, and wherein (a) represents asparagine, threonine or lysine.

61. The library of embodiment 52, wherein said loop region sequences further comprise the DE loop.

62. The library of embodiment 61, wherein said DE loop comprises 6 amino acids having a consensus sequence of X-X-X-X-X-X, wherein X represents any amino acid.

63. The library of embodiment 52, wherein said loop region sequences further comprise the AB loop.

64. The library of embodiment 63, wherein said AB loop comprises 7 residues having the consensus sequence: K-X-X-X-X-X-a, wherein X represents asparagine, aspartic acid, histidine, tyrosine, isoleucine, valine, leucine, phenylalanine, threonine, alanine, proline, or serine, and wherein (a) represents serine, threonine, alanine, or glycine.

65. The library of embodiment 63, wherein said AB loop comprises 9 residues having the consensus sequence: K-X-X-X-X-X-X-X-a, wherein X represents asparagine, aspartic acid, histidine, tyrosine, isoleucine, valine, leucine, phenylalanine, threonine, alanine, proline, or serine, and wherein (a) represents serine, threonine, alanine, or glycine.

66. The library of embodiment 52, wherein said loop region sequences further comprise the CD loop.

67. The library of embodiment 66 wherein said CD loop comprises 7, 8, or 9 residues wherein each residue in the CD loop is randomized and wherein each residue may be asparagine, aspartic acid, histidine, tyrosine, isoleucine, valine, leucine, phenylalanine, threonine, alanine, proline, or serine.

68. The library of embodiment 52, wherein said loop region sequences further comprise the EF loop.

69. The library of embodiment 68, wherein said EF loop comprises 8 having the consensus sequence X-b-L-X-P-X-c-X, wherein X represents asparagine, aspartic acid, histidine, tyrosine, isoleucine, valine, leucine, phenylalanine, threonine, alanine, proline, or serine, wherein (b) represents asparagine, lysine, arginine, aspartic acid, glutamic acid, or glycine, and wherein (c) represents isoleucine, threonine, serine, valine, alanine, or glycine.

70. The library of embodiment 51, wherein said scaffold comprises at least three loop region sequences that vary by deletion, substitution or addition by at least one amino acid from the corresponding loop sequences in the naturally occurring protein sequence.

71. The library of embodiment 70, wherein said loop region sequences comprise the BC, DE, and FG loops.

72. The library of embodiment 70, wherein said loop region sequences comprise the AB, CD, and EF loops.

73. The library of embodiment 70, wherein said loop region sequences comprise any three loops selected from the group consisting of the AB, BC, CD, DE, EF, and FG loops.

74. The polypeptide display library of embodiment 38, wherein said polypeptide is displayed on the surface of a ribosome, bacteriophage, virus, bacteria, or yeast.

75. A collection of isolated nucleic acid molecules encoding the library of any of embodiments 51-74.

76. An expression vector operably linked to the nucleic acid molecules of embodiment 75.

77. A method of obtaining a polypeptide scaffold that binds to a target, said method comprising (a) contacting a target ligand with the library of embodiment 38 under conditions that allow a scaffold:target ligand complex to form, and (b) obtaining from the complex, the scaffold that binds the target ligand.

78. The method of embodiment 77, further comprising randomizing at least one loop of said scaffold of the protein obtained in step (b) to generate a further randomized scaffold and repeating steps (a) and (b) using said further randomized scaffold.

79. The method of embodiment 78, wherein said method comprises at least two loops.

80. The method of embodiment 78, wherein said method comprises at least three loops.

81. The method of embodiment 78, further comprising randomizing at least one loop of said scaffold of the protein obtained in step (b) to generate a further randomized scaffold and repeating steps (a) and (b) using said further randomized scaffold, wherein said repetition of steps (a) and (b) further comprises contacting a target distinct from the target of said first operation of step (a) and (b).

82. The method of embodiment 78, further comprising randomizing at least one loop of said scaffold of the protein obtained step (b), wherein said loop was not randomized in said library to generate a further randomized scaffold and repeating steps (a) and (b) using said further randomized scaffold.

83. The method of embodiment 78, further comprising randomizing at least one loop of said scaffold of the protein obtained step (b), wherein said loop was not randomized in said library to generate a further randomized scaffold and repeating steps (a) and (b) using said further randomized scaffold, wherein said repetition of steps (a) and (b) further comprises contacting a target distinct from the target of said first operation of step (a) and (b).

84. The method of any of embodiments 77-83 wherein said method comprises a first randomized loop selected from the group consisting of BC, DE, and FG loops and a second loop not randomized in said library selected from the group consisting of AB, CD, and EF loops.

85. The method of any of embodiments 77-83 wherein said method comprises a first randomized loop selected from the group consisting of AB, CD, EF loops and a second loop not randomized in said library selected from the group consisting of BC, DE, and FG loops.

86. The method of any of embodiments 77-83, wherein said method further comprising randomizing at least one beta strand of said scaffold of the protein obtained in step (b) to generate a further randomized scaffold and repeating steps (a) and (b) using said further randomized scaffold.

87. The method of embodiment 86, said method further comprising at least two, three, four, five, six or seven beta strands of said scaffold of the protein obtained in step (b) to generate a further randomized scaffold and repeating steps (a) and (b) using said further randomized scaffold.

88. A method of obtaining at least two scaffolds that bind to a target said method comprising (a) contacting a target ligand with the library of embodiment 38 under conditions that allow a scaffold:target ligand complex to form, (b) engaging said scaffolds with a crosslinking agent wherein the crosslinking of said scaffolds elicits a detectable response and (c) obtaining from the complex, said scaffolds that bind the target.

89. The method of embodiment 88, wherein said scaffolds recognize the same epitope.

90. The method of embodiment 88, wherein said scaffolds recognize distinct epitopes.

91. The method of embodiment 88, wherein said crosslinking agent is selected from the group consisting of an antibody, an antibody fragment, a dimerization motif, a chemical crosslinker, a binding peptide, or an epitope tag.

92. A method of detecting a compound in a sample, said method comprising contacting said sample with a scaffold of any of embodiments 1-47 under conditions that allow the formation of a compound:scaffold complex and detecting said complex, thereby detecting said compound in said sample.

93. A method of capturing a compound in a sample, said method comprising contacting said sample with an immobilized scaffold of any of embodiments 1-47 under conditions that allow the formation of a compound:scaffold complex and removing said immobilized scaffold, thereby capturing said compound in said sample.

94. A sterile, pyrogen-free composition comprising the polypeptide of any of embodiments 1 to 47.

95. A pharmaceutical composition comprising the polypeptide of any of embodiments 1 to 47.

96. A method of preventing, treating, managing, or ameliorating a disease in a patient with the composition of embodiment 95.

97. A method of diagnosing or imaging a disease in a patient with the composition of embodiment 95 or 96.

98. The method of embodiment 96, wherein said method further comprises an additional therapy, wherein said therapy is immunotherapy, biological therapy, chemotherapy, radiation therapy, or small molecule drug therapy.

99. The method of any of embodiments 96-98 wherein said disease is an autoimmune disease, inflammatory disease, proliferative disease, infectious disease, respiratory disease, gastrointestinal disease, diabetes, lupus, or obesity.

100. A recombinant, non-naturally occurring polypeptide scaffold comprising,
   I. a plurality of predicted beta strand domains linked to a plurality of predicted loop region sequences derived from a naturally occurring protein sequence,
   II. wherein one or more of said loop region sequences vary by deletion, substitution or addition by at least one amino acid from the corresponding loop sequences in the naturally occurring protein sequence, and;
   III. wherein the beta strand domains of the polypeptide scaffold have at least 50%, at least 60%, at least 70%, at least 80%, or at least 90% homology to the corresponding domain sequences of the naturally occurring protein sequence of SEQ ID NO.2.

101. The scaffold of embodiment 100, wherein said beta strand domains comprises the polypeptide sequence encoded by SEQ ID NO. 2.

102. A recombinant, non-naturally occurring polypeptide scaffold comprising,
   I. a plurality of predicted beta strand domains linked to a plurality of predicted loop region sequences derived from a naturally occurring protein sequence, II. wherein one or more of said loop region sequences vary by deletion, substitution or addition by at least one amino acid from the corresponding loop sequences in the naturally occurring protein sequence, and;
III. wherein the beta strand domains of the polypeptide scaffold have at least 50%, at least 60%, at least 70%, at least 80%, or at least 90% homology to the corresponding domain sequences of the naturally occurring protein sequence of i ID No:3 or 4.
103. The scaffold of embodiment 102, wherein said beta strand domains comprises the protein sequence of Seq ID No:3 or 4.
104. A recombinant, non-naturally occurring polypeptide scaffold comprising,
I. a plurality of predicted beta strand domains linked to a plurality of predicted loop region sequences derived from a naturally occurring protein sequence,
II. wherein one or more of said loop region sequences vary by deletion, substitution or addition by at least one amino acid from the corresponding loop sequences in the naturally occurring protein sequence, and;
III. wherein the beta strand domains of the polypeptide scaffold have at least 50% homology to the corresponding domain sequences of the naturally occurring protein sequence, wherein said naturally occurring protein sequence is selected from SEQ ID NOs: 5-32, 68-88.
105. The scaffold of any of embodiments 100-104, wherein said plurality of beta strands is at least seven strands.
106. The scaffold of any of embodiments 100-104, wherein said plurality of loop regions is at least six regions.
107. The scaffold of embodiment 100-104, wherein said scaffold comprises seven beta strands, wherein each is designated A, B, C, D, E, and F, and six loop regions, wherein a loop region connects each beta strand and is designated AB, BC, CD, DE, EF, and FG loops.
108. The scaffold of any of embodiments 100-107, wherein said scaffold further comprises at least one disulfide bond.
109. The scaffold of any of embodiments 100-107, wherein said scaffold further comprises at least two, three, four, or more disulfide bonds.
110. The scaffold of embodiment 108 or 109, wherein said at least one disulfide bond is in a beta strand domain.
111. The scaffold of embodiment 108 or 109, wherein said at least one disulfide bond is in a loop region.
112. The scaffold of any of embodiments 100-111, wherein said scaffold binds a target.
113. The scaffold of embodiment 112, wherein said target is a cell-surface antigen, a soluble antigen, an immobilized antigen, an immunosilent antigen, an intracellular antigen, an intranuclear antigen, a self antigen, a non-self antigen, a cancer antigen, a bacterial antigen, or a viral antigen.
114. The scaffold of embodiment 112, wherein said scaffold binds with an affinity of at least a Kd of 100 μM.
115. The scaffold of embodiment 112, wherein said scaffold exhibits a melting temperature (Tm) of at least 40° C. as measured by differential scanning calorimetry (DSC) in 20 mM sodium phosphate, pH 7.0.
116. The scaffold of embodiment 112, wherein said scaffold exhibits an increased Cm of at least 10% as measured in a urea denaturation experiment compared to the same scaffold prior to engineering, under similar experimental conditions.
117. The scaffold of embodiment 112, wherein said scaffold exhibits an increased Cm of at least 10% as measured in a guanidine denaturation experiment compared to the same scaffold prior to engineering, under similar experimental conditions.
118. The scaffold of embodiment 112, wherein said scaffold exhibits an increased resistance to protease degradation by at least 10% as compared to the same scaffold prior to engineering under similar experimental conditions.
119. The scaffold of embodiment 112, wherein said scaffold is conjugated to a heterologus agent, wherein said agent is selected from the group consisting of another scaffold, Polyethylene glycol (PEG), human serum albumin (HSA), an Fc region of an antibody, an IgG molecule, a dimerization domain, a binding peptide, cytotoxic drug, radiolabel, imaging agent, His-Tag, Biotin, Flag-tag, nucleic acid, or a cytokine.
120. A multimeric scaffold comprising at least two scaffolds of any of embodiments 100-119.
121. The multimeric scaffold of embodiment 120, wherein said multimeric scaffold further comprises an epitope binding domain, wherein said epitope binding domain is selected from the group consisting of an antibody, antibody fragment, diabody, scFv, Fab, Fv, or a binding peptide.
122. The multimeric scaffold of embodiment 121, wherein said epitope binding domain is specific for a different target than said scaffold.
123. The multimeric scaffold of embodiment 121, wherein said epitope binding domain is specific for the same target than said scaffold.
124. The multimeric scaffold of any of embodiments 120-123, wherein said scaffolds are linked by another scaffold, an IgG molecule or fragment thereof, an Fc region, a dimerization domain, a chemical crosslink, a disulfide bond, or an amino acid linker.
125. An isolated nucleic acid molecule encoding the polypeptide of any of embodiments 100-124.
126. An expression vector operably linked to the nucleic acid of embodiment 125.
127. A host cell comprising the vector of embodiment 126.
128. A polypeptide display library comprising the scaffolds of any of embodiments 100-119, each scaffold comprising a plurality of beta strand domains linked to a plurality of loop region sequences derived from a naturally occurring protein sequence, wherein one or more of said loop region sequences vary by deletion, substitution or addition by at least one amino acid from the corresponding loop sequences in the naturally occurring protein sequence and wherein the beta strand domains of the polypeptide scaffold have at least 50% homology to the corresponding domain sequences of the naturally occurring protein sequence.
129. The library of embodiment 128, wherein said scaffold comprises at least two loop region sequences that vary by deletion, substitution or addition by at least one amino acid from the corresponding loop sequences in the naturally occurring protein sequence.
130. The library of embodiment 128, wherein said two loop region sequences comprise loop sequences from the group selected from BC/DE, BC/FG, DE/FG, AB/CD, AB/EF, and CD/ED loops.
131. The library of embodiment 128, wherein said scaffold comprises at least three loop region sequences that vary by deletion, substitution or addition by at least one amino acid from the corresponding loop sequences in the naturally occurring protein sequence.
132. The library of embodiment 131, wherein said loop region sequences comprise the BC, DE, and FG loops.
133. The library of embodiment 131, wherein said loop region sequences comprise the AB, CD, and EF loops.

134. The library of embodiment 128, wherein said polypeptide is displayed on the surface of a ribosome, bacteriophage, virus, bacteria, or yeast.
135. The library of embodiment 134, wherein said library has a sequence diversity of at least $10^6$.
136. A method of obtaining a scaffold that binds to a target, said method comprising (a) contacting the target ligand with the library of embodiment 128 under conditions that allow a scaffold:target ligand complex to form, and (b) obtaining, from the complex, the scaffold that binds the ligand.
137. The method of embodiment 136, further comprising randomizing at least one loop of said scaffold of the protein obtained in step (b) to generate a further randomized scaffold and repeating steps (a) and (b) using said further randomized scaffold.
138. The method of embodiment 137, wherein said method comprises randomizing at least two loops.
139. The method of embodiment 137, wherein said method comprises randomizing at least three loops.
140. The method of embodiment 137, further comprising randomizing at least one loop of said scaffold of the protein obtained in step (b) to generate a further randomized scaffold and repeating steps (a) and (b) using said further randomized scaffold, wherein said repetition of steps (a) and (b) further comprises contacting a target distinct from the target of said first operation of step (a) and (b).
141. The method of embodiment 137, further comprising randomizing at least one loop of said scaffold of the protein obtained step (b), wherein said loop was not randomized in said library to generate a further randomized scaffold and repeating steps (a) and (b) using said further randomized scaffold.
142. The method of embodiment 137, further comprising randomizing at least one loop of said scaffold of the protein obtained step (b), wherein said loop was not randomized in said library to generate a further randomized scaffold and repeating steps (a) and (b) using said further randomized scaffold, wherein said repetition of steps (a) and (b) further comprises contacting a target distinct from the target of said first operation of step (a) and (b).
143. The method of any of embodiments 136-142 wherein said method comprises a first randomized loop selected from the group consisting of BC, DE, and FG loops and a second loop not randomized in said library selected from the group consisting of AB, CD, and EF loops.
144. The method of any of embodiments 140-142 wherein said method comprises a first randomized loop selected from the group consisting of AB, CD, EF loops and a second loop not randomized in said library selected from the group consisting of BC, DE, and FG loops.
145. The method of any of embodiments 128-144, wherein said method further comprising randomizing at least one beta strand of said scaffold of the protein obtained in step (b) to generate a further randomized scaffold and repeating steps (a) and (b) using said further randomized scaffold.
146. The method of embodiment 145, said method further comprising at least two, three, four, five, six or seven beta strands of said scaffold of the protein obtained in step (b) to generate a further randomized scaffold and repeating steps (a) and (b) using said further randomized scaffold.
147. A method of obtaining at least two scaffolds that bind to a target said method comprising (a) contacting a target ligand with the library of embodiment 38 under conditions that allow a scaffold:target ligand complex to form, (b) engaging said scaffolds with a crosslinking agent wherein the crosslinking of said scaffolds elicits a detectable response and (c) obtaining from the complex, said scaffolds that bind the target.
148. The method of embodiment 147, wherein said scaffolds recognize the same epitope.
149. The method of embodiment 147, wherein said scaffolds recognize distinct epitopes.
150. The method of embodiment 147, wherein said crosslinking agent is selected from the group consisting of an antibody, an antibody fragment, a dimerization motif, a chemical crosslinker, a binding peptide, or an epitope tag.
151. A method of detecting a compound in a sample, said method comprising contacting said sample with a scaffold of embodiment 112 under conditions that allow the formation of a compound:scaffold complex and detecting said complex, thereby detecting said compound in said sample.
152. A method of capturing a compound in a sample, said method comprising contacting said sample with an immobilized scaffold of embodiment 112 under conditions that allow the formation of a compound:scaffold complex and removing said immobilized scaffold, thereby capturing said compound in said sample.
153. A method of purifying the scaffold of embodiment 101 or 102 said method comprising heating a composition containing said scaffold up to 70° C. for at least 15 minutes, and removing aggregated compounds by centrifugation.
154. A method of purifying the scaffold of embodiment 101 or 102, said method comprising adjusting a composition containing said scaffold to pH 3.0 or pH 3.5 or pH 4.0, or pH 4.5, or pH 5.0; heating the resultant composition at 50° C., or at 55° C., or at 60° C., or at 65° C., or at 70° C., for 1-30 minutes; and subsequently removing aggregated compounds by centrifugation.
155. A sterile, pyrogen-free composition comprising the scaffold of any of embodiments 100-124
156. A pharmaceutical composition comprising the scaffold of any of embodiments 100-124.
157. A method of preventing, treating, or ameliorating a disease in a patient comprising administering an effective amount of the composition of embodiment 156 to a patient.
158. A method of monitoring disease progression in a patient comprising: administering the composition of embodiment 156 to a patient in need of said monitoring; imaging the composition in said patient; and evaluating said patient.
159. The method of embodiment 157 or 158 wherein said disease is an autoimmune disease, inflammatory disease, proliferative disease, infectious disease, respiratory disease, gastrointestinal disease, diabetes, lupus, or obesity.
160. A scalable process of the invention wherein said process results in a production efficiency of at least 1 g/L of a scaffold from any of embodiments 1-47 or 100-124.
161. The process of embodiment 160, wherein said process comprises scaffolds that are purified from the culture media used in the process.
162. A method of producing a scaffold from any of embodiments 1-47 or 100-124 in which said scaffold is produced and secreted into the culture media.
163. The method of embodiment 162 wherein said method comprises using an expression vector comprises an oppA signal peptide (SEQ ID NO:227).
164. A method of assaying or detecting binding of a scaffold to a target using cell free material obtained from the method of embodiment 162.
165. A method of purifying a scaffold produced by the method of embodiment 162.
166. The scaffold of embodiment 1, wherein said scaffold specifically binds TRAIL-R2.

167. The scaffold of embodiment 166, wherein said TRAIL-R2 is human.
168. The scaffold of embodiment 166, wherein said scaffold comprises a sequence derived from a TRAIL-R2 binding scaffold selected from 2F4, 5B10, 10D9, 6F11, 8B3, 5E5, 2Hb, 7G11, 6C7, 1E03, 2B04, 1C12, 1A03, 1C10, 1B12, 2G03, 2D3, 1C06, 2F08, 1B04, 3B11, 1D8, 2A12, 1E05, 2F02, 1H05, 2A11, or 1G11.
169. The scaffold of embodiment 166, wherein said scaffold is a multimeric scaffold.
170. The scaffold of embodiment 168, wherein said multimeric scaffold comprises at least two scaffold domains.
171. The scaffold of embodiment 170, wherein said at least two scaffold domains bind the same epitope.
172. The scaffold of embodiment 170, wherein said at least two scaffold domains bind the same epitope.
173. The scaffold of embodiment 170, wherein at least one scaffold domain is linked to an Fc region derived from an IgG molecule.
174. The scaffold of embodiment 170, wherein at least one scaffold domain is linked to a CH1 region derived from an IgG molecule.
175. The scaffold of embodiment 170, wherein at least one scaffold domain is linked to a CH2 region derived from an IgG molecule.
176. The scaffold of embodiment 170, wherein at least one scaffold domain is linked to a hinge region derived from an IgG molecule.
177. The scaffold of embodiment 170, wherein at least one scaffold domain is linked to a Ckappa or Clambda region derived from an IgG molecule.
178. The scaffold of embodiment 170, wherein at least one scaffold domain is 2D3 or 1C12.
179. The scaffold of embodiment 170, wherein said scaffold comprises 1C12 linked to a hinge region derived from an IgG molecule.
180. The scaffold of embodiment 170, wherein said scaffold comprises 2D3 linked to a hinge region derived from an IgG molecule.
181. The scaffold of embodiment 170, wherein said scaffold comprises 1C12 linked to a CH1 region derived from an IgG molecule.
182. The scaffold of embodiment 170, wherein said scaffold comprises 2D3 linked to a CH1 region derived from an IgG molecule.
183. The scaffold of embodiment 170, wherein said scaffold comprises 1C12 linked to a Ckappa region of an IgG molecule.
184. The scaffold of embodiment 170, wherein said scaffold comprises 2D3 linked to a Ckappa region of an IgG molecule.
185. The scaffold of any of embodiments 166-184, wherein said scaffold comprises a BC loop sequence selected from the group consisting of SEQ ID NO:126, 128, 130, 132, 134, 136, 138, 140, 142, 144, 147, 150, 153, 156, 159, 162, 165, 168, 171, 174, 177, 180, 183, 186, 189, 192, 195, and 198.
186. The scaffold of any of claims 166-184, wherein said scaffold comprises a DE loop sequence selected from the group consisting of SEQ ID NO: 145, 148, 151, 154, 157, 160, 163, 166, 169, 172, 175, 178, 181, 184, 187, 190, 193, 196, and 199.
187. The scaffold of any of embodiments 166-184, wherein said scaffold comprises an FG loop sequence selected from the group consisting of 127, 129, 131, 133, 135, 137, 139, 141, 143, 146, 149, 152, 155, 158, 161, 164, 167, 170, 173, 176, 179, 182, 185, 188, 191, 194, 197, and 200.
188. The scaffold of any of embodiments 166-188 wherein said scaffold agonizes the TRAIL-R2 receptor upon binding.
189. The scaffold of any of embodiments 166-189 wherein said scaffold mimics the binding of TRAIL to TRAIL-R2 receptor upon binding.
190. The scaffold of any of embodiments 166-190 wherein said scaffold acts to dimerize the TRAIL-R2 receptor upon binding.
191. A method of agonizing the TRAIL-R2 receptor comprising contacting the TRAIL-R2 receptor with a scaffold of any of embodiments 166-190.
192. The method of embodiment 191, wherein said scaffold mimics the binding of TRAIL to TRAIL-R2.
193. The method of embodiment 192, wherein said scaffold acts to dimerize the TRAIL-R2 receptor.
194. A method of reducing or inhibiting cell viability comprising contacting TRAIL-R2 receptor on the cell with a scaffold of any of embodiments 166-190.
195. A method of activating or promoting apoptosis in a cell comprising contacting TRAIL-R2 receptor on the cell with a scaffold of any of embodiments 166-190.
196. A method of preventing, treating, ameliorating, or managing cancer in a patient in need thereof by administering a scaffold or a composition thereof of any of embodiments 166-190.
197. The method of embodiment 196, wherein said cancer is selected from squamous cell cancer, small-cell lung cancer, non-small cell lung cancer (NSCLC), non-Hodgkin's lymphoma, blastoma, gastrointestinal cancer, renal cancer, ovarian cancer, liver cancer, stomach cancer, bladder cancer, hepatoma, breast cancer, colon cancer, colorectal cancer, pancreatic cancer, endometrial carcinoma, salivary gland carcinoma, kidney cancer, liver cancer, prostate cancer, vulval cancer, thyroid cancer, hepatic carcinoma, head and neck cancer, lung cancer, adenocarcinoma, renal cell carcinoma, or hepatocellular carcinoma.
198. A recombinant polypeptide scaffold comprising,
I. seven beta strand domains designated A, B, C, D, E, F, and G;
II. linked to six loop regions, wherein a loop region connects each beta strand and is designated AB, BC, CD, DE, EF, and FG loops;
III. wherein at least one loop region is a non-naturally occurring variant of the cognate loop regions in any of SEQ ID NOs: 1-32 or 68-88; and
IV. wherein at least one beta strand domain have at least 50%, at least 60%, at least 70%, at least 80%, or at least 90%, at least 95%, or at least 99% homology to the cognate beta strand domains in any of SEQ ID NOs: 1-32 or 68-88.
199. The scaffold of embodiment 198, wherein said beta strand domains comprises the polypeptide sequence encoded by any of SEQ ID NOs: 1-32 or 68-88.
200. The scaffold of embodiment 199, wherein said beta strand domains comprise:
a. amino acid sequences for the A beta strand (SEQ ID NO:228), B beta strand (SEQ ID NO:229), C beta strand (SEQ ID NO:230), D beta strand (SEQ ID NO:231), E beta strand (SEQ ID NO:232), F beta strand (SEQ ID NO:233) and G beta strand (SEQ ID NO:234); or
b. amino acid sequences for the A beta strand (SEQ ID NO:235), B beta strand (SEQ ID NO:229), C beta strand (SEQ ID NO:230), D beta strand (SEQ ID NO:236), E beta strand (SEQ ID NO:232), F beta strand (SEQ ID NO:237) and G beta strand (SEQ ID NO:234).

SEQUENCES

Tn3 wild type loops (first embodiment):

```
AB (SEQ ID NO: 201) = DVTDTT
BC (SEQ ID NO: 202) = FKPLAEIDG
CD (SEQ ID NO: 203) = KDVPGDR
DE (SEQ ID NO: 204) = LTEDENQ
EF (SEQ ID NO: 205) = GNLKPD
FG (SEQ ID NO: 206) = RRGDMSSNPA
```

Tn3 wild type beta strands (first embodiment)

```
A (SEQ ID NO: 228) = RLDAPSQIEVK
B (SEQ ID NO: 229) = ALITW
C (SEQ ID NO: 230) = IELTYGI
D (SEQ ID NO: 231) = TTID
E (SEQ ID NO: 232) = YSI
F (SEQ ID NO: 233) = TEYEVSLIS
G (SEQ ID NO: 234) = KETFTT
```

Tn3 wild type loops (second embodiment):

```
AB (SEQ ID NO: 207) = KDVTDTT
BC (SEQ ID NO: 202) = FKPLAEIDG
CD (SEQ ID NO: 203) = KDVPGDR
DE (SEQ ID NO: 208) = TEDENQ
EF (SEQ ID NO: 209) = GNLKPDTE
FG (SEQ ID NO: 206) = RRGDMSSNPA
```

Tn3 wild type beta strands (second embodiment)

```
A (SEQ ID NO: 235) = RLDAPSQIEV
B (SEQ ID NO: 229) = ALITW
C (SEQ ID NO: 230) = IELTYGI
D (SEQ ID NO: 236) = TTIDL
E (SEQ ID NO: 232) = YSI
F (SEQ ID NO: 237) = YEVSLIS
G (SEQ ID NO: 234) = KETFTT
```

Protein Sequences

Upper case lettering corresponds to the Tn3 structural motif, while lower case lettering are flanking sequence appendages derived from the synthetic cDNA and expression vector.

1P:
SEQ ID NO: 5
aaLEVVAATPTSLLISWDAPAVTVRYYRITYGETGGNSPVQEFTVPGSKSTATISGLKP
GVDYTITVYAVTGRGDSPASSKPISINYRTgggtlehhhhhh SEQ ID NO: 6
LEVVAATPTSLLISWDAPAVTVRYYRITYGETGGNSPVQEFTVPGSKSTATISGLKPG
VDYTITVYAVTGRGDSPASSKPISINYRT 2P:
SEQ ID NO: 7
aaPTVDQVDDTSIVVRWSRPQAPITGYRIVYSPSVEGSSTELNLPETANSVTLSDLQPG
VQYNITIYAVEENQESTPVVIQQETgggtlehhhhhh SEQ ID NO: 8
PTVDQVDDTSIVVRWSRPQAPITGYRIVYSPSVEGSSTELNLPETANSVTLSDLQPGV
QYNITIYAVEENQESTPVVIQQET 3P:
SEQ ID NO: 9
aaPYNTEVTETTIVITWTPAPRIGFKLGVRPSQGGEAPREVTSDSGSIVVSGLTPGVEYV
YTIQVLRDGQERDAPIVNKVVTgggtlehhhhhh SEQ ID NO: 10
PYNTEVTETTIVITWTPAPRIGFKLGVRPSQGGEAPREVTSDSGSIVVSGLTPGVEYVY
TIQVLRDGQERDAPIVNKVVT 4P:
SEQ ID NO: 11
aaPPIALNWTLLNVSLTGIHADIQVRWEAPRNADIQKGWMVLEYELQYKEVNETKW
KMMDPILTTSVPVYSLKVDKEYEVRVRSKQRNSGNYGEFSEVLYVTLPgggtlehhhhhh

SEQ ID NO: 12
PPIALNWTLLNVSLTGIHADIQVRWEAPRNADIQKGWMVLEYELQYKEVNETKWK

MMDPILTTSVPVYSLKVDKEYEVRVRSKQRNSGNYGEFSEVLYVTLP

5P:
SEQ ID NO: 13
aaPPSLNVTKDGDSYSLRWETMKMRYEHIDHTFEIQYRKDTATWKDSKTETLQNAHS

MALPALEPSTRYWARVRVRTSRTGYNGIWSEWSEARSWDTEgggtlehhhhhh

SEQ ID NO: 14
PPSLNVTKDGDSYSLRWETMKMREHIDHTFEIQYRKDTATWKDSKTETLQNAHSM

ALPALEPSTRYWARVRVRTSRTGYNGIWSEWSEARSWDTE

6P:
SEQ ID NO: 15
aaPPVNFTIKVTGLAQVLLQWKPNPDQEQRNVNLEYQVKINAPKEDDYETRITESK1V

TILHKGFSASVRTILQNDHSLLASSWASAELHAgggtlehhhhhh

SEQ ID NO: 16
PPVNFTIKVTGLAQVLLQWKPNPDQEQRNVNLEYQVKINAPKEDDYETRITESK1VTI

LHKGFSASVRTILQNDHSLLASSWASAELHA

7P:
SEQ ID NO: 17
aaLSVTDVTTSSLRLNWEAPPGAFDSFLLRFGVPSPSTLEPHPRPLLQRELMVPGTRHS

AVLRDLRSGTLYSLTLYGLRGPHKADSIQGTARTgggtlehhhhhh

SEQ ID NO: 18
LSVTDVTTSSLRLNWEAPPGAFDSFLLRFGVPSPSTLEPHPRPLLQRELMVPGTRHSA

VLRDLRSGTLYSLTLYGLRGPHKADSIQGTART

8P:
SEQ ID NO: 19
aaLRALNLTEGFAVLHWKPPQNPVDTYDIQVTAPGAPPLQAETPGSAVDYPLHDLVL

HTNYTATVRGLRGPNLTSPASITFTTgggtlehhhhhh

SEQ ID NO: 20
LRALNLTEGFAVLHWKPPQNPVDTYDIQVTAPGAPPLQAETPGSAVDYPLHDLVLHT

NYTATVRGLRGPNLTSPASITFTT

9P:
SEQ ID NO: 21
aaLEAKEVTPRTALLTWTEPPVRPAGYLLSFHTPGGQTQEILLPGGITSHQLLGLFPSTS

YNARLQAMWGQSLLPPVSTSFTTgggtlehhhhhh

SEQ ID NO: 22
LEAKEVTPRTALLTWTEPPVRPAGYLLSFHTPGGQTQEILLPGGITSHQLLGLFPSTSY

NARLQAMWGQSLLPPVSTSFTT

10P:
SEQ ID NO: 23
aaIEVKDVTDTTALITWFKPLAEIDGIELTYGIKDVPGDRTTIDLTEDENQYSIGNLKPD

TEYEVSLISRRGDMSSNPAKETFTTgggtlehhhhhh

SEQ ID NO: 24
IEVKDVTDTTALITWFKPLAEIDGIELTYGIKDVPGDRTTIDLTEDENQYSIGNLKPDT

EYEVSLISRRGDMSSNPAKETFTT

11P:
SEQ ID NO: 25
aaPKFTKCRSPERETFSCHWTDEVHHGTKNLGPIQLFYTRRNTQEWTQEWKECPDYV

SAGENSCYFNSSFTSIWIPYCIKLTSNGGTVDEKCFSVgggtlehhhhhh

```
                                                     SEQ ID NO: 26
PKFTKCRSPERETFSCHWTDEVHHGTKNLGPIQLFYTRRNTQEWTQEWKECPDYVS

AGENSCYFNSSFTSIWIPYCIKLTSNGGTVDEKCFSV

12P:
                                                     SEQ ID NO: 27
aaPSGFPQNLHVTGLTTSTTELAWDPPVLAERNGRIISYTVVFRDINSQQELQNITTDT

RFTLTGLKPDTTYDIKVRAWTSKGSGPLSPSIQSRTMPVEgggtlehhhhhh

SEQ ID NO: 28
PSGFPQNLHVTGLTTSTTELAWDPPVLAERNGRIISYTVVFRDINSQQELQNITTDTRF

TLTGLKPDTTYDIKVRAWTSKGSGPLSPSIQSRTMPVE

13P:
                                                     SEQ ID NO: 29
aaPKPPIDLVVTETTATSVTLTWDSGNSEPVTYYGIQYRAAGTEGPFQEVDGVATTRY

SIGGLSPFSEYAFRVLAVNSIGRGPPSEAVRARTGEQAgggtlehhhhhh

SEQ ID NO: 30
PKPPIDLVVTETTATSVTLTWDSGNSEPVTYYGIQYRAAGTEGPFQEVDGVATTRYSI

GGLSPFSEYAFRVLAVNSIGRGPPSEAVRARTGE

14P:
                                                     SEQ ID NO: 31
aaLSPPRNLRISNVGSNSARLTWDPTSRQINGYRIVYNNADGTEINEVEVDPITTFPLKG

LTPLTEYTIAIFSIYDEGQSEPLTGVFTTgggtlehhhhhh

SEQ ID NO: 32
LSPPRNLRISNVGSNSARLTWDPTSRQINGYRIVYNNADGTEINEVEVDPITTFPLKGL

TPLTEYTIAIFSIYDEGQSEPLTGVFTT
```

DNA Sequences

Upper case lettering corresponds to the Tn3 structural motif, while lower case lettering are flanking sequence appendages.

```
1D:
                                                     SEQ ID NO: 33
gccatggccgccCTGGAAGTGGTGGCGGCGACCCCGAACCAAGCCTGCTGATTAGCTGGG

ATGCGCCGGCGGTGACCGTGCGCTATTATCGTATTACCTATGGCGAAACCGGCGG

CAATAGCCCGGTGCAGGAATTTACCGTGCCGGGCAGCAAAAGCACCGCGACCAT

TAGCGGCCTGAAACCGGGCGTGGATTATACCATTACCGTGTATGCGGTGACCGGC

CGTGGCGATAGCCCGGCGAGCAGCAAACCGATTAGCATTAACTATCGTACCggtgg cggtacc

SEQ ID NO: 34
CTGGAAGTGGTGGCGGCGACCCCGACCGACCTGCTGATTAGCTGGGATGCGCCG

GCGGTGACCGTGCGCTATTATCCGTATTACCTATGGCGAAACCGGCGGCAATAGCC

CGGTGCAGGAATTTACCGTGCCGGGCAGCAAAAGCACCGCGACCATTAGCGGCC

TGAAACCGGGCGTGGATTATACCATTACCGTGTATGCGGTGACCGGCCGTGGCG

ATAGCCCGGCGAGCAGCAAACCGATTAGCATTAACTATCGTACC

2D:
                                                     SEQ ID NO: 35
gccatggccgccCCGACCGTGGATCAGGTGGATGATACCAGCATTGTGGTGCGCTGGA

GCCGTCCGCAGGCGCCGATTACCGGCTATCGTATTGTGTATAGCCCGAGCGTGGA

AGGCAGCAGCACCGAACTGAACCTGCCGGAAACCGCGAATAGCGTGACCCTGAG
```

-continued

CGATCTGCAGCCGGGCGTGCAGTATAACATTACCATTTATGCGGTGGAAGAAAA

CCAGGAAAGCACCCCGGTGGTGATTCAGCAGGAAACCggtggcggtacc

SEQ ID NO: 36
CCGACCGTGGATCAGGTGGATGATACCAGCATTGTGGTGCGCTGGAGCCGTCCG

CAGGCGCCGATTACCGGCTATCGTATTGTGTATAGCCCGAGCGTGGAAGGCAGC

AGCACCGAACTGAACCTGCCGGAAACCGCGAATAGCGTGACCCTGAGCGATCTG

CAGCCGGGCGTGCAGTATAACATTACCATTTATGCGGTGGAAGAAAACCAGGAA

AGCACCCCGGTGGTGATTCAGCAGGAAACC

3D:

SEQ ID NO: 37
gccatggccgccCCGTATAACACCGAAGTGACCGAAACCACCATTGTGATTACCTGGAC

CCCGGCGCCGCGTATTGGCTTTAAACTGGGCGTGCGTCCGAGCCAGGGCGGTGA

AGCGCCGCGCGAAGTGACCAGCGATAGCGGCAGCATTGTGGTGAGCGGCCTGAC

CCCGGGCGTGGAATATGTGTATACCATTCAGGTGCTGCGTGATGGCCAGGAACGT

GATGCGCCGATTGTGAACAAAGTGGTGACCggtggcggtacc

SEQ ID NO: 38
CCGTATAACACCGAAGTGACCGAAACCACCATTGTGATTACCTGGACCCCGGCG

CCGCGTATTGGCTTTAAACTGGGCGTGCGTCCGAGCCAGGGCGGTGAAGCGCCG

CGCGAAGTGACCAGCGATAGCGGCAGCATTGTGGTGAGCGGCCTGACCCCGGGC

GTGGAATATGTGTATACCATTCAGGTGCTGCGTGATGGCCAGGAACGTGATGCGC

CGATTGTGAACAAAGTGGTGACC

4D:

SEQ ID NO: 39
gccatggccgccCCGCCGATCGCTCTGAATTGGACCCTGCTGAATGTTTCGCTGACCGG

TATTCATGCCGATATTCAGGTGCGTTGGGAAGCGCCGCGTAACGCCGATATTCAG

AAAGGCTGGATGGTGCTGGAATATGAACTGCAGTATAAAGAAGTGAATGAAACC

AAATGGAAAATGATGGACCCGATTCTGACCACCAGCGTGCCGGTGTACAGCCTG

AAAGTGGATAAAGAATACGAAGTCCGTGTGCGTTCTAAACAGCGTAATAGCGGC

AATTATGGTGAATTTAGTGAAGTCCTGTATGTTACCCTGCCGggtggcggtacc

SEQ ID NO: 40
CCGCCGATCGCTCTGAATTGGACCCTGCTGAATGTTTCGCTGACCGGTATTCATG

CCGATATTCAGGTGCGTTGGGAAGCGCCGCGTAACGCCGATATTCAGAAAGGCT

GGATGGTGCTGGAATATGAACTGCAGTATAAAGAAGTGAATGAAACCAAATGGA

AAATGATGGACCCGATTCTGACCACCAGCGTGCCGGTGTACAGCCTGAAAGTGG

ATAAAGAATACGAAGTCCGTGTGCGTTCTAAACAGCGTAATAGCGGCAATTATG

GTGAATTTAGTGAAGTCCTGTATGTTACCCTGCCG

5D:

SEQ ID NO: 41
gccatggccgccCCGCCGAGCCTGAACGTGACCAAAGATGGCGATAGCTATAGCCTGC

GCTGGGAAACCATGAAAATGCGCTATGAACATATTGATCATACCTTTGAAATTCA

GTATCGCAAAGATACCGCGACCTGGAAAGATAGCAAAACCGAAACCCTGCAGAA

CGCGCATAGCATGGCGCTGCCGGCGCTGGAACCGAGCACCCGTTATTGGGCGCG

TGTGCGTGTGCGTACCAGCCGTACCGGCTATAATGGCATTTGGAGCGAATGGAGC

GAAGCGCGTAGCTGGGATACCGAAggtggcggtacc

CCGCCGAGCCTGAACGTGACCAAAGATGGCGATAGCTATAGCCTGCGCTGGGAA

```
ACCATGAAAATGCGCTATGAACATATTGATCATACCTTTGAAATTCAGTATCGCA

AAGATACCGCGACCTGGAAAGATAGCAAAACCGAAACCCTGCAGAACGCGCATA

GCATGGCGCTGCCGGCGCTGGAACCGAGCACCCGTTATTGGGCGCGTGTGCGTGT

GCGTACCAGCCGTACCGGCTATAATGGCATTTGGAGCGAATGGAGCGAAGCGCG

TAGCTGGGATACCGAA
```

6D:
```
                                                   SEQ ID NO: 42
gccatggccgccCCGCCGGTGAACTTTACCATTAAAGTGACCGGCCTGGCGCAGGTGCT

GCTGCAGTGGAAACCGAACCCGGATCAGGAACAGCGTAACGTGAACCTGGAATA

TCAGGTGAAAATTAACGCGCCGAAAGAAGATGATTATGAAACCCGCATTACCGA

AAGCAAACTGGTGACCATTCTGCATAAAGGCTTTAGCGCGAGCGTGCGTACCATT

CTGCAGAACGATCATAGCCTGCTGGCGAGCAGCTGGGCGAGCGCGGAACTGCAT

GCGggtggcggtacc
```

```
                                                   SEQ ID NO: 43
CCGCCGGTGAACTTTACCATTAAAGTGACCGGCCTGGCGCAGGTGCTGCTGCAGT

GGAAACCGAACCCGGATCAGGAACAGCGTAACGTGAACCTGGAATATCAGGTGA

AAATTAACGCGCCGAAAGAAGATGATTATGAAACCCGCATTACCGAAAGCAAAC

TGGTGACCATTCTGCATAAAGGCTTTAGCGCGAGCGTGCGTACCATTCTGCAGAA

CGATCATAGCCTGCTGGCGAGCAGCTGGGCGAGCGCGGAACTGCATGCG
```

7D:
```
                                                   SEQ ID NO: 44
gccatggccgccCTGAGCGTGACCGATGTGACCACCAGCAGCCTGCGTCTGAACTGGG

AAGCGCCGCCGGGCGCGTTTGATAGCTTTCTGCTGCGTTTTGGCGTGCCGAGCCC

GAGCACCCTGGAACCGCATCCGCGTCCGCTGCTGCAGCGTGAACTGATGGTGCC

GGGCACCCGTCATAGCGCGGTGCTGCGTGATCTGCGTAGCGGCACCCTGTATAGC

CTGACCCTGTATGGCCTGCGTGGCCCGCATAAAGCGGATAGCATTCAGGGCACC

GCGCGTACCggtggcggtacc
```

```
                                                   SEQ ID NO: 45
CTGAGCGTGACCGATGTGACCACCAGCAGCCTGCGTCTGAACTGGGAAGCGCCG

CCGGGCGCGTTTGATAGCTTTCTGCTGCGTTTTGGCGTGCCGAGCCCGAGCACCC

TGGAACCGCATCCGCGTCCGCTGCTGCAGCGTGAACTGATGGTGCCGGGCACCC

GTCATAGCGCGGTGCTGCGTGATCTGCGTAGCGGCACCCTGTATAGCCTGACCCT

GTATGGCCTGCGTGGCCCGCATAAAGCGGATAGCATTCAGGGCACCGCGCGTACC
```

8D:
```
                                                   SEQ ID NO: 46
gccatggccgccCTGCGCGCGCTGAACCTGACCGAAGGCTTTGCGGTGCTGCATTGGAA

ACCGCCGCAGAACCCGGTGGATACCTATGATATTCAGGTGACCGCGCCGGGCGC

GCCGCCGCTGCAGGCGGAAACCCCGGGCAGCGCGGTGGATTATCCGCTGCATGA

TCTGGTGCTGCATACCAACTATACCGCGACCGTGCGTGGCCTGCGCGGCCCGAAT

CTGACCAGCCCGGCGAGCATTACCTTTACCACCggtggcggtacc
```

```
                                                   SEQ ID NO: 47
CTGCGCGCGCTGAACCTGACCGAAGGCTTTGCGGTGCTGCATTGGAAACCGCCGC

AGAACCCGGTGGATACCTATGATATTCAGGTGACCGCGCCGGGCGCGCCGCCGC

TGCAGGCGGAAACCCCGGGCAGCGCGGTGGATTATCCGCTGCATGATCTGGTGC
```

-continued

TGCATACCAACTATACCGCGACCGTGCGTGGCCTGCGCGGCCCGAATCTGACCAG

CCCGGCGAGCATTACCTTTACCACC

9D:
SEQ ID NO: 48
gccatggccgccCTGGAAGCGAAAGAAGTGACCCCGCGTACCGCGCTGCTGACCTGGA

CCGAACCGCCGGTGCGCCCGGCGGGTTATCTGCTGAGCTTTCATACCCCGGGCGG

CCAGACCCAGGAAATTCTGCTGCCGGGCGGCATTACCAGCCATCAGCTGCTGGG

CCTGTTTCCGAGCACCAGCTATAACGCGCGTCTGCAGGCGATGTGGGGCCAGAG

CCTGCTGCCGCCGGTGAGCACCAGCTTTACCACCggtggcggtacc

SEQ ID NO: 49
CTGGAAGCGAAAGAAGTGACCCCGCGTACCGCGCTGCTGACCTGGACCGAACCG

CCGGTGCGCCCGGCGGGTTATCTGCTGAGCTTTCATACCCCGGGCGGCCAGACCC

AGGAAATTCTGCTGCCGGGCGGCATTACCAGCCATCAGCTGCTGGGCCTGTTTCC

GAGCACCAGCTATAACGCGCGTCTGCAGGCGATGTGGGGCCAGAGCCTGCTGCC

GCCGGTGAGCACCAGCTTTACCACC

10D:
SEQ ID NO: 50
gccatggccgccATTGAAGTGAAAGATGTGACCGATACCACCGCGCTGATTACCTGGTT

TAAACCGCTGGCGGAAATTGATGGCATTGAACTGACCTATGGCATTAAAGATGT

GCCGGGCGATCGCACCACCATTGATCTGACCGAAGATGAAAACCAGTATAGCAT

TGGCAACCTGAAAACCGGATACCGAATATGAAGTGAGCCTGATTAGCCGTCGTGG

CGATATGAGCAGCAACCCGGCGAAAGAAACCTTTACCACCggtggcggtacc

SEQ ID NO: 51
ATTGAAGTGAAAGATGTGACCGATACCACCGCGCTGATTACCTGGTTTAAACCGC

TGGCGGAAATTGATGGCATTGAACTGACCTATGGCATTAAAGATGTGCCGGGCG

ATCGCACCACCATTGATCTGACCGAAGATGAAAACCAGTATAGCATTGGCAACC

TGAAAACCGGATACCGAATATGAAGTGAGCCTGATTAGCCGTCGTGGCGATATGA

GCAGCAACCCGGCGAAAGAAACCTTTACCACC

11D:
SEQ ID NO: 52
gccatggccgccCCGAAATTTACCAAATGCCGTAGCCCGGAACGCGAAACCTTTAGCTG

CCATTGGACCGATGAAGTTCATCATGGCACCAAAAATCTGGGCCCGATTCAGCTG

TTTTATACCCGCCGTAATACCCAGGAATGGACCCAGGAATGGAAAGAATGCCCG

GATTATGTTAGCGCGGGCGAAAACAGCTGCTATTTTAACAGCAGCTTTACCAGCA

TTTGGATTCCGTATTGCATTAAACTGACCAGCAACGGTGGCACCGTTGATGAAAA

ATGCTTTAGCGTGggtggcggtacc

SEQ ID NO: 53
CCGAAATTTACCAAATGCCGTAGCCCGGAACGCGAAACCTTTAGCTGCCATTGGA

CCGATGAAGTTCATCATGGCACCAAAAATCTGGGCCCGATTCAGCTGTTTTATAC

CCGCCGTAATACCCAGGAATGGACCCAGGAATGGAAAGAATGCCCGGATTATGT

TAGCGCGGGCGAAAACAGCTGCTATTTTAACAGCAGCTTTACCAGCATTTGGATT

CCGTATTGCATTAAACTGACCAGCAACGGTGGCACCGTTGATGAAAAATGCTTTA

GCGTG

12D:

SEQ ID NO: 54
gccatggcagccCCGTCTGGTTTTCCGCAGAATCTGCATGTGACCGGCCTGACCACCAG
CACCACCGAACTGGCGTGGGATCCGCCGGTGCTGGCGGAACGCAACGGCCGTAT
TATTAGCTATACCGTGGTGTTTCGTGATATTAACAGCCAGCAGGAACTGCAGAAC
ATTACCACCGATACCCGCTTTACCCTGACCGGTCTGAAACCGGATACCACCTATG
ATATTAAAGTGCGCGCCTGGACCAGCAAAGGCAGCGGCCCGCTGAGCCCGAGCA
TTCAGAGCCGCACCATGCCGGTGGAAggtggcggtacc SEQ ID NO: 55
CCGTCTGGTTTTCCGCAGAATCTGCATGTGACCGGCCTGACCACCAGCACCACCG
AACTGGCGTGGGATCCGCCGGTGCTGGCGGAACGCAACGGCCGTATTATTAGCT
ATACCGTGGTGTTTCGTGATATTAACAGCCAGCAGGAACTGCAGAACATTACCAC
CGATACCCGCTTTACCCTGACCGGTCTGAAACCGGATACCACCTATGATATTAAA
GTGCGCGCCTGGACCAGCAAAGGCAGCGGCCCGCTGAGCCCGAGCATTCAGAGC
CGCACCATGCCGGTGGAA 13D:
SEQ ID NO: 56
gccatggccgccCCGAAACCGCCGATTGATCTGGTGGTTACCGAAACCACCGCGACCA
GCGTGACCCTGACCTGGGATAGCGGCAATAGCGAACCGGTGACCTATTATGGTA
TTCAGTATCGCGCGGCGGGCACCGAAGGTCCGTTTCAGGAAGTGGATGGCGTGG
CGACCACCCGTTATAGCATTGGCGGTCTGAGCCCGTTTAGCGAATATGCGTTTCG
CGTGCTGGCGGTTAATAGCATTGGCCGCGGTCCGCCGAGCGAAGCGGTGCGTGC
GCGCACCGGCGAACAGGCGggtggcggtacc SEQ ID NO: 57
CCGAAACCGCCGATTGATCTGGTGGTTACCGAAACCACCGCGACCAGCGTGACC
CTGACCTGGGATAGCGGCAATAGCGAACCGGTGACCTATTATGGTATTCAGTATC
GCGCGGCGGGCACCGAAGGTCCGTTTCAGGAAGTGGATGGCGTGGCGACCACCC
GTTATAGCATTGGCGGTCTGAGCCCGTTTAGCGAATATGCGTTTCGCGTGCTGGC
GGTTAATAGCATTGGCCGCGGTCCGCCGAGCGAAGCGGTGCGTGCGCGCACCGG
CGAACAGGCG 14D:
SEQ ID NO: 58
gccatggccgccCTGAGCCCGCCGCGTAACCTGCGCATTAGCAACGTGGGTAGCAATA
GCGCGCGCCTGACCTGGGATCCGACCAGCCGCCAGATTAATGGCTATCGCATTGT
GTATAACAACGCCGATGGCACCGAAATTAACGAAGTGGAAGTGGATCCGATTAC
CACCTTTCCGCTGAAAGGCCTGACCCCGCTGACCGAATATACCATTGCGATTTTT
AGCATTTATGATGAAGGTCAGAGCGAACCGCTGACCGGTGTGTTTACCACCggtggc
ggtacc SEQ ID NO: 59
CTGAGCCCGCCGCGTAACCTGCGCATTAGCAACGTGGGTAGCAATAGCGCGCGC
CTGACCTGGGATCCGACCAGCCGCCAGATTAATGGCTATCGCATTGTGTATAACA
ACGCCGATGGCACCGAAATTAACGAAGTGGAAGTGGATCCGATTACCACCTTTC
CGCTGAAAGGCCTGACCCCGCTGACCGAATATACCATTGCGATTTTTAGCATTTA
TGATGAAGGTCAGAGCGAACCGCTGACCGGTGTGTTTACCACC Wild type Tn3 domain

```
RLDAPSQIEVKDVTDTTALITWFKPLAEIDGIELTYGIKDVPGDRTTIDLTEDENQYSI
GNLKPDTEYEVSLISRRGDMSSNPAKETFTT
```

Tenascin Tn3 Scaffold Protein Sequence

SEQ ID NO: 60
```
AAIEVKDVTDTTALITWFKPLAEIDGIELTYGIKDVPGDRTTIDLTED
ENQYSIGNLKPDTEYEVSLISRRGDMSSNPAKETFTTGGGTLEHHHHH
H
```

SEQ ID NO: 61
```
IEVKDVTDTTALITWFKPLAEIDGIELTYGIKDVPGDRTTIDLTEDEN
QYSIGNLKPDTEYEVSLISRRGDMSSNPAKETFTT
```

Synagis Binding Tn3 Variant SynBP01
Protein Sequence

SEQ ID NO: 62
AAIEVKDVTDTTALITWSPPSVLVGYTIELTYGIKDVPGDRTTIDLTEDE
NQYSIGNLKPDTEYEVSLISVTEFGRRRSKETFTT*GGGTLEHHHHHH*

SEQ ID NO: 63
IEVKDVTDTTALITWSPPSVLVGYTIELTYGIKDVPGDRTTIDLTEDENQ
YSIGNLKPDTEYEVSLISVTEFGRRRSKETFTT

Disulfide-stabilized Tn3s (SS1-4):

SEQ ID NO: 64
(SS1): IECKDVTDTTALCTWFKPLAEIDGIELTYGIKDVPGDRTTIDL
TEDENQYSIGNLKPDTEYEVSLISRRGDMSSNPAKETFTT

SEQ ID NO: 210
(SS2): IEVKDVTDTTALITWFKPLAEIDGIELTYIKDVPGDRTTCDL
TGEDEGNQCSIGNLKPDTEYEVSLISRRGDMSSNPAKETFTT

SEQ ID NO: 65
(SS3): IEVKDVTDTTALITWFKPLAEIDGIELTYGIKDVPGDRTTIDL
TEDENQYSIGNLKPDTEYCVSLISRRGDMSSNPAKECFTT

SEQ ID NO: 66
(SS4): IEVKDVTDTTALITWFKPLAEIDGCELTYGIKDVPGDRTTIDL
TEDENQYSIGNLKPDTEYEVSLICRRGDMSSNPAKETFTT

SEQ ID NO: 67
(SS3 + 4): IEVKDVTDTTALITWFKPLAEIDGCELTYGIKDVPGDRT
TIDLTEDENQYSIGNLKPDTEYCVSLICRRGDMSSNPAKECFTT

Scaffolds Identified from Archea
*Archaeoglobus fulgidus* DSM 4304
NCBI Accession: NC_000917
Protein Sequence:

SEQ ID NO: 68
PAISNVRVSDVTNSSATIRWDVSLAANNRVLFSTNSDLSSPQWSAWDN
STDSPMITLSGLSAGTAYYFSVYSFRPDNASLYSNSSIMSFTT

Staphylothermus Marinus F1
NCBI Accession: NC_009033
Protein Sequence:

Seq ID No: 2
SEPQNLKATAGNNNITLTWDPPIDDGGCRIVEYRIYRGTNNNNLEYYASV
NGSTTTFIDKNIVYSQTYYYKVSAVNNIVEGPKSNTASATPTSS

*Sulfolobus acidocaldarius* DSM 639
NCBI Accession: NC_007181
Protein Sequences:

1st Tn3 structural motif,
SEQ ID NO: 69
PPPKPVIRFAQAGNNSISLSWYDTNTSGYYIQWWSSIDNNKSTINVGNVS
SYLFINLTNGVTYYFRIIPYNQAGNGTSSDIISLTPGAV 2nd Tn3 structural motif,
SEQ ID NO: 70
PDSPSVKVIVGDRNATVIWSKPYNGGFPILGYYLTVKTDNSSYTINVGNV
SKYTLTNLTPEVLYEVMVVAYNKLGNSSPGIVNFVALTT 3rd Tn3 structural motif,
SEQ ID NO: 71
LTTASISVSVYKKVNGVLISWNKTENTTYNLLISDKKGKIIVNITTTNTS
YFAYIPYGIYNVTIRATNQVGTNSTSFPIVFYIPPFI 4th Tn3 structural motif,
SEQ ID NO: 72
PLVKFSIGNNSILNLKWNNVTGATFYLVYVNTTLIANVTTDSYSLNLTP
GFHVIRVVAANPIYNSSPASLGILIQQHSVTSSIT

*Sulfolobus solfataricus* P2
NCBI Accession: NC_002754
Protein Sequences:

1st Tn3 structural motif,
SEQ ID NO: 73
PLPPKITSYSAGNESVTLGWNPVRLSSGYEIIYWNNMGFNSSINVGNV
TSYTVTGLKDGITYYFEVLAYNSIGYSSPSSIIALTPASV 2nd Tn3 structural motif,
SEQ ID NO: 74
PNPPQLVSVKYGNDNVTLNWLPPTFSGGYLLLGYYVIVKNENSMVSS
HFVNSTSLTISNLTPNVTYNVFIYAVNKLGNSSPLVLTVVPITKA 3rd Tn3 structural motif,
SEQ ID NO: 75
PITKASVFAFITKLGNGILVNWTTSFPANITLELYNPNGNLISQIAAIKG
NSSYLFRVPQGNYTLVIIASNSAGVSKYVYQVVYYL 4th Tn3 structural motif,
SEQ ID NO: 76
PPASPQVSLIGFGNNLYISWNNEANVITYLVYVNNSLVYEGPSNSIVTN
ISNGTYLVKVIGVNPAGSSSPGIAVIHYTGDYVT

*Sulfolobus tokodaii* str. 7
NCBI Accession: NC_003106
Protein Sequences:

1st Tn3 structural motif,
Seq ID No: 3
PPKPQIASIASGNETITVKWYDTNASGYYITYWSNFSQKVTINVGNYTSY
TIKHLKDGVTYYIQIVPYNSLGNGTPSDIISATPSSV 2nd Tn3 structural motif,
Seq ID No: 4
PNPPIIKVKIGNLNATLTWYDTFNGGYPIEGYYLYVNGKGINVGNITSYV
LTNLTAGELYTIELIAYNKIGNSSISSVSFIAASKA 3rd Tn3 structural motif,
SEQ ID NO: 77
ASKANLTVTVYKKINGFLVSWNSTSKAKYILTVSKENVVLLNVSTTNTSY
FVKVPFGVYNISLEAVNIVGITKYAFILIYYIQ 4th Tn3 structural motif,
SEQ ID NO: 78
PASPTVNWSITLNTVSLNWSKVSGAEYYLIYDNGKLITNTTNTAFTFNL
TIGQNEIEVYAANAYYKSAPYIINDVRNYIVV Protein Sequences from Example 5
Upper case lettering corresponds to the Tn3 structural motif, while lower case lettering are flanking sequence appendages derived from the synthetic cDNA and expression vector.

*Archaeoglobus*

SEQ ID NO: 79
aaPAISNVRVSDVTNSSATIRWDVSLAANNRVLFSTNSDLSSPQWSAWDN
STDSPMITLSGLSAGTAYYFSVYSFRPDNASLYSNSSIMSFTTgggtleh
hhhhh SEQ ID NO: 80
PAISNVRVSDVTNSSATIRWDVSLAANNRVLFSTNSDLSSPQWSAWDN
STDSPMITLSGLSAGTAYYFSVYSFRPDNASLYSNSSIMSFTT Staphylothermus marinus SEQ ID NO: 81
aaSEPQNLKATAGNNNITLTWDPPIDDGGCRIVEYRIYRGTNNNNLEY
YASVNGSTTTFIDKNIVYSQTYYYKVSAVNNIVEGPKSNTASATPTSS
gggtlehhhhhh SEQ ID NO: 82
SEPQNLKATAGNNNITLTWDPPIDDGGCRIVEYRIYRGTNNNNLEYYA
SVNGSTTTFIDKNIVYSQTYYYKVSAVNNIVEGPKSNTASATPTSS

*Sulfolobus solfataricus*

SEQ ID NO: 83
aaPLPPKITSYSAGNESVTLGWNPVRLSSGYEIIYWNNMGFNSSINVGN
VTSYTVTGLKDGITYYFEVLAYNSIGYSSPSSIIALTPASVgggtlehh
hhhh SEQ ID NO: 84
PLPPKITSYSAGNESVTLGWNPVRLSSGYEIIYWNNMGFNSSINVGNVT
SYTVTGLKDGITYYFEVLAYNSIGYSSPSSIIALTPASV

*Sulfolobus tokodaii*_1

SEQ ID NO: 85
aaPPKPQIASIASGNETITVKWYDTNASGYYITYWSNFSQKVTINVGN
VTSYTIKHLKDGVTYYIQIVPYNSLGNGTPSDIISATPSSVgggtlehh
hhhh SEQ ID NO: 86
PPKPQIASIASGNETITVKWYDTNASGYYITYWSNFSQKVTINVGNVT
SYTIKHLKDGVTYYIQIVPYNSLGNGTPSDIISATPSSV

*Sulfolobus tokodaii*_2

SEQ ID NO: 87
aaPNPPIIKVKIGNLNATLTWYDTFNGGYPIEGYYLYVNGKGINVGN
ITSYVLTNLTAGELYTIELIAYNKIGNSSISSVSFIAASKAgggtlehh
hhhh SEQ ID NO: 88
PNPPIIKVKIGNLNATLTWYDTFNGGYPIEGYYLYVNGKGINVGNI
TSYVLTNLTAGELYTIELIAYNKIGNSSISSVSFIAASKA cDNA Sequences
*Archaeoglobus*

SEQ ID NO: 89
gccatggcagccCCGGCGATTAGCAATGTGCGCGTTAGCGATGTGACC
AACAGCAGCGCCACCATTCGTTGGGATGTGAGCCTGGCGGCGAAT
AATCGCGTGCTGTTTAGCACCAACAGCGATCTGAGCAGCCCGCAG
TGGAGCGCGTGGGATAACAGCACCGATAGCCCGATGATTACCCTG
AGCGGTCTGAGCGCGGGCACCGCGTATTATTTTAGCGTGTATAGCT
TTCGTCCGGATAATGCGAGCCTGTATAGCAACAGCAGCATTATGAG
CTTTACCACCggtggcggtacc SEQ ID NO: 90
CCGGCGATTAGCAATGTGCGCGTTAGCGATGTGACCAACAGCAGCG
CCACCATTCGTTGGGATGTGAGCCTGGCGGCGAATAATCGCGTGCTG
TTTAGCACCAACAGCGATCTGAGCAGCCCGCAGTGGAGCGCGTGGG
ATAACAGCACCGATAGCCCGATGATTACCCTGAGCGGTCTGAGCGCG
GGCACCGCGTATTATTTTAGCGTGTATAGCTTTCGTCCGGATAATGCGA
GCCTGTATAGCAACAGCAGCATTATGAGCTTTACCACC Staphylothermus SEQ ID NO: 91
gccatggccgccAGCGAACCGCAGAACCTGAAAGCGACCGCGGGTAATA
ACAATATTACCCTGACCTGGGATCCGCCGATTGATGATGGTGGCTGCCG
CATTGTGGAATATCGTATTTATCGTGGCACCAATAATAACAACCTGGAA
TATTATGCGAGCGTTAACGGCAGCACCACCACCTTTATTGATAAAAATA
TTGTGTATAGCCAGACCTATTATTATAAAGTGAGCGCGGTGAACAATAT
TGTGGAAGGCCCGAAAAGCAACACCGCGAGCGCGACCCCGACCAGCAGC
ggtggcggtacc -continued

SEQ ID NO: 92
AGCGAACCGCAGAACCTGAAAGCGACCGCGGGTAATAACAATATTACCC

TGACCTGGGATCCGCCGATTGATGATGGTGGCTGCCGCATTGTGGAATA

TCGTATTTATCGTGGCACCAATAATAACAACCTGGAATATTATGCGAGC

GTTAACGGCAGCACCACCACCTTTATTGATAAAAATATTGTGTATAGCC

AGACCTATTATTATAAAGTGAGCGCGGTGAACAATATTGTGGAAGGCCC

GAAAAGCAACACCGCGAGCGCGACCCCGACCAGCAGC

*S. solfataricus*_1

SEQ ID NO: 93
gccatggccgccCCGCTCCCACCGAAAATTACCAGCTATAGCGCGGGC

AACGAAAGCGTGACCCTGGGCTGGAACCCGGTGCGTCTGAGCAGC

GGCTATGAAATTATTTATTGGAACAATATGGGCTTTAACAGCAGCATT

AATGTGGGTAATGTGACCAGCTATACCGTGACCGGCCTGAAAGATG

GCATTACCTATTATTTTGAAGTGCTGGCCTATAACAGCATTGGTTATA

GCAGCCCGAGCAGCATTATCGCGCTGACCCCGGCGAGCGTGggtgg cggtacc

SEQ ID NO: 94
CCGCTCCCACCGAAAATTACCAGCTATAGCGCGGGCAACGAAAGC

GTGACCCTGGGCTGGAACCCGGTGCGTCTGAGCAGCGGCTATGAAA

TTATTTATTGGAACAATATGGGCTTTAACAGCAGCATTAATGTGGGTAA

TGTGACCAGCTATACCGTGACCGGCCTGAAAGATGGCATTACCTATTA

TTTTGAAGTGCTGGCCTATAACAGCATTGGTTATAGCAGCCCGAGCAG

CATTATCGCGCTGACCCCGGCGAGCGTG

*S. tokodaii*_1

SEQ ID NO: 95
gccatggccgccCCGCCGAAACCGCAGATTGCCAGCATTGCCAGCGGT

AATGAAACCATTACCGTGAAATGGTATGATACCAATGCGAGCGGCT

ATTATATTACCTATTGGAGCAATTTTAGCCAGAAAGTGACCATTAATG

TGGGTAACGTGACCAGCTATACCATTAAACATCTGAAAGATGGCGTG

ACCTATTATATTCAGATTGTGCCGTATAACAGCCTGGGCAATGGCAC

CCCGAGCGATATTATTAGCGCGACCCCGAGCAGCGTTggtggcggtacc

SEQ ID NO: 96
CCGCCGAAACCGCAGATTGCCAGCATTGCCAGCGGTAATGAAACCA

TTACCGTGAAATGGTATGATACCAATGCGAGCGGCTATTATATTACCTA

TTGGAGCAATTTTAGCCAGAAAGTGACCATTAATGTGGGTAACGTGAC

CAGCTATACCATTAAACATCTGAAAGATGGCGTGACCTATTATATTCAG

ATTGTGCCGTATAACAGCCTGGGCAATGGCACCCCGAGCGATATTATT

AGCGCGACCCCGAGCAGCGTT

*S. tokodaii*_2

SEQ ID NO: 97
gccatggccgccCCGAATCCGCCGATTATTAAAGTGAAAATTGGCAATC

TGAATGCGACCCTGACCTGGTATGATACCTTTAATGGTGGTTATCCGAT

TGAAGGCTATTATCTGTATGTGAACGGTAAAGGTATTAACGTGGGCAAC

ATTACCAGCTATGTGCTGACCAATCTGACCGCCGGTGAACTGTATACCA

TTGAACTGATTGCGTATAACAAAATCGGCAACAGCAGCATTAGCAGCGT

GAGCTTTATTGCGGCGAGCAAAGCGggtggcggtacc

SEQ ID NO: 98
CCGAATCCGCCGATTATTAAAGTGAAAATTGGCAATCTGAATGCGACCC

TGACCTGGTATGATACCTTTAATGGTGGTTATCCGATTGAAGGCTATTA

TCTGTATGTGAACGGTAAAGGTATTAACGTGGGCAACATTACCAGCTAT

GTGCTGACCAATCTGACCGCCGGTGAACTGTATACCATTGAACTGATTG

CGTATAACAAAATCGGCAACAGCAGCATTAGCAGCGTGAGCTTTATTGC

GGCGAGCAAAGCG

Vector Sequence

SEQ ID NO: 99
GACGAAAGGGCCTCGTGATACGCCTATTTTTATAGGTTAATGTCATGATAATAAT

GGTTTCTTAGACGTCAGGTGGCACTTTTCGGGGAAATGTGCGCGGAACCCCTATT

TGTTTATTTTTCTAAATACATTCAAATATGTATCCGCTCATGAGACAATAACCCTG

ATAAATGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCACCCAGAA

ACGCTGGTGAAAGTAAAAGATGCTGAAGATCAGTTGGGTGCTCGAGTGGGTTAC

ATCGAACTGGATCTCAACAGCGGTAAGATCCTTGAGAGTTTTCGCCCCGAAGAAC

-continued

```
GTTTTCCAATGATGAGCACTTTTAAAGTTCTGCTATGTGGCGCGGTATTATCCCGT
ATTGACGCCGGGCAAGAGCAACTCGGTCGCCGCATACACTATTCTCAGAATGACT
TGGTTGAGTACTCACCAGTCACAGAAAAGCATCTTACGGATGGCATGACAGTAA
GAGAATTATGCAGTGCTGCCATAACCATGAGTGATAACACTGCGGCCAACTTACT
TCTGACAACGATCGGAGGACCGAAGGAGCTAACCGCTTTTTTGCACAACATGGG
GGATCATGTAACTCGCCTTGATCGTTGGGAACCGGAGCTGAATGAAGCCATACC
AAACGACGAGCGTGACACCACGATGCCTGTAGCAATGGCAACAACGTTGCGCAA
ACTATTAACTGGCGAACTACTTACTCTAGCTTCCCGGCAACAATTAATAGACTGG
ATGGAGGCGGATAAAGTTGCAGGACCACTTCTGCGCTCGGCCCTTCCGGCTGGCT
GGTTTATTGCTGATAAATCTGGAGCCGGTGAGCGTGGGTCTCGCGGTATCATTGC
AGCACTGGGGCCAGATGGTAAGCCCTCCCGTATCGTAGTTATCTACACGACGGG
GAGTCAGGCAACTATGGATGAACGAAATAGACAGATCGCTGAGATAGGTGCCTC
ACTGATTAAGCATTGGTAACTGTCAGACCAAGTTTACTCATATATACTTTAGATT
GATTTAAAACTTCATTTTTAATTTAAAAGGATCTAGGTGAAGATCCTTTTTGATAA
TCTCATGACCAAAATCCCTTAACGTGAGTTTTCGTTCCACTGAGCGTCAGACCCC
GTAGAAAAGATCAAAGGATCTTCTTGAGATCCTTTTTTTCTGCGCGTAATCTGCT
GCTTGCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATACCAAA
TACTGTCCTTCTAGTGTAGCCGTAGTTAGGCCACCACTTCAAGAACTCTGTAGCA
CCGCCTACATACCTCGCTCTGCTAATCCTGTTACCAGTGGCTGCTGCCAGTGGCG
ATAAGTCGTGTCTTACCGGGTTGGACTCAAGACGATAGTTACCGGATAAGGCGC
AGCGGTCGGGCTGAACGGGGGGTTCGTGCATACAGCCCAGCTTGGAGCGAACGA
CCTACACCGAACTGAGATACCTACAGCGTGAGCTATGAGAAAGCGCCACGCTTC
CCGAAGGGAGAAAGGCGGACAGGTATCCGGTAAGCGGCAGGGTCGGAACAGGA
GAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGC
GGAGCCTATGGAAAAACGCCAGCAACGCGGCCTTTTTACGGTTCCTGGCCTTTTG
CTGGCCTTTTGCTCACATGTTCTTTCCTGCGTTATCCCCTGATTCTGTGGATAACC
GTATTACCGCCTTTGAGTGAGCTGATACCGCTCGCCGCAGCCGAACGACCGAGCG
CAGCGAGTCAGTGAGCGAGGAAGCGGAAGAGCGCCCAATACGCAAACCGCCTCT
CCCCGCGCGTTGGCCGATTCATTAATGCAGCTGGCACGACAGGTTTCCCGACTGG
AAAGCGGGCAGTGAGCGCAACGCAATTAATGTGAGTTAGCTCACTCATTAGGCA
CCCCAGGCTTTACACTTTATGCTTCCGGCTCGTATGTTGTGTGGAATTGTGAGCGG
ATAACAATTTCACACAGGAAACAGCTATGACCATGATTACGCCAAGCTTTGGAG
CCTTTTTTTTGGAGATTTTCAACGTGAAAAAATTATTATTCGCAATTCCTTTAGTT
GTTCCTTTCTATGCGGCCCAGCCGGCCATGGCCGCCATTGAAGTGAAAGATGTGA
CCGATACCACCGCGCTGATTACCTGGTTTAAACCGCTGGCGGAAATTGATGGCTG
TGAACTGACCTATGGCATTAAAGATGTGCCGGGCGATCGCACCACCATAGATCTG
ACCGAAGATGAAAACCAGTATAGCATTGGTAACCTGAAACCGGATACCGAATAT
GAAGTGAGCCTGATTTGCCGTCGTGGCGATATGAGCGGCGCGCCGGCGAAAGAA
```

-continued

ACCTTTACCACCGGTGGCGGTACCCCAACCGACCCGCCAACCACTCCACCAACTG
ATAGCCCAGGCGGTACTGGTGGCTCTGGTTCCGGTGATTTTGATTATGAAAAGAT
GGCAAACGCTAATAAGGGGGCTATGACCGAAAATGCCGATGAAAACGCGCTACA
GTCTGACGCTAAAGGCAAACTTGATTCTGTCGCTACTGATTACGGTGCTGCTATC
GATGGTTTCATTGGTGACGTTTCCGGCCTTGCTAATGGTAATGGTGCTACTGGTG
ATTTTGCTGGCTCTAATTCCCAAATGGCTCAAGTCGGTGACGGTGATAATTCACC
TTTAATGAATAATTTCCGTCAATATTTACCTTCCCTCCCTCAATCGGTTGAATGTC
GCCCTTTTGTCTTTAGCGCTGGTAAACCATATGAATTTTCTATTGATTGTGACAAA
ATAAACTTATTCCGTGGTGTCTTTGCGTTTCTTTTATATGTTGCCACCTTTATGTAT
GTATTTTCTACGTTTGCTAACATACTGCGTAATAAGGAGTCTTAAGAATTCGACG
GTCACAGCTTGTCTGTAAGCGGATGCCGGGAGCAGACAAGCCCGTCAGGGCGCG
TCAGCGGGTGTTGGCGGGTGTCGGGGCTGGCTTAACTATGCGGCATCAGAGCAG
ATTGTACTGAGAGTGCACCATAAAATTGTAAACGTTAATATTTTGTTAAAATTCG
CGTTAAATTTTTGTTAAATCAGCTCATTTTTTAACCAATAGGCCGAAATCGGCAA
AATCCCTTATAAATCAAAAGAATAGCCCGAGATAGGGTTGAGTGTTGTTCCAGTT
TGGAACAAGAGTCCACTATTAAAGAACGTGGACTCCAACGTCAAAGGGCGAAAA
ACCGTCTATCAGGGCGATGGCCCACTACGTGAACCATCACCCAAATCAAGTTTTT
TGGGGTCGAGGTGCCGTAAAGCACTAAATCGGAACCCTAAAGGGAGCCCCCGAT
TTAGAGCTTGACGGGGAAAGCCGGCGAACGTGGCGAGAAAGGAAGGGAAGAAA
GCGAAAGGAGCGGGCGCTAGGGCGCTGGCAAGTGTAGCGGTCACGCTGCGCGTA
ACCACCACACCCGCCGCGCTTAATGCGCCGCTACAGGGCGCGTACTATGGTTGCT
TTGACGTATGCGGTGTGAAATACCGCACAGATGCGTAAGGAGAAAATACCGCAT
CAGGCGCCATTCGCCATTCAGGCTGCGCAACTGTTGGGAAGGGCGATCGGTGCG
GGCCTCTTCGCTATTACGCCAGCTGGCGAAAGGGGGATGTGCTGCAAGGCGATT
AAGTTGGGTAACGCCAGGGTTTTCCCAGTCACGACGTTGTAAAACGACGGCCAG
TTCCGGGAGCTGCATGTGTCAGAGGTTTTCACCGTCATCACCGAAACGCGCGA

| Clone | BC loop | Seq ID NO: | FG loop | Seq ID NO: |
|---|---|---|---|---|
| SYNAGIS ® specific binding scaffolds | | | | |
| SynBP01 | SPPSVLVGYTG | 100 | VTEFGRRRS | 101 |
| 2 | FKPLAEIDG | 102 | RKIIGLLSNPA | 103 |
| 3 | FKPLAEIDG | 102 | GTVVGQKSNPA | 104 |
| 4 | SPGERIWMFTG | 105 | PNYERISNPA | 106 |
| 5 | SPSGRVILWTG | 107 | DNLYGRISNPA | 108 |
| 6 | ATPGCRNGKIVG | 109 | TTSVGATSNPA | 110 |
| Lysozyme specific binding scaffolds | | | | |
| 1 | FKPLAEIDG | 111 | YNRYGLCPS | 112 |
| 2 | FKPLAEIDG | 111 | SNRIGMCPS | 113 |

-continued

| | | | | |
|---|---|---|---|---|
| 3 | AQPTSPNGSIXG | 114 | RRGDMSSNPA | 115 |
| 4 | FKPLAEIDG | 102 | DTVHGRLSNPA | 116 |
| 5 | FKPLAEIDG | 102 | RKVLGRLSNPA | 117 |
| 6 | FKPLAEIDG | 102 | RKLVGALRS | 118 |
| 7 | FKPLAEIDG | 102 | RKVLRYSNPA | 119 |
| 8 | SPCNGGKRCTG | 120 | RRGDMSSNPA | 121 |
| 9 | FKPLAEIDG | 102 | FKWLGAIRS | 122 |

| 10 | FKPLAEIDG | 102 | GNCVGNLWS | 123 |
| 11 | SPAWITWHRTG | 124 | HTPLGHLRS | 125 |

TRAIL-R2 two-loop binders

| Clone name | BC loop | SEQ ID NO. | FG loop | SEQ ID NO. |
|---|---|---|---|---|
| 2F4 | SPCIMVCLRTG | 126 | RRGDMSGAPA | 127 |
| 5B10 | SPCLFVCLRTG | 128 | RRGDMSGAPA | 129 |
| 10D9 | SPPLFCCQKTG | 130 | FKLTGFLYS | 131 |
| 6F11 | SPSVARMLETG | 132 | ITLCGRGVS | 133 |
| 8B3 | SPPEYAFYYTG | 134 | VKNCGLFSNPA | 135 |
| 5E5 | SLAPGYRLG | 136 | VKLCMRGNPA | 137 |
| 2H6 | ATPSVFDSHIEG | 138 | WKHHGDAWS | 139 |
| 7G11 | AKPSIVNGFISG | 140 | DKCFGAMKS | 141 |
| 6C7 | AKPMSCSGYIQG | 142 | AKLTGWLCS | 143 |

TRAIL-R2 three-loop binders

| Clone | BC loop | Seq Id. | DE loop | Seq Id. | FG loop | Seq Id. |
|---|---|---|---|---|---|---|
| 1E03 | AAPFFGSSYISG | 144 | HYYVTR | 145 | VNLSGHMPS | 146 |
| 2B04 | APPMLTDSEING | 147 | TSSYWS | 148 | STLRRNAIS | 149 |
| 1C12 | AKPEKWDGSIYG | 150 | NSRHTA | 151 | FTPYGAKSNPA | 152 |
| 1A03 | APPPFSNSCIIG | 153 | RPGRAS | 154 | STGTGLPSNPA | 155 |
| 1C10 | SPCCPYDRYTG | 156 | QSSRSH | 157 | ITTFGHVSNPA | 158 |
| 1B12 | AKPRQGGSNISG | 159 | YHKGLH | 160 | PKMTGYTYS | 161 |
| 2G03 | SPGPLLRHTTG | 162 | RPIPRA | 163 | RNRPQQSNPA | 164 |
| 2D3 | SPGGFQKITTG | 165 | VNRRNH | 166 | LTYKARAIS | 167 |
| 1C06 | SPRMYTWIQTG | 168 | THLSGS | 169 | LKLTRTHIS | 170 |
| 2F08 | SHAGGIRIG | 171 | HVWQVY | 172 | MTPYLLGNPA | 173 |
| 1B04 | SPSHGVESSTG | 174 | HGLQRV | 175 | AKICGHLVS | 176 |
| 3B11 | SPCQLLALITG | 177 | NSRHYH | 178 | YTSTGQRSNPA | 179 |
| 1D8 | SPCQMLSSLTG | 180 | NIERPK | 181 | FTMTGYRSNPA | 182 |
| 2A12 | SPCCQEFTLTG | 183 | HNHHHH | 184 | ITDAGNKSNPA | 185 |
| 1E05 | SPCSPCQLVTG | 186 | SCTRAK | 187 | INKLGDTSNPA | 188 |
| 2F02 | SPSRGGTSLTG | 189 | DQVRAT | 190 | HTNSGQPSNPA | 191 |
| 1H05 | SPGMFDQVRTG | 192 | GKYWER | 193 | RNQYGQHQS | 194 |
| 2A11 | SPPFRAGHVTG | 195 | VTARCQ | 196 | TTGNGLRSNPA | 197 |
| 1G11 | SWAQANPGG | 198 | WHSITF | 199 | KTKVQSSNPA | 200 |

EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

Example 1

Recombinant Expression of Candidate Scaffolds

Figure 1:
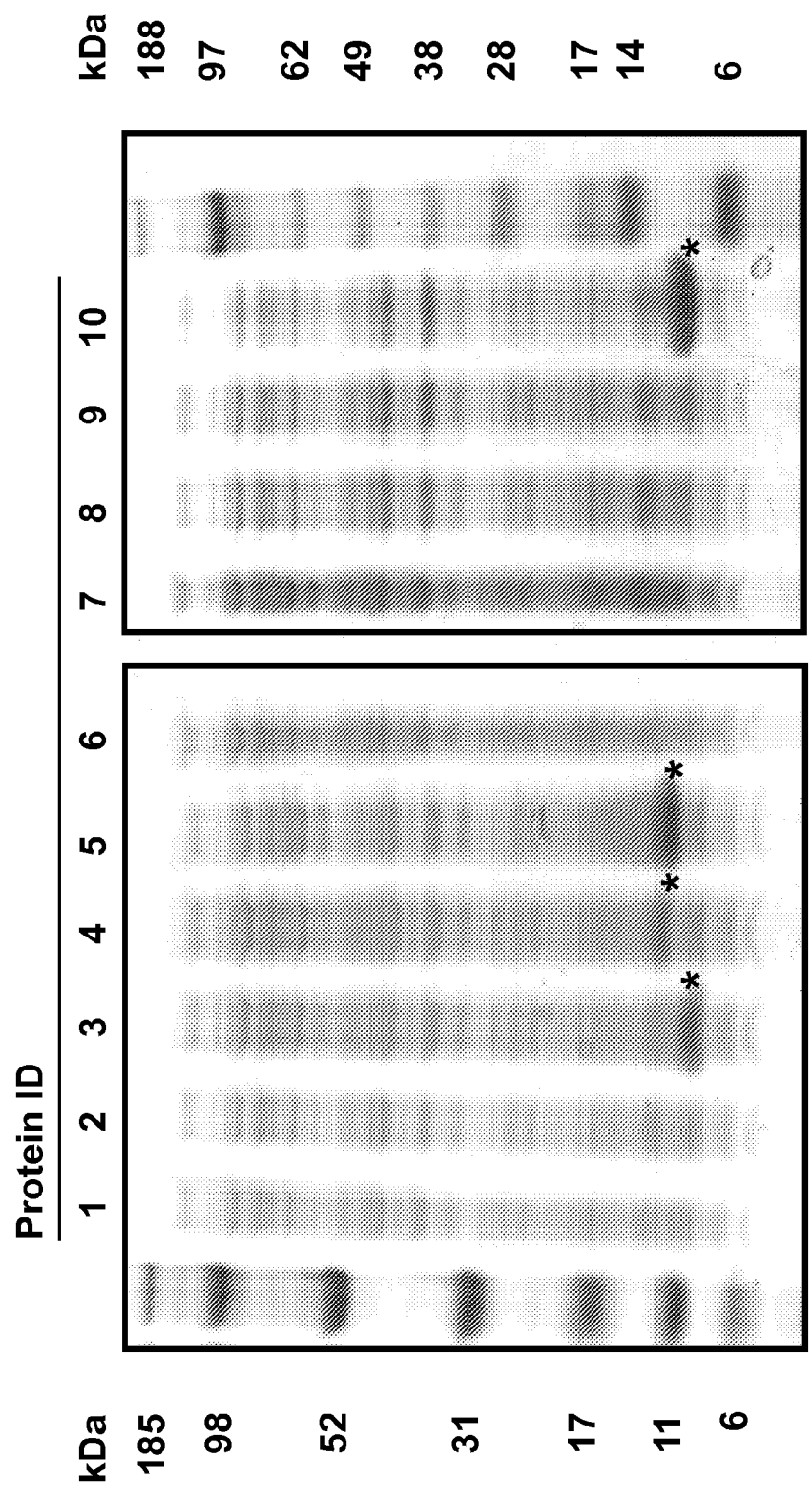
FIG. 1. Recombinant total cell expression of scaffolds. Presented here is a Coomassie stained PAGE gel of various recombinant lysates from *E. coli* cultures expressing protein scaffolds. Highly expressed scaffolds are indicated with an asterisk (*).

This example demonstrates that candidate scaffolds may be recombinantly expressed in *E. coli* in sufficient quantity to be visible against the background of host proteins on a Coomassie stained on a polyacrylamide gel (FIG. 1). Represented in FIG. 1 is the PAGE analysis of crude *E. coli* lysates expressing candidate scaffolds. Some of the candidate scaffolds exhibited higher expression levels (exemplified by lanes 3, 4, 5, and 10) and were selected for further development. Specifically, Lane 3 represents the 6$^{th}$ domain of Fibronectin III, Lane 4 represents the scaffold from β-common receptor, Lane 5 represents the candidate scaffold from growth hormone receptor and Lane 10 represents the Tn3 structural motif.

Recombinant Expression

A panel of human-derived Tn3 structural motif sequences were selected for heterologous expression in *E. coli* (Table 1). Synthetic cDNAs encoding each of these proteins, and optimized for codon usage in *E. coli*, were supplied by GenScript Corporation as per the sequences shown. Each cDNA contained flanking Nco I and Kpn I restriction sites, and following digestion with these enzymes, the inserts were cloned into a modified pET22b vector (Novagen) containing corresponding Nco I/Kpn I sites.

In other embodiments, vectors may comprise any number of restrictions sites to facilitate the engineering of the scaffolds of the invention. In some embodiments, vectors of the invention comprise at least one restriction site. In other embodiments, vectors of the invention comprise at least one restriction site flanking at least one loop sequence. In other embodiments, vectors of the invention comprise at least one restriction site selected from the group consisting of NcoI, BglII, BstEII, AscI, and KpnI. In further embodiments, the vector comprises a leader sequence. In other embodiments, the vector comprises a linker sequence. In a specific embodiment, vectors of the invention comprise the polynucleotide sequence defined by SEQ ID NO:99.

Transformants of BL21 DE3 *E. coli* harboring Tn3 structural motif expression plasmids were grown overnight at 37° C. in Luria Broth containing 50 μg/mL carbenicillum. Overnight cultures were diluted 1 in 20 into Super Broth media containing 50 μg/mL carbenicillum and 2% w/v glucose and incubated at 37° C. with shaking until the optical density at 600 nm was 0.6. At this time, protein expression was induced by addition of IPTG to 200 μM, and cultures were transferred to a 30° C. incubator with shaking. After 5 h at 30° C., a small aliquot of culture was removed for SDS-PAGE analysis, and the remainder of cells were pelleted by centrifugation, and frozen overnight at −20° C. SDS-PAGE analysis of whole cell lysates suggested that Tn3 structural motifs 3, 4, 5, 10 were highly overexpressed in *E. coli* as determined by gel bands at approximately 10 kDa (FIG. 1). In a separate experiment, it was also determined that Tn3 structural motif 12 was overexpressed.

Purification

Figure 2:
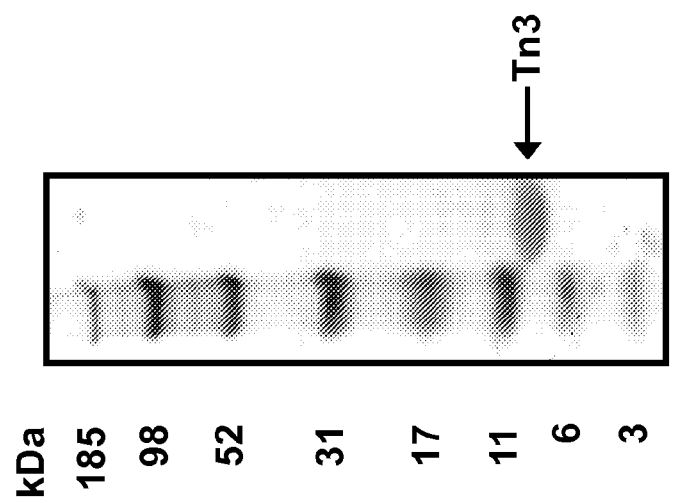
FIG. 2. Expression and purification of a Tn3 based scaffold. Presented here is a Coomassie stained PAGE gel documenting the Tn3 based scaffold after recombinant expression and purification. The Tn3 scaffold was readily purified to homogeneity.

Frozen cell pellets were resuspended in lysis buffer (50 mM NaH$_2$PO$_4$, 300 mM NaCl, 10 mM imidazole, pH 8.0) containing 1 mg/mL lysozyme (Sigma) and 200 units/mL of DNase (Invitrogen). Lysis was effected by sonication, and clarified lysate was separated from cell debris by centrifugation followed by filtration through a 0.8 μm filter. Lysates were loaded onto HiTrap chelating columns charged with Ni$^{2+}$, washed with 15 column volumes of wash buffer (50 mM NaH$_2$PO$_4$, 300 mM NaCl, 20 mM imidazole, pH 8.0) and eluted with 4 column volumes of elution buffer (50 mM NaH$_2$PO$_4$, 300 mM NaCl, 250 mM imidazole, pH 8.0). The concentrations of purified protein were determined by UV absorbance at 280 nm according to Gill and von Hippel (*Anal. Biochem.* 182: 319, 1989). Post purification yields of the various Tn3 proteins are reported in Table 1. The Tn3 structural motif derived from human tenascin C (Tn3) gave the highest yield, which corresponded to 110 mg of purified Tn3 obtained from a 400 mL culture. SDS-PAGE analysis of a purified Tn3 sample is shown in FIG. 2.

TABLE 1

| Protein # | Parent Protein | Expression level (mg/L) | Protein sequence | DNA sequence |
|---|---|---|---|---|
| 1 | Fibronectin | 2 mg/ml | 1P | 1D |
| 2 | Fibronectin | — | 2P | 2D |
| 3 | Fibronectin | 83 | 3P | 3D |
| 4 | Growth hormone R | 48 | 4P | 4D |
| 5 | β-common R | 9 | 5P | 5D |
| 6 | IL-5R | — | 6P | 6D |
| 7 | Tenascin XB | — | 7P | 7D |
| 8 | Tenascin XB | — | 8P | 8D |
| 9 | Tenascin XB | — | 9P | 9D |
| 10 | Tenascin C (Tn3) | 265 | 10P | 10D |
| 11 | Growth hormone R | — | 11P | 11D |
| 12 | PTPR-F | 105 | 12P | 12D |
| 13 | PTPR-F | 3 | 13P | 13D |
| 14 | Collagen type XIV | 1 | 14P | 14D |

Characterization

Given the high yield of soluble Tn3 produced in *E. coli*, this protein was analysed for its stability and solution properties.

Stability

Figure 3A:
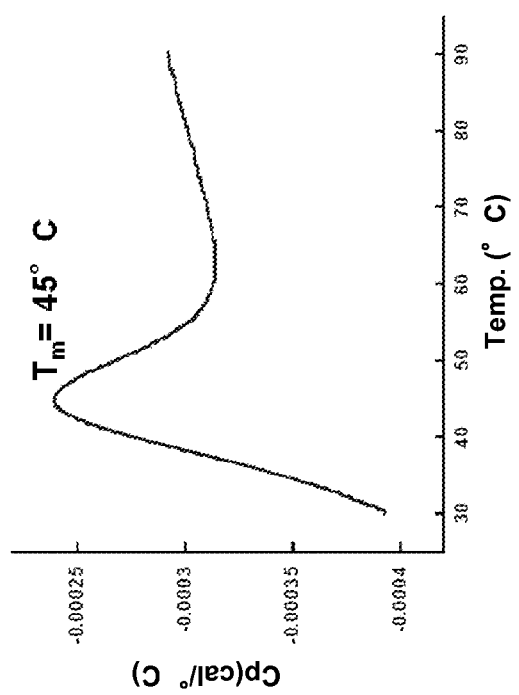
FIG. 3A. Melting temperature determination for a Tn3 based scaffold. The graph illustrates the thermal melting curve determination of the Tn3 based scaffold as measured by differential scanning calorimetry. The $T_m$ was determined to be about 45° C. at pH 7.0.

Thermal unfolding of Tn3 was assessed by differential scanning calorimetry (DSC). A 1 mg/mL Tn3 sample in 20 mM sodium phosphate at pH 7.0 exhibited a melting temperature (Tm) of 45° C. (FIG. 3A), moreover, thermal unfolding was reversible as evidenced by superimposable thermograms when the same sample was cooled and reheated. Tn3 was more stable to thermal unfolding at lower pH or high salt. The Tm in 20 mM sodium acetate pH 5.0 was 56° C., and 55° C. in 20 mM sodium phosphate pH 7.0 containing 1 M NaCl.

Figure 3B:
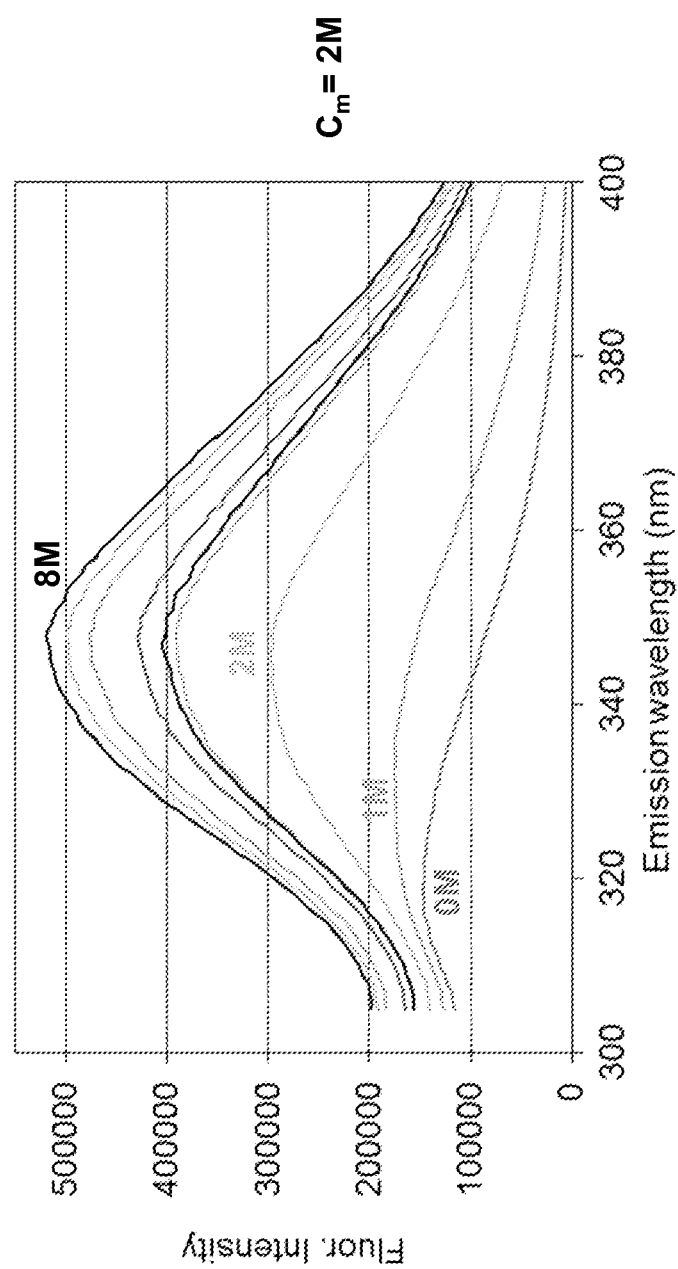
FIG. 3B. Urea denaturation profile of a Tn3 based scaffold. The graph represents the denaturation profile of a Tn3 based scaffold in various concentrations of urea at pH 7.5. The change in intrinsic fluorescence of the molecules was used as a measure of unfolding of the molecule. For the Tn3 scaffold, unfolding results in an increase in fluorescence intensity and shift to a higher wavelength. As demonstrated in the figure, the molecule is folded at low concentrations of urea (less than or equal to 1M) and became denatured at higher concentrations of urea. The molarity at which 50% of the molecules are unfolded was calculated to be about 2M.

Unfolding of Tn3 by chaotropic agents was monitored by intrinsic fluorescence. Samples of 0.1 mg/mL Tn3 containing different concentrations of urea or guanidine hydrochloride were prepared in 20 mM sodium phosphate pH 7.0., or 20 mM Tris pH 7.5. Fluorescence emission spectra were acquired on a Photon Technology QuantaMaster spectrofluorometer at an excitation wavelength of 280 nm. In the absence of chaotrope, folded samples of Tn3 exhibited an emission maxima at 319 nm. Unfolding of Tn3 by urea or GuHCl resulted in a red shift of the maxima to 348 nm, in addition to an increase in fluorescence intensity. The midpoint of unfolding at pH 7.0 or 7.5 occurred at approximately 2M urea (FIG. 3B) or 0.8M GuHCl.

The stability of Tn3 to proteolytic degradation was tested by incubation with thermolysin. Tn3 (45 μM) in digest buffer (20 mM Tris pH 7.5 containing 10 mM CaCl$_2$) was incubated at room temperature with thermolysin (0.45 μM). Aliquots of the digest were removed at different time points, and the reaction quenched by addition of excess EDTA. Samples were then analysed by SDS-PAGE (see the WT lanes in FIG. 10I). As demonstrated by FIG. 10I, the wild-type Tn3 domain is rapidly degraded when incubated with thermolysin.

Figure 3C:
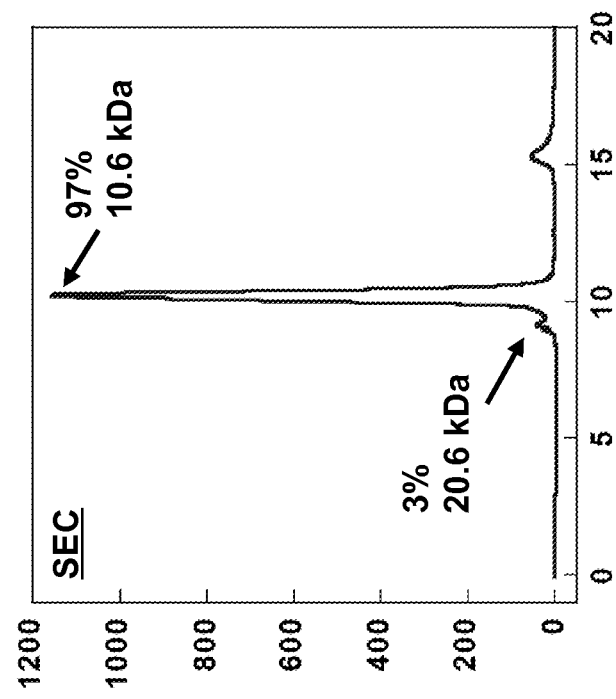
FIG. 3C. A Tn3 scaffold exists in a monomeric state. The graph represents the results of a size exclusion chromatography analysis of a purified Tn3 scaffold to determine the relative proportions of contaminating fragments and/or higher order structures. As represented by the percentages on the graph, over 97% of the scaffold eluted in monomeric form (determined to be around 11 kDa by an online light scattering detector) while only a small fraction (around 3%) eluted at a peak of about 21 kDa, possibly as a dimer.

Size exclusion chromatography with multi-angle light scattering (SEC-MALS) was used to determine whether Tn3 was monomeric in solution. Size exclusion separation was carried out using a Bio-Rad Bio-Sil SEC 125-5 column (7.8× 300 mm) at a flow rate of 0.75 mL/min. The mobile phase was phosphate-buffered saline (PBS) at pH7.2. Triple detection was accomplished using a Wyatt Technologies DAWN EOS multi-angle light scattering detector coupled with a Wyatt Technologies Optilab rEX differential refractive index detector and an Agilent 1100 Series variable wavelength UV detector. SEC-MALS analysis showed that the monomer content of a 4.5 mg/mL Tn3 stored at 4° C. for 2 months was 97% (FIG. 3C). The experimentally-derived monomer mass was 10.6 kDa which is in close agreement with the calculated mass of 10.8 kDa. The Tn3 scaffold remains as a monomer as a monomer even through extended periods of storage.

Example 2

Identification of Loop Length and Sequence Diversity

An ideal scaffold is highly soluble and stable. It should be small enough for structural analysis, yet large enough to accommodate a multitude of changes to facilitate binding of a target. In an effort to facilitate the identification and engineering of non-antibody protein scaffolds as well as design of combinatorial libraries of scaffolds, a bioinformatics analysis of scaffold sequences was performed.

The Tn3 structural motif is small, monomeric, soluble and stable. In addition, Tn3 structural motifs are present in many different human proteins, providing important information on conserved residues which are often important for the stability and folding as well as regions of diversity which can be exploited to introduce novel binding functions. From sequence analysis, large variations are seen in the BC and FG loops, suggesting that the loops are not crucial to stability. Using this property, a strategy was developed to identify candidate protein scaffolds and analyze the loop length and sequence diversity in an effort to characterize the natural extent of variation that occurs in these two parameters.

A search of the available protein databases identified a number of protein scaffolds based on the Tn3 structural motif. Candidate scaffolds contained a similar predicted structure to Tn3 structural motifs, namely 7 beta strands each separated by a loop region. An analysis of the location of the beta strands and the loop regions revealed a pattern of diversity that may aide in the prediction of loop length and sequence compositions for candidate scaffolds for which a structure is not available. A length diversity analysis was performed for the BC, DE, and FG loops of candidate scaffolds in accessible protein databases.

Figure 4A:
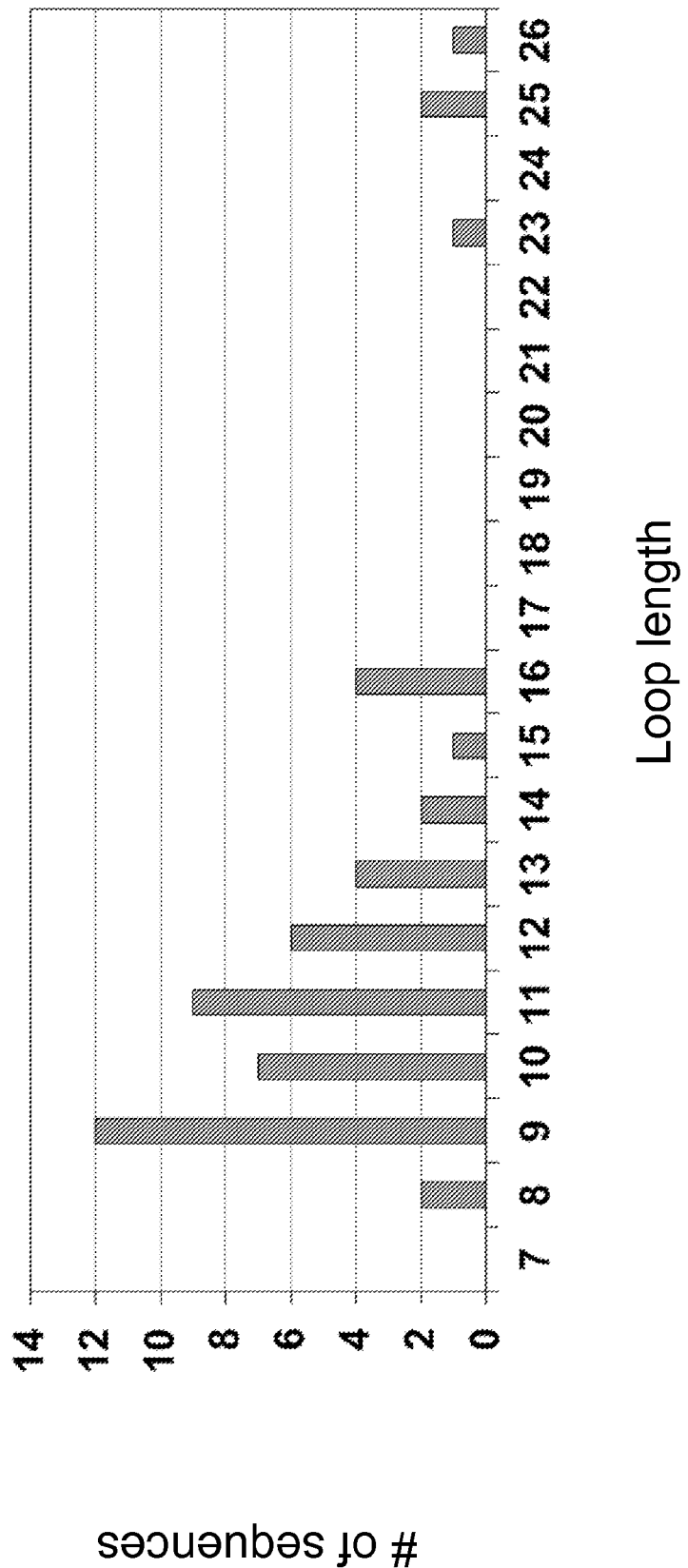
FIG. 4. The BC loops of scaffolds demonstrate loop length diversity. The graph represents the length diversity of the BC loop of various Tn3 related protein scaffolds. (A) represents the loop length diversity exhibited by sequences derived from a subset of Tn3 related scaffolds from the PDB database (51 sequences). (B) represents the loop length diversity exhibited by sequences derived from the Swiss-prot database (397 sequences). As presented, the BC loop of various Tn3 related scaffolds exhibit lengths from 7-26 amino acid residues. According to the scheme used herein, the length of the BC loops in Tn3 is 9 residues.
Figure 4B:
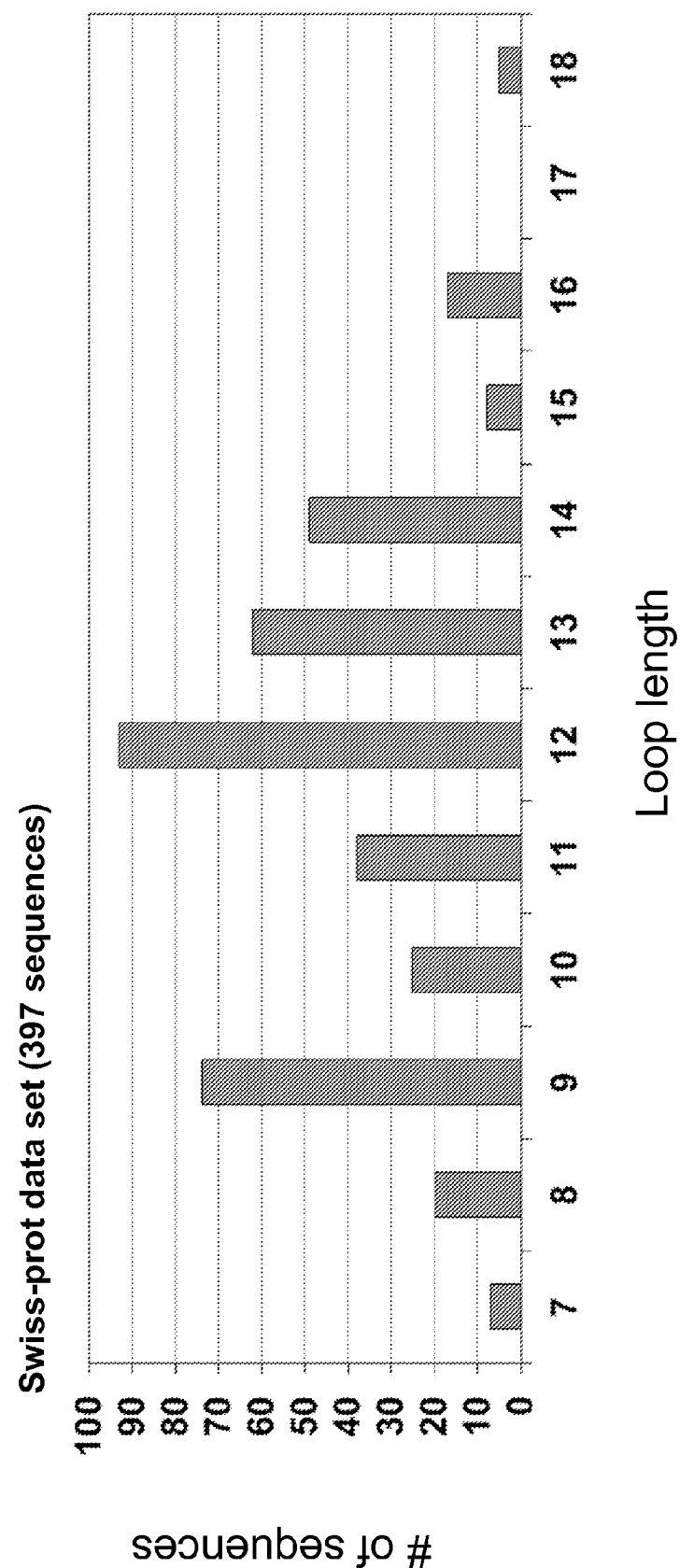
Figure 5:
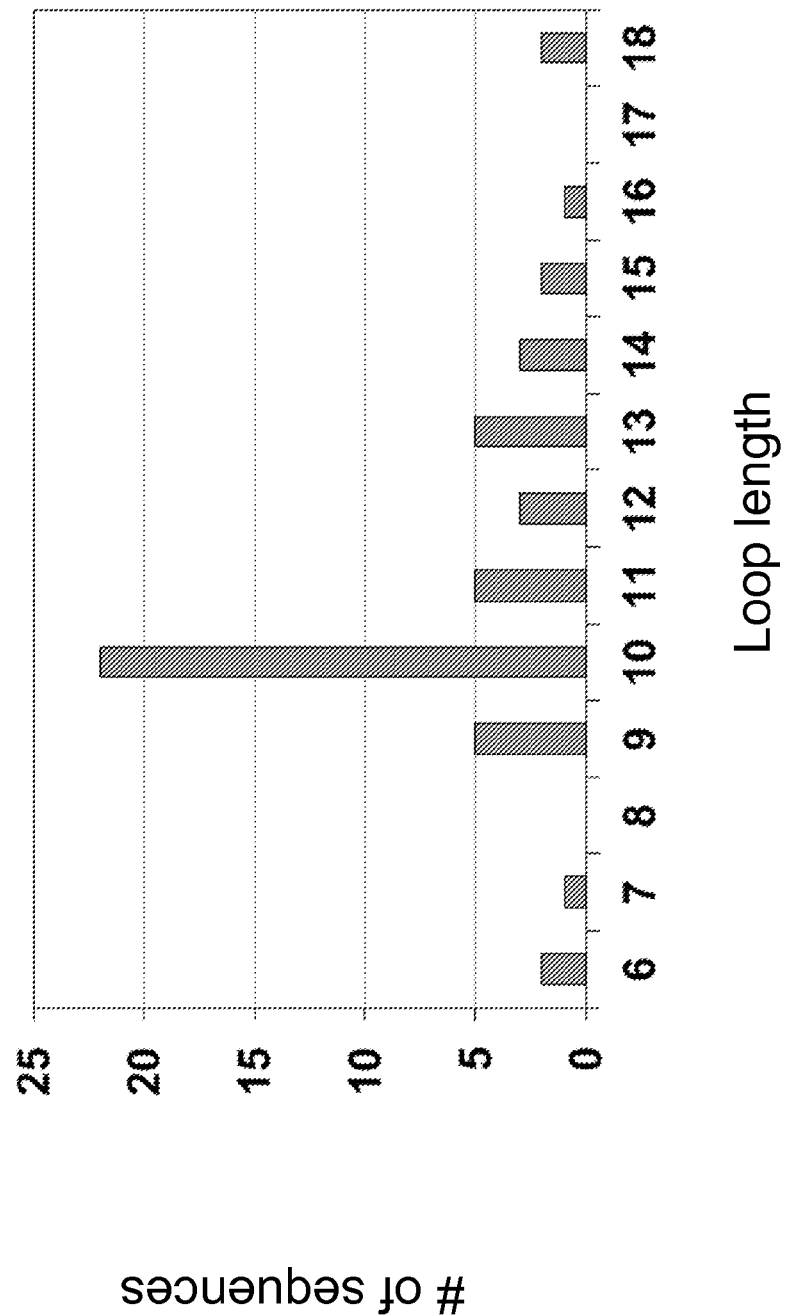
FIG. 5. The FG loops of scaffolds demonstrate loop length diversity. The graph represents the length diversity of the FG loops of various Tn3 related protein scaffolds. The figure depicts the FG loop length diversity exhibited by sequences derived from a subset of Tn3 related scaffolds from the PDB database. As presented, the FG loop of Tn3 scaffolds exhibit lengths of 6-18 amino acid residues. According to the scheme used herein, the length of the FG loop in Tn3 is 10 residues.
Figure 6:
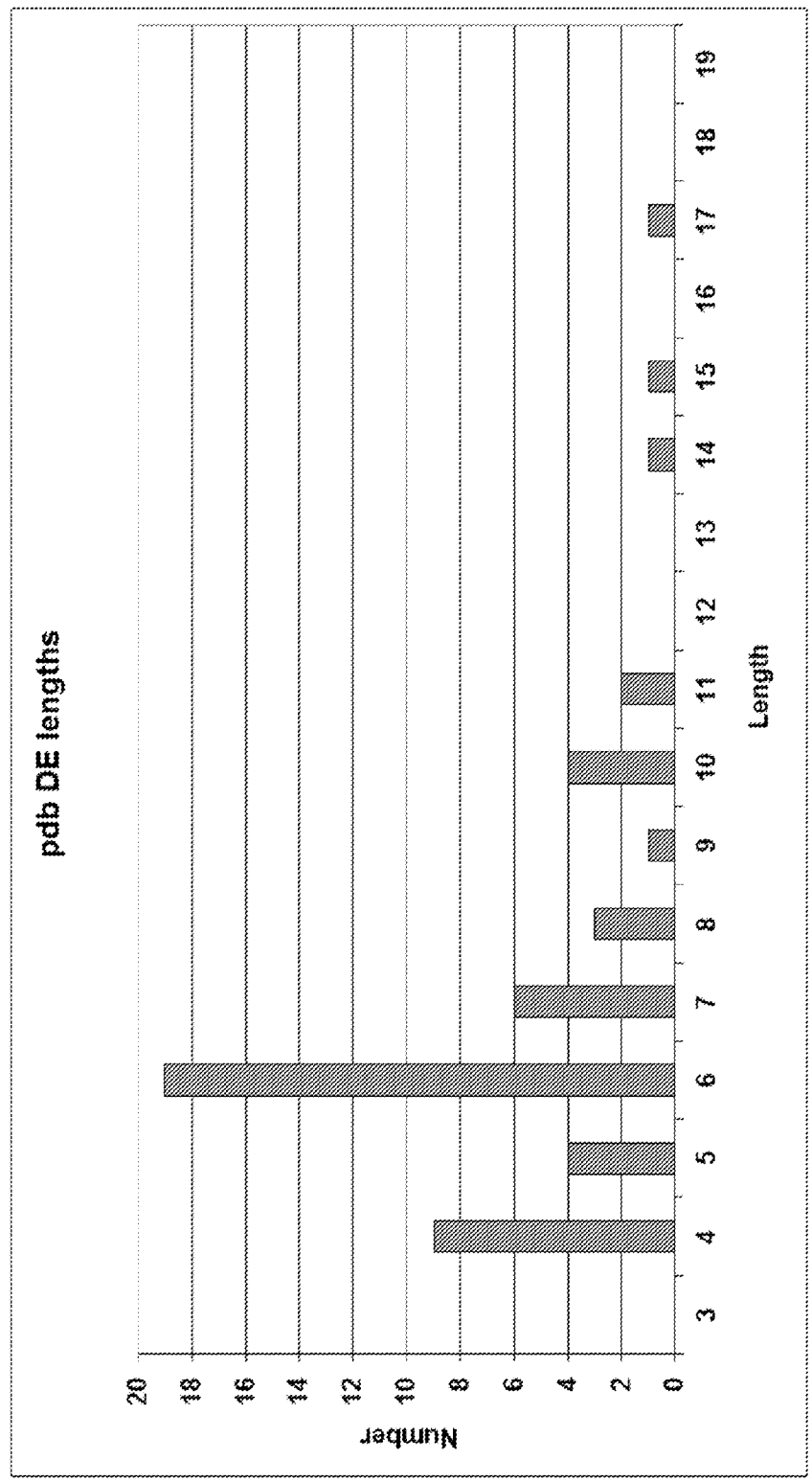
FIG. 6. The DE loops of scaffolds demonstrate loop length diversity. The graph represents the length diversity of the DE loops of various Tn3 protein scaffolds. The figure depicts the DE loop length diversity exhibited by sequences derived from a subset of Tn3 related scaffolds from the PDB database. As presented, the DE loop of Tn3 related scaffolds exhibit lengths from about 4 to about 17 amino acid residues. According to the scheme used herein, the length of the DE loop in Tn3 is 6 residues.

A compilation of identified scaffold sequences has lead to the development of the loop length diversity graphs presented in FIGS. 4, 5, and 6. Presented in FIG. 4A is the BC loop length diversity obtained from the analysis of 51 sequences from the Protein Data Bank (PDB). It is apparent from the graph that the BC loop length in this collection of sequences ranges from about 8 amino acid residues to about 26 amino acid residues, with the 9 amino acid residue loop being the most predominant. Presented in FIG. 4B is loop length diversity obtained from the analysis of 397 sequences identified from the Swiss-prot database. It is apparent from the graph that the BC loop length in this collection of sequences ranges from about 7 amino acid residues to about 19 amino acid residues, with the 12 amino acid residue loop being the most predominant. Presented in FIG. 5 is the FG loop length diversity obtained from the analysis of 51 sequences identified from the PDB database. It is apparent from the graph that the FG loop length in this collection of sequences ranges from about 6 amino acid residues to about 18 amino acid residues, with the 10 amino acid residue loop being the most predominant. A similar analysis as described herein was performed for the DE loop sequences. Presented in FIG. 6 is the DE loop length diversity, demonstrating that the length of DE loops range from about 4 amino acid residues to about 17 amino acid residues with the 6 residue loop being the most predominant length.

Figure 7A:
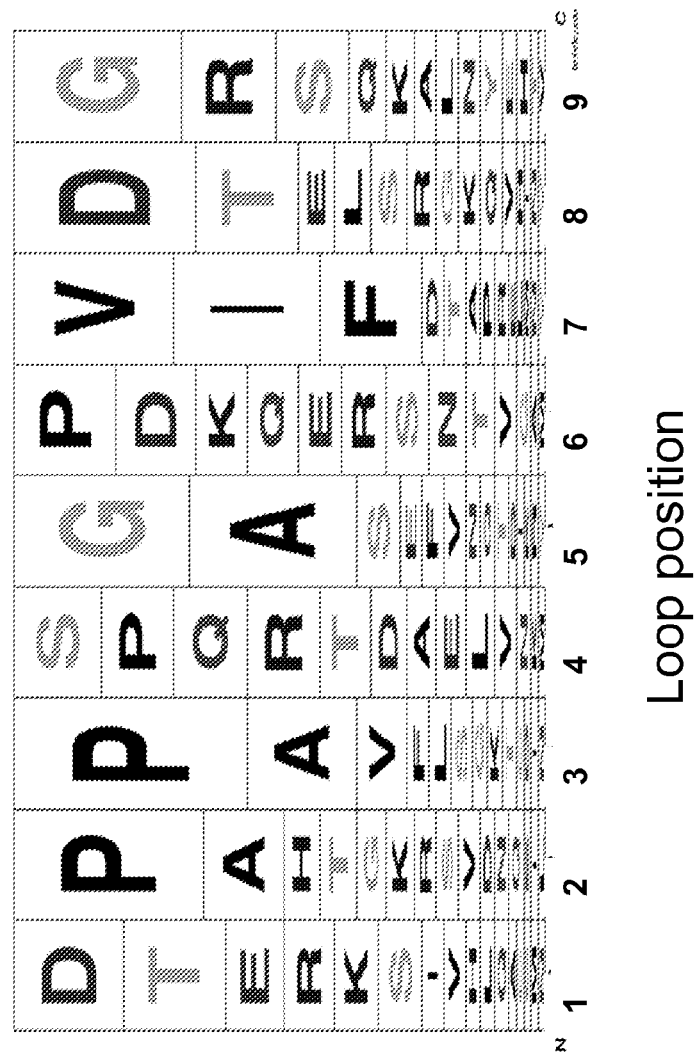
FIG. 7A. The 9 amino acid residue BC loops of scaffolds demonstrate sequence diversity. The graph represents the sequence diversity exhibited by 9 amino acid residue BC loops from the Swiss-Prot database (73 sequences). Using the alignment tool, Weblogo, the relative incidence of an amino acid occurring at a particular position in a 9 amino acid long BC loop is represented by the size of the single letter code above the particular position. For example, at position 3 of the analyzed BC loops of 9 amino acid residues, the most prevalent amino acid is Proline (P), followed by Alanine (A), followed by Valine (V).
Figure 7B:
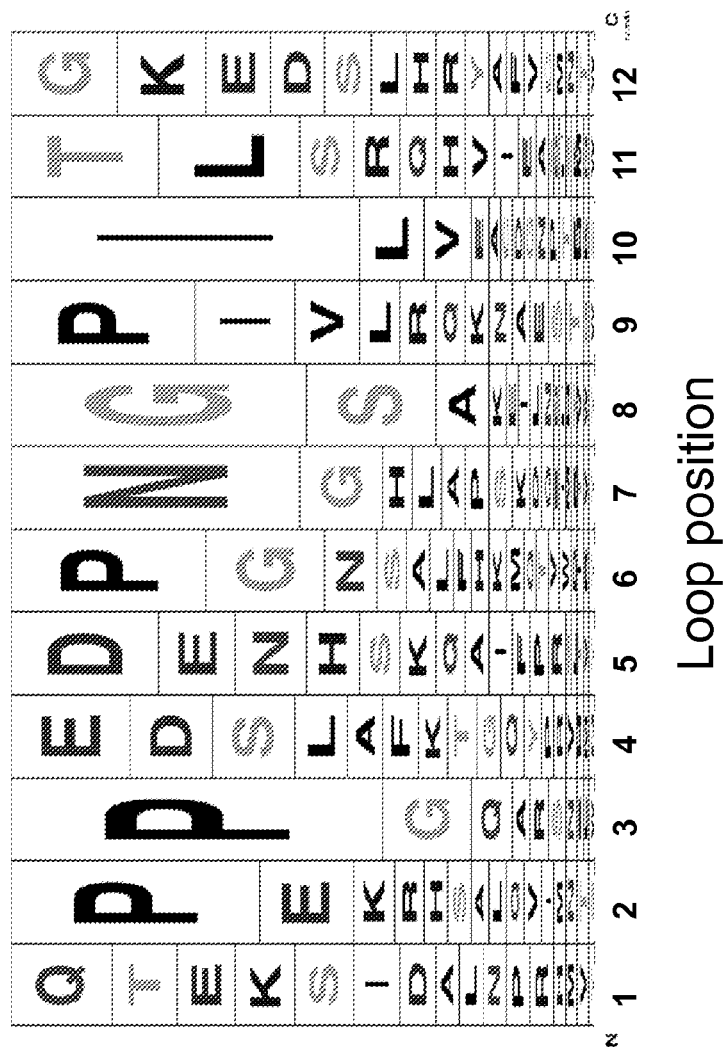
FIG. 7B. The 12 amino acid residue BC loops of scaffolds demonstrate sequence diversity. The graph represents the sequence diversity exhibited by 12 amino acid residue BC loops from the Swiss-Prot data set (99 sequences). Using the alignment tool, Weblogo, the relative incidence of an amino acid occurring at a particular position in a 12 amino acid long BC loop is represented by the size of the single letter code above the particular position. For example, at position 3 of the analyzed BC loops of 12 amino acid residues, the most prevalent amino acid is Proline (P), followed by Glycine (G), followed by Glutamine (Q).
Figure 8:
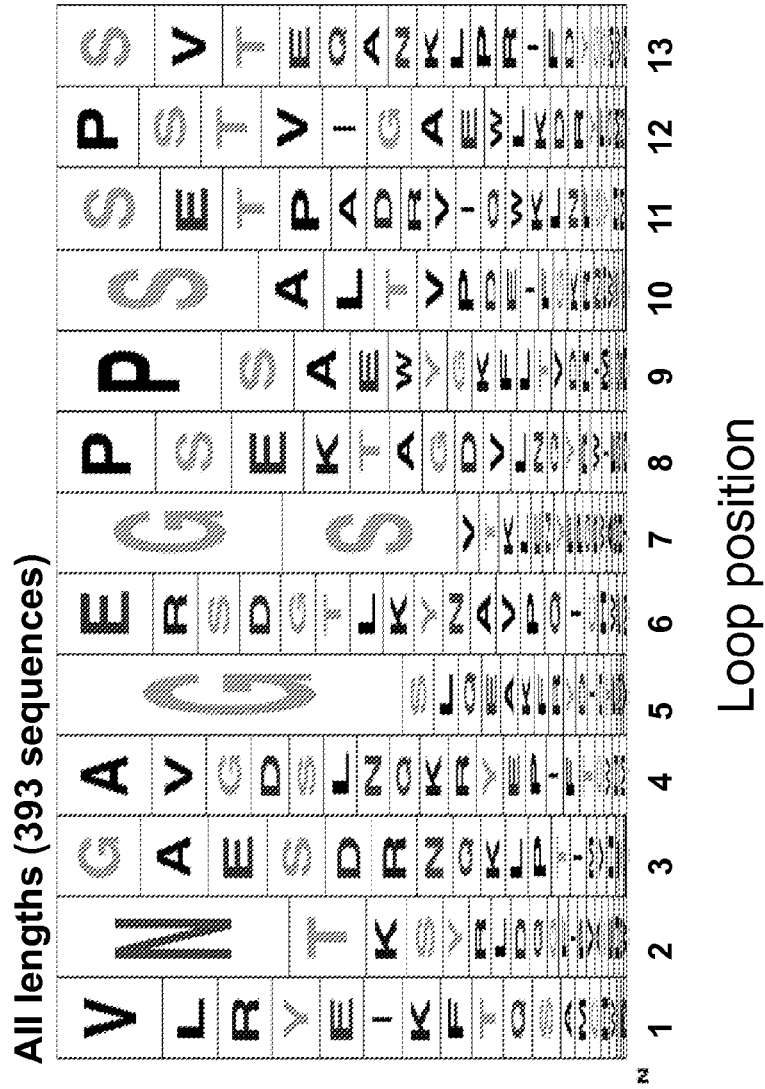
FIG. 8. The FG loops of scaffolds demonstrate sequence diversity. The graph represents the sequence diversity exhibited by FG loops from all of the lengths from the Swiss-Prot data set (393 sequences). Using the alignment tool, Weblogo, the relative incidence of an amino acid occurring at a particular position in the FG loop is represented by the size of the single letter code above the particular position. For example, at position 2 of the analyzed FG loops, the most prevalent amino acid is Asparagine (N), followed by Threonine (T), followed by Lysine (K).

In addition to the length diversity, for the more abundant loop lengths a sequence diversity analysis was performed in an attempt to guide the establishment of consensus sequences. Presented in FIG. 7A is the sequence diversity graph of 9 amino acid residue BC loops. The prevalence of a particular amino acid at each position is represented by the relative size of the box containing that residue over each position. For example, at position 3 of a 9 amino acid residue loop, there is a preference of a proline or an alanine. Also, at position 5 there is a preference for glycine and alanine. At position 7 there is a preference for the amino acids valine, isoleucine, and phenylalanine. Other positions in the loop show greater sequence diversity suggesting that these positions may be suitable for complete randomization in construction of libraries of the Tn3 scaffold. Presented in FIG. 7B is the sequence diversity graph of 12 amino acid residue BC loops. In this analysis, for example, at position 3 a Proline residue is preferred. Also, positions 1, 4, 5 and 12 appear to be suitable for complete randomization as they do not exhibit selectivity for an amino acid residue. Presented in FIG. 8 is the sequence diversity graph for all lengths of FG loops. From this analysis, position 2 is often asparagine, position 5 prefers glycine, position 7 is often glycine or serine. Also, positions 1, 3, 4, 6, 8, 9, 11, 12, and 13 represent candidate positions for complete randomization in library construction as they do not demonstrate selectivity for amino acid residues. The data from this analysis suggests a potential benefit of limiting loop diversity at positions showing a sequence conservation such that a greater proportion of molecules in a library may maintain WT-like stability, expression and solubility.

Example 3

Construction of a Phage Displayed Tn3 Library and Selection of Specific Binders

Given the loop and sequence diversity established above, a directed approach to the development of libraries was performed. More specifically, loops BC and FG were randomized in a restricted fashion. The following strategy was employed for the BC and FG loops.

Library Design and Construction

A synthetic cDNA encoding Tn3, corresponding to the Nco I-Kpn I fragment of seq. ID 10D (See section 6 for sequence), was cloned into a phage display vector enabling display of Tn3 protein on the surface of M13 bacteriophage as a fusion to a fragment of the gene III coat protein. The construct encoded a 20 amino acid Thr/Pro-rich linker sequence between the C-terminus of Tn3 and codons 251-406 of M13 gene III.

Libraries of randomly mutated Tn3 were prepared by Kunkel mutagenesis (Kunkel T A et al., Methods Enzym. 204, 125, 1991) using degenerate oligonucleotides. Three degenerate oligonucleotides were used to randomize the coding sequence of the BC loop, and three for the FG loop (Table 2). This strategy resulted in the introduction of characterized sequence and loop length diversity into the Tn3 library, consistent with patterns of diversity described for natural Tn3 domains.

TABLE 2

Degenerate oligonucleotides for Tn3 library construction

| Oligo name | Loop randomized | Sequence | Seq ID |
|---|---|---|---|
| BC9 | BC | ACCGCGCTGATTACCTGGTCTNNK SCGNNKGSTNNKNNKNNKGGCATTG AACTGACCTATGGC | 211 |
| BC11 | BC | ACCGCGCTGATTACCTGGTCTCCG BSTNNKNNKNNKNNKNNKNNKACCG GCATTGAACTGACCTATGGC | 212 |
| BC12 | BC | ACCGCGCTGATTACCTGGGCGVMA CCGNNKNNKNNKRRCRGCNNKATTNN KGGTATTGAACTGACCTATGGC | 213 |
| FG9 | FG | TATGAAGTGAGCCTGATTAGCNNK AMSNNKNNKGGTNNKNNKNNKAGCA AAGAAACCTTTACCACC | 214 |
| FG10 | FG | TATGAAGTGAGCCTGATTAGCNNK AMSNNKNNKNNKNNKRGCAACCCGG CGAAAGAAACCTTTACCACC | 215 |
| FG11 | FG | TATGAAGTGAGCCTGATTAGCNNK AMSNNKNNKGGTNNKNNKAGCAAC CCGGCGAAAGAAACCTTTACCACC | 216 |

Following transformation of electrocompetent *E. coli* with randomly mutated phagemid constructs, M13KO7 helper phage was added and cultures were grown overnight at 37° C. in 500 mL of 2YT medium containing carbenicillum. Phage was then isolated from culture supernatants by precipitation with a saline polyethylene glycol solution and resuspended in a small volume of PBS.

Panning of Libraries for a Specific SYNAGIS® Binding Scaffold

SYNAGIS® was passively adsorbed onto microtitre plate wells, and free sites were blocked with PBS containing 10 mg/mL BSA or casein. Phage stocks were diluted with PBS containing 2 mg/mL BSA or casein and 0.1% v/v Tween-20. Diluted phage samples (100 μL; ~$10^{12}$ phage) were added to SYNAGIS®-coated wells and incubated for 2 h at room temperature with gentle shaking. Plates were then washed 10-15 times with PBS containing 0.1% v/v Tween 20, and bound phage were eluted with 100 μL/well of 0.1M HCl, then neutralized by addition of 1.0M Tris-HCl, pH 8.0. Eluted phage were re-propagated by infection of XL-1 Blue *E. coli* and harvested from overnight cultures co-infected with M13KO7 helper phage in 50 mL 2YT medium containing 50 μg/mL carbenicillum. The library was panned against SYNAGIS® in this manner for a total of four rounds, using BSA in the blocking and diluent buffers in the first and third rounds, and casein in rounds 2 and 4.

Screening of SYNAGIS® Binding Clones

After the final round of panning, eluted phage were serially diluted and used to infect XL-1 Blue *E. coli* for 1 h prior to plating overnight on LB agar containing 50 μg/mL carbenicillum. Individual colonies were picked and grown overnight in 2YT/carbenicillum at 37° C. Cultures were then diluted 1:100 in 2YT/carbenicillum, grown to an optical density (600 nm) of 0.4, and M13KO7 helper phage were added followed by overnight incubation at 37° C. with shaking. Following centrifugation, 50 µL of culture supernatant was diluted with an equal volume of PBS containing 0.1% v/v Tween 20 and 2% w/v skim milk powder, and used for analysis by ELISA. Clones that gave the highest response for binding to SYNAGIS® but not BSA/casein-coated ELISA plates were then selected for sequencing. To determine the sequences of Tn3 variants displayed by the selected clones, 1 µL of culture supernatant was used in a PCR to amplify a fragment encompassing the encoded Tn3 sequence. This PCR product was then treated with ExoSAPit, (USB Corp., Cleveland, Ohio) to degrade unconsumed deoxynucleotides and primers, and sequenced directly.

Identification of the SYNAGIS®-binding Tn3 Variant SynBP01

Figure 9B:
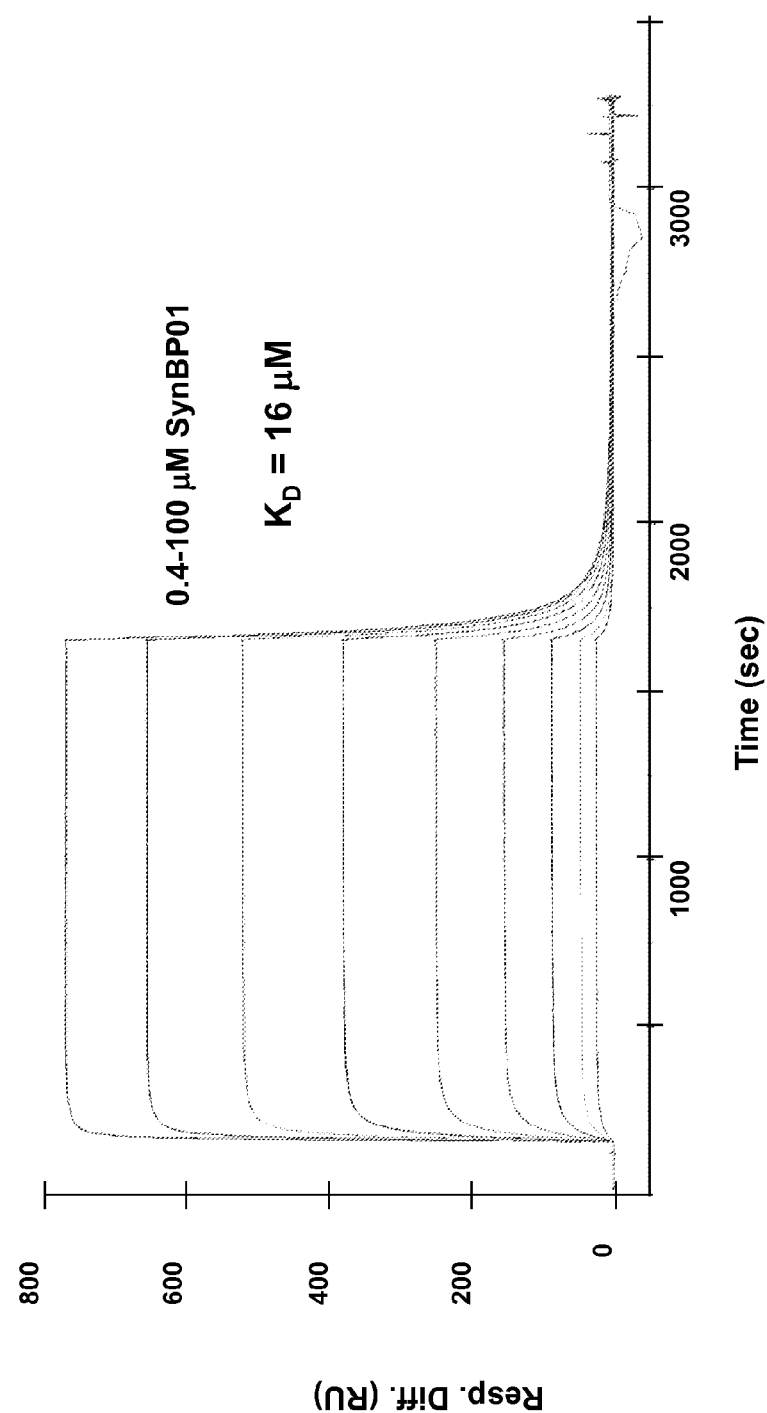
FIG. 9B. The $K_D$, determination of SYNAGIS® specific binding scaffold. The tracing represents an experiment characterizing the specific binding affinity for the SynBP01 scaffold for SYNAGIS® by a BIACORE® assay. Using immobilized SYNAGIS®and mobile phase SynBP01 at various concentrations it was determined that the binding affinity ($K_D$) was about 16 μM.
Figure 9C:
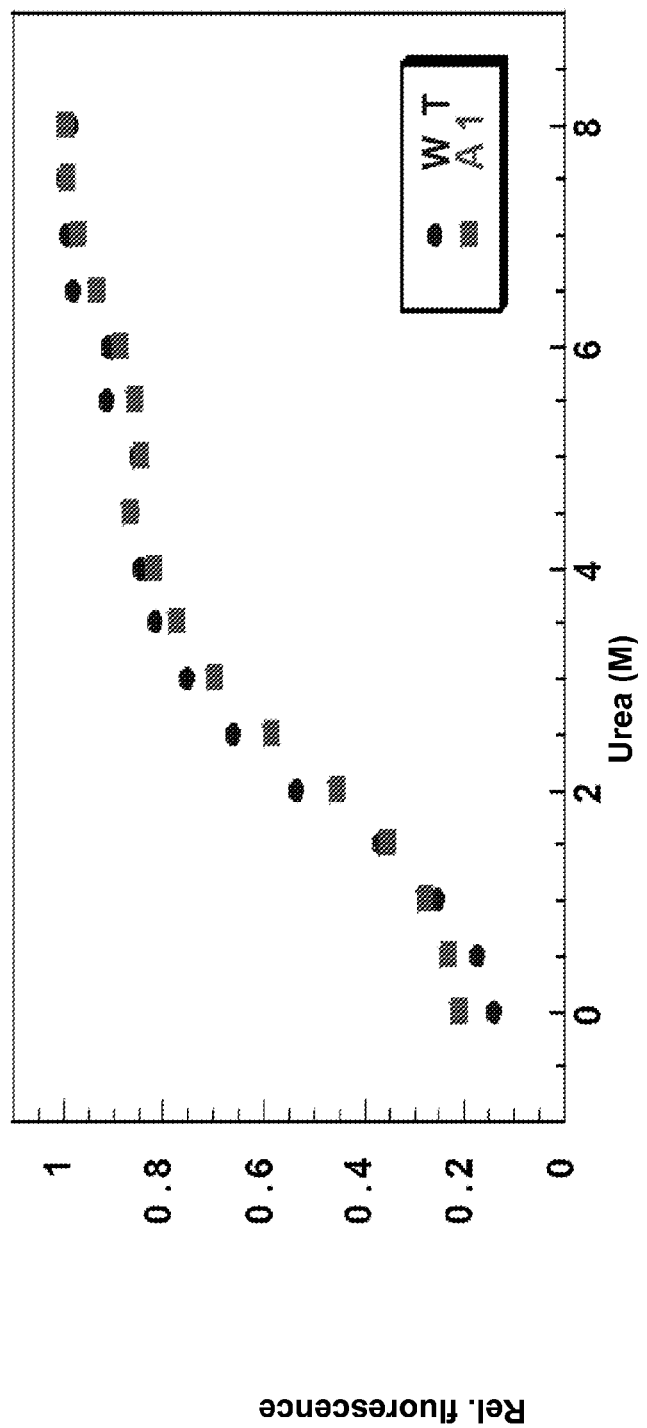
FIG. 9A. Expression and purification of a SYNAGIS® specific Tn3 scaffold. Presented here is a Coomassie stained PAGE gel documenting the SYNAGIS® specific Tn3 scaffold (SynBP01) after recombinant expression and purification. The SynBP01 scaffold was readily purified to homogeneity.
Figure 9D:
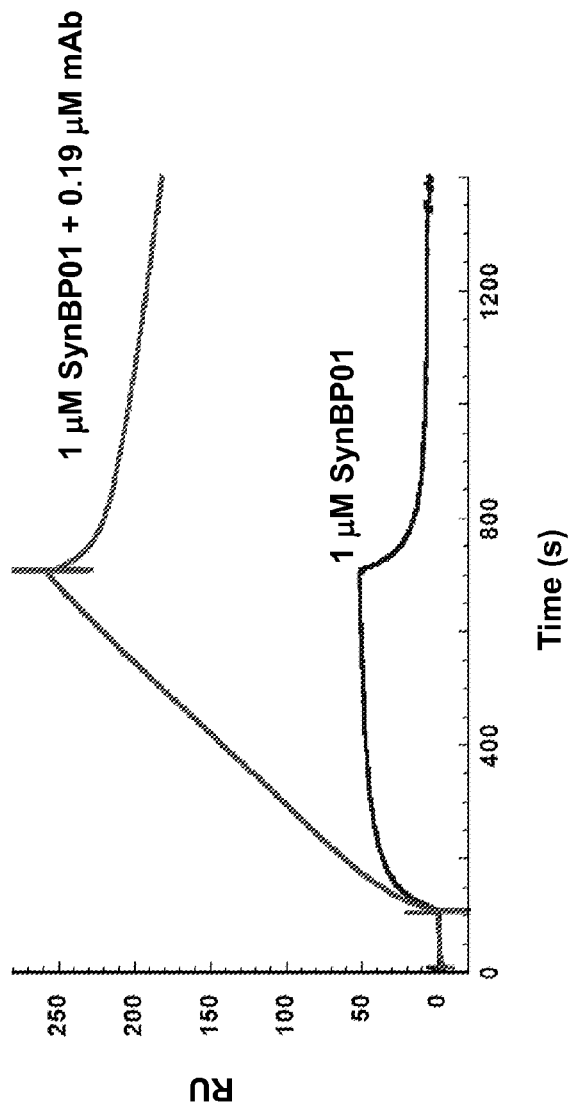

DNA sequencing of SYNAGIS®-binding Tn3 variants identified 3 unique clones. The clone with the highest signal in a SYNAGIS®-binding ELISA, SynBP01, contained novel BC and FG loop sequences as shown in Table 3. To express soluble SynBP01, the NcoI-KpnI cDNA fragment was excised from the phage display vector and cloned into the corresponding sites of the *E. coli* expression vector previously described. Recombinant SynBP01 was then expressed in *E. coli*, and purified as previously described for wild type Tn3. The yield of purified SynBP01 was 18 mg from 400 mL of *E. coli* culture, and was greater than 95% pure as judged by SDS-PAGE analysis (FIG. 9A). As this recovery is close to the capacity of the 1 mL nickel chelate affinity column used, it is likely that this yield under represents the actual expression level of SynBP01.

Determination of SYNAGIS® Binding Affinity Exhibited by SynBP01

The equilibrium dissociation constant ($K_D$) for binding of SynBP01 to SYNAGIS® was measured by surface plasmon resonance on a BIAcore 3000 instrument. SYNAGIS® was covalently immobilized on the biosensor chip via primary amino groups. Equilibrium binding of SynBP01 was measured by injecting samples of SynBP01 in HBS-EP buffer (10 mM HEPES, 150 mM NaCl, 3 mM EDTA, pH 7.5, 0.005% v/v Tween 20) over the chip at a flow rate of 10 μL/min (FIG. 9B). Following each equilibrium binding measurement, SynBP01 was allowed to completely dissociate by running HBS-EP buffer over the chip for at least 25 mM prior to injection of the next SynBP01 sample. Binding profiles were analyzed by using BIAevaluation software (Biacore AB, Uppsala, Sweden), and the $K_D$ for binding of SynBP01 to SYNAGIS® was calculated as 16 μM.

Examination of the Stability of SynBP01

The stability of SynBP01 to unfolding by urea at pH 7.0 was measured as described previously for Tn3 (See Example 1). To facilitate a comparison of chaotrope-induced unfolding of Tn3 and SynBP01, the relative fluorescence emission intensity at 360 nm was plotted as a function of chaotrope concentration for each protein.

A comparison of urea-induced unfolding of Tn3 and SynBP01 at pH 7.0 (FIG. 9C) showed that the concentration of urea required to achieve 50% unfolding was similar for both proteins. This indicates that the stability of SynBP01 is similar to that of wild type Tn3.

In other library screens, additional SYNAGIS® and Lysozyme specific binding scaffolds were identified. The specific BC and FG loops sequences are as follows:

TABLE 3

BC and FG loop sequences of SYNAGIS ® and Lysozyme specific binding scaffolds

| Clone | BC loop | Seq ID NO: | FG loop | Seq ID NO: |
|---|---|---|---|---|
| SYNAGIS ® specific binding scaffolds | | | | |
| SynBP01 | SPPSVLVGYTG | 100 | VTEFGRRRS | 101 |
| 2 | FKPLAEIDG | 102 | RKIIGLLSNPA | 103 |
| 3 | FKPLAEIDG | 102 | GTVVGQKSNPA | 104 |
| Lysozyme specific binding scaffolds | | | | |
| 1 | FKPLAEIDG | 102 | YNRYGLCPS | 112 |
| 2 | FKPLAEIDG | 102 | SNRIGMCPS | 113 |
| 3 | AQPTSPNGSIXG | 114 | RRGDMSSNPA | 115 |
| 4 | FKPLAEIDG | 102 | DTVHGRLSNPA | 116 |
| 5 | FKPLAEIDG | 102 | RKVLGRLSNPA | 117 |
| 6 | FKPLAEIDG | 102 | RKLVGALRS | 118 |
| 7 | FKPLAEIDG | 102 | RKVLRYSNPA | 119 |
| 8 | SPCNGGKRCTG | 120 | RRGDMSSNPA | 121 |
| 9 | FKPLAEIDG | 102 | FKWLGAIRS | 122 |
| 10 | FKPLAEIDG | 102 | GNCVGNLWS | 123 |
| 11 | SPAWITWHRTG | 124 | HTPLGHLRS | 125 | mAb Capture of Paired Scaffolds

Bivalent or bispecific scaffolds, containing 2 identical or 2 distinct scaffolds, may be useful therapeutic molecules based on their ability to simultaneously bind 2 target proteins. A method of directly screening pairs of scaffolds for a desired bivalent or bispecific activity, without having to reformat and express tandem or fusion scaffolds, would vastly simply the process of identifying useful scaffold pairs. Only those pairs identified in the screen would then require reformatting into a form suitable for preparation of a bivalent or bispecific scaffold (for example, a multimeric scaffold).

Full length IgG antibody molecules contain two antigen binding sites, and can therefore bind two target antigens simultaneously. Thus, noncovalent monoclonal antibody capture of scaffolds would result in presentation of two scaffolds on each antigen-binding arm of the antibody. If the scaffold captured in this way were oriented so that the binding surface formed by the BC, DE and FG loops were available for binding to other proteins, then this could form the basis for screening pairs of scaffolds. For this reason, capture by an antibody which recognizes an epitope involving the C-terminus of the scaffold, or any/all of the AB, CD, EF loops would be most suitable. Antibody capture of 2 identical scaffolds would result in formation of a homodimeric mAb-scaffold complex that could mimic the activity of a bivalent scaffold. Capture of 2 different scaffolds would result in a mixture of homo- and heterodimeric mAb-scaffold complexes, wherein the heterodimeric complex could mimic the activity of a bispecific scaffold.

To demonstrate the feasibility of this assay strategy, different concentrations of PentaHis, an anti-histidine tag monoclonal antibody (Qiagen), was incubated for 2 h with 1 μM SynBP01 in HBS-EP buffer. PentaHis capture of SynBP01 was not expected to interfere with its ability to bind SYN- AGIS®, given the C-terminal hexahistidine tag should be on the opposite side of the molecule to the binding surface formed by the BC, DE and FG loops (FIG. 9D). The PentaHis-SynBP01 samples were then injected over a BIAcore® chip onto which SYNAGIS® had been immobilized as previously described. The sensorgrams were corrected for background by subtraction of corresponding sensorgrams for injection of PentaHis in the absence of SynBP01, and then compared to the sensorgram obtained for injection of 1 µM SynBP01 in the absence of PentaHis.

Binding of the PentaHis-SynBP01 complex to SYNAGIS® was significantly stronger than binding of free SynBP01, as exemplified by the sensorgram corresponding to the complex of 0.19 µM PentaHis with 1 µM SynBP01 (FIG. 9D) In particular, PentaHis-complexed SynBP01 had a much slower dissociation rate from the SYNAGIS® surface, indicative of bivalent binding, than did free SynBP01. Control experiments verified that PentaHis did not exhibit any detectable binding to SynBP01 when injected alone, nor did injection of a SynBP01/irrelevant mouse mAb mixture (isotype matched with PentaHis) show any evidence of enhanced binding relative to SynBP01 alone.

Example 4

Design, Expression and Characterization of Disulfide-stabilized Tn3 Variants Design of Disulfide-containing Tn3 Variants While many naturally occurring Tn3 structural motifs lack disulfide bonds, others do contain one or more disulfide bonds. Thus, rather than attempt de novo design of disulfide bonds in Tn3 by measuring distances and angles between amino acid side chains, we introduced cysteine residues into the Tn3 scaffold at positions analogous to Tn3 structural domains that contain naturally occurring disulfides.

Figure 10F:
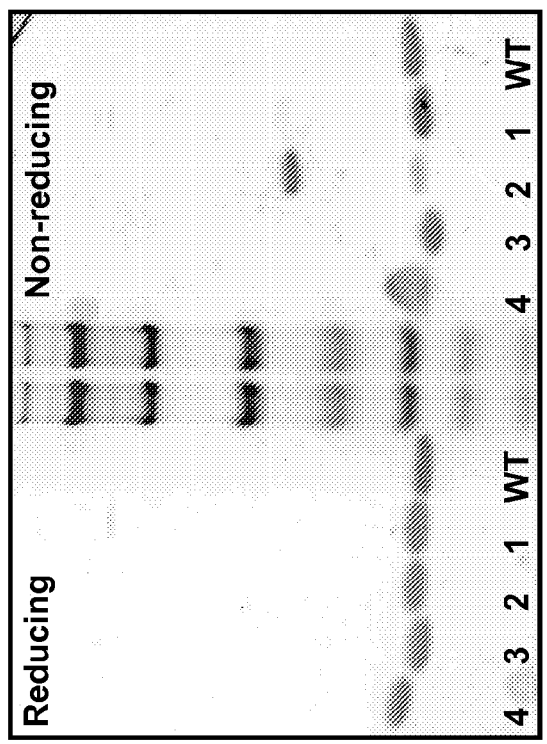
FIG. 10K. The $Tn3^{SS4}$ disulfide engineered scaffold exists in a monomeric state. The figure depicts a tracing from a Size exclusion chromatography/multiple-angle light scattering (SEC-MALS) analysis of the $Tn3^{SS4}$ scaffold. The data demonstrates that the purified $Tn3^{SS4}$ scaffold existed in a monomeric state, determined to be about 11 kDa by an online light scattering detector.


FIG. 10L. RP-HPLC chromatograms of the purified $Tn3^{SS3+4}$ disulfide engineered scaffolds. Depicted in the graphic are the reverse-phase HPLC chromatograms of $Tn3^{SS3+4}$ after purification, following reduction, and after refolding to form disulfide bonds. The tracings demonstrated that the cysteines contained within the scaffolds are only partially oxidized following protein purification (upper tracing) are completely reduced by treatment with DTT (middle tracing) and are completely oxidized to two disulfide bonds after refolding (lower tracing).

FIG. 10M. The dual disulfide containing scaffold $Tn3^{SS3+4}$ exhibits an elevated level of stability. The graph depicts the results from a guanidine hydrochloride denaturation assay comparing the stability of the Tn3 (WT) scaffold (circles) to the single disulfide containing scaffold, $Tn3^{SS4}$ (squares) and to the double disulfide containing scaffold, $Tn3^{SS3+4}$ (triangles). As presented in the graph, the refolded double disulfide scaffold, $Tn3^{SS3+4}$ exhibited a greater resistance to guanidine mediated denaturation, and therefore more stable, as compared to the single refolded disulfide containing scaffold, $Tn3^{SS4}$ as well as the Tn3 scaffold.
Figure 10G:
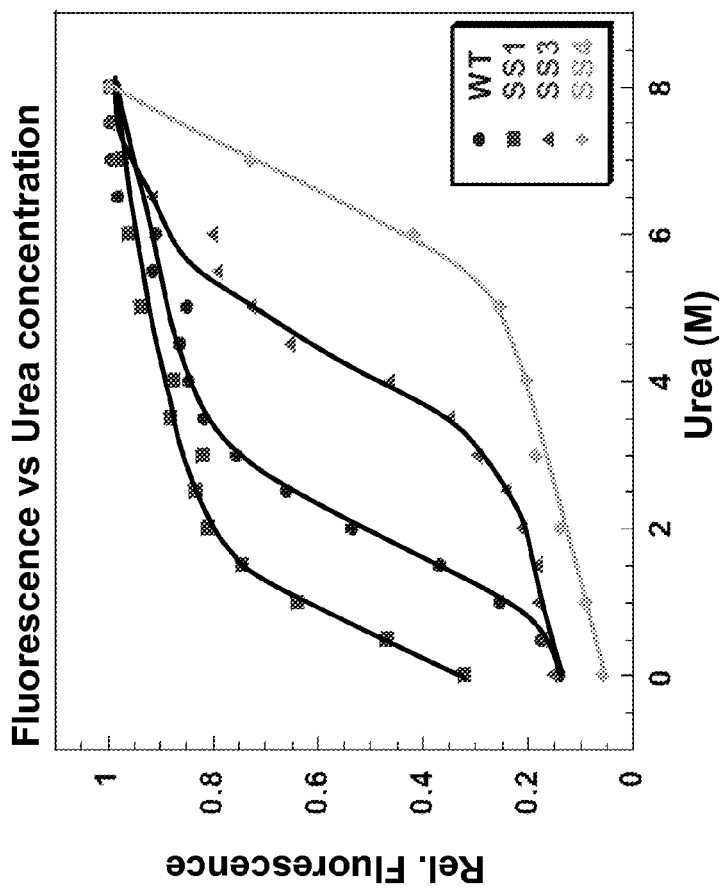

The three dimensional structures of 21 Tn3 structural motifs that naturally contain disulfide bonds were superimposed. The PDB codes and sequences for these structures is shown in FIG. 10A-C. Within these 21 structures, disulfide bonds occurred at various positions within the scaffold, however, a number of these were analogous in that the disulfide bonds were overlaid within the family of superimposed structures. Three examples were found of disulfide bonds that were represented more than twice across the 21 structures. Two of these three correspond to the previously described disulfide bond pair commonly conserved within cytokine receptors (Bazan et al., PNAS, 87, 6934, 1990). A total of 8 and 12 instances of these two disulfides were noted in the 21 structures. The third disulfide occurs less frequently (5 cases/21 structures), and results in a crosslink between the F- and G-strands.

Three cysteine-containing Tn3 mutants were designed in an effort to introduce disulfide bonds at positions corresponding to these 3 naturally occurring disulfides. A fourth cysteine-containing mutant was also designed to introduce a disulfide which occurs naturally in one of the Tn3 structural motifs from mouse G-CSF receptor (PDB code 1pgr). Although there was only one instance of this disulfide in the 21 structures, it results in a disulfide cross-link between the C- and F-strands that is buried within the protein core and occurs close to the BC and FG loop. For each of the Tn3 mutants, designated $Tn3^{SS1-4}$, 2 cysteines were introduced at positions determined from the structure-based sequence alignment of Tn3 with those of the disulfide-containing Tn3 proteins (FIG. 10A-C). As disulfide 2 occurs across at the base of the DE loop in Tn3 structural motifs which often have longer DE loops than Tn3, 2 glycine residues were also inserted into the mutant corresponding to $Tn3^{SS2}$. The disulfide engineering strategy is graphically depicted in FIG. 10D.

Disulfide Mutant Generation and Recombinant Expression

Expression constructs for $Tn3^{SS1-4}$ were generated by site-directed mutagenesis of the wild type expression construct described in Example 1. Recombinant protein was expressed in *E. coli* and purified by immobilized nickel chelate affinity chromatography as described in Example 1. All Tn3 mutants expressed at a level in excess of 50 mg/L.

Refolding of $Tn3^{SS1-4}$

Cytoplasmic expression of proteins in *E. coli* generally results in the isolation of cysteine-containing proteins in the reduced state, or with some degree of inappropriate disulfide formation. To determine whether recombinant $Tn3^{SS1-4}$ proteins were oxidized (i.e. disulfide-containing) or reduced (i.e. lacking disulfide bonds), purified material was analyzed by reverse phase HPLC, and compared to material that was first pre-incubated with the strong reducing agent DTT in the presence of guanidine hydrochloride. In all cases, DTT-treated material chromatographed as a single peak, while untreated samples showed the presence of a 2$^{nd}$ minor peak indicative of partial oxidation to the disulfide-containing form (Representative HPLC analyses of $Tn^{SS3}$ and $Tn^{SS4}$ are depicted in FIG. 10E).

In order to effect complete conversion of reduced $Tn3^{SS1-4}$ to the corresponding disulfide-containing proteins, samples were diluted to 1 mg/mL with 6M guanidine hydrochloride containing 10 mM DTT and buffered at pH 8. After 10 minutes incubation at room temperature, samples were dialyzed overnight against 0.5M guanidine hydrochloride buffered at pH 8.5 with 20 mM Tris-HCl. HPLC-analysis of material refolded in this way typically showed 30-70% conversion into the disulfide-containing species (FIG. 10E). Further conversion to 90-100% of the disulfide-containing species was affected by overnight incubation at 37° C., or by storing samples at 4° C. for >2 weeks. Alternatively, near quantitative refolding to the disulfide-containing product could be affected by overnight dialysis of reduced and denatured protein into buffer containing 0.5M guanidine hydrochloride, 4 mM reduced glutathione, 0.8 mM oxidized glutathione and buffered at pH 8.5 with 20 mM Tris-HCl.

Characterization

To determine purity and whether disulfide bonds within refolded $Tn3^{SS1-4}$ samples were inter- or intramolecular, samples were analyzed by SDS-PAGE under reducing and non-reducing conditions (FIG. 10F). In the presence of reducing agent, all refolded $Tn3^{SS1-4}$ samples migrated at a similar position to Tn3. In the absence of reducing agent, $Tn3^{SS1}$, $Tn3^{SS3}$ and $Tn3^{SS4}$ migrated similarly to Tn3, and were therefore expected to contain an intramolecular disulfide as designed. By contrast, $Tn3^{SS2}$ migrated primarily as a dimer, with a small amount of protein migrating as a monomer. Accordingly, $Tn3^{SS2}$ appears to form intermolecular disulfide-linked dimers and was therefore not studied further.

Stability

Unfolding of $Tn3^{SS1,3,4}$ by chaotropic agents was monitored by intrinsic fluorescence as previously described for wild type Tn3. To facilitate a comparison of chaotrope-induced unfolding of wild type and disulfide-containing Tn3, the relative fluorescence emission intensity at 360 nm was plotted as a function of chaotrope concentration for each protein.

A comparison of urea-induced unfolding of Tn3 and $Tn3^{SS1,3,4}$ at pH 7.0 (FIG. 10G) showed that $Tn3^{SS1}$ was less stable than the wild type protein, but that $Tn3^{SS3}$ and $Tn3^{SS4}$ were considerably more stable. At pH 7.0, the concentration of urea required to achieve 50% unfolding (Cm) of wild type Tn3 was 2M. By contrast, the Cm for unfolding of Tn3$^{SS3}$ was 4M urea, while for Tn3$^{SS4}$ Cm was at least 6M, but could not be accurately determined as this protein was not fully unfolded at the highest concentration of urea used in these experiments (8M).

Figure 10H:
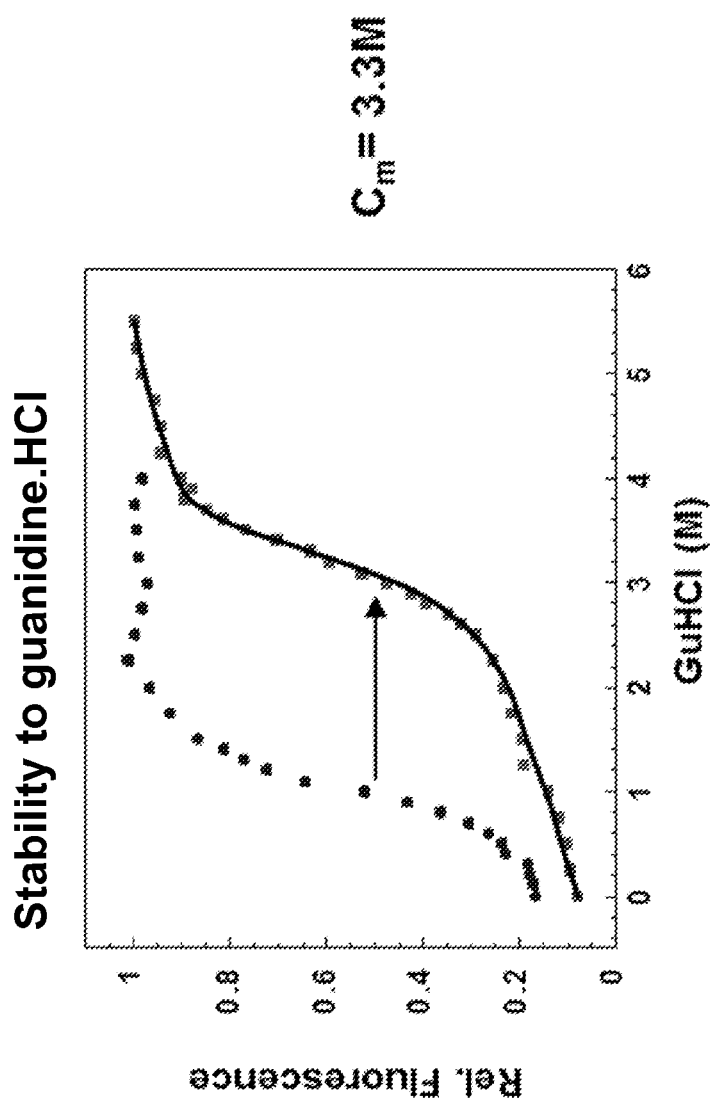

Unfolding of Tn3$^{SS4}$ by guanidine hydrochloride (GuHCl) at pH 5.0 was also determined by fluorescence and compared to unfolding of wild type Tn3. Given GuHCl is a stronger denaturant than urea, a complete unfolding transition was obtained by analyzing the fluorescence of protein samples in concentrations of GuHCl ranging from 0 to 5.5M (FIG. 10H). The Cm for unfolding of wild type Tn3 at pH 5.0 was 1M GuHCl and approx. 3.2M for Tn3$^{SS4}$.

Figure 10I:
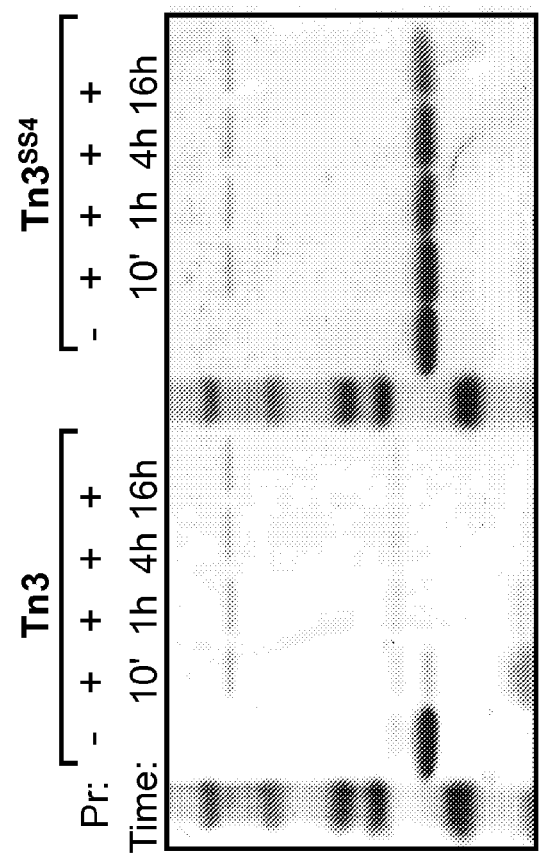

The stability of Tn3$^{SS4}$ to proteolytic degradation was tested by incubation with thermolysin as previously described in Example 1 for the wild type protein. In contrast to the wild type protein, Tn3$^{SS4}$ resisted proteolysis, even after overnight incubation at room temperature (FIG. 10I).

Figure 10J:
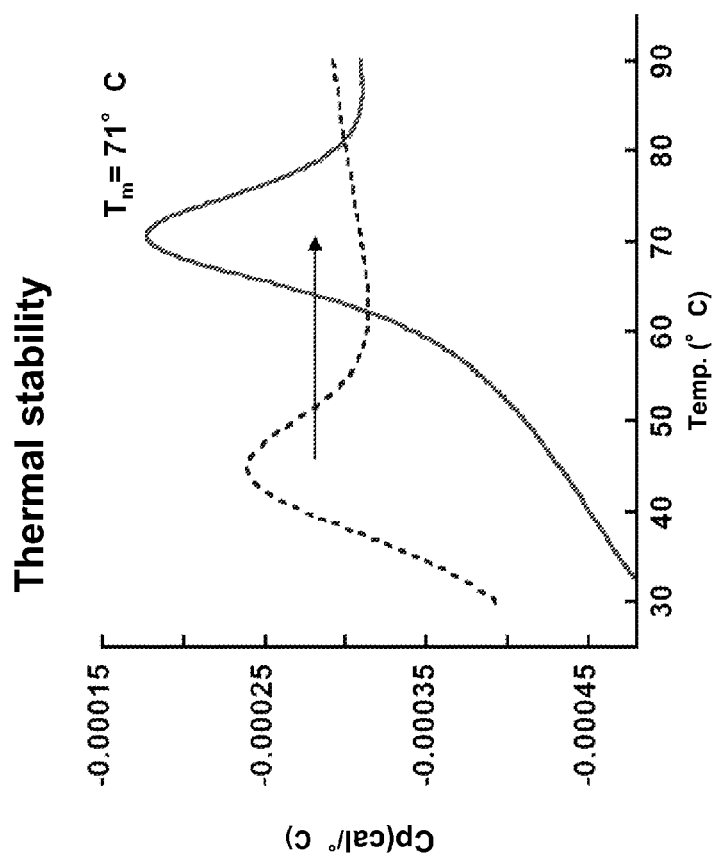

Thermal unfolding of Tn3$^{SS4}$ was assessed by differential scanning calorimetry (DSC) as previously described. A 1 mg/mL Tn3$^{SS4}$ sample in 20 mM sodium phosphate at pH 7.0 exhibited a melting temperature (Tm) of 71° C., which is 26° C. higher than the Tm of the wild type protein under the same conditions (FIG. 10J). The Tm was slightly elevated for Tn3$^{SS4}$ in 20 mM sodium acetate pH 5.0. At this pH, the Tm for Tn3$^{SS4}$ was 74° C. which is 18° C. higher than the wild type protein. As with the wild type protein, thermal unfolding of Tn3$^{SS4}$ appeared completely reversible at pH 7.0, but resulted in precipitation at pH 5.0.

Size exclusion chromatography with multi-angle light scattering (SEC-MALS) was used to determine whether Tn3$^{SS4}$ was monomeric in solution, using the same conditions previously described for the wild type protein. SEC-MALS analysis of a 2.0 mg/mL Tn3$^{SS4}$ sample revealed that the protein was completely in the monomeric state (FIG. 10K). The experimentally-derived monomer mass was 10.7 kDa which is in close agreement with the calculated mass of 10.8 kDa.

Preparation of a Dual-Disulfide Containing Tn3 Variant

Given the enhanced stability of both the Tn3$^{SS3}$ and Tn3$^{SS4}$ variants relative to the wild type protein, a new Tn3 variant was prepared to determine whether the stabilizing effect of each disulfide bond would be additive in the context of a combination mutant.

A construct for recombinant expression of this tetra-cysteine variant, designated Tn3$^{SS3+4}$ was prepared by methods previously described and contained 4 cysteine residues at positions corresponding to disulfides 3 and 4 (see FIG. 10D). Protein was expressed and purified as previously described in Example 1. The yield of purified protein obtained for this variant was 22 mg from 200 mL E. coli culture. As this is the maximum binding capacity of the column used for purification, the actual expression level is at least 110 mg/L.

Refolding of Tn3$^{SS3+4}$

Purified Tn3$^{SS3+4}$ was analyzed by reverse phase HPLC, and compared to material that was first preincubated with the strong reducing agent DTT in the presence of guanidine hydrochloride. While the DTT-treated material chromatographed as a single peak, untreated Tn3$^{SS3+4}$ showed the presence of 3 additional earlier eluting peaks most likely due to partial formation of either or both potential disulfides bonds (FIG. 10L).

In order to refold Tn3$^{SS3+4}$ to the correct dual disulfide-containing protein, the sample was diluted to 1 mg/mL with 6M guanidine hydrochloride containing 10 mM DTT and buffered at pH 8. After 10 minutes incubation at room temperature, the sample was dialyzed overnight against 0.5M guanidine hydrochloride buffered at pH 8.5 with 20 mM Tris.HCl, and containing 4 mM reduced glutathione. HPLC-analysis of the refolded material indicated >95% conversion of the reduced protein to a single peak corresponding to the earliest eluting peak in the unfolded preparation. This product, by virtue of its elution time profile, was presumed to contain the 2 correctly formed disulfide bonds. (FIG. 10L).

Characterization of Tn3$^{SS3+4}$

Figure 10M:
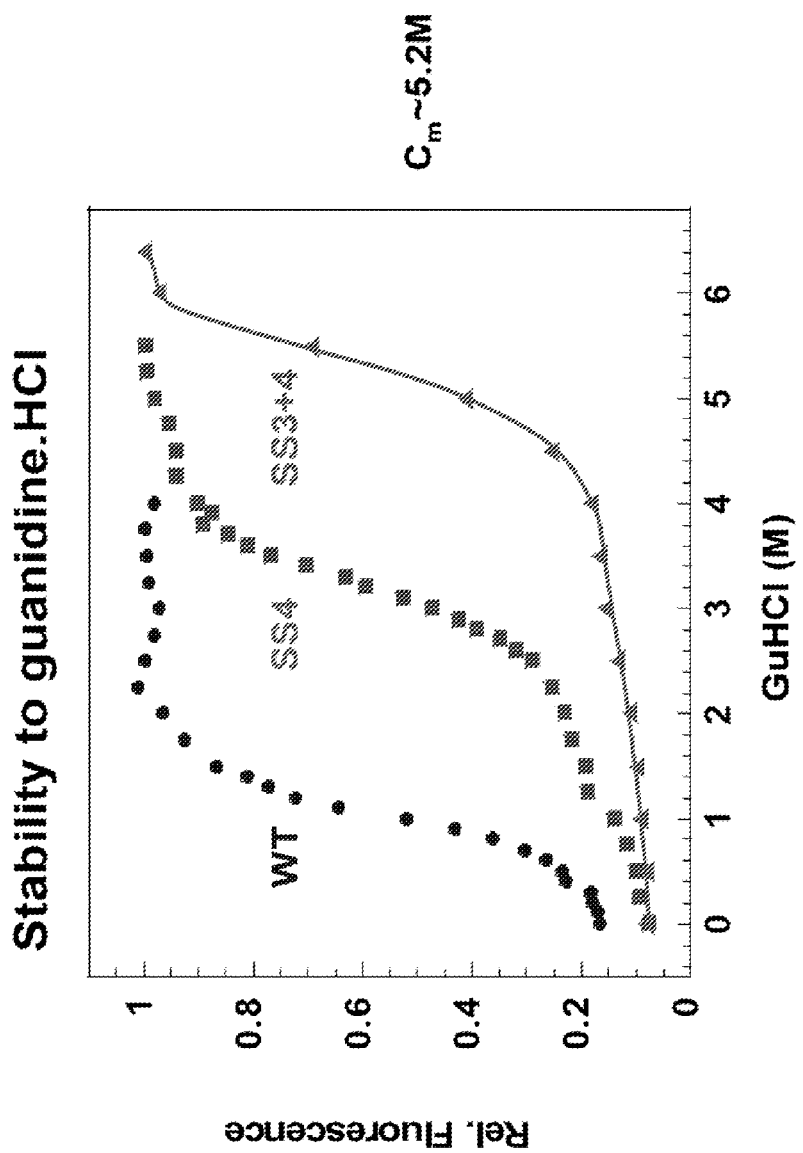

Unfolding of Tn3$^{SS3+4}$ by guanidine hydrochloride (GuHCl) at pH 5.0 was determined by fluorescence and compared to previous data for Tn3 and Tn3$^{SS4}$. The Cm for unfolding of Tn3$^{SS3+4}$ at pH 5.0 was between 5.0-5.5M GuHCl (FIG. 10M) which is considerably higher than the Cm for wild type or Tn3$^{SS4}$. The significant enhancement in stability to GuHCl-induced denaturation suggests that the stabilizing effects of disulfides 3 and 4 are additive when both sets of mutations are combined into the one scaffold.

Example 5

Identification, Expression and Characterization of Tn3 Structural Motifs Derived from Hyperthermophilic Organisms Tn3 Structural Motif Identification A BLAST search was performed to identity putative Tn3 structural motif sequences encoded in the 48 archaeal genomes within the NCBI database. The search was further restricted to the genomes of hyperthermophilic organisms, which we define here as organisms which grow optimally at temperatures of 70° C. or higher. Tn3 was used as a query sequence, and this led to the identification of a Tn3 structural motif within a hypothetical protein from the organism *Archaeoglobus fulgidus*. This Tn3 structural motif was in turn used as the query sequence to identify further Tn3 structural motifs, and those in turn were used as query sequences. A total of 14 potential Tn3-coding sequences were identified within hypothetical proteins from 5 hyperthermophilic organisms. The sequences obtained are represented in Section 6 herein.

Hyperthermophile Tn3 Expression and Purification

Five of the predicted hyperthermophile-derived Tn3 proteins were selected for expression in *E. coli*. Synthetic cDNAs encoding each of these proteins, and optimized for codon usage in *E. coli*, were supplied by GenScript Corporation as per the sequences shown. Each cDNA contained flanking Nco I and Kpn I restriction sites, and following digestion with these enzymes, the inserts were cloned into a modified pET22b vector (Novagen) containing corresponding Nco I/Kpn I sites. Recombinant expression of the encoded C-terminal hexahistidine-tagged proteins and purification from *E. coli* lysates was performed according to the procedure previously described for human-derived Tn3 structural motifs. The Tn3 structural motif from Staphylothermus marinus, and both Tn3 structural motifs from *Sulfolobus tokodaii* expressed well, while Tn3 structural motifs from *Sulfolobus solfataricus* and *Archeoglobus fulgidus* expressed at a low level (FIG. 11A).

Characterization

The stability of each Tn3 structural motif, with the exception of the Tn3 from *Sulfolobus solfataricus*, was analyzed by DSC, fluorescence, and thermolysin-treatment as previously described (See Example 1).

The thermograms for Tn3 structural motifs at from *S. tokodaii* at pH 7.0 did not exhibit a defined peak corresponding to thermal unfolding. Rather, the data showed that *S. tokodaii*

Figure 11B:
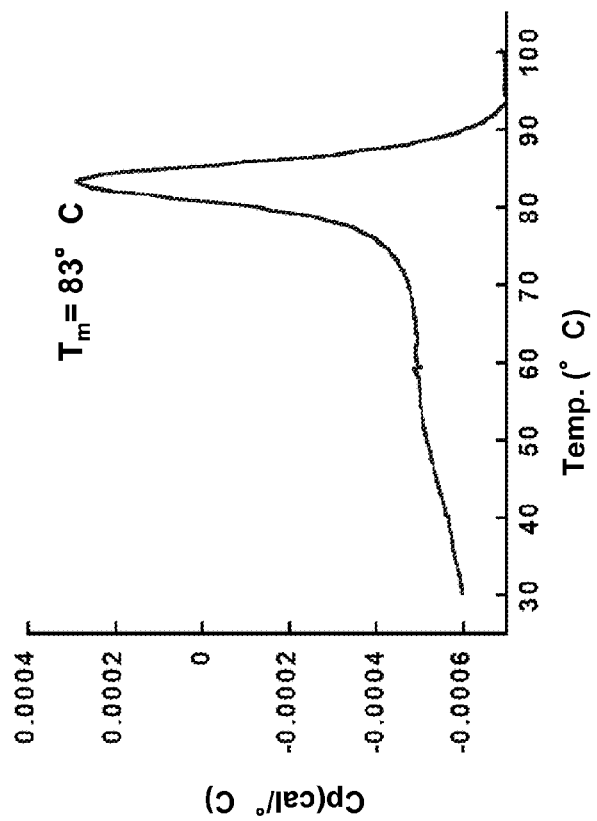
FIG. 11B. A scaffold from *Staphylothermus marinus* exhibits a high level of thermal stability. The graph depicts the thermal stability of a scaffold from *Staphylothermus marinus*. The putative scaffold was recombinantly expressed, purified, and subjected to the thermal stability test. As presented in the graph, the scaffold from *Staphylothermus marinus* exhibits a high melting temperature (around 83° C. at pH 7.0).
Figure 11C:
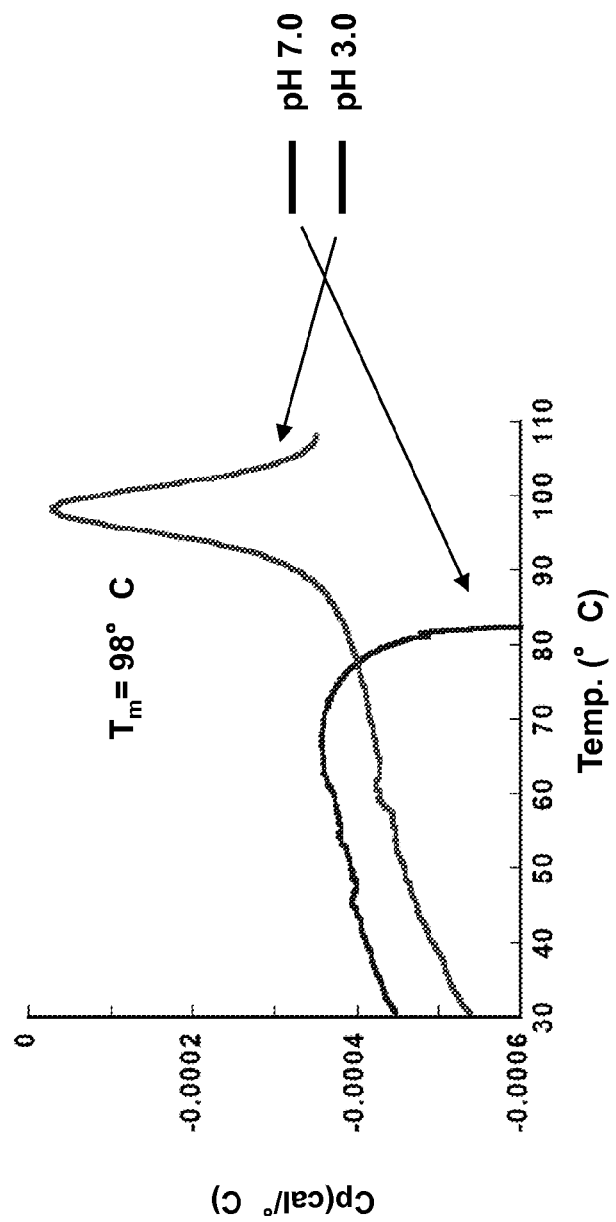
FIG. 11C. A scaffold from *Sulfolobus tokodaii* exhibits a high level of stability. The panel depicts the thermal stability of a scaffold from *Sulfolobus tokodaii*. The putative scaffold was recombinantly expressed, purified, and subjected to the thermal stability test in a differential scanning calorimeter. As presented in the graph, the scaffold from *Sulfolobus tokodaii* exhibits a high melting temperature (around 98° C.) at pH 3.0. The scaffold also exhibits a high level of stability at pH 7.0, however, it aggregates and falls out of solution at temperatures greater than 75° C.

1Tn3 precipitated at temperatures above 70° C., while *S. tokodaii* 1Tn3 precipitated above 50° C. (FIG. 11C). The thermogram for the Tn3 structural motif from *A. fulgidis* showed a characteristic peak with Tm for unfolding of 77° C., as with the Tn3 structural motif from S. marinus which had a Tm of 83° C. (FIG. 11B). Thermal unfolding was not reversible for either of these two proteins, which precipitated at temperatures above Tm.

Figure 11D:
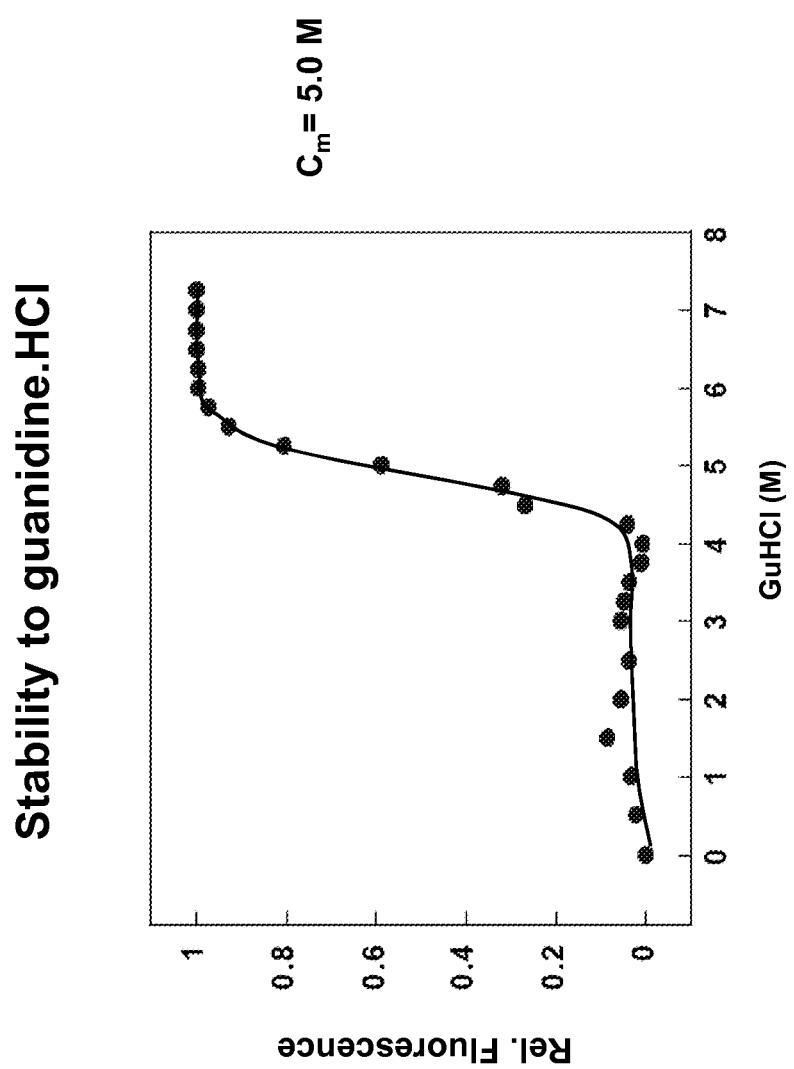
FIG. 11D. A scaffold from *Staphylothermus marinus* exhibits a high level of stability. The graph depicts the results from a guanidine hydrochloride denaturation assay demonstrating the high protein stability of a scaffold from *Staphylothermus marinus*. As presented in the graph, a high concentration of guanidine hydrochloride are required to unfold the scaffold (50% of the molecules are unfolded at a guanidine concentration of 5.0 M), which exemplified high stability.

Unfolding of the Tn3 structural motifs at pH 7.0 by guanidine hydrochloride (GuHCl) was analyzed by fluorescence. All Tn3 structural motifs required high concentrations of GuHCl to effect unfolding, with the midpoints of unfolding ranging from 4.5M to 6M GuHCl, as exemplified for the Tn3 from S. marinus (FIG. 11D).

Figure 11E:
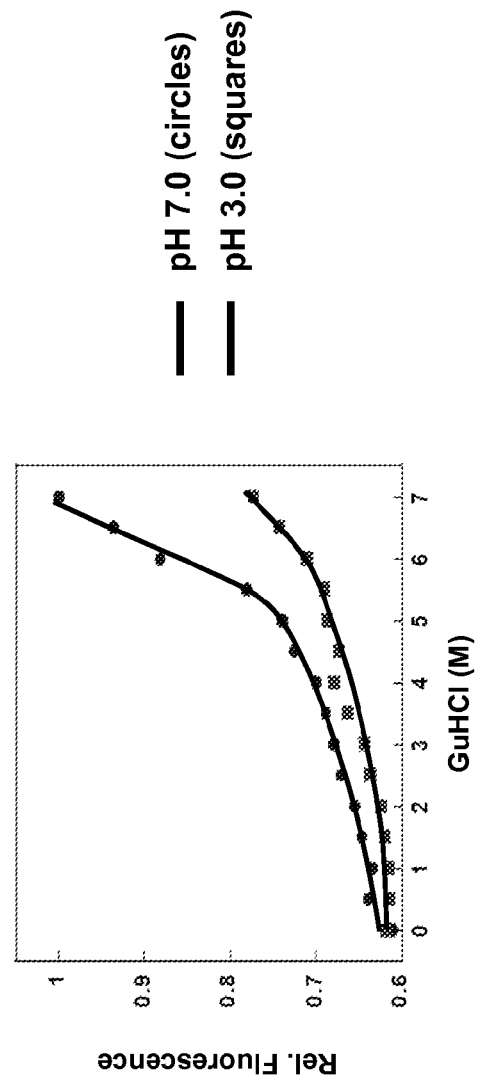
FIG. 11E. A scaffold from *Sulfolobus tokodaii* exhibits a high level of stability. The panel depicts the results from a guanidine hydrochloride denaturation assay demonstrating the high protein stability of a scaffold from *Sulfolobus tokodaii*. Protein unfolding is correlated with an increase in relative fluorescence of the molecule. As presented in the graph, a high concentration of guanidine-HCl is required to unfold the scaffold at either pH 7.0 (circles) or at pH 3.0 (squares), which exemplified high stability.
Figure 11F:
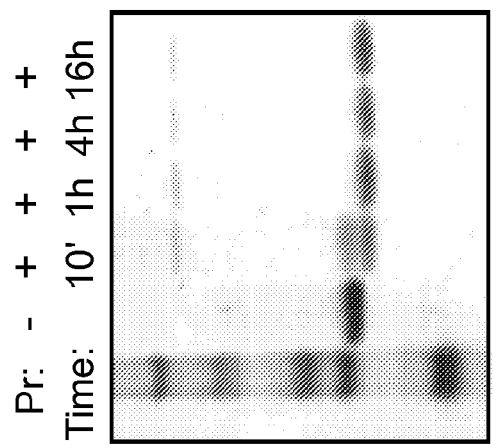
FIG. 11F. A scaffold from *Staphylothermus marinus* exhibits a high level of protease resistance. The graph depicts the results from a protease sensitivity assay measuring the stability of a scaffold from *Staphylothermus marinus*. In this experiment, the relative protease resistance correlates with the protein stability. For the scaffold, incubation for ten minutes with thermolysin results in a small level of degradation which remains stable over time. The *Staphylothermus marinus* scaffold exhibited thermolysin resistance over the entire 16 hour time course.
Figure 11G:
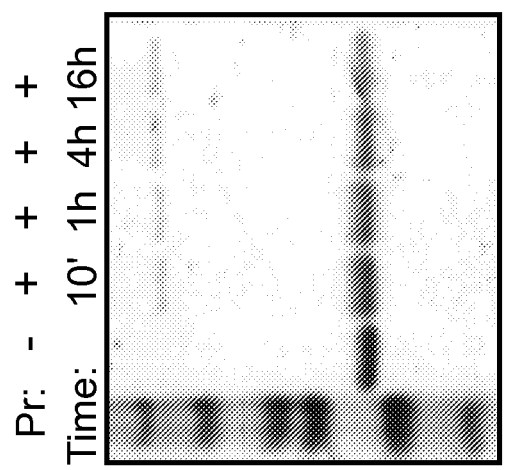
FIG. 11G. A scaffold from *Sulfolobus tokodaii* exhibits a high level of protease resistance. The panel depicts the results from a protease sensitivity assay measuring the stability of a scaffold from *Sulfolobus tokodaii*. In this experiment, the relative protease resistance correlates with the protein stability. The *Sulfolobus tokodaii* scaffold exhibited thermolysin resistance over the entire 16 hour time course.

Stability to proteolysis by thermolysin was analysed using the same conditions previously described (See Example 1), where samples of 45 µM Tn3 were incubated with thermolysin at 0.45 µM. All Tn3 structural motifs were resistant to proteolysis, although rapid cleavage of small 1-2 kDa fragments was observed for Tn3 proteins from *A. fulgidis*, S. marinus and *S. tokodaii* 2Tn3 which we assume are N- and/or C-terminal fragments that do not form part of the core Tn3 structural motif. A significant proportion of all 4 core Tn3 structural motifs remained undigested after 16 hr thermolysin treatment, as exemplified for the Tn3 from S. marinus and *S. tokodaii* (2Tn3) (FIG. 11F+G).

The stability of the Tn3 structural motifs from *S. tokodaii* was also assessed at pH 3.0 in 20 mM sodium citrate buffer, given this organism is acidophilic in addition to being hyperthermophilic. Both *S. tokodaii* 1 Tn3 and 2Tn3 were more stable to GuHCl-induced unfolding at pH 3.0 compared to pH 7.0, with 1Tn3 being more stable than 2Tn3. Thermal unfolding of *S. tokodaii* 1Tn3 at pH 3.0 in 20 mM sodium citrate was also assessed by DSC.

In contrast to thermal unfolding at pH 7.0, the thermogram at pH 3.0 showed a characteristic peak indicating a Tm of 98° C., moreover, unfolding at this pH was partially reversible. A comparison of thermal and GuHCl-mediated unfolding for *S. tokodaii* 1Tn3 is shown in (FIGS. 11C and 11E.)

Exploiting Stability for Purification of Tn3 Structural Motifs

Figure 11H:
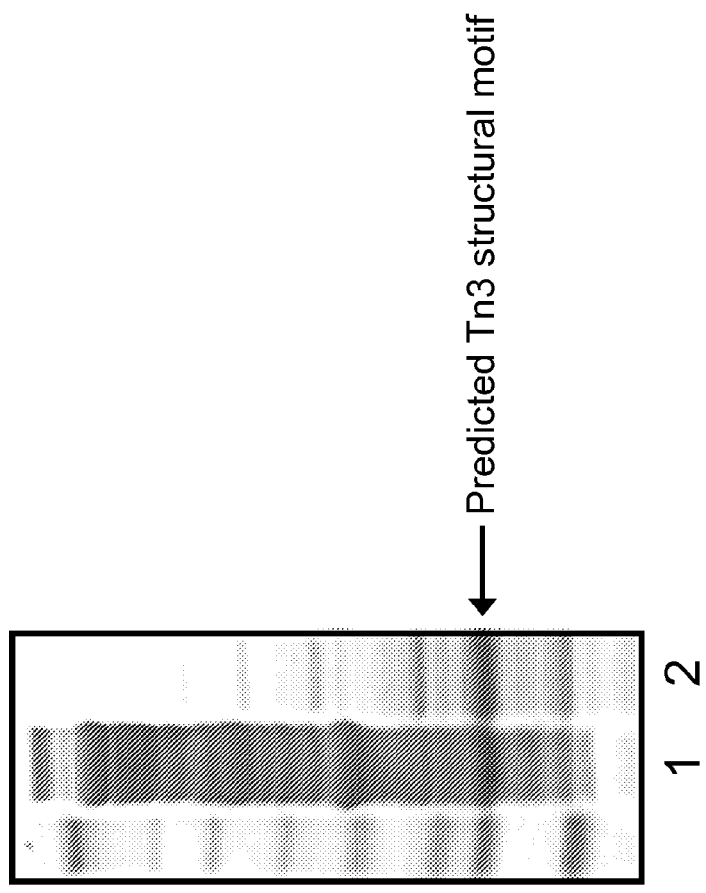
FIG. 11H. A scaffold from *Staphylothermus marinus* is purified from a host cell. The panel depicts one step in the purification of the *Staphylothermus marinus* scaffold. Due to the high level of stability exhibited by this scaffold, it is possible to heat the crude *E. coli* lysate containing the recombinant scaffold to remove the bulk of the host cell proteins while retaining the scaffold. Lane 1 represents the crude lysate prior to heat treatment. Coomassie staining of a PAGE gel containing the crude lysate demonstrates that the candidate scaffold was present. Heat treatment of the crude lysate at 70° C. for 15 minutes resulted in a loss of much of the host cell proteins while the scaffold remains intact (Lane 2).

The stability of hyperthermophile-derived Tn3 structural motifs to extremes of temperature, pH and proteolysis were exploited to purify these proteins from crude *E. coli* lysates. The Tn3 proteins from S. marinus and *S. tokodaii* (1Tn3) were expressed in *E. coli* and soluble lysates prepared as previously described. Lysate containing S. marinus Tn3 was heated at 70° C. for 15 minutes, precipitated protein was removed by centrifugation, then supernatant was analyzed by SDS-PAGE and compared to lysate which had not been heated (FIG. 11H). As seen on the gel, a majority of *E. coli* contaminants were removed by the heat treatment resulting in significant purification of the Tn3 protein. Similarly, treatment of soluble *E. coli* lysate with thermolysin at 55° C. for 45 minutes also resulted in significant removal of *E. coli*-derived proteins and concomitant purification of the S. marinus Tn3 (FIG. 11I).

Figure 11J:
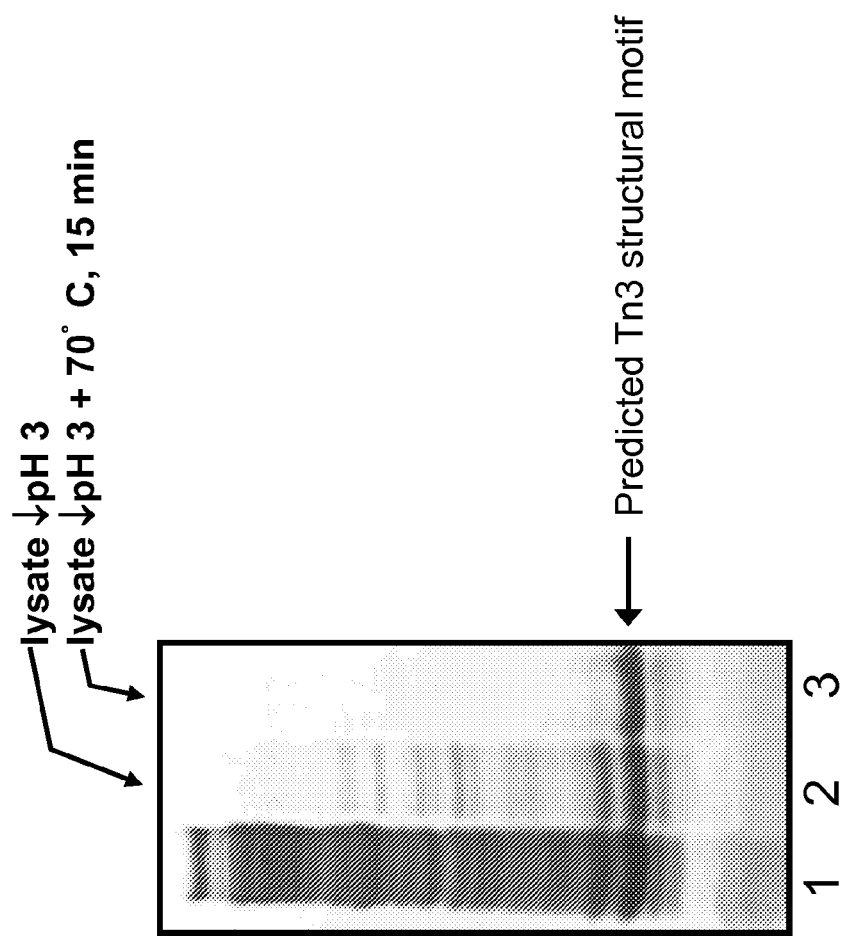
FIG. 11J. A scaffold from *Sulfolobus tokodaii* is purified from a host cell. The panel depicts the purification of the *Sulfolobus tokodaii* scaffold. Due to the high level of stability exhibited by this scaffold, it is possible to incubate the crude lysate containing the recombinant scaffold at pH 3.0 and raise the temperature to 70° C. for 15 min to remove the majority of the host cell proteins while retaining the soluble scaffold. Lane 1 represents the crude *E. coli* lysate prior to acidification or heat treatment. Lane 2 represents the soluble protein remaining after lowering the pH of the crude lysate to 3.0. Lane 3 represents the soluble protein after lowering the pH to 3.0 and incubation at 70° C. for 15 min. The scaffold was resistant and remained in solution through these treatments.

The pH and high temperature stability of *S. tokodaii* 1Tn3 protein were utilized to remove *E. coli* proteins from crude lysate. Dilution of lysate, which was buffered at pH 7, with 4 volumes of 200 mM sodium citrate pH 3.0 resulted in significant precipitation of *E. coli*-derived proteins. After removal of precipitate by centrifugation, the supernatant was then heated at 70° C. for 15 minutes, and newly precipitated protein was again removed by centrifugation. SDS-PAGE analysis of untreated, pH 3-treated, and pH 3/heat-treated samples shows the dramatic removal of background *E. coli* proteins by these 2 steps (FIG. 11J).

Example 6

Loop Swapping Analysis of SynBP01

Summary

Figure 12:
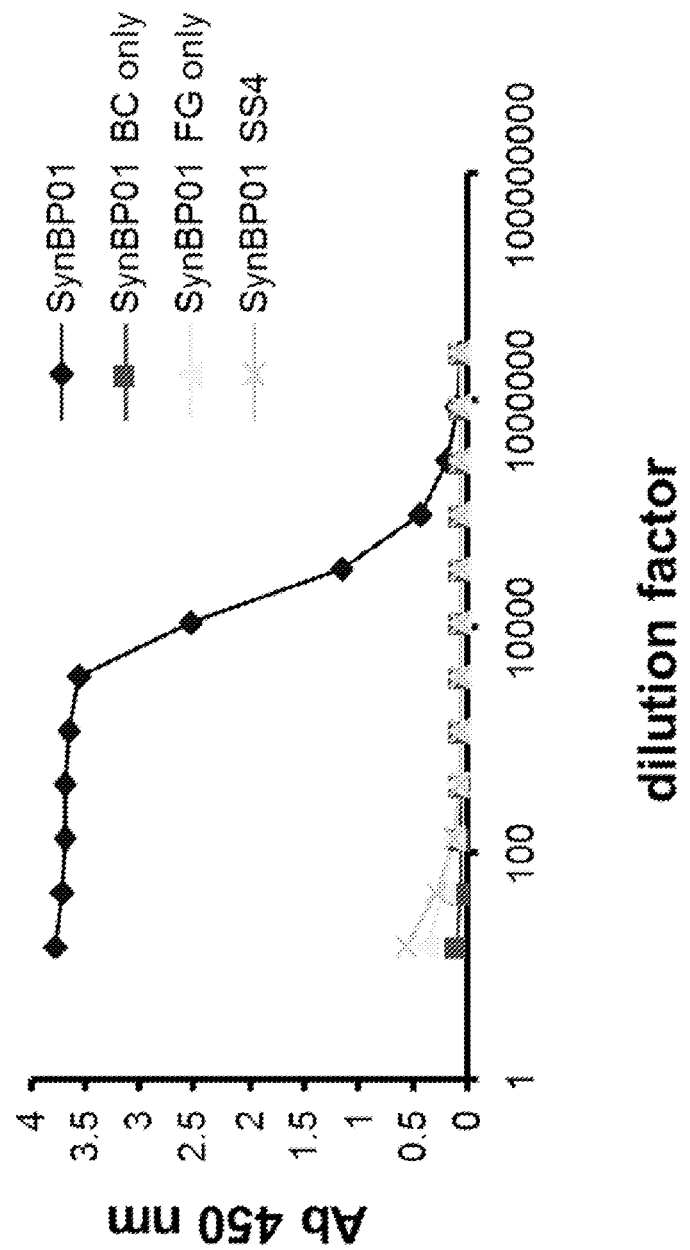
FIG. 12. Two loops are required for binding of SynBP01 to SYNAGIS®. This panel depicts the binding of SynBP01 and variants thereof to plate bound SYNAGIS®. In this experiment, the BC and FG loops of SynBP01 were transferred to a wild-type scaffold to create single loop variants of SynBP01.

Three different variants of SynBP01 were constructed to test if one loop or both the BC and FG loops were contributing to the binding interface of the Tn3 (FIG. 12). In addition, the Tn3$^{SS4}$ mutation was added to test its affect on binding to SYNAGIS®. These variants differed in amino acid sequence from SynBP01 as follows:

"SynBP01-BC only"—FG loop sequence replaced with RRGDMSSNPA (SEQ ID NO:206)
"SynBP01-FG only"—BC loop sequence replaced with FKPLAEIDG (SEQ ID NO:202)
"SynBP-1 SS4"—substitution of Ile and Ser, shown by line 4 in FIG. 10D, with Cys.

Experimental Procedure

Phage display vector encoding gene 3 fragment fusions of SynBP01 and its 3 variants were transformed into *E. coli*, and these bacteria were then used to prepare phage displaying each of these Tn3 proteins as described in Example 3. Plates were coated with SYNAGIS® at 10 µg/ml in PBS pH 7.2 overnight at 4° C. Plates were blocked with PBS containing 0.1% v/v Tween-20 plus 4% w/v skim milk powder (PBST 4% milk). Diluted phage stocks were added to column 1 and a 3-fold serial dilution was performed across the plate using PBST 1% milk as diluent. Plates were incubated at room temperature for 2 hours with gentle shaking. After washing, bound phage were labeled with anti-M13 HRP conjugated antibody (GE Healthcare, Piscataway, N.J.) and detected colorimetrically by addition of TMB substrate (KPL Laboratories, Gaithersburg, Md.). The absorbance was read at 450 nm after quenching the color development by addition of 2.5M phosphoric acid.

Results: The data presented in FIG. 12 demonstrates that both the BC and FG loops are required for binding of the Tn3 scaffold to SYNAGIS®. SynBP01 variants containing a substitution of either loop with the wild type Tn3 sequence did not exhibit binding to plate bound SYNAGIS®. These results demonstrate that at least two loops of the Tn3 scaffold act cooperatively to present a functional binding surface.

In addition, the introduction of the SS4 disulfide bond into the SynBP01 scaffold ablates binding to SYNAGIS® (FIG. 12). A loss of activity for the SS4-containing variant of SynBP01 is probably due to a subtle conformational effect given this disulfide is not expected to result in a large change in the structure of a Tn3 scaffold protein. This further suggests that binding of SYNAGIS® is exquisitely dependent on the three dimensional structure of SynBP01.

Example 7

Construction of a 2 Loop Library on the $Tn3^{SS4}$ Scaffold

A new library was constructed based upon the $Tn3^{SS4}$ scaffold shown in FIG. 10D. The BC loop diversity was introduced using PCR and the FG loop diversity was introduced using Kunkel mutagenesis (Table 5). A library of approximately $1.12\times10^{10}$ members was constructed.

TABLE 5

Degenerate oligonucleotides for Tn3^SS4 library construction

| Oligo | Loop | Sequence | Seq ID |
|---|---|---|---|
| BC9 | BC | ACCGCGCTGATTACCTGGTCTNNKSCGNNKG STNNKNNKNNKGGCTGTGAACTGACCTATGGC | 217 |
| BC11 | BC | ACCGCGCTGATTACCTGGTCTCCGBSTNNKN NKNNKNNKNNKNNKACCGGCTGTGAACTGACC TATGGC | 218 |
| BC12 | BC | ACCGCGCTGATTACCTGGGCGVMACCGNNKNN KNNKRRCRGCNNKATTNNKGGTTGTGAACT GACCTATGGC | 219 |
| FG9 | FG | TATGAAGTGAGCCTGATTTGCNNKAMSNNKN NKGGTNNKNNKNNKAGCAAAGAAACCTTTAC CACC | 220 |
| FG10 | FG | TATGAAGTGAGCCTGATTTGCNNKAMSNNKN NKNNKNNKRGCAACCCGGCGAAAGAAACCTT TACCACC | 221 |
| FG11 | FG | TATGAAGTGAGCCTGATTTGCNNKAMSNNKN NKGGTNNKNNKAGCAACCCGGCGAAAGAAACC TTTACCACC | 222 |

Experimental Procedure

The BC loop diversity was made by using the BC9, 11, or 12 primers in Table 5. These primers annealed on their 3' ends to the Tn3 DNA and the degeneracy formed a library upon completion of the PCR. These PCR products were amplified with flanking primers to make a complete Tn3 gene which was then digested with NcoI and KpnI and ligated into the phage display vector. The DNA was transformed into E. coli by electroporation. The final diversity of the BC library was estimated to be about $3.4 \times 10^9$ members.

After electroporation, the BC library was incubated for 1 hour at 37° C. with shaking. M13KO7 helper phage was added and after one hour the cells were diluted to a larger volume and grown at 37° C. with shaking overnight. The next day phage were removed and concentrated from the supernatant by precipitation with PEG 8000.

BC library phage was used to infect CJ236 E. coli. After a one hour infection, cells were diluted into 2xYT with 100 μg/mL carbenicillum and grown overnight with shaking at 37° C. The next day phage were removed and concentrated from the supernatant by precipitation with PEG 8000. Single stranded DNA was recovered by using a Qiagen (Valencia, Calif.) QIAprep spin M13 kit. This DNA served as the template for Kunkel mutagenesis using the FG primers in Table 5.

Example 8

Panning the Two Loop Tn3^SS4 Library for SYNAGIS® Specific Scaffolds

SYNAGIS® was biotinylated with 15 molar equivalents of EZ Link sulfo-NHS-SS-biotin (Pierce, Rockford, Ill.). After incubation for 1 hour at room temperature, the sample was dialyzed in PBS overnight to remove unconjugated biotin. The next day M280 streptavidin beads (Dynal, Carlsbad, Calif.) and the two loop library were blocked in PBS containing 10 mg/ml BSA for 1 hour. 10 ug of biotinylated SYNAGIS® were added to the blocked phage and incubated at room temperature on an end-over-end rotating mixer for two hours. SYNAGIS® was captured with the blocked streptavidin beads for 30 min on the rotating mixer at room temperature. After three washes with PBST to remove unbound phage, the bound phage were eluted with 75 mM DTT. XL-1 Blue E. coli were infected with eluted phage, co-infected with M13KO7 helper phage and repropagated overnight as described in Example 3. The next day, phage were harvested from overnight culture media as described in Example 3.

The second round of panning was the same as the first with casein used at 10 mg/ml as the blocking reagent. The beads used for the second round were Spherotech (Lake Forest, Ill.) avidin-coated magnetic particles. For the third round, casein was used as the blocking reagent and M280 streptavidin beads were used to capture SYNAGIS®. For the fourth round BSA was used as the blocking reagent and Spherotech avidin magnetic particles were used to capture SYNAGIS®. After 4 rounds of panning, E. coli were infected with eluted phage and plated. Individual colonies were cultured in 96 well format, infected with M13KO7, and culture supernatant was used in a phage ELISA to identify SYNAGIS® binding clones. Three new SS4 stabilized clones were identified, the sequences of which are shown in Table 6.

TABLE 6

BC and FG loop sequences of SYNAGIS® specific binding scaffolds

| Clone | BC loop | Seq ID NO: | FG loop | Seq ID NO: |
|---|---|---|---|---|
| SYNAGIS® specific binding scaffolds | | | | |
| 4 | SPGERIWMFTG | 105 | PNYERISNPA | 106 |
| 5 | SPSGRVILWTG | 107 | DNLYGRISNPA | 108 |
| 6 | ATPGCRNGKIVG | 109 | TTSVGATSNPA | 110 |

Example 9

Panning the Two Loop Tn3^SS4 Library for TRAIL-R2 Specific Scaffolds

M280 streptavidin beads were washed with PBST and biotinylated goat anti-human IgG Fc fragment specific antibody (Jackson ImmunoResearch, West Grove, Pa.) was added. After overnight incubation at 4° C., a control IgG1 antibody or TRAIL-R2/Fc fusion protein (R & D Systems, Minneapolis, Minn.) was added, and again incubated overnight at 4° C. The beads were washed with PBST and blocked in PBST 2% milk prior to use.

The two loop Tn3^SS4 phage library was incubated overnight at 4° C. with the control IgG1 antibody-coated beads to deplete the library of binders to the beads or human IgG1 Fc. The depleted library was then added to TRAIL-R2 coated beads and incubated for 2 hours at room temperature on a rocking platform. Beads were washed with PBST and added to XL-1 Blue E. coli to propagate bound phage as described in Example 8. This panning procedure was repeated for 4 more rounds, except that incubation with control antibody beads for background depletion was performed for 1 hour rather than overnight. Individual clones were analyzed by phage ELISA after the fourth and fifth rounds of panning to identify TRAIL-R2 binding variants.

Following the sequencing of positive clones from the TRAIL-R2 phage ELISA, nine unique binding clones were identified (Table 7). A lower case q indicates that a TAG stop codon was at that position. A suppressor strain such as XL-1 Blue allows for expression of genes with a TAG stop codon by inserting a glutamine at this position.

TABLE 7

BC and FG loop sequences of TRAIL-R2
specific binding scaffolds

| Clone name | BC loop | SEQ ID NO. | FG loop | SEQ ID NO. |
|---|---|---|---|---|
| 2F4 | SPCIMVCLRTG | 126 | RRGDMSGAPA | 127 |
| 5B10 | SPCLFVCLRTG | 128 | RRGDMSGAPA | 129 |
| 10D9 | SPPLFCCqKTG | 130 | FKLTGFLYS | 131 |
| 6F11 | SPSVARMLETG | 132 | ITLCGRGVS | 133 |
| 8B3 | SPPEYAFYYTG | 134 | VKNCGLFSNPA | 135 |
| 5E5 | SLAPGYRLG | 136 | VKLCMRGNPA | 137 |
| 2H6 | ATPSVFDSHIEG | 138 | WKHHGDAWS | 139 |
| 7G11 | AKPSIVNGFISG | 140 | DKCFGAMKS | 141 |
| 6C7 | AKPMSCSGYIqG | 142 | AKLTGWLCS | 143 |

Example 10

Binding Affinity Determination for a TRAIL-R2 Specific Scaffold

Goat anti-human-Fc IgG was immobilized at a density of ~7700 RUs onto a flow cell of a CM5 Biacore sensor chip surfaces using a standard amino coupling protocol (BIAcore, Inc.). Separately, a blank surface was also prepared on the same chip using the identical coupling protocol, minus the protein. This blank surface was used as a reference cell throughout the experiment, and served to correct for both non-specific binding and certain housekeeping artifacts.

TRAIL-R2/Fc protein was prepared at 100 nM in instrument buffer in (HBS-EP buffer, BIAcore, Inc., consisting of the following: 10 mM HEPES buffer, pH7.4, 150 mM NaCl, 3 mM EDTA, and 0.005% P20.), then injected over both the Fc-capture and control surfaces at a flow rate of 75 uL/min. Capture levels of the ligand approximated 800 RUs.

After baseline stabilization, solutions of the Tn3 clone 5E5 (Table 7) were injected over both the captured ligand and control surfaces. Between injections, the Fc-capture surface was regenerated with two 1 min. injections of 10 mM Gly, pH2.

Several buffer and control protein injections were also interspersed throughout the injection series. Later, these buffer injections were used, along with the reference cell data, to correct the raw data sets for injection artifacts and/or non-specific 'binding' through a technique commonly referred to as "double-referencing." (Myszka, D. G. (1999) *J. Mol. Recognit.* 12, pp. 279-284). Sensorgram overlays of the fully corrected data were generated using the BIAevaluation 4.1 software (BIAcore, Inc, Uppsala, Sweden). The affinity of 5E5 for binding to TRAIL-R2 was calculated by measuring the $k_{on}$ and $k_{off}$ values in the BIAevaluation software for the sensorgram shown in FIG. 13. This analysis resulted in anestimated $K_d$ of 700 nM for 5E5 binding to TRAIL-R2.

Example 11

Competition for Binding to TRAIL-R2 with Clones 5E5 and 7G11

Soluble 5E5 and 7G11 (TRAIL-R2 specific clones isolated in Example 9) were expressed and used in a competition phage ELISA assay to assess whether they specifically bind TRAIL-R2. TRAIL-R2 coated plates were incubated with phage displaying TRAIL-2 specific Tn3' sin the presence or absence of soluble Tn3 clones 7G11 or 5E5. As shown in FIG. 14, soluble 5E5 competes with phage displayed 5E5 and all other phage displayed clones except 2H6 and 7G11. Soluble 7G11 only competes with phage displayed 7G11 and 2H6. This experiment indicates that all clones are specific for TRAIL-R2 and that there are two different epitopes on TRAIL-R2 recognized by this panel of Tn3 proteins.

Example 12

Construction of a Three Loop Tn3$^{SS4}$ Library

A phage displayed three loop library based on the Tn3$^{SS4}$ scaffold was made by randomizing the sequences of the BC, DE, and FG loops using the primers shown in Table 8. Briefly, single stranded DNA from the two loop Tn3 BC loop library with Tn3$^{SS4}$ (from Example 7) was used as a template for a PCR with the DE rev primer in Table 8. This PCR generated a product that contained a portion of the Tn3 gene with BC and DE randomization. A second PCR used this BC, DE loop randomized PCR product as template for amplification with the FG primers listed in Table 8. The resulting PCR products were amplified with flanking primers to make a complete Tn3 gene which was then cut NcoI to KpnI and ligated into the phage display vector. The DNA was transformed into *E. coli* by electroporation.

After electroporation, the library was incubated for 1 hour at 37° C. with shaking. M13KO7 helper phage was added and after one hour the cells were diluted to a larger volume and grown at 37° C. with shaking overnight. The next day phage were purified from the culture supernatant by precipitation with a saline PEG 8000 solution. The library size was estimated to contain about $1.5 \times 10^9$ members based on the number of *E. coli* transformants.

TABLE 8

Degenerate oligonucleotides for three loop
Tn3$^{SS4}$ library construction

| Sequence Name | Sequence | SEQ ID: |
|---|---|---|
| DE rev | CCGGTTTCAGGTTACCAATGCTATAMNNMNNMN NMNNMNNMNNCAGATCTATGGTGGTGCGATCGCC | 223 |
| FG9 rev | CCGCCACCGGTGGTAAAGGTTTCTTTGCTMNNM NNMNNACCMNNMNNSKTMNNGCAAATCAGGCTC ACTTCATATTCGG | 224 |
| FG10 rev | CCGCCACCGGTGGTAAAGGTTTCTTTCGCCGGG TTGCYMNNMNNMNNMNNSKTMNNGCAAATCAG GCTCACTTCATATTCGG | 225 |
| FG11 rev | CCGCCACCGGTGGTAAAGGTTTCTTTCGCCGGGT TGCTMNNAMNNACCMNNMNNSKTMNNGCAATCA GGCTCACTTCATATTCGG | 226 |

Example 13

Panning the Three Loop Tn3$^{SS4}$ Library for TRAIL-R2 Specific Scaffolds

The three loop Tn3$^{SS4}$ library constructed in Example 12 was panned against TRAIL-R2, and specific clones identified in by phage ELISA as described in Example 9 In total, 19 new Tn3s were identified that bound to TRAIL-R2 (Table 9).

TABLE 9

BC, DE, and FG loop sequences of
TRAIL-R2 specific binding scaffolds

| Clone | BC loop | Seq Id. | DE loop | Seq Id. | FG loop | Seq Id. |
|---|---|---|---|---|---|---|
| 1E03 | AAPFFGSSY-ISG | 144 | HYYVTR | 145 | VNLSGHMPS | 146 |
| 2B04 | APPMLTDSE-ING | 147 | TSSYWS | 148 | STLRRNAIS | 149 |
| 1C12 | AKPEKWDG-SIYG | 150 | NSRHTA | 151 | FTPYGAKSNPA | 152 |
| 1A03 | APPPFSN-SCIIG | 153 | RPGRAS | 154 | STGTGLPSNPA | 155 |
| 1C10 | SPCCPYDRYTG | 156 | QSSRSH | 157 | ITTFGHVSNPA | 158 |
| 1B12 | AKPRqGGSNISG | 159 | YHKGLH | 160 | PKMTGYTYS | 161 |
| 2G03 | SPGPLLRHTTG | 162 | RPIPRA | 163 | RNRPQqSNPA | 164 |
| 2D3 | SPGGFqKITTG | 165 | VNRRNH | 166 | LTYKARAIS | 167 |
| 1C06 | SPRMYTWIqTG | 168 | THLSGS | 169 | LKLTRTHIS | 170 |
| 2F08 | SHAGGIRIG | 171 | HVVVqVY | 172 | MTPYLLGNPA | 173 |
| 1B04 | SPSHGVESSTG | 174 | HGLqRV | 175 | AKICGHLVS | 176 |
| 3B11 | SPCqLLALITG | 177 | NSRHYH | 178 | YTSTGQRSNPA | 179 |
| 1D8 | SPCqMLSSLTG | 180 | NIERPK | 181 | FTMTGYRSNPA | 182 |
| 2A12 | SPCCqEFTLTG | 183 | HNHHHH | 184 | ITDAGNKSNPA | 185 |
| 1E05 | SPCSPCqLVTG | 186 | SCTRAK | 187 | 1IKLGDTSNPA | 188 |
| 2F02 | SPSRGGTSLTG | 189 | DqVRAT | 190 | HTNSGqPSNPA | 191 |
| 1H05 | SPGMFDqVRTG | 192 | GKYWER | 193 | RNQYGqHqS | 194 |
| 2A11 | SPPFRAGHVTG | 195 | VTARCq | 196 | TTGNGLRSNPA | 197 |
| 1G11 | SWAqANPGG | 198 | WHSITF | 199 | KTKVqSSNPA | 200 |

The amber stop codon in the nucleotide sequences of clones 2D3 and 1 G11 was replaced with a glutamine codon by site-directed mutagenesis. These Tn3 clones, along with 1E3, 1C12, and 2B4 were cloned into a E. coli expression vector (described in Example 1) and transformed into BL21 DE3 cells. After induction with IPTG, the transformed bacteria were grown for 5 hours at 30° C. The cells were pelleted, lysed by sonication, and the soluble fraction was purified on a HiTrap chelating HP column (GE Healthcare, Piscataway, N.J.). Tn3 clones 2B4 and 1C12 were obtained in good yield, however, a poor recovery of the remaining three clones was the result of overexpression leading to accumulation of the proteins into inclusion bodies. In this case, a high yield of Tn3 was subsequently obtained by solubilizing the inclusion bodies in buffered 6M guanidine hydrochloride (GuHCl), then purifying on a HiTrap chelating column under denaturing conditions. All Tn3s were subsequently refolded by dialysis of reduced and denatured samples into native buffer in the presence of a cysteine/cystine redox pair.

Example 14

Determining Epitope Diversity

Figure 15B:
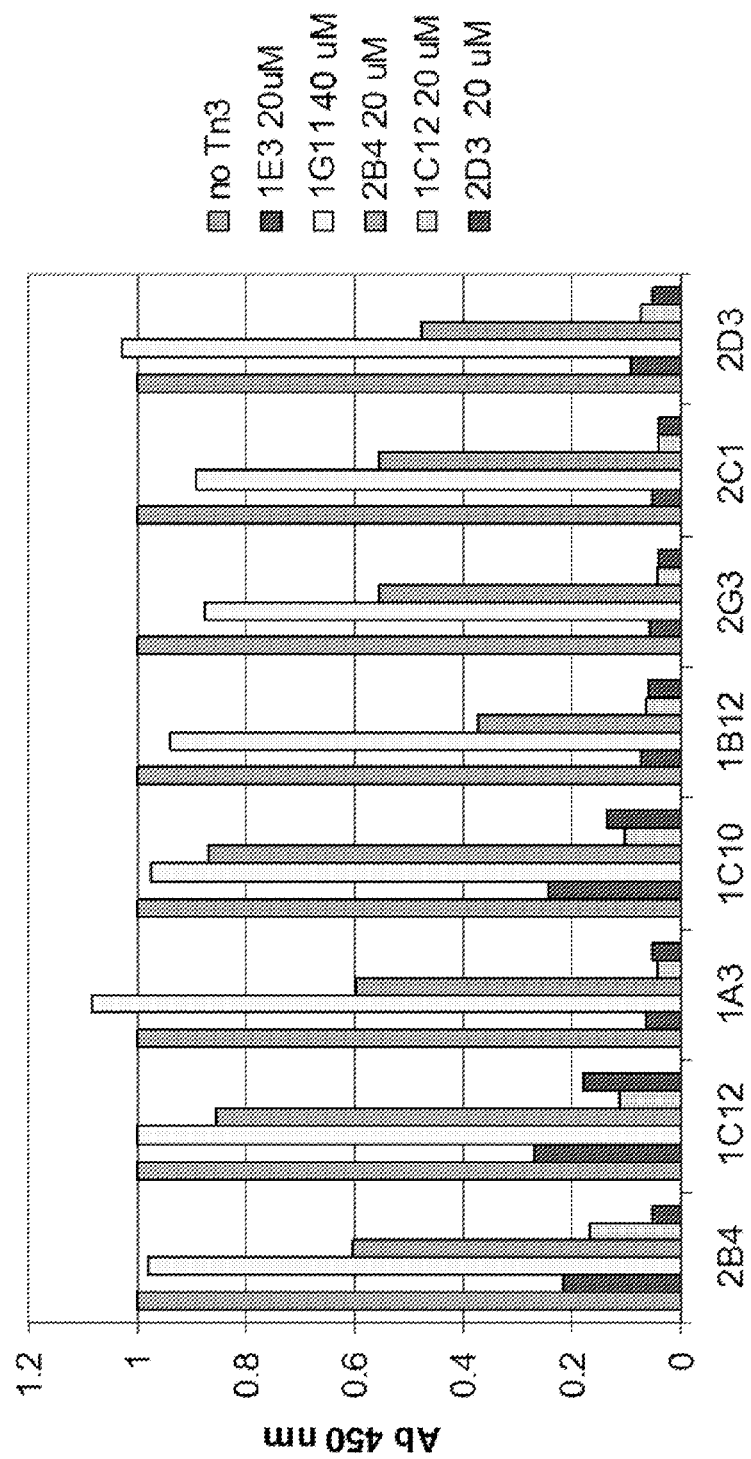
Figure 15C:
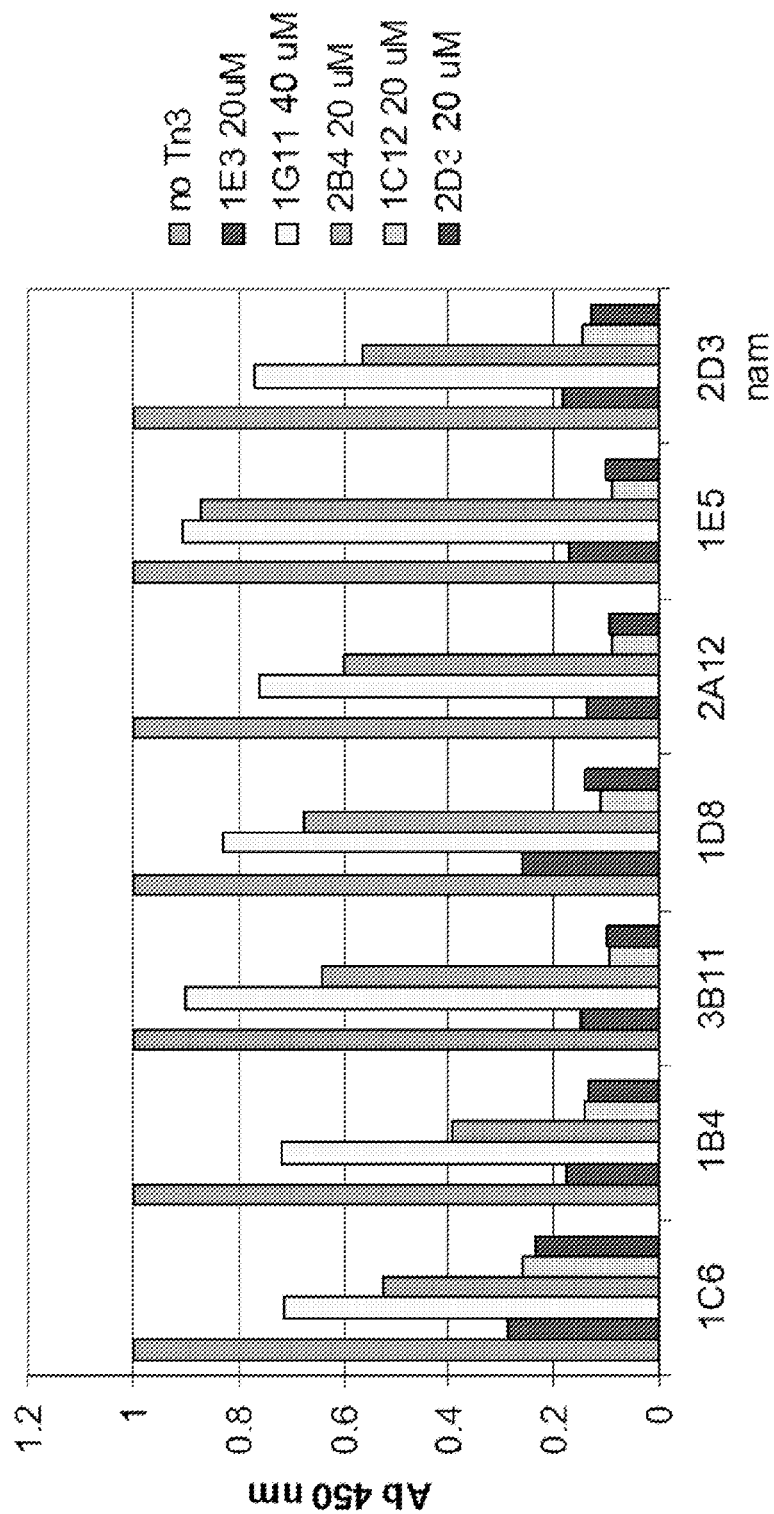

A selection of the phage displayed clones from Table 9 were tested to see if soluble forms of Tn3s 1E3, 1G11, 2B4, 1C12 and 2D3 would compete for binding to TRAIL-R2 in a phage ELISA. The assay was performed in a similar manner to the competition for binding in Example 11, and the results are shown in FIG. 15 A, B, and C. Soluble Tn3 clones 1E3, 1C12, and 2D3 significantly inhibited the binding of most of the phage linked Tn3s to TRAIL R2, with the exception of clones 8B3 and 7G11. Soluble 1G11 did not significantly compete with any of the phage bound clones. Soluble 2B4 showed little to moderate inhibition in most cases. The fact that 1E3, 1C12, and 2D3 competed with the same set of phage linked Tn3s indicates that these three soluble Tn3s and the phage linked Tn3s likely bind to the same epitope on TRAIL-R2.

Example 15

Cell Viability Assays Using Tn3 Monomers Linked to an Anti-His Monoclonal Antibody Colo 205 is a cell line which is highly sensitive to TRAIL-induced killing. TRAIL-R2 binding Tn3s, when multimerized via binding to a complex of mouse anti-His tag antibody and anti-mouse IgG, were tested for their ability to induce killing of Colo205 cells. Colo205 cells in 100 ul of RPMI 1640 medium with 10% FBS were plated into each well of a flat bottom 96-well culture plate and incubated overnight at 37° C. Tn3 proteins 7G11 and 5E5 (Table 7), 1C12, 2D3 and 1E3 (Table 9) and Tn3$^{SS4}$ (Example 4) were incubated with mouse anti-His tag antibody (Penta-His; Qiagen Inc) and rabbit anti mouse IgG in a molar ratio of 2:1:0.5. Serial dilutions of each Tn3 complex was made in RPMI 1640 medium containing 10% FBS to a final concentration of 5 μM, 1.66 μM, 0.55 μM, 0.185 μM and 0 μM based on the Tn3 content. After removal of medium from cells cultured overnight, 100 of the Tn3-antibody complexes was added. Each assay point was performed in triplicate.

After addition of Tn3 complexes, the cells were incubated for 3 days in at 37° C., after which cell viability was measured in a CellTiter-Glo® luminescent cell viability assay (Promega Corp., Madison, Wis.) according to the manufacturers instructions. The percent viability for cells treated with a TRAIL-R2 binding Tn3s was calculated by dividing the luminescent signal obtained in the CellTiter-Glo® assay by the corresponding signal obtained for cells treated with the same concentration of non TRAIL-R2 binding control Tn.

Figure 16:
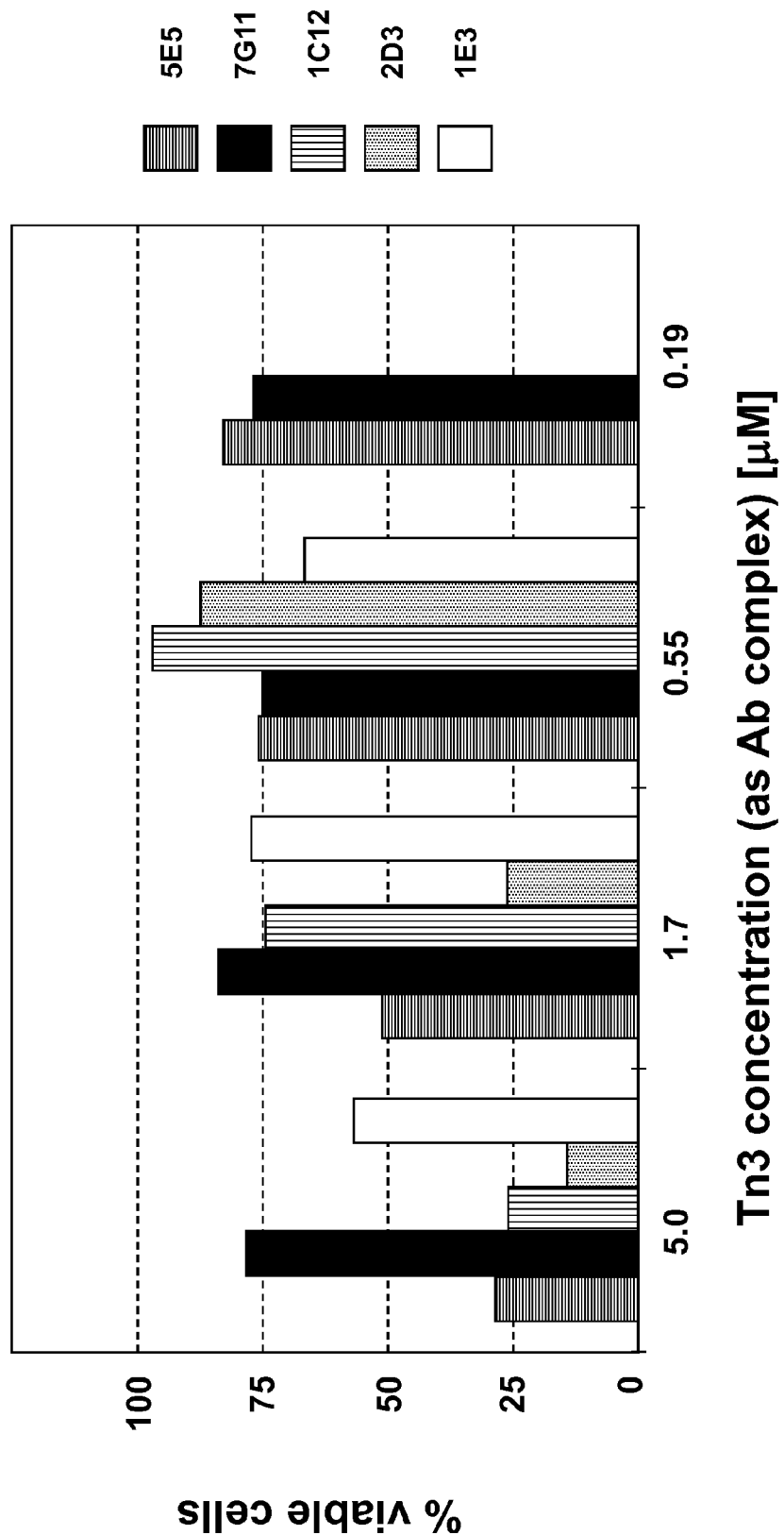

The cell viability assay (FIG. 16) showed that Tn3 clones 5E5, 1C12 and 2D3, when multimerized via antibody complexation, were able to inhibit Colo205 viability in a dose-dependent manner relative to treatment of cells with a non-TRAIL-R2 binding Tn3. Inhibition of cell viability was presumably due to cellular apoptosis triggered by TRAIL-R2 ligation, although pathway-specific assays would be needed to confirm this. Clones 7G11 and 1E3 did not show detectable activity at the concentrations used in the assay. Additional cell assays showed that none of the active Tn3 proteins affected cell viability when assayed without an anti-His tag capture antibody. This demonstrates that activity is dependent on the presentation of multimerized TRAIL-R2 binding moieties. Clone 5E5 also lacked activity if the anti-IgG antibody was not present, however, clones 1C12 and 2D3 were active in the absence of anti-IgG, suggesting that dimeric presentation via anti His-tag antibody capture is sufficient to trigger TRAIL-R2 signaling.

Example 16

Construction of Polyvalent Anti TRAIL R2Tn3 Antibody Fusions

Given the requirement for presentation of oligomeric Tn3 complexes to effect TRAIL-R2-dependent cell killing, Tn3 fusion constructs were designed for the production of bi- and tetravalent Tn3-containing proteins (FIG. 17). A bivalent Tn3 construct was designed by fusion of Tn3 to the Fc region of human IgG1, while a two chain tetravalent Tn3 construct was designed based on co-expression of a Tn3-Cκ fusion with Tn3-IGHG1, i.e Tn3 fused to a human C-kappa region, and to the heavy chain constant region of human IgG1. The latter construct is similar in nature to an antibody, except that the light and heavy chain variable regions were replaced with a Tn3 moiety.

Figure 17A:
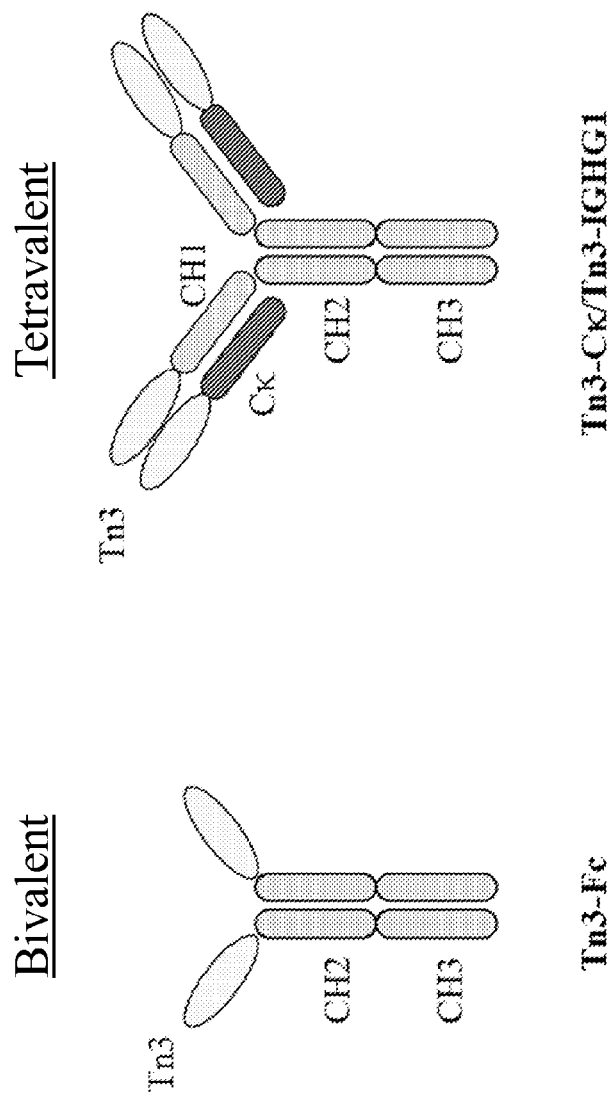
Figure 18:
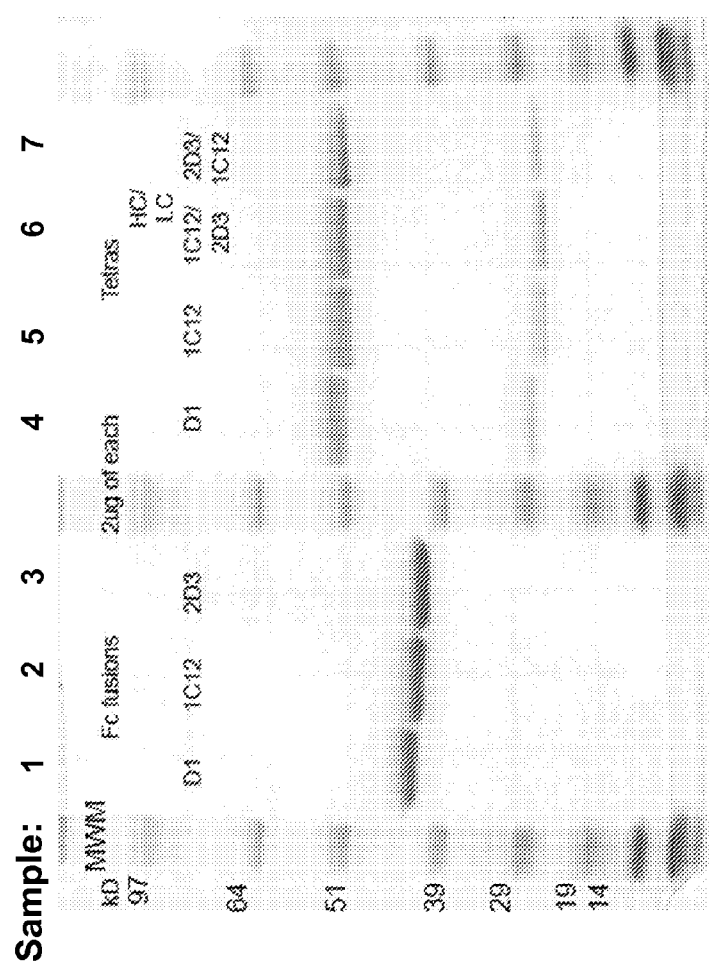

The constructs shown in FIGS. 17A and B, were expressed in 293F cells transiently transfected with the in-house pOE expression vector coding for each of the proteins. After 10 days in culture, media (250 mL) was harvested, and the protein was purified by protein A affinity chromatography. Presented in Table 10 are the expression levels of a selection of multivalent Tn3 constructs. 1C12 and a control SYNAGIS® binding Tn3 named D1 (from Example 8 Seq ID NO: 105 and Seq ID NO 106) expressed well as either the Fc fusion, or two chain Tn3-Cκ/Tn3-IGHG1 fusions. Hybrid tetravalent fusions of 1C12 and 2D3 (1C12 linked to IGHG1, 2D3 linked to Cκ and vice versa) along with the 2D3 Fc fusion yielded lower amounts of material, while the two chain 2D3-Cκ/2D3-IGHG1 fusion did not express SDS-PAGE analysis of the protein A purified proteins is shown in FIG. 18.

TABLE 10

Yield of Different Fc fusion and Tetravalent Antibody Fusion Constructs

| # | Name | Final |
|---|---|---|
| 1 | D1-Fc | 15 mg |
| 2 | 1C12-Fc | 15 mg |
| 3 | 2D3-Fc | 3.5 mg |
| 4 | D1-Cκ/D1-IGHG1 | 13 mg |
| 5 | 1C12-Cκ/1C12-IGHG1 | 10 mg |
| 6 | 2D3-Cκ/1C12-IGHG1 | 4 mg |
| 7 | 1C12-Cκ/2D3-IGHG1 | 4 mg |

Biosensor Assays of 1C12, 1C12 Fc, and 1C12 Tetravalent

Figure 19:
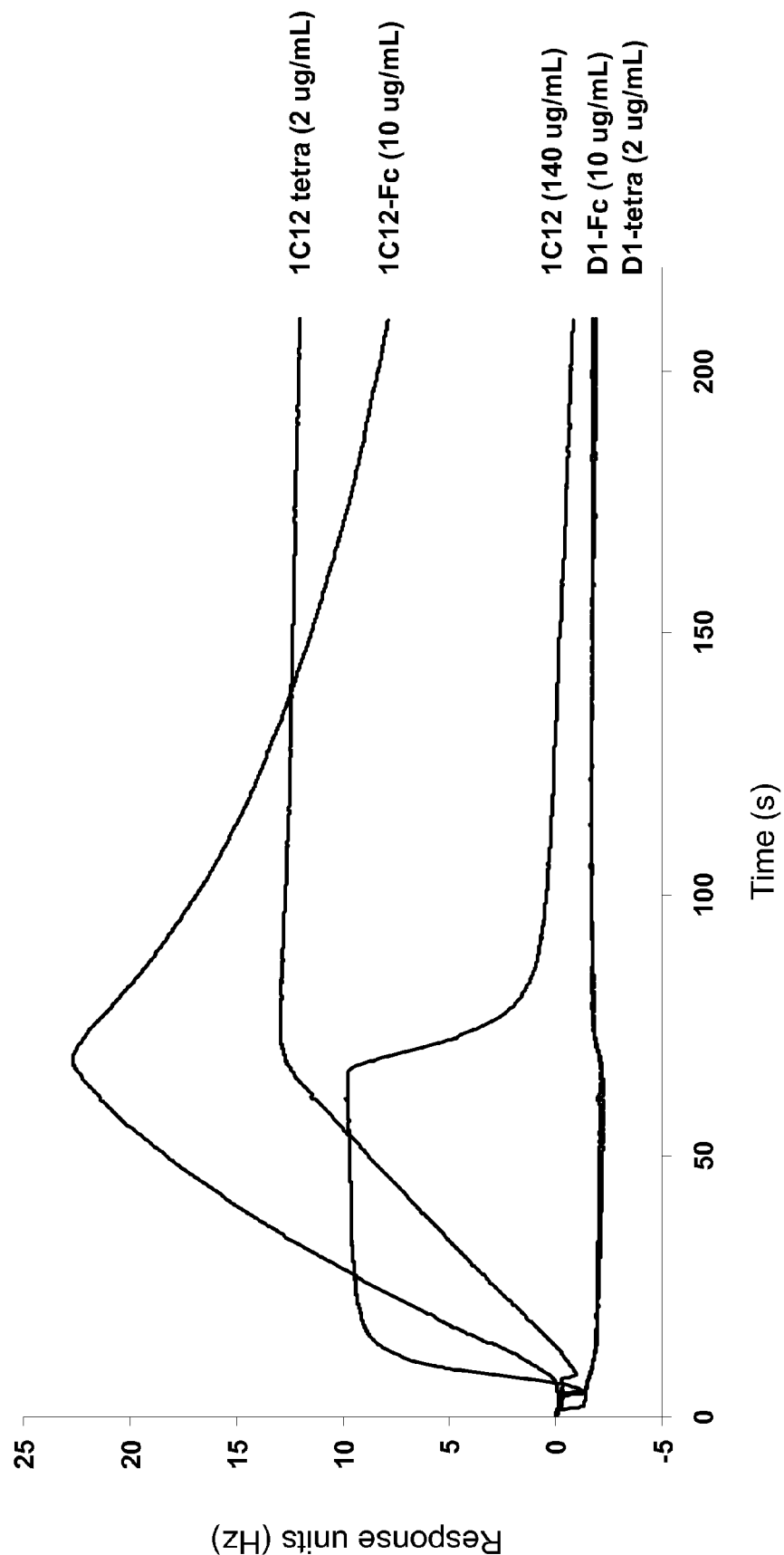

A qualitative comparison of binding by monomeric 1C12, 1C12-Fc and 1C12-Cκ/1C12-IGHG1 proteins was performed by injecting samples of each of these proteins over a TRAIL-R2 chip on an Attana biosensor instrument. As shown in FIG. 19, complexes of TRAIL-R2 with oligomerized forms of 1C12 show a substantial improvement in affinity relative to monomeric 1C12. The specificity of binding was demonstrated by injection of D1-Fc and D1-Cκ/D1-IGHG1 proteins which did not interact with immobilized TRAIL-R2. The dissociation rates for the different 1C12 constructs followed the order 1C12>1C12-Fc>1C12-Cκ/1C12-IGHG1, consistent with the bi- and tetravalent constructs exhibiting avidity in their interaction with TrailR2.

Example 17

Cell Viability Assays Using Polyvalent Anti TRAIL-R2Tn3 Fusion Proteins

Figure 20A:
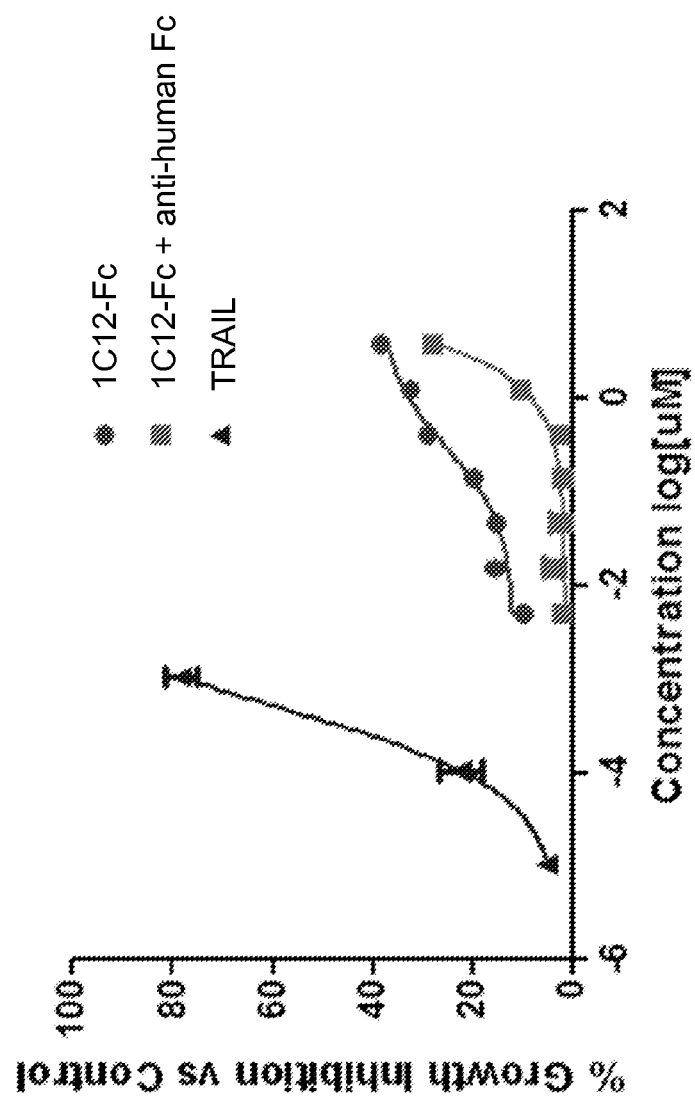
Figure 21B:
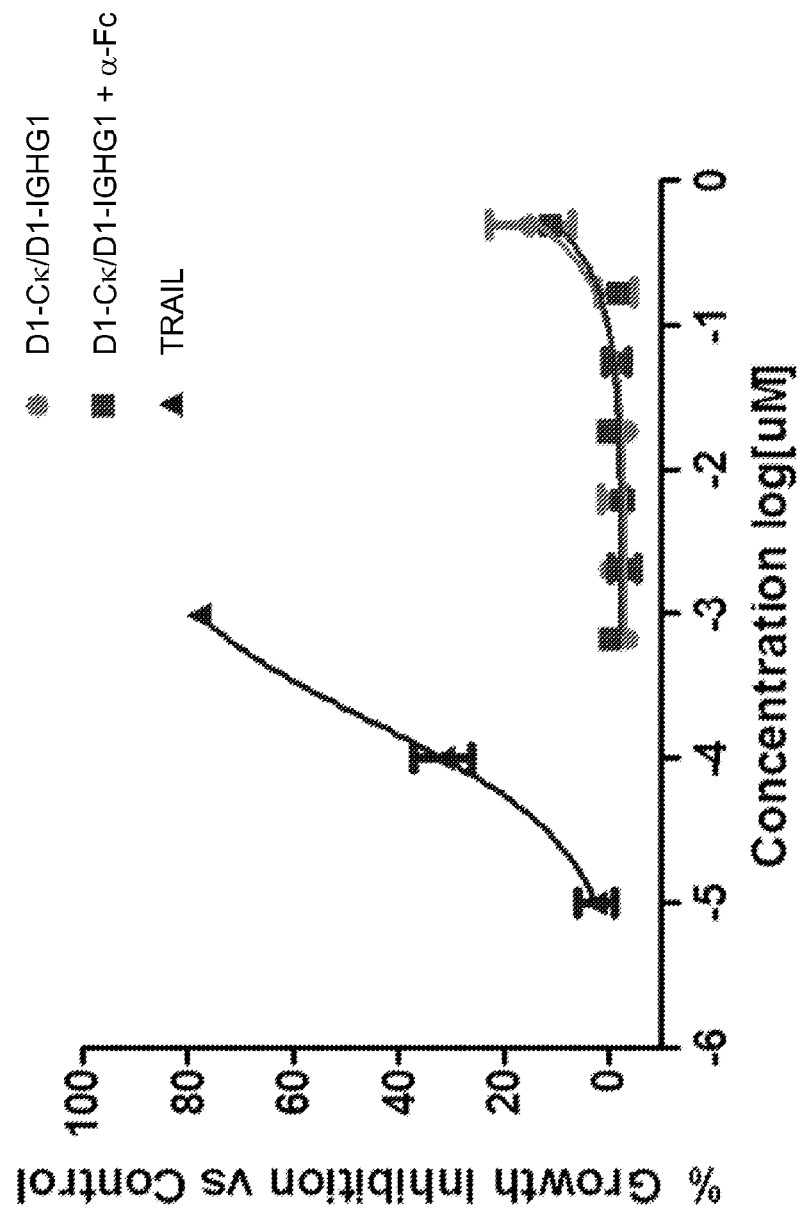
Figure 22B:
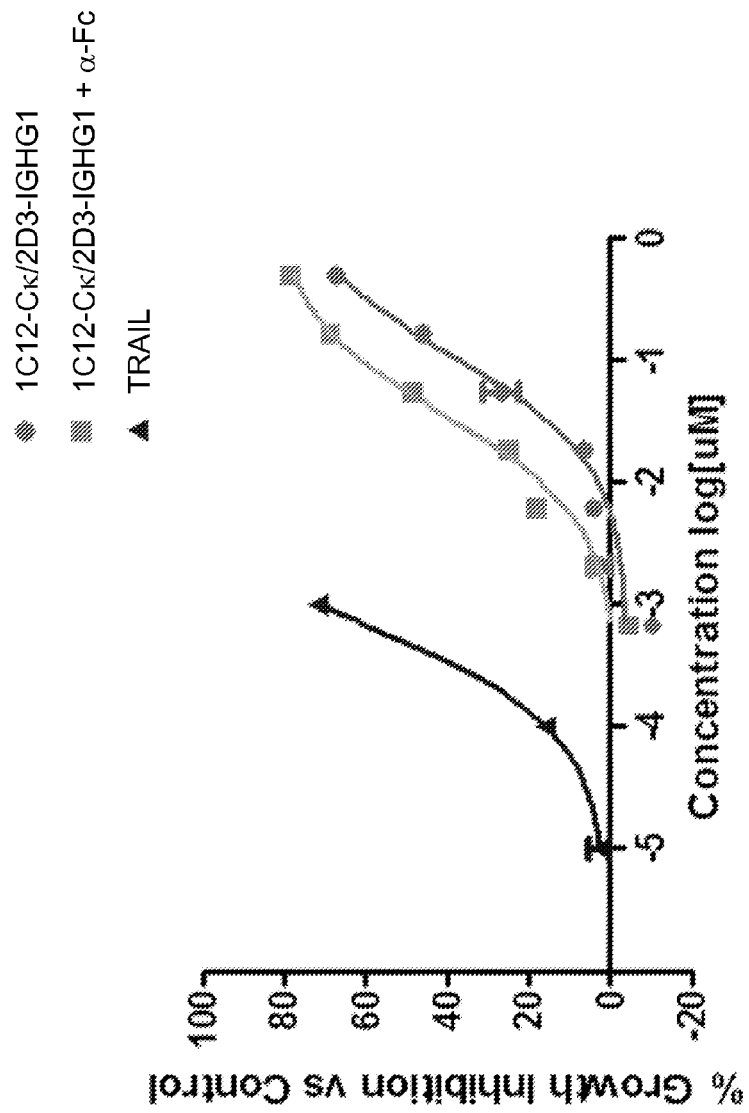

H2122 cells were plated in 96 well plates at a density of 10000 cells/well in 50 ul of complete medium (RPMI 1640 medium supplemented with 10% FBS). Cells were incubated overnight at 37° C. The next day, polyvalent Tn3 fusion proteins (Fc fusions or two chain tetravalent constructs) alone or in combination with goat anti-human Fc were serially diluted in complete medium. To achieve a dose curve, a 3-fold dilution scheme was used (highest final concentration was 3.6 uM). The goat anti-human Fc was added at a 1:2 molar ratio (i.e. half of the concentration of the Tn3-containing molecule). Tn3 and anti-human Fc alone and in combination were prepared at a 2× concentration (50 ul of each treatment were added per well). All treatments were done in triplicate wells. Commercially available TRAIL ligand (Chemicon Cat# GF092) was used as a positive control for Trail-induced cell death. The final concentrations for Trail were 1, 0.1, and 0.01 nM. After 48 hrs, the CellTiter-Glo kit from Promega was used to determine cell viability. Briefly, cells are allowed to equilibrate for about 10 min to room temperature. CellTiter-Glo buffer and substrate were mixed to prepare the CellTiter-Glo reagent as indicated by manufacturer. Each well received 100 ul of the CellTiter-Glo reagent and the plate was incubated for 10 min at room temperature prior to reading luminescence in a Wallac Plate reader. Results are shown in FIGS. 20-22. Each of the 1C12 and 2D3 containing polyvalent constructs were able to inhibit the viability of H2122 cells, presumably by activating TRAIL-R2 dependent apoptosis, moreover this activity was not dependent on higher order crosslinking via coordination with an anti-Fc antibody. The tetrameric form of 1C12 was more potent in the cell assay than its dimer form (compare FIGS. 20 and 21), consistent with the killing activity being a function of the valency. Fc-cross-linking did not increase the potency of killing and appeared to reduce the activity of the monospecific 1C12 constructs. Neither D1-Fc nor D1-Cκ/D1-IGHG1 control proteins, which do not bind TRAIL-R2, affected cell viability. The bispecific tetravalent constructs (FIG. 22) had the greatest potency in inhibiting H2122 cell viability, and this increased slightly if co-incubated with anti-Fc antibody. The improvement in activity for the 2D3/1C12 bispecific constructs relative to monospecific 1C12-Cκ/C12-IGHG1 may be due to superior potency for 2D3 vs 1C12 Tn3 units, or because 2D3 and 1C12 recognize different epitopes on TRAIL-R2 which could result in higher order aggregation of cell surface TRAIL-R2.

Example 18

Bacterial Secretion of Tn3 Scaffolds

Figure 23:

A bacterial expression vector was designed to secrete correctly folded Tn3 scaffold in *E. coli*. This system would allow for correct disulfide bond formation within Tn3 and therefore avoid the refolding process that is required for material expressed intracellularly as described in Example 4. To create a secretion vector, an intracellular Tn3 expression vector, similar to that described in Example 4, but containing a Ptac promoter instead of T7, was modified by insertion of the signal peptide sequence from *E. coli* oligopeptide binding protein (oppA). This signal sequence, cloned immediately upstream of Tn3, was chosen because oppA is a highly expressed *E. coli* protein. An extended 8×His tag was encoded downstream of Tn3 to facilitate purification. To simplify the transfer of Tn3 cassettes between this and other plasmids, a modified form of this vector was also created by introducing an Nco I site at the 3' end of the oppA signal sequence. This modification results in a single amino acid substitution (L25M) at the penultimate position within the oppA signal sequence (FIG. 23). These vectors were referred to as pSec-oppA-Tn3 and pSec-oppA(L25M)-Tn3.

Figure 24A:
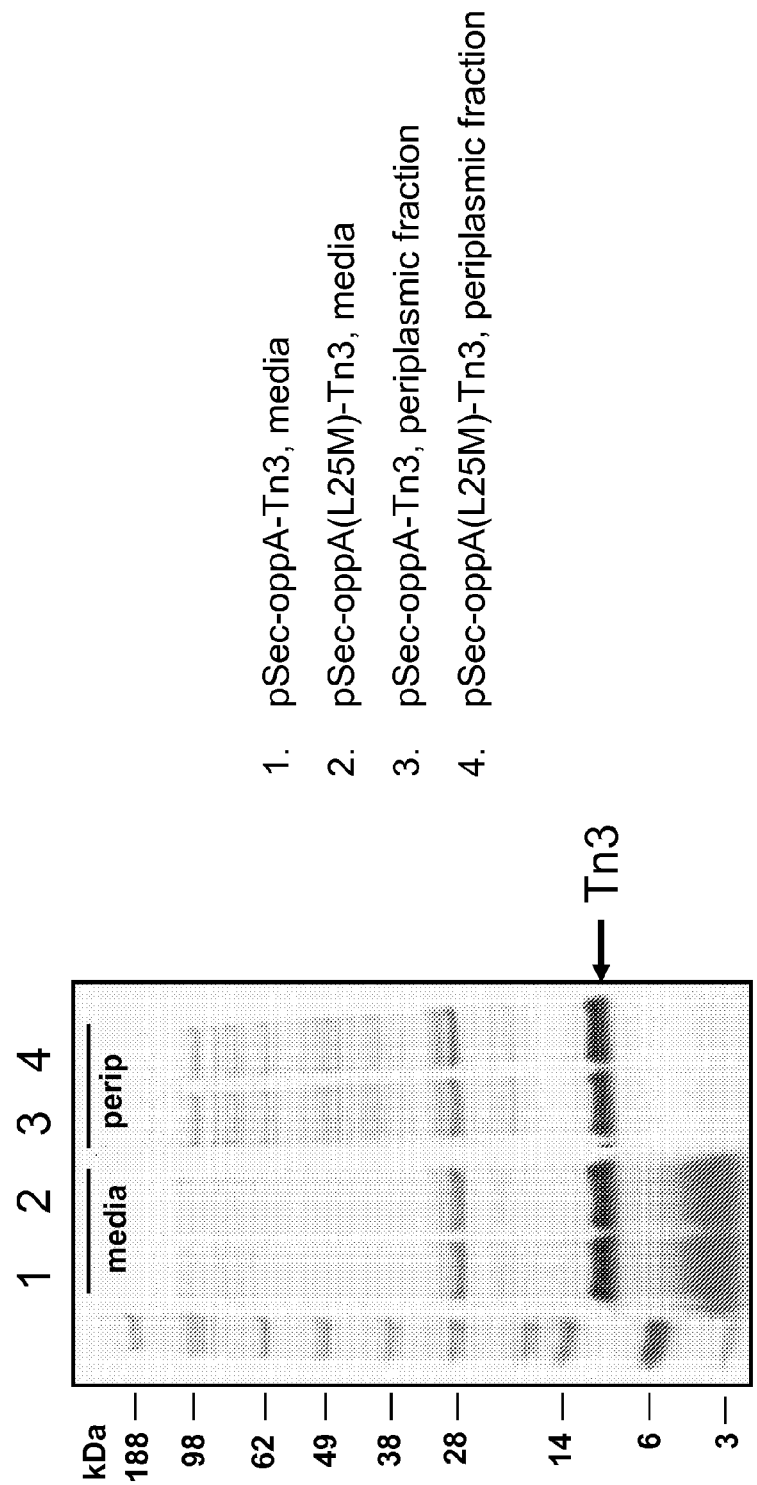

Superbroth media containing carbenicillum (100 ug/mL, 1% glucose) was innoculated with *E. coli* BL21 DE3 cultures transformed with pSec-oppA-Tn3 or pSec-oppA(L25M)-Tn3. Cultures were grown at 37° C. to an OD of 0.5-0.8 then induced with 0.2 mM IPTG. After shaking at 37° C. for 5 hours, cells were separated from the media by centrifugation. Periplasmic extracts were prepared by resuspending the cell pellet in 1/10 volume of ice-cold extraction buffer (10 mM Tris, pH 8 and 1 mM EDTA), incubating on ice for 10 min, then centrifuging to remove cells. Samples of periplasmic extract and media were analyzed by SDS-PAGE. Tn3 could be detected in both media and periplasmic fractions, and expression levels were similar for constructs containing the wild type or L25M oppA signal peptides (FIG. 24A). As pSec-oppA(L25M)-Tn3 contains a convenient 5' Tn3 cloning site, this construct is preferred for the expression of Tn3 clones derived from display libraries.

Figure 24B:
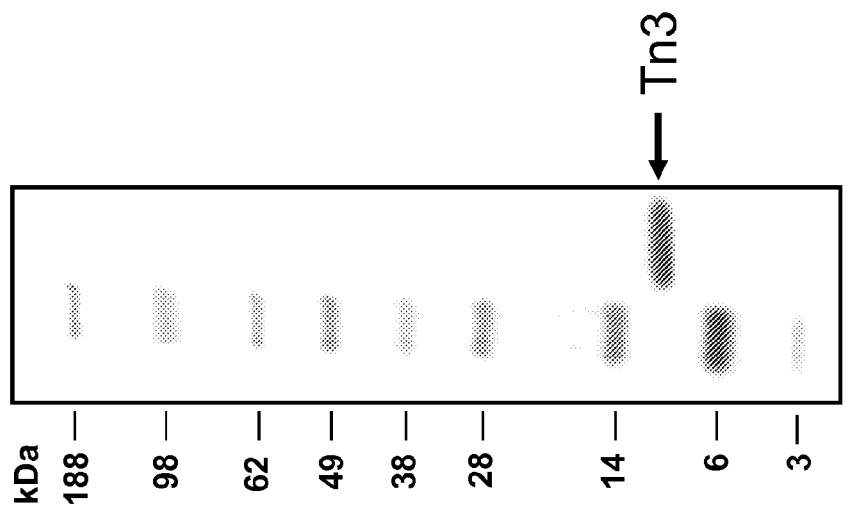
Figure 24C:
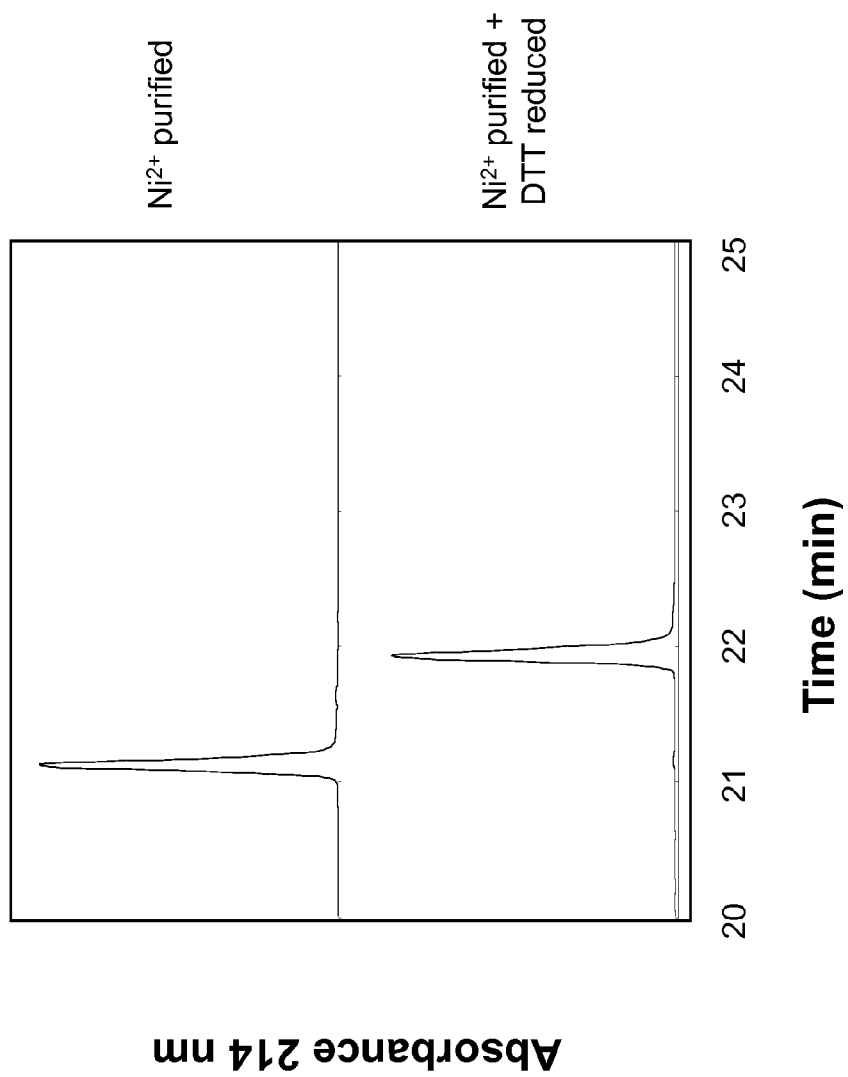
Figure 25:
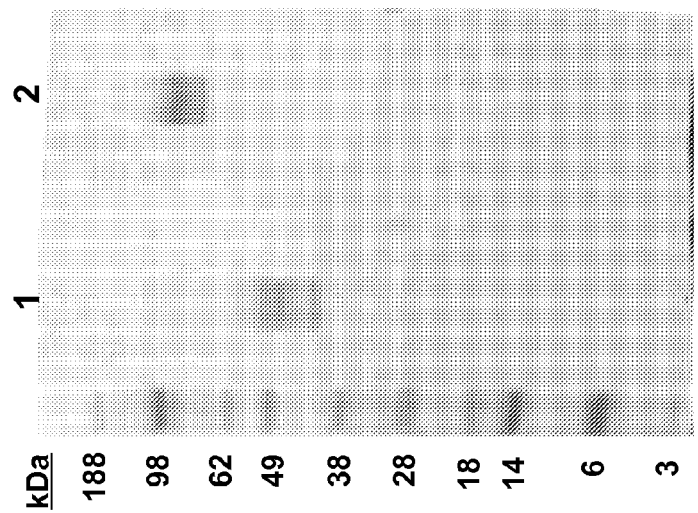

Purification of Tn3 from media was effected by precipitating the secreted protein with 65% w/v ammonium sulfate, resuspending the pellet in 50 mM Tris pH 8 buffer, then purifying on a HiTrap chelating column charged with $Ni^{2+}$ as previously described. SDS-PAGE analysis of the purified sample is shown in FIG. 24B. Purified Tn3 was analyzed by reverse phase HPLC (as described herein), either with or without DTT pretreatment to reduce any disulfide bonds. Tn3 eluted as a single peak, and the elution time shifted after reduction with DTT indicating the purified sample contained a disulfide bond as expected (FIG. 23C). Non-reducing SDS-PAGE and size exclusion chromatography of this material were consistent with a single monomeric species, and mass spectrometric analysis gave a molecular weight. of 10,896 Da which is within 3 Da of the predicted molecular weight for the mature, disulfide-containing sequence shown in FIG. 28A.

Finally, the expression level of secreted Tn3 in media was determined in a biosensor assay. Anti-His tag antibody (Penta-His, Qiagen Inc.) was immobilized onto an Attana A100 carboxyl sensor chip via standard amine coupling. *E. coli* BL21 DE3 were transformed with pSec-oppA(L25M)-Tn3, and protein expression was induced as described above. Dilutions of clarified media were injected over the chip, and levels of bound His-tag containing Tn3 were compared to that generated from injection of purified Tn3 standard. By this technique, the level of Tn3 detected in crude media was 250 mg/L.

Example 19

Generation of SynBP01-Fc Fusion

Summary: A chimeric fusion of a SYNAGIS®-binding Tn3 and the Fc region of IgG1 was generated.

Methods: Expression of SynBP01-Fc

As described above, SynBP01 is a Tn3 variant which was identified from a library of BC loop and FG loop-randomized Tn3 variants panned against SYNAGIS®. Flanking NheI and KasI sites were introduced by silent mutagenesis and utilized to subclone this construct into the pOE-Fc vector. The pOE-Fc vector contains the CH2 and CH3 domains of IgG1 Fc, which is 3' to the KasI restriction sites. The vector generated by subcloning SynBP01 into pOE-Fc was named pOE-SynBP01.

293EBNA cells (120 mL culture volume) were transfected with pOE-SynBP01 through Lipofectamine 2000 (Invitrogen), using standard methods. Supernatant was harvested 10 days post-transfection, and SynBP01-Fc was purified through Protein A affinity chromatography (GE Healthcare), eluting with 0.1M glycine, 0.15M NaCl, pH 3.08, and neutralizing with Tris-HCl buffer at pH 8. The purified sample was then dialyzed against PBS buffered at pH 7.2. The yield of purified SynBP01-Fc was 4 mg, indicating an expression level of 33 mg/L.

BIAcore Analysis of SynBP01-Fc

BIAcore analysis of this molecule was conducted on a BIAcore 3000 (GE Healthcare), as described in Example 3. This experiment was designed to determine whether the SynBP01-Fc was competent to bind SYNAGIS, and to detect qualitatively the difference in apparent affinity between the original SynBP01 binder and the Fc fusion.

Results: When injected at equivalent 1 μM concentrations, SynBP01-Fc yielded an approximately 6-fold increase in total response units compared to SynBP01 (FIG. 26). Moreover, SynBP01-Fc had a substantially reduced off-rate relative to SynBP01, due primarily to the increased avidity of the bivalent Fc fusion. Although the dissociation constant ($K_D$) of the SynBP01-Fc/SYNAGIS® interaction was not determined in this experiment, as the binding surface had not been prepared for a kinetic analysis, it is evident that the $K_D$ is improved from the $K_D$ of 16 μM seen with the SynBP01/SYNAGIS® interaction in Example 3.

Example 20

Site-specific PEGylation of STn3 Scaffold

Modification of a protein through PEGylation is frequently used to improve its therapeutic properties, such as decreased immunogenicity, improved pharmacokinetics and bioavailability by increasing the effective size of small proteins so as to avoid renal clearance. Site-specific modification with PEG, that is attachment at one or more specific residues in the protein, can avoid inactivation of a target proteins activity that could otherwise result from attachment of PEG at or near a functional site within a protein. To demonstrate site-specific PEGylation of a Tn3-like scaffold protein, a cysteine residue was engineered at the C-terminus of STn3 (*S. tokodaii* 1Tn3 from Example 5). As the wild type sequence of STn3 does not contain cysteine, treatment of the engineered scaffold with a Cys-specific PEGylation reaction would lead to site-specific attachment of PEG. STn3 had previously been expressed as a fusion to a C-terminal 6×His tag, in a variant of the pET-22b vector (Novagen). This vector contains the linker sequence GGGLE between the protein and the His tag. A variation on the QuikChange (Stratagene) mutagenesis method was used to mutate the leucine residue in the linker to a cysteine, which can be modified by a maleimide reagent. This protein is referred to as STn3(CTC), and was expressed and purified from BL21(DE3) cells using an IMAC column as described in Example 1.

The PEGylation reagent, Sunbright ME-200MA (NOF), was added to STn3(CTC) at a 4:1 molar excess (PEG reagent: protein), and was allowed to incubate at room temperature for 72 hours. Protein PEGylation was monitored by SDS-PAGE (FIG. 27A, lane 5), which revealed that the majority of the protein had been PEGylated by a single PEG moiety. As PEGylation typically has the effect of masking surface charge of a protein, the pH for cation-exchange chromatography was lowered from 6.0 (for wild-type purification) to 4.5, to ensure that the protein would effectively bind the column. The protein was purified on a 1 mL SP XL column (GE Healthcare) using 50 mM acetic acid, pH 4.5. A sodium chloride gradient was used to elute the protein, with the protein peak occurring at approximately 120 mM NaCl. Successful removal of residual unPEGylated STn3(CTC) from the PEGylated product is demonstrated by SDS-PAGE analysis of fractions obtained from the cation exchange purification fractions are shown in FIG. 27B, lanes 1-5.)

Example 21

Analysis of AB, CD and EF loops and Design of Randomized Library

To design Tn3 libraries which were randomized in the AB, CD and EF loops, a bioinformatic analysis was performed to derive information regarding the length and sequence diversity of these loops in naturally occurring Fn3 domains. Due to the difficulty in predicting the AB, CD and EF loop regions based on sequence information alone, the three dimensional structures of 103 different Fn3 domains from the pdb database were superimposed, and this was used to align the corresponding amino acid sequences (data not shown). The locations of the loops regions were used to extract length and sequence diversity information for each of the loops. The variation in length for each of the AB, CD and EF loops is shown graphically in FIG. 28.

As with loops on the opposite side of the Tn3 molecule, the AB, CD and EF loops vary in length and sequence composition for different Fn3 domains. The AB and CD loops are usually 5 to 9 amino acids long, although exceptions occur for some Fn3 domains which have AB and/or CD loops longer or shorter than this. The most common length within this data set was 6 residues for the CD loop (31% of sequences), and 7 residues for the AB loop (61% of sequences). Length variation occurs less frequently for the EF loop, and an 8 residue loop is most commonly observed (80% of sequences). Both the AB and CD loops show significant diversity in sequence and do not show overt preferences for specific amino acids in particular positions. An exception is the final position in the AB loop which is often Ser or Thr (58/103 sequences). The sequences of EF loops reveals strongly preferred amino acids at specific positions, though this is restricted to those that are 8 residues long. A Leu at position 3 within these loops is strongly conserved (76/82 sequences), and given the sidechain of this residue is buried in each of the structures, it is likely to be important for the structural integrity of the scaffold. A Pro residue is also commonly observed at position 5 (44/82 sequences), while Gly, Asn, Asp and Ser are often in position 2 (71/82 sequences) and Thr in position 7 (40/82).

A further practical consideration in the design of these Tn3 libraries was to identify an alternative to the "NNK" (N=A, G, T, C; K=G, T) mixed codon scheme typically used in degenerate oligonucleotides to code for any amino acid. Although the "NNK" mixture gives 32 different codons which code for all 20 amino acids, they are not encoded equally (Table 11). For instance, 3/32 codons in the "NNK" scheme code for Leu (CTG, CTT, TTG), but only 1/32 codes for Asp (GAT). In addition, the "NNK" mixture encodes one stop codon (TAG) and a Cys codon (TGT), neither of which is desirable when generating naiive libraries. In considering an alternative scheme, we took note of the fact that synthetic antibody libraries have been described which encode CDR sequences composed of a small subset of amino acids. Antibody libraries with CDR's composed of just 4 amino acids (Tyr, Ala, Asp, Ser), or even a binary pair (Tyr, Ser) have been shown to yield specific high affinity mAbs to protein antigens (Fellouse et al., Proc. Natl. Acad. Sci. USA. 2004, 101: 12467-72; J. Mol. Biol. 2005, 348: 1153-62). Similarly, a library of scaffold proteins with randomized loop sequences comprising just Tyr and Ser also yielded specific binders to a protein target (Koide et al., Proc. Natl. Acad. Sci. USA. 2007, 104: 6632-7). Although libraries containing highly restricted sets of amino acids are able to produce specific binding proteins, it is likely that the diversity of binders that are obtained from such a library will be limited. We therefore designed an alternate "NHT" mixed codon scheme for introducing diversity into a Tn3 library (H=A, T, C). "NHT" mixes code for a reasonable subset of the 20 amino acids, but avoid the disadvantages described with "NNK" mixed codons (Table 12). This scheme generates 12 codons that code for 12/20 amino acids, that is, each codon codes for a unique amino acid. Moreover, there are no stop or Cys codons.

TABLE 11

Amino acids encoded by "NNK" codon mixtures

| A | AAG = Lys | ATG = Met | ACG = Thr | AGG = Arg | G |
| | AAT = Asn | ATT = Ile | ACT = Thr | AGT = Ser | T |
| G | GAG = Glu | GTG = Val | GCG = Ala | GGG = Gly | G |
| | GAT = Asp | GTT = Val | GCT = Ala | GGT = Gly | T |
| C | CAG = Gln | CTG = Leu | CCG = Pro | CGG = Arg | G |
| | CAT = His | CTT = Leu | CCT = Pro | CGT = Arg | T |
| T | TAG = STOP | TTG = Leu | TCG = Ser | TGG = Trp | G |
| | TAT = Tyr | TTT = Phe | TCT = Ser | TGT = Cys | T |
| | A | T | C | G | |

TABLE 12

Amino acids encoded by "NHT" codon mixtures

| A | AAT = Asn | ATT = Ile | ACT = Thr |
| G | GAT = Asp | GTT = Val | GCT = Ala |
| C | CAT = His | CTT = Leu | CCT = Pro |
| T | TAT = Tyr | TTT = Phe | TCT = Ser |
| | A | T | C |

The final design for Tn3 libraries containing randomized AB, CD and EF loops is shown below. This design incorporates diversity observed in natural Fn3 sequences, two different lengths for the AB and CD loops, and uses "NHT" codon mixes.

AB Loop (7 and 9 Residues):
  Tn3 wild type amino acid sequence: KDVTDTT (SEQ ID NO:207)
  Library amino acid sequence (7 aa): Kxxxxxa
  DNA sequence: AAA-NHT-NHT-NHT-NHT-NHT-RST (SEQ ID NO:262)
  Library amino acid sequence (9 aa): Kxxxxxxxa
  DNA sequence: AAA-NHT-NHT-NHT-NHT-NHT-NHT-NHT-RST (SEQ ID NO:263)

CD Loop (7 and 9 Residues):
  Tn3 wild type amino acid sequence: KDVPGDR (SEQ ID NO:203)
  Library amino acid sequence (7 aa): xxxxxxx
  DNA sequence: NHT-NHT-NHT-NHT-NHT-NHT-NHT (SEQ ID NO:264)
  Library amino acid sequence (9 aa): xxxxxxxxx
  DNA sequence: NHT-NHT-NHT-NHT-NHT-NHT-NHT-NHT-NHT (SEQ ID NO:265)

EF Loop (8 Residues):
  Tn3 wild type amino acid sequence: GNLKPDTE (SEQ ID NO:209)
  Library amino acid sequence: xbLxPxcx
  DNA sequence: NHT-RRB-CTG-NHT-CCG-NHT-RBT-NHT (SEQ ID NO:266)
  Amino acid codes: x=N/D/H/Y/I/V/L/F/T/A/P/S; a=S/T/A/G; b=N/K/S/R/D/E/G; c=I/T/SN/A/G Nucleotide codes: N=G/A/T/C; H=A/T/C; R=A/G; S=G/C; B=T/C/G Design, Expression and Characterization of Charge Engineered Tn3 Variants with Enhanced Stability Design of Charge Engineered Tn3 Variants The stability of Tn3 to thermal unfolding is greater at pH 5 compared to pH 7, and greater in pH 7 buffer containing 1M salt than the same buffer without salt (FIG. 29). As high salt concentrations can mask surface protein charge, while buffer acidification can result in neutralization of negatively charged Asp and Glu side chains, these observations suggest that surface negative charge on Tn3 has a destabilizing effect.

To explore the potential for enhancing the stability of Tn3 through engineering of surface charge, the locations of Asp and Glu side chains were mapped onto the three dimensional structure of Tn3. From a total of 18 Asp and Glu residues contained in Tn3 (SEQ ID 1), a panel of 8 mutants were designed in which individual Asp or Glu residues were replaced with the neutral isoteric residues Asn or Gln (FIG. 30A). The selection of the 8 substitution sites was biased towards Asp and Glu residues that were in close proximity to another Asp or Glu, given proximity of like charges can contribute to destabilization through electrostatic repulsion.

Charge Mutant Generation and Recombinant Expression

Expression constructs for Tn3 mutants were generated by site-directed mutagenesis of the wild type expression construct as described previously. Recombinant protein was expressed in *E. coli* and purified by immobilized nickel chelate affinity chromatography as described previously. All Tn3 mutants expressed at high levels and were readily purified, although the preparation of the E54Q mutant did contain some impurities as evidenced by SDS-PAGE analysis (FIG. 30B).

Characterization of Stability

Unfolding of charge mutants by urea was monitored by intrinsic fluorescence as previously described for wild type Tn3. To facilitate a comparison of urea-induced unfolding profiles of wild type and charge mutants of Tn3, the relative fluorescence emission intensity at 360 nm was plotted as a function of urea concentration for each protein.

A comparison of urea-induced unfolding at pH 7.0 for wild type Tn3 and the various charge mutants (FIG. 31A) showed that 3 of the mutants (D40N, E54Q and E67Q) had the same or slighty lower stability than the wild type protein. Five of the mutants (E33Q, D49N, E52Q, D53N, E86Q) showed small but clearly defined increases in the midpoints of urea-induced unfolding, suggestive of an increase in protein stability. The concentration of urea required to induce 50% unfolding was approximately 0.5M higher for best 3 mutants (E33Q, D49N and E86Q) than for wild type Tn3.

Preparation and Analysis of Tn3 Variants Containing Multiple Charge Mutations

Given the enhanced stability of a number of the Tn3 charge variants, new Tn3 variants containing combined charge mutations were prepared to investigate whether additive improvements in stability could be obtained. To this end, three new variants were prepared containing paired mutations (D49N/E86Q and E33Q/D49N) or a triple mutation (E33Q/D49N/E86Q). These mutants were recombinantly expressed and purified, and their urea denaturation profiles were characterized by fluorescence.

When compared to the single charge mutants of Tn3, each of the combination mutants showed further enhancement of stability as determined by the increase in urea concentration required for unfolding (FIG. 31B). While the midpoint of urea-induced unfolding of the individual charge mutants E33Q, D49N and E86Q occurred at ~2.5M urea, the midpoint of unfolding for each of the D49N/E86Q, E33Q/D49N and E33Q/D49N/E86Q mutants corresponded to ~3.0M urea. This indicates that combined replacement of multiple destabilizing Asp or Glu residues can lead to an additive improvement in Tn3 stability, although in the examples studied here, a triple mutant was no more stable than a double mutant.

To further characterize the stabilities of the combination charge mutants relative to wild type Tn3, these proteins were analyzed by DSC at pH 7 as previously described. This analysis further confirmed that the charge mutations led to an improvement in the stability of the Tn3 scaffold. While the wild type protein had a mid-point of thermal unfolding ($T_m$) of 45° C., the E33Q/D49N Tn3 mutant had a Tm of 50° C., while D49N/E86Q and E33Q/D49N/E86Q mutants had Tm's of 52° C. (FIG. 32).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

We claim:

1. A recombinant polypeptide scaffold comprising:
   I. seven beta strand domains designated A, B, C, D, E, F, and G, having the amino acids of:
      a) SEQ ID NO:239 for the A beta strand, SEQ ID NO:229 for the B beta strand, SEQ ID NO:230 for the C beta strand, SEQ ID NO: 236 for the D beta strand, SEQ ID NO:232 for the E beta strand, SEQ ID NO:245 for the F beta strand and SEQ ID NO:246 for the G beta strand; or
      b) SEQ ID NO:239 for the A beta strand, SEQ ID NO:229 for the B beta strand, SEQ ID NO:247 for the C beta strand, SEQ ID NO: 236 for the D beta strand, SEQ ID NO:232 for the E beta strand, SEQ ID NO:248 for the F beta strand, and SEQ ID NO:234 for the G beta strand;
   II. linked to six loop regions such that a loop region connects each beta strand domain, is designated AB, BC, CD, DE, EF, and FG and corresponds to the cognate loop regions of SEQ ID NO:1, the cognate loop regions of SEQ ID NO: 1 consisting of residues:
      a) from 11 to 17 inclusive in an AB loop;
      b) from 23 to 31 inclusive in an BC loop;
      c) from 39 to 45 inclusive in an CD loop;
      d) from 51 to 56 inclusive in an DE loop;
      e) from 23 to 31 inclusive in an EF loop;
      f) from 23 to 31 inclusive in an FG loop,
   at least one of said loop regions being a non-naturally occurring variant of the cognate loop region in SEQ ID NO: 1; and
   III. a disulfide bond linking the F and G beta strand domains or linking the C and F beta strand domains, wherein said scaffold binds a target.

2. The scaffold of claim 1, wherein said BC loop is a non-naturally occurring variant and consists of 9 amino acids having a sequence of S-X-a-X-b-X-X-X-G, wherein X represents any amino acid, wherein (a) represents proline or alanine and wherein (b) represents alanine or glycine.

3. The scaffold of claim 1, wherein said BC loop is a non-naturally occurring variant and consists of 11 amino acids having a sequence of S-P-c-X-X-X-X-X-X-T-G (SEQ ID NO: 258), wherein X represents any amino acid and wherein (c) represents proline, serine or glycine.

4. The scaffold of claim 1, wherein said BC loop is a non-naturally occurring variant and consists of 12 amino acids having a sequence of A-d-P-X-X-X-e-f-X-I-X-G (SEQ ID NO: 257), wherein X represents any amino acid, wherein (d) represents proline, glutamate or lysine, wherein (e) represents asparagine or glycine, and wherein (f) represents serine or glycine.

5. The scaffold of claim 1, wherein said FG loop is a non-naturally occurring variant and consists of 9 amino acids having a sequence of X-a-X-X-G-X-X-X-S, wherein X represents any amino acid and wherein (a) represents asparagine, threonine or lysine.

6. The scaffold of claim 1, wherein said FG loop is a non-naturally occurring variant and consists of 10 amino acids having a sequence of X-a-X-X-X-X-b-N-P-A, wherein X represents any amino acid, wherein (a) represents asparagine, threonine or lysine and wherein (b) represents serine or glycine.

7. The scaffold of claim 1, wherein said FG loop is a non-naturally occurring variant and consists of 11 amino acids having a sequence of X-a-X-X-G-X-X-S-N-P-A (SEQ ID NO: 259), wherein X represents any amino acid, and wherein (a) represents asparagine, threonine or lysine.

8. The scaffold of claim 1, wherein said DE loop is a non-naturally occurring variant and consists of 6 amino acids having a sequence of X-X-X-X-X-X, wherein X represents any amino acid.

9. The scaffold of claim 1, wherein said AB loop is a non-naturally occurring variant and consists of 7 residues having the sequence: K-X-X-X-X-X-a, wherein X represents asparagine, aspartic acid, histidine, tyrosine, isoleucine, valine, leucine, phenylalanine, threonine, alanine, proline, or serine, and wherein (a) represents serine, threonine, alanine, or glycine.

10. The scaffold of claim 1, wherein said AB loop is a non-naturally occurring variant and consists of 9 residues having the sequence: K-X-X-X-X-X-X-X-a, wherein X represents asparagine, aspartic acid, histidine, tyrosine, isoleucine, valine, leucine, phenylalanine, threonine, alanine, proline, or serine, and wherein (a) represents serine, threonine, alanine, or glycine.

11. The scaffold of claim 1, wherein said CD loop is a non-naturally occurring variant and consists of 7, 8, or 9 residues wherein each residue in the CD loop is randomized and wherein each residue may be asparagine, aspartic acid, histidine, tyrosine, isoleucine, valine, leucine, phenylalanine, threonine, alanine, proline, or serine.

12. The scaffold of claim 1, wherein said EF loop is a non-naturally occurring variant and consists of 8 residues having the sequence X-b-L-X-P-X-c-X, wherein X represents asparagine, aspartic acid, histidine, tyrosine, isoleucine, valine, leucine, phenylalanine, threonine, alanine, proline, or serine, wherein (b) represents asparagine, lysine, arginine, aspartic acid, glutamic acid, or glycine, and wherein (c) represents isoleucine, threonine, serine, valine, alanine, or glycine.

13. The scaffold of claim 1, wherein said beta strand domains have the amino acid sequences of: SEQ ID NO:239 for the A beta strand, SEQ ID NO:229 for the B beta strand, SEQ ID NO:230 for the C beta strand, SEQ ID NO: 236 for the D beta strand, SEQ ID NO:232 for the E beta strand, SEQ ID NO:245 for the F beta strand and SEQ ID NO:246 for the G beta strand.

14. The scaffold of claim 1, wherein said beta strand domains have the amino acids of: SEQ ID NO: 239 for the A beta strand, SEQ ID NO:229 for the B beta strand, SEQ ID NO: 247 for the C beta strand, SEQ ID NO: 236 for the D beta strand, SEQ ID NO: 232 for the E beta strand, SEQ ID NO: 248 for the F beta strand and SEQ ID NO: 234 for the G beta strand.

15. The scaffold of claim 1, wherein said BC and FG loops are non-naturally occurring variants.

16. The scaffold of claim 1, wherein said BC, DE and FG loops are non-naturally occurring variants.

17. The scaffold of claim 1, wherein the target is TRAIL-R2.

* * * * *